United States Patent
Rosinger et al.

(10) Patent No.: US 8,962,523 B2
(45) Date of Patent: Feb. 24, 2015

(54) HERBICIDE/SAFENER COMBINATION

(75) Inventors: Christopher Hugh Rosinger, Hofheim (DE); Erwin Hacker, Hochheim (DE); Hartmut Ahrens, Egelsbach (DE); Hansjörg Dietrich, Liederbach am Taunus (DE); Frank Ziemer, Kriftel (DE)

(73) Assignee: Bayer Cropscience AG, Monheim (DE)

( * ) Notice: Subject to any disclaimer, the term of this patent is extended or adjusted under 35 U.S.C. 154(b) by 398 days.

(21) Appl. No.: 12/626,158

(22) Filed: Nov. 25, 2009

(65) Prior Publication Data
US 2010/0137137 A1  Jun. 3, 2010

(30) Foreign Application Priority Data
Nov. 29, 2008 (EP) .................................... 08020782

(51) Int. Cl.
*A01N 25/26* (2006.01)
*A01N 25/32* (2006.01)

(52) U.S. Cl.
CPC ..................................... *A01N 25/32* (2013.01)
USPC ............................. 504/100; 504/103; 504/105

(58) Field of Classification Search
None
See application file for complete search history.

(56) References Cited

U.S. PATENT DOCUMENTS

| | | | |
|---|---|---|---|
| 5,215,570 A * | 6/1993 | Burckhardt et al. | 504/104 |
| 6,251,827 B1 | 6/2001 | Ziemer et al. | |
| 6,635,306 B2 | 10/2003 | Steckl et al. | |
| 6,784,137 B2 * | 8/2004 | Balko et al. | 504/244 |
| 6,849,578 B1 | 2/2005 | Wellmann et al. | |
| 7,314,849 B2 * | 1/2008 | Balko et al. | 504/244 |
| 7,498,468 B2 * | 3/2009 | Balko et al. | 568/1 |
| 7,786,044 B2 * | 8/2010 | Epp et al. | 504/260 |
| 2004/0110637 A1 | 6/2004 | Ziemer et al. | |
| 2007/0054805 A1 * | 3/2007 | Krause et al. | 504/102 |
| 2007/0179060 A1 | 8/2007 | Balko et al. | |
| 2009/0062121 A1 * | 3/2009 | Satchivi et al. | 504/105 |
| 2010/0130361 A1 * | 5/2010 | Yerkes et al. | 504/105 |

FOREIGN PATENT DOCUMENTS

| | | |
|---|---|---|
| WO | 2009029518 | 3/2009 |
| WO | 2010059671 | 5/2010 |
| WO | 2010059676 | 5/2010 |
| WO | 2010059680 | 5/2010 |

OTHER PUBLICATIONS

International Search Report of PCT/EP2009-008304 dated Jul. 15, 2011.
European Search Report to Application No. EP 08 02 0782, dated Aug. 10, 2009 (3 pages).

* cited by examiner

*Primary Examiner* — Alton Pryor
(74) *Attorney, Agent, or Firm* — Miles and Stockbridge

(57) ABSTRACT

A composition comprising
(A) one or more compounds of the formula (I) or salts thereof,

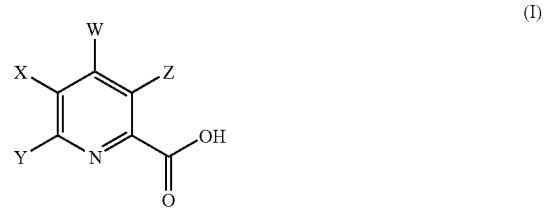

(I)

in which the individual indices have the meaning defined in the description and
(B) one or more safeners
is described.

16 Claims, No Drawings

HERBICIDE/SAFENER COMBINATION

The present invention relates to agrochemically effective herbicide/safener combinations, to processes for their preparation, and to their use for controlling harmful plants.

It is known from various documents that certain pyridine derivatives have herbicidal properties. For example, WO 2003/011853, WO 2006/062979 and WO 2007/082098 describe pyridine derivatives which control a broad spectrum of weeds. WO 2009/029518, prior art which has been subsequently published, discloses mixtures of auxin herbicides with further herbicidal active ingredients and, in some cases, safeners. An increase in the selectivity or crop plant compatibility as a result of using safeners is not demonstrated, but merely synergistic effects of the various herbicidal active ingredients. WO 1999/16744 discloses safeners from the class of acylsulfamoylbenzamides. An effect of herbicidal active ingredients of the present invention is not disclosed. WO 2001/035740 discloses mixtures of pyridine herbicides such as propoxycarbazone with further active ingredients. The present pyridine herbicides, however, are structurally different from the substance class disclosed therein.

Some of the already disclosed active ingredients and active ingredient combinations with auxin herbicides are not fully compatible with a number of important crop plants, such as, for example, various cereal species, corn or rice. Consequently, in some crops, they cannot be used in a manner which ensures the desired broad herbicidal activity against harmful plants.

It is therefore an object of the present invention to find herbicidal compositions in which the selectivity of the aforementioned herbicides in respect of important crop plants is increased. Surprisingly, this object is achieved by the herbicide/safener combination according to the invention.

The present invention therefore provides a composition comprising
(A) one or more compounds of the formula (I) or their salts,

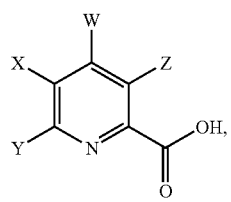

in which
X is hydrogen, halogen, $C_1$-$C_6$-alkyl, $C_1$-$C_6$-alkoxy, $C_1$-$C_6$-alkylthio, aryloxy, nitro, $C_1$-$C_6$-haloalkyl, $C_1$-$C_6$-haloalkoxy, thiocyano or cyano;
Y is an aryl group selected from a group consisting of phenyl, indanyl and naphthyl, or is a heteroaryl group selected from the group of 5- and 6-membered heteroaromatic rings, comprising one or more heteroatoms, where the heteroaromatic rings may be optionally annelated with another aromatic system; the aryl group or the heteroaryl group may be unsubstituted or substituted by one or more substituents from a group consisting of halogen, hydroxy, nitro, cyano, aryloxy, formyl, $C_1$-$C_6$-alkyl, cyclopropyl, $C_2$-$C_6$-alkenyl, $C_2$-$C_6$-alkynyl, $C_1$-$C_6$-alkoxy, halogenated $C_1$-$C_6$-alkyl, $C_1$-$C_4$-alkoxy-substituted $C_1$-$C_4$-alkyl, halogenated $C_1$-$C_6$-alkoxy, $C_1$-$C_4$-alkoxy-substituted $C_1$-$C_4$-alkoxy, $C_1$-$C_6$-acyl, fluorinated acetyl, fluorinated propionyl, where the two last-mentioned groups may each contain two or more fluorine atoms in the alkyl radical, $C_1$-$C_6$-alkylthio, $C_1$-$C_6$-alkylsulfinyl, $C_1$-$C_6$-alkylsulfonyl, halogenated $C_1$-$C_6$-alkylthio, aryl, amino, $C_1$-$C_4$-monoalkylamino, $C_2$-$C_8$-dialkylamino, $C_1$-$C_6$-alkylcarbonyloxy, $C_1$-$C_6$-alkylcarbonylamino, (C=O)OH, $C_1$-$C_6$-alkoxycarbonyl, (C=O)NH$_2$, $C_1$-$C_6$-alkylaminocarbonyl, $C_1$-$C_6$-dialkylaminocarbonyl, —CH$_2$CH$_2$O—, —CH$_2$CH$_2$CH$_2$O—, —OCH$_2$O—, —O(CH$_2$)$_2$O—;
Z is halogen, $C_1$-$C_6$-alkyl, $C_1$-$C_6$-alkoxy, $C_1$-$C_6$-alkylthio, aryloxy, nitro, $C_1$-$C_6$-haloalkyl, $C_1$-$C_6$-haloalkoxy, thiocyano or cyano;
W is NO$_2$, N$_3$, NR$^1$R$^2$, N=CR$^3$R$^4$ or NHN=CR$^3$R$^4$;
R$^1$ and R$^2$ independently of one another are hydrogen, $C_1$-$C_6$-alkyl, $C_3$-$C_6$-alkenyl, $C_3$-$C_6$-alkynyl, aryl, heteroaryl, hydroxy, $C_1$-$C_6$-alkoxy, amino, $C_1$-$C_6$-acyl, $C_1$-$C_6$-alkoxycarbonyl, $C_1$-$C_6$-alkylaminocarbonyl, $C_1$-$C_6$-alkylsulfonyl, $C_1$-$C_6$-trialkylsilyl or $C_1$-$C_6$-dialkylphosphonyl; or
R$^1$ and R$^2$ together with N are a five- or six-membered saturated or unsaturated ring, which may optionally additionally contain O, S or N heteroatoms;
R$^3$ and R$^4$ independently of one another are hydrogen, $C_1$-$C_6$-alkyl, $C_3$-$C_6$-alkenyl, $C_3$-$C_6$-alkynyl, aryl or heteroaryl; or
R$^3$ and R$^4$ together with =C are a five- or six-membered saturated ring;
or herbicidally active derivatives of the carboxylic acid group
and
(B) one or more safeners,
where in general and in all embodiments, compositions are excluded which comprise the following combinations of further herbicidal active ingredients and safeners:
pinoxaden and cloquintocet-mexyl,
pyroxsulam and cloquintocet-mexyl,
clodinafop-propargyl and cloquintocet-mexyl,
mesosulfuron-methyl and iodosulfuron-methyl-sodium and mefenpyr-diethyl,
fenoxaprop-P-ethyl and mefenpyr-diethyl.

The present invention further provides the use of the safeners for increasing the selectivity and/or crop plant compatibility of the herbicides of the formula (I).

The herbicide/safener combinations according to the invention can comprise additional further components, for example crop protection composition active ingredients of a different type and/or formulation auxiliaries and/or additives customary in crop protection, or can be used together with these.

The herbicides (A) and the safeners (B) can be applied in a known manner, for example together (for example as a coformulation or as a tank mix) or else at different times (splitting), for example to the plants, plant parts, plant seeds or the area on which the plants grow. It is possible, for example, to apply the individual active ingredients or the herbicide/safener combination in several portions (sequential application), for example pre-emergence applications, followed by post-emergence applications or early post-emergence applications, followed by medium or late post-emergence applications. Preference is given here to the joint or almost simultaneous application of the active ingredients of the combination in question. It is also possible to use the individual active ingredients or the herbicide/safener combination for treating seed material.

Compound of the Formula (I)
The specified formula (I) encompasses all stereoisomers and mixtures thereof, in particular also racemic mixtures, and—if enantiomers are possible—both enantiomers and in particular the respective biologically effective enantiomer.

In a first embodiment of the present invention, preferred herbicides (A) are compounds of the formula (I) and salts thereof, in which the radical
X is hydrogen or fluorine.

In a second embodiment of the present invention, preferred herbicides (A) are compounds of the formula (I) and salts thereof, in which the radical
Y is a phenyl group or a pyridinyl, benzofuranyl, benzothienyl, thienyl or thiazolyl group, where the phenyl group or the heteroaryl group may be substituted by one or more substituents selected from the group consisting of halogen, $C_1$-$C_2$-alkyl, $C_1$-$C_2$-alkoxy, $C_1$-$C_2$-haloalkyl and $C_1$-$C_2$-haloalkoxy.

In this second embodiment, particularly preferred herbicides (A) are compounds of the formula (I) and salts thereof in which the radical
Y is a phenyl group or a pyridinyl, benzofuranyl, benzothienyl, thienyl or thiazolyl group, where the phenyl group or the heteroaryl group is substituted by one or more substituents selected from the group consisting of halogen, $C_1$-$C_2$-alkyl, $C_1$-$C_2$-alkoxy, $C_1$-$C_2$-haloalkyl and $C_1$-$C_2$-haloalkoxy.

In this second embodiment, yet further preferred herbicides (A) are compounds of the formula (I) and salts thereof in which the radical
Y is a tri- or tetrasubstituted phenyl group, where the phenyl group is substituted by substituents, independently of one another selected from the group consisting of halogen, $C_1$-$C_2$-alkyl, $C_1$-$C_2$-alkoxy, $C_1$-$C_2$-haloalkyl and $C_1$-$C_2$-haloalkoxy.

In a third embodiment of the present invention, preferred herbicides (A) are compounds of the formula (I) and salts thereof, in which the radical
Z is halogen.

In this third embodiment, particularly preferred herbicides (A) are compounds of the formula (I) and salts thereof, in which the radical
Z is chlorine.

In a fourth embodiment of the present invention, preferred herbicides (A) are compounds of the formula (I) and salts thereof, in which the radical W is $NH_2$ or $N(R^1)(R^2)$, where
$R^1$ and $R^2$, in each case independently of one another, are hydrogen or $C_1$-$C_6$-alkyl.

The amino group at the 4 position may be unsubstituted or substituted by one or more $C_1$-$C_6$-alkyl, $C_3$-$C_6$-alkenyl, $C_3$-$C_6$-alkynyl, aryl, heteroaryl, hydroxy, $C_1$-$C_6$-alkoxy or amino substituents. The amino group may also be derivatized as an amide, a carbamate, a urea, a sulfonamide, a silylamine, a phosphoramidate, an imine or a hydrazone. These derivatives may be cleaved to give the amine. Preference is given to an unsubstituted amino group or an amino group substituted by one or two alkyl substituents.

It is assumed that the carboxylic acids of the formula (I) are the compounds which actually kill or control the undesired vegetation and these are usually preferred. Analogs of these compounds in which the acid group of the picolinic acid has been derivatized in order to form a related substituent which can be converted into an acid in the plants or in the environment essentially have the same herbicidal effect and are within the scope of the invention. Consequently, a "herbicidally active derivative" is any desired salt, ester, acyl hydrazide, imidate, thioimidate, amidine, amide, orthoester, acyl cyanide, acyl halide, thio ester, thione ester, dithiol ester, nitrile or any other desired acid derivative known to the person skilled in the art which (a) does not substantially impair the herbicidal effect of the active ingredient, namely of the 6-aryl- or heteroaryl-4-aminopicolinic acid, and (b) is or can be hydrolyzed, oxidized or metabolized in plants or in the earth to give the picolinic acid of the formula (I) which, depending on the pH, is present in the dissociated or the undissociated form. The preferred herbicidally active derivatives of the carboxylic acid are agriculturally acceptable salts, esters and amides. A "herbicidally active derivative" with regard to the amine functionality in the 4 position is likewise any desired salt, silylamine, phosphorylamine, phosphinimine, phosphoroamidate, sulfonamide, sulfilimine, sulfoximine, aminal, hemiaminal, amide, thioamide, carbamate, thiocarbamate, amidine, urea, imine, nitro, nitroso, azide, or any other desired nitrogen-containing derivative known to the person skilled in the art which (a) does not substantially impair the herbicidal effect of the active ingredient, namely of the 6-aryl- or heteroaryl-4-aminopicolinic acid, and (b) is or can be hydrolyzed in plants or in the earth to give a free amine of the formula (I). N-oxides, which can likewise be cleaved to give the starting pyridine of the formula (I) are likewise encompassed within the context of the invention.

Suitable salts include those which are derived from alkali metals or alkaline earth metals and those which are derived from ammonia and amines. Preferred cations include sodium, potassium, magnesium, and ammonium cations of the formula:

$$R_5R_6R_7NH$$

in which $R_5$, $R_6$ and $R_7$, in each case independently of one another, are hydrogen or $C_1$-$C_{12}$-alkyl, $C_3$-$C_{12}$-alkenyl or $C_3$-$C_{12}$-alkynyl, where each is optionally substituted by one or more hydroxy, $C_1$-$C_4$-alkoxy, $C_1$-$C_4$-alkylthio or phenyl groups, with the proviso that $R_5$, $R_6$ and $R_7$ are sterically compatible. Additionally, in each case two of $R_5$, $R_6$ and $R_7$ together may be an aliphatic difunctional unit which comprises 1 to 12 carbon atoms and up to two oxygen or sulfur atoms. Salts of the compounds of the formula (I) can be prepared by treating the compounds of the formula (I) with a metal hydroxide, such as, for example, sodium hydroxide, or an amine, such as, for example, ammonia, trimethylamine, diethanolamine, 2-methylthiopropylamine, bisallylamine, 2-butoxyethylamine, morpholine, cyclododecylamine, or benzylamine. The amine salts are often the preferred forms of the compounds of the formula (I) since they are water-soluble and are suitable for producing the desired water-based herbicide compositions.

Suitable esters include those which are derived from $C_1$-$C_{12}$-alkyl, $C_3$-$C_{12}$-alkenyl or $C_3$-$C_{12}$-alkynyl alcohols, such as, for example, methanol, isopropanol, butanol, 2-ethylhexanol, butoxyethanol, methoxypropanol, allyl alcohol, propargyl alcohol or cyclohexanol. Esters can be prepared by coupling the picolinic acid with the alcohol using any desired number of suitable activating agents, such as, for example, those which are used in peptide couplings, such as, for example, dicyclohexylcarbodiimide (DCC) or carbonyldiimidazole (CDI), by reacting the corresponding acid chloride of a picolinic acid of the formula (I) with a suitable alcohol or by reacting the corresponding picolinic acid of the formula (I) with a suitable alcohol in the presence of an acid catalyst. Suitable amides include those which are derived from ammonia or from $C_1$-$C_{12}$-alkyl, $C_3$-$C_{12}$-alkenyl or $C_3$-$C_{12}$-alkynyl mono- or disubstituted amines, such as, for example, but not limited to, dimethylamine, diethanolamine, 2-methylthiopropylamine, bisallylamine, 2-butoxyethylamine, cyclododecylamine, benzylamine or cyclic or aromatic amines with or without additional heteroaromatics such as, for example, but not limited to, aziridine, azetidine, pyrrolidine, pyrrole, imidazole, tetrazole or morpholine. Amides can be prepared by reacting the corresponding picolinoyl chloride, mixed anhydride, or carboxylic acid ester of the formula (I) with ammonia or a suitable amine.

The compounds of the formula (I) can also form salts through adduct formation of a suitable inorganic or organic acid, such as, for example, HCl, HBr, $H_2SO_4$ or $HNO_3$, but also oxalic acid or sulfonic acids onto a basic group, such as, for example, amino or alkylamino. Suitable substituents which are present in deprotonated form, such as, for example, sulfonic acids or carboxylic acids, can form internal salts with groups that for their part are protonatable, such as amino groups. Salts can likewise be formed by, in the case of suitable substituents, such as, for example, sulfonic acids or carboxylic acids, replacing the hydrogen by a cation suitable for agriculture. These salts are, for example, metal salts, in particular alkali metal salts or alkaline earth metal salts, in particular sodium and potassium salts, or else ammonium salts, salts with organic amines or quaternary ammonium salts with cations of the formula [NRR'R''R''']$^+$, in which R to R''', in each case independently of one another, are an organic radical, in particular alkyl, aryl, aralkyl or alkylaryl.

In particular, the compounds of the formula (I) can also include N-oxides. Corresponding pyridine N-oxides are accessible via an oxidation of the corresponding pyridines. Suitable oxidation methods are described, for example, in Houben-Weyl, Methoden der organischen Chemie [Methods in organic chemistry], expanded and subsequent volumes to the 4th edition, volume E 7b, p. 565 f.

Unless specifically defined otherwise, the following definitions apply in general for the radicals of the formula (I).

In formula (I), the radicals alkyl, alkoxyalkyl, hydroxyalkyl and alkoxyalkoxyalkyl may in each case be straight-chain or branched.

Within the context of the present invention, the term "alkyl" is understood in particular as meaning the radicals methyl; ethyl; n-propyl; isopropyl; n-butyl; sec-butyl; tert-butyl; or the various isomers of pentyl or hexyl.

Within the context of the present invention, the term "alkoxyalkyl" is understood as meaning alkyl provided with an alkoxy substituent. Examples of the radical "alkoxyalkyl" include $CH_3OCH_2$, $CH_3OCH_2CH_2$, $CH_3CH_2OCH_2$, $CH_3CH_2CH_2CH_2OCH_2$, $CH_3CH_2OCH_2CH_2$, $CH_3CH_2CH_2CH_2OCH_2CH_2$ or $CH_3CH_2CH_2CH_2OCH_2CHMe$.

Within the context of the present invention, the term "alkoxyalkoxy" is understood as meaning alkoxy provided with an alkoxy substituent.

Within the context of the present invention, the term "alkoxyalkoxyalkyl" is understood as meaning a radical in which an alkoxyalkoxy substituent is bonded to an alkyl radical. Examples of "alkoxyalkoxyalkyl" include $CH_3OCH_2OCH_2$, $CH_3OCH_2OCH_2CH_2$, $CH_3CH_2OCH_3OCH_2$ and $CH_3OCH_3CH_2OCH_2CH_2$.

Within the context of the present invention, the term "hydroxyalkyl" is understood as meaning alkyl provided with a hydroxy substituent. Examples of "hydroxyalkyl" include $HOCH_2CH_2$, $HOCH_2CH_2CH_2$ and $HOCH_2CH_2CH_2CH_2$.

For radicals with carbon atoms, preference is in principle given to those having 1 to 6 carbon atoms, preferably 1 to 4 carbon atoms, in particular 1 or 2 carbon atoms.

The present invention also provides mixtures comprising stereoisomers which are encompassed by formula (I) or by the formulae of component B (safener). Such compounds of the formula (I) or of the formulae of component B (safener) comprise, for example, one or more asymmetrically substituted carbon atoms or sulfoxides. The possible stereoisomers defined by their specific spatial form, such as enantiomers and diastereomers, are all encompassed by the formula (I) or by the formulae of component B (safener) and can be obtained by customary methods from mixtures of the stereoisomers or else be prepared by stereoselective reactions in combination with the use of stereochemically pure starting substances or auxiliaries.

Examples of compounds used as herbicide (A) are listed below:

Methyl 4-amino-3-chloro-6-(5-bromo-2-thiazolyl)pyridine-2-carboxylate (compound I-1)

Methyl 4-amino-3,5-dichloro-6-(5-chloro-2-furanyl)pyridine-2-carboxylate (compound I-2)

Methyl 4-amino-3-chloro-6-(1-methyl-1H-pyrazol-3-yl)pyridine-2-carboxylate (compound I-3)

Methyl 4-amino-3-chloro-6-(1-methyl-1H-pyrazol-5-yl)pyridine-2-carboxylate (compound I-4)

Methyl 4-amino-3-chloro-6-(3-pyrazolyl)pyridine-2-carboxylate (compound I-5)

Methyl 4-amino-3-chloro-6-(4-triazolyl)pyridine-2-carboxylate (compound I-6)

Methyl 4-amino-3-chloro-6-(5-oxazolyl)pyridine-2-carboxylate (compound I-7)

Methyl 4-amino-3-chloro-6-(2-(5-methyl-1,3,4-thiadiazolyl))pyridine-2-carboxylate (compound I-8)

Methyl 4-amino-3-chloro-6-(2-benzothiazolyl)pyridine-2-carboxylate (compound I-9)

Methyl 4-amino-3-chloro-6-(1-methyl-1H-tetrazol-5-yl)pyridine-2-carboxylate (compound I-10)

Methyl 4-amino-3-chloro-6-(2-methyl-2H-tetrazol-5-yl)pyridine-2-carboxylate (compound I-11)

Methyl 4-amino-3-chloro-6-(3,4-dimethylphenyl)pyridine-2-carboxylate (compound I-12)

Methyl 4-amino-3-chloro-6-(2,4-dichlorophenyl)pyridine-2-carboxylate (compound I-13)

Methyl 4-amino-3-chloro-5-fluoro-6-(4-chlorophenyl)pyridine-2-carboxylate (compound I-14)

Methyl 4-amino-3,5-dichloro-6-(4-methoxyphenyl)pyridine-2-carboxylate (compound I-15)

Methyl 4-amino-3-chloro-6-phenylpyridine-2-carboxylate (compound I-16)

Methyl 4-amino-3-chloro-6-(4-methoxyphenyl)pyridine-2-carboxylate (compound I-17)

Methyl 4-amino-6-(4-methylphenyl)-3-(trifluoromethyl)pyridine-2-carboxylate (compound I-18)

Methyl 4-amino-3-chloro-6-(4-chlorophenyl)pyridine-2-carboxylate (compound I-19)

Methyl 4-amino-3-chloro-6-(4-methylphenyl)pyridine-2-carboxylate (compound I-20)

Methyl 4-amino-3-chloro-6-(3-methylphenyl)pyridine-2-carboxylate (compound I-21)

Methyl 4-amino-3-chloro-6-(4-thiomethoxyphenyl)pyridine-2-carboxylate (compound I-22)

Methyl 4-amino-3-chloro-6-(2-methoxyphenyl)pyridine-2-carboxylate (compound I-23)

Methyl 4-amino-3-chloro-6-(3-methoxyphenyl)pyridine-2-carboxylate (compound I-24)

Methyl 4-amino-3-chloro-6-(2-methylphenyl)pyridine-2-carboxylate (compound I-25)

Methyl 4-amino-3-chloro-6-(2-chlorophenyl)pyridine-2-carboxylate (compound I-26)

Methyl 4-amino-3-chloro-6-(3-chlorophenyl)pyridine-2-carboxylate (compound I-27)

Methyl 4-amino-3-chloro-6-[4-(trifluoromethyl)phenyl]pyridine-2-carboxylate (compound I-28)
Methyl 4-amino-3-chloro-6-(3,4-methylenedioxyphenyl)pyridine-2-carboxylate (compound I-29)
Methyl 4-amino-3-chloro-6-(4-ethylphenyl)pyridine-2-carboxylate (compound I-30)
Methyl 4-amino-3-chloro-6-(4-acetylphenyl)pyridine-2-carboxylate (compound I-31)
Methyl 4-amino-3-chloro-6-(5-bromo-2-methoxyphenyl)pyridine-2-carboxylate (compound I-32)
Methyl 4-amino-3-chloro-6-(2-fluorophenyl)pyridine-2-carboxylate (compound I-33)
Methyl 4-amino-3-chloro-6-(3,5-difluorophenyl)pyridine-2-carboxylate (compound I-34)
Methyl 4-amino-3-chloro-6-(4-isopropylphenyl)pyridine-2-carboxylate (compound I-35)
Methyl 4-amino-3-chloro-6-(4-biphenyl)pyridine-2-carboxylate (compound I-36)
Methyl 4-amino-3-chloro-6-(2-fluorophenyl)pyridine-2-carboxylate (compound I-37)
Methyl 4-amino-3-chloro-6-(4-chloro-3-methylphenyl)pyridine-2-carboxylate (compound I-38)
Methyl 4-amino-3-chloro-6-(3-chloro-4-fluorophenyl)pyridine-2-carboxylate (compound I-39)
Methyl 4-amino-3-chloro-6-(3,4-dichlorophenyl)pyridine-2-carboxylate (compound I-40)
Methyl 4-amino-3-chloro-6-(4-formylphenyl)pyridine-2-carboxylate (compound I-41)
Methyl 4-amino-3-chloro-6-(3-cyanophenyl)pyridine-2-carboxylate (compound I-42)
Methyl 4-amino-3-chloro-6-(4-fluorophenyl)pyridine-2-carboxylate (compound I-43)
Methyl 4-amino-3,5-dichloro-6-[4-(trifluoromethyl)phenyl]pyridine-2-carboxylate (compound I-44)
Methyl 4-amino-3-chloro-6-(4-chloro-2-methylphenyl)pyridine-2-carboxylate (compound I-45)
Methyl 4-amino-3-chloro-6-(3,5-bis(trifluoromethyl)phenyl)pyridine-2-carboxylate (compound I-46)
Methyl 4-amino-3-chloro-6-(2-naphthyl)pyridine-2-carboxylate (compound I-47)
Methyl 4-amino-3-chloro-5-fluoro-6-(4-methylphenyl)pyridine-2-carboxylate (compound I-48)
Methyl 4-acetamido-3-chloro-5-fluoro-6-(2,4-dichlorophenyl)pyridine-2-carboxylate (compound I-49)
Methyl 4-amino-3-chloro-6-(3,4-difluoromethylenedioxyphenyl)pyridine-2-carboxylate (compound I-50)
Methyl 4-amino-3-chloro-6-(3,5-difluorophenyl)pyridine-2-carboxylate (compound I-51)
Methyl 4-acetamido-3-chloro-6-(4-chloro-2-fluorophenyl)pyridine-2-carboxylate (compound I-52)
Methyl 4-acetamido-3-chloro-6-(4-chlorophenyl)pyridine-2-carboxylate (compound I-53)
Methyl 4-acetamido-3-chloro-6-(2-chloro-4-fluorophenyl)pyridine-2-carboxylate (compound I-54)
Methyl 4-acetamido-3-chloro-6-(2,6-difluorophenyl)pyridine-2-carboxylate (compound I-55)
Methyl 4-amino-3-chloro-6-[4-(trifluoromethoxy)phenyl]pyridine-2-carboxylate (compound I-56)
Methyl 4-acetamido-3-chloro-6-(2,5-dichlorophenyl)pyridine-2-carboxylate (compound I-57)
Methyl 4-amino-3-chloro-6-(2-chloro-4-fluorophenyl)pyridine-2-carboxylate (compound I-58)
Methyl 4-amino-3-chloro-6-(4-chloro-2-fluorophenyl)pyridine-2-carboxylate (compound I-59)
Methyl 4-acetamido-3-chloro-6-(4-chloro-3-fluorophenyl)pyridine-2-carboxylate (compound I-60)
Methyl 4-amino-3-chloro-6-(4-chloro-3-fluorophenyl)pyridine-2-carboxylate (compound I-61)
Methyl 4-amino-3-chloro-6-[2-chloro-4-(trifluoromethyl)phenyl]pyridine-2-carboxylate (compound I-62)
Methyl 4-acetamido-3-chloro-6-(3,4-dimethoxyphenyl)pyridine-2-carboxylate (compound I-63)
Methyl 4-amino-3-chloro-6-(3,4-dimethoxyphenyl)pyridine-2-carboxylate (compound I-64)
Methyl 4-amino-3-chloro-5-fluoro-6-(4-chlorophenyl)pyridine-2-carboxylate (compound I-65)
Methyl 4-acetamido-3-chloro-6-(4-chloro-2-methoxyphenyl)pyridine-2-carboxylate (compound I-66)
Methyl 4-amino-3-chloro-6-(3,4-ethylenedioxyphenyl)pyridine-2-carboxylate (compound I-67)
Methyl 4-amino-3-chloro-6-(4-chloro-2-methoxyphenyl)pyridine-2-carboxylate (compound I-68)
Methyl 4-acetamido-3-chloro-6-(3,4-methylenedioxyphenyl)pyridine-2-carboxylate (compound I-69)
Methyl 4-acetamido-3-chloro-6-(4-chloro-3-methoxymethylphenyl)pyridine-2-carboxylate (compound I-70)
Methyl 4-amino-3-chloro-6-(4-chloro-3-methoxymethylphenyl)pyridine-2-carboxylate (compound I-71)
Methyl 4-acetamido-3-chloro-6-(2-chloro-3,4-methylenedioxyphenyl)pyridine-2-carboxylate (compound I-72)
Methyl 4-amino-3-chloro-6-(2-chloro-3,4-methylenedioxyphenyl)pyridine-2-carboxylate (compound I-73)
Methyl 4-acetamido-3-chloro-6-(5-indanyl)pyridine-2-carboxylate (compound I-74)
Methyl 4-amino-3-chloro-6-(5-indanyl)pyridine-2-carboxylate (compound I-75)
Methyl 4-acetamido-3-chloro-6-(2,3-dihydro-5-benzofuranyl)pyridine-2-carboxylate (compound I-76)
Methyl 4-amino-3-chloro-6-(2,3-dihydro-5-benzofuranyl)pyridine-2-carboxylate (compound I-77)
Methyl 4-acetamido-3-chloro-6-(5-chloro-2-fluoro-4-methylphenyl)pyridine-2-carboxylate (compound I-78)
Methyl 4-amino-3-chloro-6-(5-chloro-2-fluoro-4-methylphenyl)pyridine-2-carboxylate (compound I-79)
Methyl 4-amino-3-chloro-6-(4-methoxy-3-methylphenyl)pyridine-2-carboxylate (compound I-80)
Methyl 4-acetamido-3-chloro-6-(2,5-dimethoxyphenyl)pyridine-2-carboxylate (compound I-81)
Methyl 4-amino-3-chloro-6-(2,5-dimethoxyphenyl)pyridine-2-carboxylate (compound I-82)
Methyl 4-acetamido-3-chloro-6-(4-methylphenyl)pyridine-2-carboxylate (compound I-83)
Methyl 4-amino-3-chloro-5-fluoro-6-(3,4-methylenedioxyphenyl)pyridine-2-carboxylate (compound I-84)
Methyl 4-amino-3-chloro-5-fluoro-6-(2,3-dihydro-5-benzofuranyl)pyridine-2-carboxylate (compound I-85)
Methyl 4-amino-3,5-dichloro-6-(4-chlorophenyl)pyridine-2-carboxylate (compound I-86)
Methyl 4-acetamido-3-chloro-6-(1-methyl-1H-pyrazol-4-yl)pyridine-2-carboxylate (compound I-87)
Methyl 4-amino-3-chloro-5-fluoro-6-(2,4-dichlorophenyl)pyridine-2-carboxylate (compound I-88)
Methyl 4-N-pyrrolyl-3-chloro-6-(4-methylphenyl)pyridine-2-carboxylate (compound I-89)
Methyl 4-amino-3,5-difluoro-6-(4-chlorophenyl)pyridine-2-carboxylate (compound I-90)
Methyl 4-amino-3,5-difluoro-6-(4-methylphenyl)pyridine-2-carboxylate (compound I-91)
Methyl 4-amino-3,5-difluoro-6-(2-chloro-4-methylphenyl)pyridine-2-carboxylate (compound I-92)
Methyl 4-amino-3,5-difluoro-6-(4-chloro-2-fluorophenyl)pyridine-2-carboxylate (compound I-93)

Methyl 4-amino-3,5-difluoro-6-[4-(trifluoromethyl)phenyl]pyridine-2-carboxylate (compound I-94)
Methyl 4-amino-3,5-difluoro-6-(3,4-methylenedioxyphenyl)pyridine-2-carboxylate (compound I-95)
Methyl 4-amino-3-chloro-6-(2-benzofuranyl)pyridine-2-carboxylate (compound I-96)
Methyl 4-acetamido-3-chloro-6-(2-benzothienyl)pyridine-2-carboxylate (compound I-97)
Methyl 4-amino-3-chloro-6-(5-chloro-2-thienyl)pyridine-2-carboxylate (compound I-98)
Methyl 4-acetamido-6-(2-benzofuranyl)-3-chloropyridine-2-carboxylate (compound I-99)
Methyl 4-amino-3-chloro-6-(3,5-dimethyl-4-isoxazolyl)pyridine-2-carboxylate (compound I-100)
Methyl 4-acetamido-3-chloro-6-(3-thienyl)pyridine-2-carboxylate (compound I-101)
Methyl 4-amino-3-chloro-6-(3-pyridyl)pyridine-2-carboxylate (compound I-102)
Methyl 4-acetamido-3-chloro-6-(2-thiazolyl)pyridine-2-carboxylate (compound I-103)
Methyl 4-amino-3,5-dichloro-6-(2-furanyl)pyridine-2-carboxylate (compound I-104)
Methyl 4-amino-3,5-dichloro-6-(2-thienyl)pyridine-2-carboxylate (compound I-105)
Methyl 4-amino-3-chloro-6-(2-thienyl)pyridine-2-carboxylate (compound I-106)
Methyl 4-amino-3-chloro-6-(6-methoxy-4-pyridinyl)pyridine-2-carboxylate (compound I-107)
Methyl 4-amino-3-chloro-6-(6-hydroxy-3-pyridinyl)pyridine-2-carboxylate (compound I-108)
Methyl 4-amino-3-chloro-6-(2-pyridinyl)pyridine-2-carboxylate (compound I-109)
Methyl 4-amino-3-chloro-6-(2-furanyl)pyridine-2-carboxylate (compound I-110)
Methyl 4-amino-3-chloro-6-(5-chloro-2-pyridyl)pyridine-2-carboxylate (compound I-111)
Methyl 4-acetamido-3-chloro-6-(3-(6-methyl)pyridazyl)pyridine-2-carboxylate (compound I-112)
Methyl 4-amino-3-chloro-5-fluoro-6-(2-thiazolyl)pyridine-2-carboxylate (compound I-113)
Methyl 4-amino-3-chloro-6-(2-(5-methylthiazolyl))pyridine-2-carboxylate (compound I-114)
Methyl 4-amino-3,5-dichloro-6-(5-thiazolyl)pyridine-2-carboxylate (compound I-115)
Methyl 4-acetamido-3-chloro-6-(5-(2-chloro)pyrimidinyl)pyridine-2-carboxylate (compound I-116)
Methyl 4-acetamido-3-chloro-6-(5-pyrimidinyl)pyridine-2-carboxylate (compound I-117)
Methyl 4-acetamido-3-chloro-6-(3-(6-methyl)pyridazinyl)pyridine-2-carboxylate (compound I-118)
Methyl 4-acetamido-3-chloro-6-(3-bromo-5-isoxazoyl)pyridine-2-carboxylate (compound I-119)
Methyl 4-acetamido-3-chloro-6-(3-bromo-4-isoxazoyl)pyridine-2-carboxylate (compound I-120)
Methyl 4-amino-3-chloro-6-(3-(6-methyl)pyridazinyl)pyridine-2-carboxylate (compound I-121)
Methyl 4-amino-3-chloro-6-(3-thienyl)pyridine-2-carboxylate (compound I-122)
Methyl 4-amino-3-chloro-6-(2-thiazolyl)pyridine-2-carboxylate (compound I-123)
Methyl 4-amino-3-chloro-6-(1-methyl-1H-pyrazol-4-yl)pyridine-2-carboxylate (compound I-124)
Methyl 4-amino-3-chloro-6-(2-benzothienyl)pyridine-2-carboxylate (compound I-125)
Methyl 4-amino-3-chloro-6-(5-pyrimidinyl)pyridine-2-carboxylate (compound I-126)
Methyl 4-amino-3-chloro-6-(6-hydroxy-3-pyridinyl)pyridine-2-carboxylate (compound I-127)
Methyl 4-amino-3-chloro-6-(6-chloro-3-pyridinyl)pyridine-2-carboxylate (compound I-128)
Methyl 4-amino-3-chloro-6-(4-(2-methylthiazolyl))pyridine-2-carboxylate (compound I-129)
Methyl 4-amino-3-chloro-6-(3-bromo-5-isoxazoyl)pyridine-2-carboxylate (compound I-130)
Methyl 4-amino-3-chloro-6-(3-bromo-4-isoxazoyl)pyridine-2-carboxylate (compound I-131)
4-Amino-3-chloro-6-(3,4-dimethylphenyl)pyridine-2-carboxylic acid (compound I-132)
4-Amino-3,5-dichloro-6-(phenyl)pyridine-2-carboxylic acid (compound I-133)
4-Amino-3,5-dichloro-6-(4-methoxyphenyl)pyridine-2-carboxylic acid (compound I-134)
4-Amino-3-chloro-6-(phenyl)pyridine-2-carboxylic acid (compound I-135)
4-Amino-3-chloro-6-(4-methylphenyl)pyridine-2-carboxylic acid (compound I-136)
4-Amino-3-chloro-6-(4-thiomethylphenyl)pyridine-2-carboxylic acid (compound I-137)
4-Amino-3-chloro-6-(3-methylphenyl)pyridine-2-carboxylic acid (compound I-138)
4-Amino-3-chloro-6-(2-methoxyphenyl)pyridine-2-carboxylic acid (compound I-139)
4-Amino-3-chloro-6-(2-chlorophenyl)pyridine-2-carboxylic acid (compound I-140)
4-Amino-3-chloro-6-(4-methoxyphenyl)pyridine-2-carboxylic acid (compound I-141)
4-Amino-3-chloro-6-(2-fluorophenyl)pyridine-2-carboxylic acid (compound 142)
4-Amino-3-chloro-6-(3-chlorophenyl)pyridine-2-carboxylic acid (compound I-143)
4-Amino-3-chloro-6-(4-acetylphenyl)pyridine-2-carboxylic acid (compound I-144)
4-Amino-3-chloro-6-(2,4-difluorophenyl)pyridine-2-carboxylic acid (compound I-145)
4-Amino-3-chloro-6-(2,4-dichlorophenyl)pyridine-2-carboxylic acid (compound I-146)
4-Amino-3-chloro-6-(4-isopropylphenyl)pyridine-2-carboxylic acid (compound I-147)
4-Amino-3-chloro-6-(4-biphenyl)pyridine-2-carboxylic acid (compound I-148)
4-Amino-3-chloro-6-(4-chloro-3-methylphenyl)pyridine-2-carboxylic acid (compound I-149)
4-Amino-3-chloro-6-(3,4-dichlorophenyl)pyridine-2-carboxylic acid (compound I-150)
4-Amino-3-chloro-6-(3-chloro-4-fluorophenyl)pyridine-2-carboxylic acid (compound I-151)
4-Amino-3-chloro-6-[4-(trifluoromethyl)phenyl]pyridine-2-carboxylic acid (compound I-152)
4-Amino-3-chloro-6-(3,4-methylenedioxyphenyl)pyridine-2-carboxylic acid (compound I-153)
4-Amino-3-chloro-6-(4-chlorophenyl)pyridine-2-carboxylic acid (compound I-154)
4-Amino-3-chloro-6-(4-chloro-2-methylphenyl)pyridine-2-carboxylic acid (compound I-155)
4-Amino-3-chloro-6-(4-fluorophenyl)pyridine-2-carboxylic acid (compound I-156)
4-Amino-3-chloro-6-[3-(trifluoromethyl)phenyl]pyridine-2-carboxylic acid (compound I-157)
4-Amino-3-chloro-6-(2-fluoro-4-methylphenyl)pyridine-2-carboxylic acid (compound I-158)
4-Amino-3-chloro-6-(4-hydroxymethylphenyl)pyridine-2-carboxylic acid (compound I-159)

4-Amino-3-chloro-6-[4-(fluoromethyl)phenyl]pyridine-2-carboxylic acid (compound I-160)
4-Amino-3-chloro-6-[bis-3,5-(trifluoromethyl)phenyl]pyridine-2-carboxylic acid (compound I-161) 4-Amino-3-chloro-6-(2-naphthyl)pyridine-2-carboxylic acid (compound I-162)
4-Amino-3-chloro-5-fluoro-6-(4-methylphenyl)pyridine-2-carboxylic acid (compound I-163)
4-Amino-3-chloro-6-(3-chloro-4-methylphenyl)pyridine-2-carboxylic acid (compound I-164)
4-Amino-3-chloro-6-(2-methylphenyl)pyridine-2-carboxylic acid (compound I-165)
4-Amino-3-chloro-6-(3,4-difluoromethylenedioxyphenyl)pyridine-2-carboxylic acid (compound I-166)
4-Amino-3-chloro-6-(3,5-difluorophenyl)pyridine-2-carboxylic acid (compound I-167)
4-Amino-3-chloro-6-(4-chloro-2-fluorophenyl)pyridine-2-carboxylic acid (compound I-168)
4-Amino-3-chloro-6-(2,6-difluorophenyl)pyridine-2-carboxylic acid (compound I-169)
4-Amino-3-chloro-6-(2-chloro-4-fluorophenyl)pyridine-2-carboxylic acid (compound I-170)
4-Amino-3,5-dichloro-6-[4-(trifluoromethyl)phenyl]pyridine-2-carboxylic acid (compound I-171)
4-Amino-3-chloro-5-fluoro-6-(4-fluorophenyl)pyridine-2-carboxylic acid (compound I-172)
4-Amino-3-chloro-5-fluoro-6-(4-chlorophenyl)pyridine-2-carboxylic acid (compound I-173)
4-Amino-3-chloro-6-[4-(trifluoromethoxy)phenyl]pyridine-2-carboxylic acid (compound I-174)
4-Amino-3-chloro-6-(4-ethylphenyl)pyridine-2-carboxylic acid (compound I-175)
4-Amino-3-chloro-6-(2-fluorophenyl)pyridine-2-carboxylic acid (compound I-176)
4-Amino-3-chloro-6-(2,5-dichlorophenyl)pyridine-2-carboxylic acid (compound I-177)
4-Amino-3-chloro-6-(2,4-dimethylphenyl)pyridine-2-carboxylic acid (compound I-178)
4-Amino-3-chloro-6-(4-chloro-3-(trifluoromethyl)phenyl)pyridine-2-carboxylic acid (compound I-179)
3-chloro-6-(4-methylphenyl)-4-(N-pyrrolyl)pyridine-2-carboxylic acid (compound I-180)
4-Amino-3-chloro-6-(4-chloro-3-fluorophenyl)pyridine-2-carboxylic acid (compound I-181)
4-Amino-3-chloro-6-(4-chloro-2-(trifluoromethyl)phenyl)pyridine-2-carboxylic acid (compound I-182)
4-Amino-3-chloro-5-fluoro-6-(4-chlorophenyl)pyridine-2-carboxylic acid (compound I-183)
4-Amino-3-chloro-6-(2-chloro-4-(trifluoromethyl)phenyl)pyridine-2-carboxylic acid (compound I-184)
4-Amino-3-chloro-6-(3,4-dimethoxyphenyl)pyridine-2-carboxylic acid (compound I-185)
4-Amino-3-chloro-6-(4-chloro-2-methoxyphenyl)pyridine-2-carboxylic acid (compound I-186)
4-Amino-3-chloro-6-(2-chloro-3,4-methylenedioxyphenyl)pyridine-2-carboxylic acid (compound I-187)
4-Amino-3-chloro-6-(5-indanyl)pyridine-2-carboxylic acid (compound I-188)
4-Amino-3-chloro-5-fluoro-6-(4-chloro-2-fluorophenyl)pyridine-2-carboxylic acid (compound I-189)
4-Amino-3-chloro-6-(2-chloro-4-methylphenyl)pyridine-2-carboxylic acid (compound I-190)
4-Amino-3-chloro-6-(4-methyl-3-thiomethylphenyl)pyridine-2-carboxylic acid (compound I-191)
4-Amino-3-chloro-6-(5-chloro-2-fluoro-4-methylphenyl)pyridine-2-carboxylic acid (compound I-192)
4-Amino-3-chloro-6-(4-methoxy-3-methylphenyl)pyridine-2-carboxylic acid (compound I-193)
4-Amino-3-chloro-6-(2,5-dimethoxyphenyl)pyridine-2-carboxylic acid (compound I-194)
4-Amino-3-chloro-6-(4-chloro-3-methoxymethylphenyl)pyridine-2-carboxylic acid (compound I-195)
4-Amino-3-chloro-5-fluoro-6-(3,4-methylenedioxyphenyl)pyridine-2-carboxylic acid (compound I-196)
4-Amino-3-chloro-5-fluoro-6-(2,3-dihydro-5-benzofuranyl)pyridine-2-carboxylic acid (compound I-197)
4-Amino-3,5-dichloro-6-(4-chlorophenyl)pyridine-2-carboxylic acid (compound I-198)
4-Amino-3-chloro-5-fluoro-6-(2,4-dichlorophenyl)pyridine-2-carboxylic acid (compound I-199)
4-Amino-3,5-difluoro-6-(4-(trifluoromethyl)phenyl)pyridine-2-carboxylic acid (compound I-200)
4-Amino-3-chloro-6-(2,3-dihydro-5-benzofuranyl)pyridine-2-carboxylic acid (compound I-201)
4-Amino-3,5-difluoro-6-(6-chlorophenyl)pyridine-2-carboxylic acid (compound I-202)
4-Amino-3,5-difluoro-6-(4-methylphenyl)pyridine-2-carboxylic acid (compound I-203)
4-Amino-3,5-difluoro-6-(2-chloro-4-methylphenyl)pyridine-2-carboxylic acid (compound I-204)
4-Amino-3,5-difluoro-6-(2,4-dichlorophenyl)pyridine-2-carboxylic acid (compound I-205)
4-Amino-3,5-difluoro-6-(4-chloro-2-fluorophenyl)pyridine-2-carboxylic acid (compound I-206)
4-Amino-3,5-difluoro-6-(3,4-methylenedioxyphenyl)pyridine-2-carboxylic acid (compound I-207)
4-Amino-3,5-dichloro-6-(2-thienyl)pyridine-2-carboxylic acid (compound I-208)
4-Amino-3-chloro-6-(4-pyridinyl)pyridine-2-carboxylic acid (compound I-209)
4-Amino-3,5-dichloro-6-(2-furfuryl)pyridine-2-carboxylic acid (compound I-210)
4-Amino-3-chloro-6-(2-thienyl)pyridine-2-carboxylic acid (compound I-211)
4-Amino-3-chloro-6-(2-furfuryl)pyridine-2-carboxylic acid (compound I-212)
4-Amino-3-chloro-6-(6-methoxy-3-pyridinyl)pyridine-2-carboxylic acid (compound I-213)
4-Amino-3-chloro-6-(2-pyridinyl)pyridine-2-carboxylic acid (compound I-214)
4-Amino-3-chloro-6-(5-chloro-2-thienyl)pyridine-2-carboxylic acid (compound I-215)
4-Amino-3-chloro-6-(3-thienyl)pyridine-2-carboxylic acid (compound I-216)
4-Amino-3-chloro-6-(2,3-dihydro-5-benzofuranyl)pyridine-2-carboxylic acid (compound I-217)
4-Amino-3-chloro-6-(5-methyl-2-thienyl)pyridine-2-carboxylic acid (compound I-218)
4-Amino-6-(2-benzofuranyl)-3-chloropyridine-2-carboxylic acid (compound I-219)
4-Amino-3-chloro-6-(2-pyrazinyl)pyridine-2-carboxylic acid (compound I-220)
4-Amino-3-chloro-5-fluoro-6-(6-chloro-3-pyridinyl)pyridine-2-carboxylic acid (compound I-221)
4-Amino-3-chloro-6-(2-thiazolyl)pyridine-2-carboxylic acid (compound I-222)
4-Amino-3-chloro-6-(1-methyl-1H-pyrazol-5-yl)pyridine-2-carboxylic acid (compound I-223)
4-Amino-3-chloro-6-(2-benzothienyl)pyridine-2-carboxylic acid (compound I-224)
4-Amino-3-chloro-6-(6-chloro-3-pyridinyl)pyridine-2-carboxylic acid (compound I-225)

4-Amino-3-chloro-6-(2-benzoxazolyl)pyridine-2-carboxylic acid (compound I-226)
4-Amino-3-chloro-6-(2-(5-methyl-1,3,4-oxadiazolyl))pyridine-2-carboxylic acid (compound I-227)
4-Amino-3-chloro-6-(5-pyrimidinyl)pyridine-2-carboxylic acid (compound I-228)
4-Amino-3-chloro-6-(2-(5-methyl-1,3,4-thiadiazolyl))pyridine-2-carboxylic acid (compound I-229)
4-Amino-3-chloro-6-(2-benzothiazolyl)pyridine-2-carboxylic acid (compound I-230)
4-Amino-3-chloro-6-(5-oxazolyl)pyridine-2-carboxylic acid (compound I-231)
4-Amino-3-chloro-6-(2-benzoxazolyl)pyridine-2-carboxylic acid (compound I-232)
4-Amino-3-chloro-6-(3-(6-methyl)pyridazinyl)pyridine-2-carboxylic acid (compound I-233)
4-Amino-3-chloro-6-(3-(6-methyl)pyridazyl)pyridine-2-carboxylic acid (compound I-234)
4-Amino-3-chloro-6-(4-(2-methylthiazolyl))pyridine-2-carboxylic acid (compound I-235)
4-Amino-3,5-dichloro-6-(4-(2-methylthiazolyl))pyridine-2-carboxylic acid (compound I-236)
4-Amino-3,5-dichloro-6-(5-chloro-2-furanyl)pyridine-2-carboxylic acid (compound I-237)
4-Amino-3-chloro-5-fluoro-6-(4-(2-methylthiazolyl))pyridine-2-carboxylic acid (compound I-238)
4-Amino-3-chloro-6-(2-methoxy-5-pyrimidinyl)-2-carboxylic acid (compound I-239)
4-Amino-3-chloro-6-(2-(5-methylthiazolyl))pyridine-2-carboxylic acid (compound I-240)
4-Amino-3,5-dichloro-6-(5-thiazolyl)pyridine-2-carboxylic acid (compound I-241)
Methyl 4-amino-3-chloro-6-(4-hydroxymethylphenyl)pyridine-2-carboxylate (compound I-242)
Methyl 4-amino-3-chloro-6-[4-(fluoromethyl)phenyl]pyridine-2-carboxylate (compound I-243)
n-Decyl 4-amino-3-chloro-5-fluoro-6-(4-chlorophenyl)pyridine-2-carboxylate (compound I-244)
(2-Butoxyethyl) 4-amino-3-chloro-5-fluoro-6-(4-chlorophenyl)pyridine-2-carboxylate (compound I-245)
(2-Ethylhexyl) 4-amino-3-chloro-5-fluoro-6-(4-chlorophenyl)pyridine-2-carboxylate (compound I-246)
(2-Methylheptyl) 4-amino-3-chloro-5-fluoro-6-(4-chlorophenyl)pyridine-2-carboxylate (compound I-247)
(2-Butoxyethyl) 4-amino-3-chloro-6-(4-methylphenyl)pyridine-2-carboxylate (compound I-248)
n-Butyl 4-amino-3-chloro-6-(4-methylphenyl)pyridine-2-carboxylate (compound I-249)
(Ethoxybutyl) 4-amino-3-chloro-6-(4-methylphenyl)pyridine-2-carboxylate (compound I-250)
(2-Ethylbutyl) 4-amino-3-chloro-6-(4-methylphenyl)pyridine-2-carboxylate (compound I-251)
Ethyl 4-amino-3-chloro-5-fluoro-6-(4-chlorophenyl)pyridine-2-carboxylate (compound I-252)
(Butoxyethyl) 4-amino-3-chloro-5-fluoro-6-(4-chlorophenyl)pyridine-2-carboxylate (compound I-253)
(2-Ethylhexyl) 4-amino-3-chloro-5-fluoro-6-(4-chlorophenyl)pyridine-2-carboxylate (compound I-254)
Ethyl 4-amino-3-chloro-6-(2,4-dichlorophenyl)pyridine-2-carboxylate (compound I-255)
n-Propyl 4-amino-3-chloro-6-(2,4-dichlorophenyl)pyridine-2-carboxylate (compound I-256)
n-Butyl 4-amino-3-chloro-6-(2,4-dichlorophenyl)pyridine-2-carboxylate (compound I-257)
n-Pentyl 4-amino-3-chloro-6-(2,4-dichlorophenyl)pyridine-2-carboxylate (compound I-258)
(2-Ethylhexyl) 4-amino-3-chloro-6-(2,4-dichlorophenyl)pyridine-2-carboxylate (compound I-259)
n-Decyl 4-amino-3-chloro-6-(2,4-dichlorophenyl)pyridine-2-carboxylate (compound I-260)
(2-Methylethyl) 4-amino-3-chloro-6-(2,4-dichlorophenyl)pyridine-2-carboxylate (compound I-261)
n-Hexyl 4-amino-3-chloro-6-(2,4-dichlorophenyl)pyridine-2-carboxylate (compound I-262)
Ethyl 4-amino-3-chloro-6-(4-methylphenyl)pyridine-2-carboxylate (compound I-263)
4-Amino-3-chloro-5-fluoro-6-(4-chlorophenyl)-2-(N-benzyl)picolinamide (compound I-264)
Methyl 4-N-methylamino-3-chloro-5-fluoro-6-(4-chlorophenyl)pyridine-2-carboxylate (compound I-265)
Methyl 4-acetamido-3-chloro-6-(4-(2-methylthiazolyl))pyridine-2-carboxylate (compound I-266)
Methyl 4-amino-3,5-dichloro-6-(4-(2-methylthiazolyl))pyridine-2-carboxylate (compound I-267)
Methyl 4-amino-3-chloro-5-fluoro-6-(4-(2-methylthiazolyl))pyridine-2-carboxylate (compound I-268)
Methyl 4-amino-3-chloro-6-(4-(2,2,2-trifluoromethylthiazolyl))pyridine-2-carboxylate (compound I-269)
Methyl 4-amino-3-chloro-5-fluoro-6-(4-(2,2,2-trifluoromethylthiazolyl))pyridine-2-carboxylate (compound I-270)
Methyl 4-amino-3-chloro-6-(4-chloro-2-fluoro-3-thiomethylphenyl)pyridine-2-carboxylate (compound I-271)
Methyl 4-amino-3-chloro-6-(4-chloro-3-cyano-2-fluorophenyl)pyridine-2-carboxylate (compound I-272)
Methyl 4-amino-3-chloro-6-(4-chloro-2-fluoro-3-methoxymethylphenyl)pyridine-2-carboxylate (compound I-273)
Methyl 4-amino-3-chloro-6-(4-chloro-2-fluoro-3-difluoromethylphenyl)pyridine-2-carboxylate (compound I-274)
Methyl 4-amino-3-chloro-6-(4-chloro-2-fluoro-3-fluoromethylphenyl)pyridine-2-carboxylate (compound I-275)
Methyl 4-amino-3-chloro-6-(4-cyano-2-fluoro-3-methoxyphenyl)pyridine-2-carboxylate (compound I-276)
Methyl 4-amino-3-chloro-6-(2,4-dichloro-3-ethoxyphenyl)pyridine-2-carboxylate (compound I-277)
Methyl 4-amino-3-chloro-6-[4-chloro-2-fluoro-3-(2,2-difluoroethoxy)phenyl]pyridine-2-carboxylate (compound I-278)
Methyl 4-amino-3-chloro-6-(4-chloro-2-fluoro-5-ethoxyphenyl)pyridine-2-carboxylate (compound I-279)
Methyl 4-amino-3-chloro-6-[2,4-dichloro-3-(2,2-difluoroethoxy)phenyl]pyridine-2-carboxylate (compound I-280)
Methyl 4-amino-3-chloro-6-[4-chloro-2-fluoro-3-(methoxyethoxy)phenyl]pyridine-2-carboxylate (compound I-281)
Methyl 4-amino-3-chloro-5-fluoro-6-(2-fluoro-3,4-methylenedioxyphenyl)pyridine-2-carboxylate (compound I-282)
Methyl 4-amino-3-chloro-6-(2,4-dichloro-3-methylthiophenyl)pyridine-2-carboxylate (compound I-283)
Methyl 4-amino-3-chloro-5-fluoro-6-(4-chloro-2-fluoro-3-methoxyphenyl)pyridine-2-carboxylate (compound I-284)
Methyl 4-amino-3-chloro-5-fluoro-6-(4-chloro-2-fluoro-5-methoxyphenyl)pyridine-2-carboxylate (compound I-285)
Methyl 4-amino-3-chloro-6-(4-chloro-3-dimethylamino-2-fluorophenyl)pyridine-2-carboxylate (compound I-286)
Methyl 4-amino-3-chloro-6-[4-chloro-3-(diethylamino)-2-fluorophenyl]pyridine-2-carboxylate (compound I-287)
Methyl 4-acetylamino-3-chloro-6-(4-chloro-2-fluoro-5-methoxyphenyl)pyridine-2-carboxylate (compound I-288)

Methyl 4-acetylamino-3-chloro-6-(4-chloro-2-fluoro-3-methylphenyl)pyridine-2-carboxylate (compound I-289)
Methyl 4-acetylamino-3-chloro-6-(4-chloro-2-fluoro-3-methoxyphenyl)pyridine-2-carboxylate (compound I-290)
Methyl 4-acetylamino-3-chloro-6-(4-chloro-2-fluoro-3-ethoxyphenyl)pyridine-2-carboxylate (compound I-291)
Methyl 4-acetylamino-3-chloro-6-(2,4-dichloro-3-methoxyphenyl)pyridine-2-carboxylate (compound I-292)
Methyl 4-acetylamino-3-chloro-6-(2,4-difluoro-3-methylphenyl)pyridine-2-carboxylate (compound I-293)
Methyl 4-acetylamino-3-chloro-6-(2,4-dichloro-3-methylphenyl)pyridine-2-carboxylate (compound I-294)
Methyl 4-amino-3-chloro-6-[4-chloro-2-fluoro-3-(1-fluoro-1-methylethyl)phenyl]-pyridine-2-carboxylate (compound I-295)
Methyl 4-amino-3-chloro-6-(4-chloro-5-dimethylamino-2-fluorophenyl)pyridine-2-carboxylate (compound I-296)
Methyl 4-amino-6-(4-bromo-2-fluoro-3-methoxyphenyl)-3-chloropyridine-2-carboxylate (compound I-297)
Methyl 4-acetylamino-3-chloro-6-(2,4-difluoro-3-methoxyphenyl)pyridine-2-carboxylate (compound I-298)
Methyl 4-acetylamino-3-chloro-6-(2-chloro-4-fluoro-3-methoxyphenyl)pyridine-2-carboxylate (compound I-299)
Methyl 4-acetylamino-3-chloro-6-[2,4-dichloro-3-(difluoromethyl)phenyl]pyridine-2-carboxylate (compound I-300)
Methyl 4-acetylamino-3-chloro-6-[4-chloro-2-fluoro-3-(1,2,2,2-tetrafluoroethyl)phenyl)pyridine-2-carboxylate (compound I-301)
Methyl 4-acetylamino-3-chloro-6-[4-chloro-2-fluoro-3-(1-fluoropropyl)phenyl]pyridine-2-carboxylate (compound I-302)
Methyl 4-acetylamino-3-chloro-6-(2,3,4-trifluorophenyl)pyridine-2-carboxylate (compound I-303)
Methyl 4-acetylamino-3-chloro-6-(4-chloro-2-fluoro-3-methoxymethoxyphenyl)pyridine-2-carboxylate (compound I-304)
Methyl 4-acetylamino-3-chloro-6-(4-chloro-2-fluoro-3-difluoromethoxyphenyl)pyridine-2-carboxylate (compound I-305)
Methyl 4-amino-3-chloro-6-(2-fluoro-3-methoxy-4-methylphenyl)pyridine-2-carboxylate (compound I-306)
Methyl 4-amino-3-chloro-6-[2,4-dichloro-3-(dimethylamino)phenyl]pyridine-2-carboxylate (compound I-307)
Methyl 4-amino-3-chloro-6-[4-chloro-2-fluoro-3-(methylamino)phenyl]pyridine-2-carboxylate (compound I-308)
Methyl 4-amino-3-chloro-6-[4-chloro-2-fluoro-3-(methoxycarbonyl)phenyl]pyridine-2-carboxylate (compound I-309)
Methyl 4-acetylamino-3-chloro-6-(4-chloro-2,6-difluoro-3-methoxyphenyl)pyridine-2-carboxylate (compound I-310)
Methyl 4-amino-3-chloro-6-(4-chloro-2-fluoro-3-ethoxyphenyl)pyridine-2-carboxylate (compound I-311)
Methyl 4-amino-3-chloro-6-(4-chloro-2-fluoro-3-methoxyphenyl)pyridine-2-carboxylate (compound I-312)
Methyl 4-amino-3-chloro-6-(4-chloro-2-fluoro-5-methoxyphenyl)pyridine-2-carboxylate (compound I-313)
Methyl 4-amino-3-chloro-6-(2,4-dichloro-3-methoxyphenyl)pyridine-2-carboxylate (compound I-314)
Methyl 4-amino-3-chloro-6-(2-fluoro-3-methoxy-4-trifluoromethylphenyl)pyridine-2-carboxylate (compound I-315)
Methyl 4-amino-3-chloro-6-(2-fluoro-3,4-methylenedioxyphenyl)pyridine-2-carboxylate (compound I-316)
Methyl 4-amino-3-chloro-6-(2,4-difluoro-3-methylphenyl)pyridine-2-carboxylate (compound I-317)
Methyl 4-amino-3-chloro-6-(2,4-dichloro-3-methylphenyl)pyridine-2-carboxylate (compound I-318)
Methyl 4-amino-3-chloro-6-(4-chloro-2-fluoro-3-methylphenyl)pyridine-2-carboxylate (compound I-319)
Methyl 4-amino-3-chloro-6-[4-chloro-3-(dimethylamino)-2,6-difluorophenyl]pyridine-2-carboxylate (compound I-320)
Methyl 4-amino-3-chloro-6-(2,6-difluoro-3-methoxy-4-methylphenyl)pyridine-2-carboxylate (compound I-321)
Methyl 4-amino-6-(4-bromo-2-chloro-3-methoxyphenyl)-3-chloropyridine-2-carboxylate (compound I-322)
Methyl 4-amino-3-chloro-6-(2-chloro-4-difluoromethyl-6-fluoro-3-methoxyphenyl)-pyridine-2-carboxyliate (compound I-323)
Methyl 4-amino-3-chloro-6-(4-chloro-3-difluoromethyl-2,6-difluorophenyl)pyridine-2-carboxylate (compound I-324)
Methyl 4-amino-3-chloro-6-(2-chloro-4,6-difluoro-3-methoxyphenyl)pyridine-2-carboxylate (compound I-325)
Methyl 4-amino-3-chloro-6-(2,4,6-trifluoro-3-methoxyphenyl)pyridine-2-carboxylate (compound I-326)
Methyl 4-amino-3-chloro-6-(2,4-dichloro-6-fluoro-3-methoxyphenyl)pyridine-2-carboxylate (compound I-327)
Methyl 4-amino-3-chloro-6-(4-chloro-2,6-difluoro-3-methoxyphenyl)pyridine-2-carboxylate (compound I-328)
Methyl 4-amino-3-chloro-6-(4-chloro-2,6-difluoro-3-ethoxyphenyl)pyridine-2-carboxylate (compound I-329)
Methyl 4-amino-3-chloro-6-(4-chloro-3-butoxy-2-fluorophenyl)pyridine-2-carboxylate (compound I-330)
Methyl 4-amino-3-chloro-6-[4-chloro-2-fluoro-3-(1-fluoroethyl)phenyl]pyridine-2-carboxylate (compound I-331)
Methyl 4-amino-3-chloro-6-(2,4-dichloro-3-difluoromethylphenyl)pyridine-2-carboxylate (compound I-332)
Methyl 4-amino-3-chloro-6-[2,4-dichloro-3-(1-fluoro-1-ethyl)phenyl]pyridine-2-carboxylate (compound I-333)
Methyl 4-amino-3-chloro-6-(4-chloro-3-ethyl-2-fluorophenyl)pyridine-2-carboxylate (compound I-334)
Methyl 4-amino-3-chloro-6-[4-chloro-2-fluoro-3-(1,2,2,2-tetrafluoroethyl)phenyl]-pyridine-2-carboxylate (compound I-335)
Methyl 4-amino-3-chloro-6-[4-chloro-2-fluoro-3-(1-fluoropropyl)phenyl]pyridine-2-carboxylate (compound I-336)
Methyl 4-amino-3-chloro-6-(2,3,4-trifluorophenyl)pyridine-2-carboxylate (compound I-337)
Methyl 4-amino-3-chloro-6-(4-chloro-2-fluoro-3-methoxymethoxyphenyl)pyridine-2-carboxylate (compound I-338)
Methyl 4-amino-3-chloro-6-(4-chloro-2-fluoro-3-difluoromethoxyphenyl)pyridine-2-carboxylate (compound I-339)
Methyl 4-amino-3-chloro-6-(2,4-difluoro-3-methoxyphenyl)pyridine-2-carboxylate (compound I-340)
Methyl 4-amino-3-chloro-6-(4-difluoromethyl-2-fluoro-3-methoxyphenyl)pyridine-2-carboxylate (compound I-341)
Methyl 4-amino-3-chloro-6-(2-fluoro-4-fluoromethyl-3-methoxyphenyl)pyridine-2-carboxylate (compound I-342)
Methyl 4-amino-3-chloro-6-(2,4-difluoro-5-methoxyphenyl)pyridine-2-carboxylate (compound I-343)
Methyl 4-amino-3-chloro-6-(2-chloro-4-fluoro-3-methoxyphenyl)pyridine-2-carboxylate (compound I-344)
Methyl 4-amino-3-chloro-6-(4-chloro-2,6-difluoro-3-methylphenyl)pyridine-2-carboxylate (compound I-345)

Methyl 4-amino-6-(2-bromo-4-chloro-3-methoxyphenyl)-3-chloropyridine-2-carboxylate (compound I-346)
Methyl 4-amino-6-(4-bromo-2,6-difluoro-3-methoxyphenyl)-3-chloropyridine-2-carboxylate (compound I-347)
Methyl 4-amino-3-chloro-6-(3-difluoromethyl-2,4,6-trifluorophenyl)pyridine-2-carboxylate (compound I-348)
Methyl 4-amino-3-chloro-6-(2-chloro-4-difluoromethyl-3-methoxyphenyl)pyridine-2-carboxylate (compound I-349)
Methyl 4-amino-3-chloro-6-(2,4-difluoro-3-ethoxyphenyl)pyridine-2-carboxylate (compound I-350)
Methyl 4-amino-3-chloro-6-(4-chloro-3-cyclopropyl-2-fluorophenyl)pyridine-2-carboxylate (compound I-351)
Methyl 4-amino-3-chloro-6-[4-chloro-2-fluoro-3-(2,2,2-trifluoroacetyl)phenyl]pyridine-2-carboxylate (compound I-352)
Methyl 4-amino-3-chloro-6-(4-chloro-2-fluoro-3-methanesulfinylphenyl)pyridine-2-carboxylate (compound I-353)
Methyl 4-amino-3-chloro-6-(4-chloro-2-fluoro-3-methanesulfonylphenyl)pyridine-2-carboxylate (compound I-354)
Methyl 4-amino-3-chloro-6-(4-chloro-2-fluoro-3-fluoromethylthiophenyl)pyridine-2-carboxylate (compound I-355)
Ethyl 4-amino-3-chloro-6-(4-chloro-2-fluoro-3-methoxyphenyl)pyridine-2-carboxylate (compound I-356)
2-Butoxyethyl 4-amino-3-chloro-6-(4-chloro-2-fluoro-3-methoxyphenyl)pyridine-2-carboxylate (compound I-357)
n-Butyl 4-amino-3-chloro-6-(4-chloro-2,6-difluoro-3-methoxyphenyl)pyridine-2-carboxylate (compound I-358)
n-Butyl 4-amino-3-chloro-6-(2,4-dichloro-3-methoxyphenyl)pyridine-2-carboxylate (compound I-359)
n-Butyl 4-amino-3-chloro-6-(4-bromo-2-fluoro-3-methoxyphenyl)pyridine-2-carboxylate (compound I-360)
n-Butyl 4-amino-3-chloro-6-[4-chloro-2-fluoro-3-(1-fluoroethyl)phenyl]pyridine-2-carboxylate (compound I-361)
2-Butoxyethyl 4-amino-3-chloro-6-(4-chloro-2-fluoro-3-methoxyphenyl)pyridine-2-carboxylate (compound I-362)
4-Amino-3-chloro-6-(2,6-difluoro-3-methoxy-4-methylphenyl)pyridine-2-carboxylic acid (compound I-363)
4-Amino-3-chloro-6-(4-chloro-2,6-difluoro-3-dimethylaminophenyl)pyridine-2-carboxylic acid (compound I-364)
Methyl 4-amino-3-chloro-6-(4-cyano-2,6-difluoro-3-methoxyphenyl)pyridine-2-carboxylate (compound I-365)
4-Amino-3-chloro-6-(4-chloro-2-fluoro-3-(2,2-difluoroethoxy)phenyl)pyridine-2-carboxylic acid (compound I-366)
4-Amino-3-chloro-6-(2,4-difluoro-3-methylphenyl)pyridine-2-carboxylic acid (compound I-367)
4-Amino-3-chloro-6-(2,4-dichloro-3-methylphenyl)pyridine-2-carboxylic acid (compound I-368)
4-Amino-3-chloro-6-(4-chloro-2-fluoro-3-methylphenyl)pyridine-2-carboxylic acid (compound I-369)
4-Amino-3-chloro-6-(4-chloro-2-fluoro-3-methoxyphenyl)pyridine-2-carboxylic acid (compound I-370)
4-Amino-3-chloro-6-(4-chloro-2-fluoro-5-methoxyphenyl)pyridine-2-carboxylic acid (compound I-371)
4-Amino-3-chloro-6-(4-chloro-2-fluoro-3-ethoxyphenyl)pyridine-2-carboxylic acid (compound I-372)
4-Amino-3-chloro-6-(2,4-dichloro-3-methoxyphenyl)pyridine-2-carboxylic acid (compound I-373)
4-Amino-3-chloro-6-(4-chloro-2-fluoro-3-methylthiophenyl)pyridine-2-carboxylic acid (compound I-374)
4-Amino-3-chloro-6-(4-chloro-2-fluoro-3-methoxymethylphenyl)pyridine-2-carboxylic acid (compound I-375)
4-Amino-3-chloro-6-(4-chloro-2-fluoro-3-difluoromethylphenyl)pyridine-2-carboxylic acid (compound I-376)
4-Amino-3-chloro-6-(2-fluoro-3-methoxy-4-trifluoromethylphenyl)pyridine-2-carboxylic acid (compound I-377)
4-Amino-3-chloro-6-(2-fluoro-3,4-methylenedioxyphenyl)pyridine-2-carboxylic acid (compound I-378)
4-Amino-3-chloro-6-(4-chloro-2-fluoro-5-ethoxyphenyl)pyridine-2-carboxylic acid (compound I-379)
4-Amino-3-chloro-6-(2,4-dichloro-3-methoxyphenyl)pyridine-2-carboxylic acid (compound I-380)
4-Amino-3-chloro-6-(4-chloro-5-dimethylamino-2-fluorophenyl)pyridine-2-carboxylic acid (compound I-381)
4-Amino-3-chloro-6-(4-chloro-3-dimethylamino-2-fluorophenyl)pyridine-2-carboxylic acid (compound I-382)
4-Amino-3-chloro-6-(4-chloro-2-fluoro-3-methoxyethoxyphenyl)pyridine-2-carboxylic acid (compound I-383)
4-Amino-3-chloro-6-(4-chloro-2-fluoro-3-fluoromethylphenyl)pyridine-2-carboxylic acid (compound I-384)
4-Amino-3-chloro-5-fluoro-6-(2-fluoro-3,4-methylenedioxyphenyl)pyridine-2-carboxylic acid (compound I-385)
4-Amino-3-chloro-6-[4-chloro-3-(diethylamino)-2-fluorophenyl]pyridine-2-carboxylic acid (compound I-386)
4-Amino-3-chloro-6-[2,4-dichloro-3-(dimethylamino)phenyl]pyridine-2-carboxylic acid (compound I-387)
4-Amino-3-chloro-6-[4-chloro-2-fluoro-3-(methylamino)phenyl]pyridine-2-carboxylic acid (compound I-388)
4-Amino-3-chloro-6-(2-fluoro-3-methoxy-4-methylphenyl)pyridine-2-carboxylic acid (compound I-389)
4-Amino-6-(4-bromo-2-fluoro-3-methoxyphenyl)-3-chloropyridine-2-carboxylic acid (compound I-390)
4-Amino-6-(4-bromo-2-chloro-3-methoxyphenyl)-3-chloropyridine-2-carboxylic acid (compound I-391)
4-Amino-3-chloro-6-(4-chloro-2-fluoro-5-methoxyphenyl)-5-fluoropyridine-2-carboxylic acid (compound I-392)
4-Amino-3-chloro-6-(4-chloro-2-fluoro-3-methoxyphenyl)-5-fluoropyridine-2-carboxylic acid (compound I-393)
4-Amino-3-chloro-6-(4-chloro-3-butoxy-2-fluorophenyl)pyridine-2-carboxylic acid (compound I-394)
4-Amino-6-[2,4-dichloro-3-(1-fluoroethyl)phenyl]pyridine-2-carboxylic acid (compound I-395)
4-Amino-3-chloro-6-(2,4-dichloro-3-difluoromethylphenyl)pyridine-2-carboxylic acid (compound I-396)
4-Amino-3-chloro-6-[2,4-dichloro-3-(1-fluoro-1-methylethyl)phenyl]pyridine-2-carboxylic acid (compound I-397)
4-Amino-3-chloro-6-(4-chloro-3-ethyl-2-fluorophenyl)pyridine-2-carboxylic acid (compound I-398)
4-Amino-3-chloro-6-[4-chloro-2-fluoro-3-(1,2,2,2-tetrafluoroethyl)phenyl]pyridine-2-carboxylic acid (compound I-399)
Methyl 4-amino-3-chloro-6-[4-chloro-2-fluoro-3-(1-fluoropropyl)phenyl]pyridine-2-carboxylate (compound I-400)
4-Amino-3-chloro-6-(2,3,4-trifluorophenyl)pyridine-2-carboxylic acid (compound I-401)
4-Amino-3-chloro-6-(4-chloro-2-fluoro-3-methoxymethoxyphenyl)pyridine-2-carboxylic acid (compound I-402)
4-Amino-3-chloro-6-(4-chloro-2,6-difluoro-3-methoxyphenyl)pyridine-2-carboxylic acid (compound I-403)
4-Amino-3-chloro-6-(4-chloro-3-difluoromethoxy-2-fluorophenyl)pyridine-2-carboxylic acid (compound I-404)
4-Amino-3-chloro-6-(4-chloro-2-fluoro-3-methoxyphenyl)pyridine-2-carboxylic acid, triethylamine salt (compound I-405)
4-Amino-3-chloro-6-(2,4-dichloro-3-methoxyphenyl)pyridine-2-carboxylic acid, triethylamine salt (compound I-406)

The application rate of the herbicides of the formula (I) (A) can vary within a wide range with the external conditions such as temperature, humidity, the type of herbicide used, for example between 0.001 g and 2000 g of a.i./ha (ai/ha means hereinbelow "active substance per hectare"=based on 100% pure active ingredient).

In the case of applications at application rates of from 0.01 g to 1000 g of a.i./ha of the herbicides of the formula (I) (A), in the pre-emergence and post-emergence method, a relatively broad spectrum of harmful plants is controlled, e.g. annual and perennial monocotyledonous or dicotyledonous weeds and also of undesired crop plants. For the combinations according to the invention, the application rates are generally lower, e.g. in the range from 0.1 g to 800 g of a.i./ha, preferably 1 g to 500 g of a.i./ha, particularly preferably 10 g to 400 g of a.i./ha.

The herbicides of the formula (I) are suitable for controlling harmful plants, e.g. in plant crops, for example in economically important arable crops, e.g. monocotyledonous arable crops such as cereals (e.g. wheat, barley, rye, oats), rice, corn, millet, or dicotyledonous arable crops such as sugar beet, rapeseed, cotton, sunflowers and leguminous plants, for example of the genera Glycine (for example *Glycine max.* (soybean), such as non-transgenic *Glycine max.* (e.g. conventional cultivars such as STS cultivars) or transgenic *Glycine max.* (e.g. RR-soybean or LL-soybean) and hybrids thereof), *Phaseolus, Pisum, Vicia* and *Arachis*, or vegetable crops from various botanical groups, such as potato, leek, cabbage, carrot, tomato, onion, and also permanent crops and plantation crops such as pip and stone fruit, berry fruit, grapevine, Hevea, bananas, sugar cane, coffee, tea, citrus fruits, nut plantations, lawns, palm crops and forest plantations. For the application of the herbicide/safener combinations (A)+(B) according to the invention, these crops are likewise preferred, particular preference being given to the use in cereals (e.g. wheat, barley, rye, oats), rice, corn, millet, sugar beet, sugar cane, sunflowers, rapeseed and cotton. The herbicide/safener combinations (A)+(B) can also be used in tolerant and nontolerant mutant crops and tolerant and nontolerant transgenic crops, preferably of corn, rice, cereals, rapeseed and soybean, e.g. those which are resistant to imidazolinone herbicides, atrazine, glufosinates or glyphosates.

The compounds of the formula (I) are known from WO 03/011853 A and can be obtained by the processes described therein.

Safeners (B):

The safeners present as component (B) are understood as meaning compounds which are suitable for reducing phytotoxic effects of crop protection composition active ingredients such as herbicides on crop plants.

Within the context of the present invention, the compounds of the formula (I) are combined with the following safener compounds:

S1) compounds from the group of heterocyclic carboxylic acid derivatives:

S1$^a$) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;

S1$^b$) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

S1$^c$) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

S1$^d$) compounds of the triazolecarboxylic acid type (S1$^d$), preferably compounds such as fenchlorazole(-ethyl), i.e. ethyl 1-(2,4-dichloro-phenyl)-5-trichloromethyl-(1H)-1,2,4-triazole-3-carboxylate (S1-7), and related compounds, as described in EP-A-174 562 and EP-A-346 620;

S1$^e$) compounds of the 5-benzyl- or 5-phenyl-2-isoxazoline-3-carboxylic acid type, or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazoline-carboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or of the ethyl 5-(4-fluorophenyl)-5-phenyl-2-isoxazoline-3-carboxylate type (S1-13), as described in the patent application WO-A-95/07897.

S2) Compounds from the group of 8-quinolinyloxy derivatives (S2):

S2$^a$) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminum, iron, ammonium, quaternary ammonium, sulfonium or phosphonium salts, as described in WO-A-2002/34048;

S2$^b$) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Active ingredients of the dichloroacetamide type (S3), which are often used as pre-emergence safeners (soil-acting safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7),
"TI-35" (1-dichloroacetylazepane) from TRI-Chemical RT (S3-8),
"diclonon" (dicyclonone) (synonym: "BAS145138" or "LAB145138") (RS)-1-dichloroacetyl-3,3,8a-trimethylperhydropyrrolo[1,2-a]pyrimidin-6-one from BASF (S3-9),
"furilazole" or "MON 13900" ((RS)-3-dichloroacetyl-5-(2-furyl)-2,2-dimethyloxazolidine) (S3-10), and also its (R)-isomer (S3-11).

S4) Compounds from the class of the acylsulfonamides (S4):
S4$^a$) N-acylsulfonamides of the formula (S4$^a$) and their salts, as described in WO-A-97/45016,

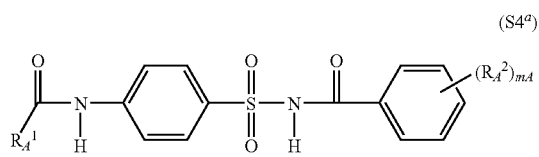

(S4$^a$)

in which
$R_A^1$ is $(C_1-C_6)$alkyl, $(C_3-C_6)$cycloalkyl, where the 2 last-mentioned radicals are substituted by $v_A$ substituents from the group consisting of halogen, $(C_1-C_4)$alkoxy, $(C_1-C_6)$haloalkoxy and $(C_1-C_4)$alkylthio and, in the case of cyclic radicals, also by $(C_1-C_4)$alkyl and $(C_1-C_4)$haloalkyl;
$R_A^2$ is halogen, $(C_1-C_4)$alkyl, $(C_1-C_4)$alkoxy, $CF_3$;
$m_A$ is 1 or 2;
$v_A$ is 0, 1, 2 or 3;

S4$^b$) compounds of the 4-(benzoylsulfamoyl)benzamide type of the formula (S4$^b$) and salts thereof, as described in WO-A-99/16744,

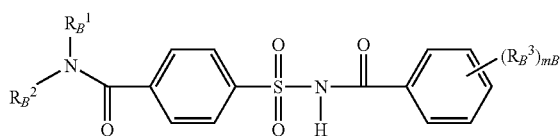

(S4$^b$)

in which
$R_B^1$, $R_B^2$ independently of one another are hydrogen, $(C_1-C_6)$alkyl, $(C_3-C_6)$cycloalkyl, $(C_3-C_6)$alkenyl, $(C_3-C_6)$alkynyl,
$R_B^3$ is halogen, $(C_1-C_4)$alkyl, $(C_1-C_4)$haloalkyl or $(C_1-C_4)$alkoxy and
$m_B$ is 1 or 2,
e.g. those in which
$R_B^1$=cyclopropyl, $R_B^2$=hydrogen and $(R_B^3)$=2-OMe (S4-1, "cyprosulfamide"),
$R_B^1$=cyclopropyl, $R_B^2$=hydrogen and $(R_B^3)$=5-Cl-2-OMe (S4-2),
$R_B^1$=ethyl, $R_B^2$=hydrogen and $(R_B^3)$=2-OMe (S4-3),
$R_B^1$=isopropyl, $R_B^2$=hydrogen and $(R_B^3)$=5-Cl-2-OMe (S4-4) and
$R_B^1$=isopropyl, $R_B^2$=hydrogen and $(R_B^3)$=2-OMe (S4-5).

S4$^c$) Compounds from the class of the benzoylsulfamoylphenylureas of the formula (S4$^c$), as described in EP-A-365484

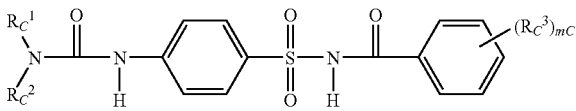

(S4$^c$)

in which
$R_C^1$, $R_C^2$ independently of one another are hydrogen, $(C_1-C_8)$alkyl, $(C_3-C_8)$cycloalkyl, $(C_3-C_6)$alkenyl, $(C_3-C_6)$alkynyl,
$R_C^3$ is halogen, $(C_1-C_4)$alkyl, $(C_1-C_4)$alkoxy, $CF_3$
$m_C$ is 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.

S5) Active ingredients from the class of hydroxyaromatics and aromatic-aliphatic carboxylic acid derivatives (S5), e.g. ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), e.g. 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of the diphenylmethoxyacetic acid derivatives (S7), e.g. methyl diphenylmethoxyacetate (CAS Reg. No. 41858-19-9) (S7-1), ethyl diphenylmethoxyacetate or diphenylmethoxyacetic acid, as described in WO-A-98/38856.

S8) Compounds of the formula (S8), as described in WO-A-98/27049

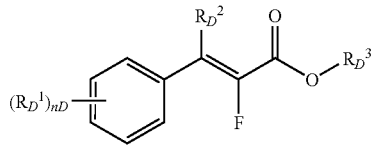

(S8)

in which the symbols and the indices have the following meanings:
$R_D^1$ is halogen, $(C_1-C_4)$alkyl, $(C_1-C_4)$haloalkyl, $(C_1-C_4)$alkoxy, $(C_1-C_4)$haloalkoxy,
$R_D^2$ is hydrogen or $(C_1-C_4)$alkyl
$R_D^3$ is hydrogen, $(C_1-C_8)$alkyl, $(C_2-C_4)$alkenyl, $(C_2-C_4)$alkynyl, or aryl, where each of the aforementioned C-containing radicals is unsubstituted or substituted by one or more, preferably up to three, identical or different radicals from the group consisting of halogen and alkoxy; or salts thereof
$n_D$ is an integer from 0 to 2.

S9) Active ingredients from the class of the 3-(5-tetrazolylcarbonyl)-2-quinolones (S9), e.g. 1,2-dihydro-4-hydroxy-1-ethyl-3-(5-tetrazolylcarbonyl)-2-quinolone (CAS Reg No.: 219479-18-2), 1,2-dihydro-4-hydroxy-1-methyl-3-(5-tetrazolyl-carbonyl)-2-quinolone (CAS Reg. No. 95855-00-8), as described in WO-A-1999/000020.

S10) Compounds of the formulae (S10$^a$) or (S10$^b$) as described in WO-A-2007/023719 and WO-A-2007/023764

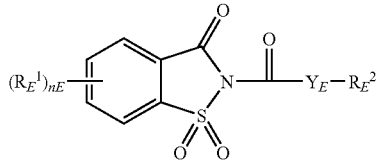

(S10$^a$)

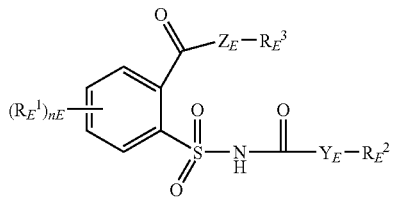

(S10$^b$)

in which $R_E^1$ is halogen, $(C_1-C_4)$alkyl, methoxy, nitro, cyano, $CF_3$, $OCF_3$ $Y_E$, $Z_E$ independently of one another are O or S, $n_E$ is an integer from 0 to 4, $R_E^2$ is $(C_1-C_{16})$alkyl, $(C_2-C_6)$alkenyl, $(C_3-C_6)$cycloalkyl, aryl; benzyl, halobenzyl, $R_E^3$ is hydrogen or $(C_1-C_6)$alkyl.

S11) Active ingredients of the oxyimino compound type (S11), which are known as seed dressings, such as, for example, "oxabetrinil" ((Z)-1,3-dioxolan-2-ylmethoxyimino(phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and "cyometrinil" or "CGA-43089" ((Z)-cyanomethoxyimino (phenyl)acetonitrile) (S11-3), which is known as seed dressing safener for millet against metolachlor damage.

S12) Active ingredients from the class of the isothiochromanones (S12), such as, for example, methyl[(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as seed dressing safener for corn against thiocarbamate herbicide damage, "fenclorim" (4,6-dichloro-2-phenylpyrimidine) (S13-2), which is known as safener for pretilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL 304415" (CAS Reg. No. 31541-S7-8) (4-carboxy-3,4-dihydro-2H-1-benzopyran-4-acetic acid) (S13-4) from American Cyanamid, which is known as safener for corn against imidazolinone damage, "MG 191" (CAS Reg. No. 96420-72-3) (2-dichloromethyl-2-methyl-1,3-dioxolane) (S13-5) from Nitrokemia, which is known as safener for corn, "MG-838" (CAS Reg. No. 133993-74-5) (2-propenyl 1-oxa-4-azaspiro[4.5]decane-4-carbodithioate) (S13-6) from Nitrokemia "disulfoton" (O,O-diethyl S-2-ethylthioethyl phosphorodithioate) (S13-7), "dietholate" (O,O-diethyl O-phenylphosphorothioate) (S13-8), "mephenate" (4-chlorophenyl methylcarbamate) (S13-9).

S14) Active ingredients which, besides a herbicidal effect against harmful plants, also have a safener effect on crop plants such as rice, such as, for example, "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), (S14-1), which is known as safener for rice against imazosulfuron herbicide damage, "cumyluron"="JC-940" (3-(2-chlorophenylmethyl)-1-(1-methyl-1-phenylethyl)urea, see JP-A-60087254) which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulfonyl)benzene) from Kumiai (CAS Reg. No. 54091-06-4), which is known as safener against some herbicide damage in rice.

The cited documents contain detailed information relating to preparation processes and starting materials and name preferred compounds. Reference is expressly made to these documents; they form part of this description by way of citation.

Examples of preferred combinations of herbicidal active ingredients (A) and safeners (B) are shown in the table below:

(I-1)+(S1-1); (I-1)+(S1-2); (I-1)+(S1-3); (I-1)+(S1-4); (I-1)+(S1-5); (I-1)+(S1-6); (I-1)+(S1-7); (I-1)+(S1-8); (I-1)+(S1-9); (I-1)+(S1-10); (I-1)+(S1-11); (I-1)+(S1-12); (I-1)+(S1-13); (I-1)+(S2-1); (I-1)+(S2-2); (I-1)+(S2-3); (I-1)+(S2-4); (I-1)+(S2-5); (I-1)+(S2-6); (I-1)+(S2-7); (I-1)+(S2-8); (I-1)+(S2-9); (I-1)+(S2-10); (I-1)+(S3-1); (I-1)+(S3-2); (I-1)+(S3-3); (I-1)+(S3-4); (I-1)+(S3-5); (I-1)+(S3-6); (I-1)+(S3-7); (I-1)+(S3-8); (I-1)+(S3-9); (I-1)+(S3-10); (I-1)+(S3-11); (I-1)+(S4-1); (I-1)+(S4-2); (I-1)+(S4-3); (I-1)+(S4-4); (I-1)+(S4-5); (I-1)+(S7-1); (I-1)+(S11-1); (I-1)+(S11-2); (I-1)+(S11-3); (I-1)+(S12-1); (I-1)+(S13-1); (I-1)+(S13-2); (I-1)+(S13-3); (I-1)+(S13-4): (I-1)+(S13-5); (I-1)+(S13-6); (I-1)+(S13-7); (I-1)+(S13-8); (I-1)+(S13-9); (I-1)+(S14-1)

(I-2)+(S1-1); (I-2)+(S1-2); (I-2)+(S1-3); (I-2)+(S1-4); (I-2)+(S1-5); (I-2)+(S1-6); (I-2)+(S1-7); (I-2)+(S1-8); (I-2)+(S1-9); (I-2)+(S1-10); (I-2)+(S1-11); (I-2)+(S1-12); (I-2)+(S1-13); (I-2)+(S2-1); (I-2)+(S2-2); (I-2)+(S2-3); (I-2)+(S2-4); (I-2)+(S2-5); (I-2)+(S2-6); (I-2)+(S2-7); (I-2)+(S2-8); (I-2)+(S2-9); (I-2)+(S2-10); (I-2)+(S3-1); (I-2)+(S3-2); (I-2)+(S3-3); (I-2)+(S3-4); (I-2)+(S3-5); (I-2)+(S3-6); (I-2)+(S3-7); (I-2)+(S3-8); (I-2)+(S3-9); (I-2)+(S3-10); (I-2)+(S3-11); (I-2)+(S4-1); (I-2)+(S4-2); (I-2)+(S4-3); (I-2)+(S4-4); (I-2)+(S4-5); (I-2)+(S7-1); (I-2)+(S11-1); (I-2)+(S11-2); (I-2)+(S11-3); (I-2)+(S12-1); (I-2)+(S13-1); (I-2)+(S13-2); (I-2)+(S13-3); (I-2)+(S13-4): (I-2)+(S13-5); (I-2)+(S13-6); (I-2)+(S13-7); (I-2)+(S13-8); (I-2)+(S13-9); (I-2)+(S14-1)

(I-3)+(S1-1); (I-3)+(S1-2); (I-3)+(S1-3); (I-3)+(S1-4); (I-3)+(S1-5); (I-3)+(S1-6); (I-3)+(S1-7); (I-3)+(S1-8); (I-3)+(S1-9); (I-3)+(S1-10); (I-3)+(S1-11); (I-3)+(S1-12); (I-3)+(S1-13); (I-3)+(S2-1); (I-3)+(S2-2); (I-3)+(S2-3); (I-3)+(S2-4);

(I-3)+(S2-5); (I-3)+(S2-6); (I-3)+(S2-7); (I-3)+(S2-8); (I-3)+(S2-9); (I-3)+(S2-10); (I-3)+(S3-1); (I-3)+(S3-2); (I-3)+(S3-3); (I-3)+(S3-4); (I-3)+(S3-5); (I-3)+(S3-6); (I-3)+(S3-7); (I-3)+(S3-8); (I-3)+(S3-9); (I-3)+(S3-10); (I-3)+(S3-11); (I-3)+(S4-1); (I-3)+(S4-2); (I-3)+(S4-3); (I-3)+(S4-4); (I-3)+(S4-5); (I-3)+(S7-1); (I-3)+(S11-1); (I-3)+(S11-2); (I-3)+(S11-3); (I-3)+(S12-1); (I-3)+(S13-1); (I-3)+(S13-2); (I-3)+(S13-3); (I-3)+(S13-4): (I-3)+(S13-5); (I-3)+(S13-6); (I-3)+(S13-7); (I-3)+(S13-8); (I-3)+(S13-9); (I-3)+(S14-1)

(I-4)+(S1-1); (I-4)+(S1-2); (I-4)+(S1-3); (I-4)+(S1-4); (I-4)+(S1-5); (I-4)+(S1-6); (I-4)+(S1-7); (I-4)+(S1-8); (I-4)+(S1-9); (I-4)+(S1-10); (I-4)+(S1-11); (I-4)+(S1-12); (I-4)+(S1-13); (I-4)+(S2-1); (I-4)+(S2-2); (I-4)+(S2-3); (I-4)+(S2-4); (I-4)+(S2-5); (I-4)+(S2-6); (I-4)+(S2-7); (I-4)+(S2-8); (I-4)+(S2-9); (I-4)+(S2-10); (I-4)+(S3-1); (I-4)+(S3-2); (I-4)+(S3-3); (I-4)+(S3-4); (I-4)+(S3-5); (I-4)+(S3-6); (I-4)+(S3-7); (I-4)+(S3-8); (I-4)+(S3-9); (I-4)+(S3-10); (I-4)+(S3-11); (I-4)+(S4-1); (I-4)+(S4-2); (I-4)+(S4-3); (I-4)+(S4-4); (I-4)+(S4-5); (I-4)+(S7-1); (I-4)+(S11-1); (I-4)+(S11-2); (I-4)+(S11-3); (I-4)+(S12-1); (I-4)+(S13-1); (I-4)+(S13-2); (I-4)+(S13-3); (I-4)+(S13-4): (I-4)+(S13-5); (I-4)+(S13-6); (I-4)+(S13-7); (I-4)+(S13-8); (I-4)+(S13-9); (I-4)+(S14-1)

(I-5)+(S1-1); (I-5)+(S1-2); (I-5)+(S1-3); (I-5)+(S1-4); (I-5)+(S1-5); (I-5)+(S1-6); (I-5)+(S1-7); (I-5)+(S1-8); (I-5)+(S1-9); (I-5)+(S1-10); (I-5)+(S1-11); (I-5)+(S1-12); (I-5)+(S1-13); (I-5)+(S2-1); (I-5)+(S2-2); (I-5)+(S2-3); (I-5)+(S2-4); (I-5)+(S2-5); (I-5)+(S2-6); (I-5)+(S2-7); (I-5)+(S2-8); (I-5)+(S2-9); (I-5)+(S2-10); (I-5)+(S3-1); (I-5)+(S3-2); (I-5)+(S3-3); (I-5)+(S3-4); (I-5)+(S3-5); (I-5)+(S3-6); (I-5)+(S3-7); (I-5)+(S3-8); (I-5)+(S3-9); (I-5)+(S3-10); (I-5)+(S3-11); (I-5)+(S4-1); (I-5)+(S4-2); (I-5)+(S4-3); (I-5)+(S4-4); (I-5)+(S4-5); (I-5)+(S7-1); (I-5)+(S11-1); (I-5)+(S11-2); (I-5)+(S11-3); (I-5)+(S12-1); (I-5)+(S13-1); (I-5)+(S13-2); (I-5)+(S13-3); (I-5)+(S13-4): (I-5)+(S13-5); (I-5)+(S13-6); (I-5)+(S13-7); (I-5)+(S13-8); (I-5)+(S13-9); (I-5)+(S14-1)

(I-6)+(S1-1); (I-6)+(S1-2); (I-6)+(S1-3); (I-6)+(S1-4); (I-6)+(S1-5); (I-6)+(S1-6); (I-6)+(S1-7); (I-6)+(S1-8); (I-6)+(S1-9); (I-6)+(S1-10); (I-6)+(S1-11); (I-6)+(S1-12); (I-6)+(S1-13); (I-6)+(S2-1); (I-6)+(S2-2); (I-6)+(S2-3); (I-6)+(S2-4); (I-6)+(S2-5); (I-6)+(S2-6); (I-6)+(S2-7); (I-6)+(S2-8); (I-6)+(S2-9); (I-6)+(S2-10); (I-6)+(S3-1); (I-6)+(S3-2); (I-6)+(S3-3); (I-6)+(S3-4); (I-6)+(S3-5); (I-6)+(S3-6); (I-6)+(S3-7); (I-6)+(S3-8); (I-6)+(S3-9); (I-6)+(S3-10); (I-6)+(S3-11); (I-6)+(S4-1); (I-6)+(S4-2); (I-6)+(S4-3); (I-6)+(S4-4); (I-6)+(S4-5); (I-6)+(S7-1); (I-6)+(S11-1); (I-6)+(S11-2); (I-6)+(S11-3); (I-6)+(S12-1); (I-6)+(S13-1); (I-6)+(S13-2); (I-6)+(S13-3); (I-6)+(S13-4): (I-6)+(S13-5); (I-6)+(S13-6); (I-6)+(S13-7); (I-6)+(S13-8); (I-6)+(S13-9); (I-6)+(S14-1)

(I-7)+(S1-1); (I-7)+(S1-2); (I-7)+(S1-3); (I-7)+(S1-4); (I-7)+(S1-5); (I-7)+(S1-6); (I-7)+(S1-7); (I-7)+(S1-8); (I-7)+(S1-9); (I-7)+(S1-10); (I-7)+(S1-11); (I-7)+(S1-12); (I-7)+(S1-13); (I-7)+(S2-1); (I-7)+(S2-2); (I-7)+(S2-3); (I-7)+(S2-4); (I-7)+(S2-5); (I-7)+(S2-6); (I-7)+(S2-7); (I-7)+(S2-8); (I-7)+(S2-9); (I-7)+(S2-10); (I-7)+(S3-1); (I-7)+(S3-2); (I-7)+(S3-3); (I-7)+(S3-4); (I-7)+(S3-5); (I-7)+(S3-6); (I-7)+(S3-7); (I-7)+(S3-8); (I-7)+(S3-9); (I-7)+(S3-10); (I-7)+(S3-11); (I-7)+(S4-1); (I-7)+(S4-2); (I-7)+(S4-3); (I-7)+(S4-4); (I-7)+(S4-5); (I-7)+(S7-1); (I-7)+(S11-1); (I-7)+(S11-2); (I-7)+(S11-3); (I-7)+(S12-1); (I-7)+(S13-1); (I-7)+(S13-2); (I-7)+(S13-3); (I-7)+(S13-4): (I-7)+(S13-5); (I-7)+(S13-6); (I-7)+(S13-7); (I-7)+(S13-8); (I-7)+(S13-9); (I-7)+(S14-1)

(I-8)+(S1-1); (I-8)+(S1-2); (I-8)+(S1-3); (I-8)+(S1-4); (I-8)+(S1-5); (I-8)+(S1-6); (I-8)+(S1-7); (I-8)+(S1-8); (I-8)+(S1-9); (I-8)+(S1-10); (I-8)+(S1-11); (I-8)+(S1-12); (I-8)+(S1-13); (I-8)+(S2-1); (I-8)+(S2-2); (I-8)+(S2-3); (I-8)+(S2-4); (I-8)+(S2-5); (I-8)+(S2-6); (I-8)+(S2-7); (I-8)+(S2-8); (I-8)+(S2-9); (I-8)+(S2-10); (I-8)+(S3-1); (I-8)+(S3-2); (I-8)+(S3-3); (I-8)+(S3-4); (I-8)+(S3-5); (I-8)+(S3-6); (I-8)+(S3-7); (I-8)+(S3-8); (I-8)+(S3-9); (I-8)+(S3-10); (I-8)+(S3-11); (I-8)+(S4-1); (I-8)+(S4-2); (I-8)+(S4-3); (I-8)+(S4-4); (I-8)+(S4-5); (I-8)+(S7-1); (I-8)+(S11-1); (I-8)+(S11-2); (I-8)+(S11-3); (I-8)+(S12-1); (I-8)+(S13-1); (I-8)+(S13-2); (I-8)+(S13-3); (I-8)+(S13-4): (I-8)+(S13-5); (I-8)+(S13-6); (I-8)+(S13-7); (I-8)+(S13-8); (I-8)+(S13-9); (I-8)+(S14-1)

(I-9)+(S1-1); (I-9)+(S1-2); (I-9)+(S1-3); (I-9)+(S1-4); (I-9)+(S1-5); (I-9)+(S1-6); (I-9)+(S1-7); (I-9)+(S1-8); (I-9)+(S1-9); (I-9)+(S1-10); (I-9)+(S1-11); (I-9)+(S1-12); (I-9)+(S1-13); (I-9)+(S2-1); (I-9)+(S2-2); (I-9)+(S2-3); (I-9)+(S2-4); (I-9)+(S2-5); (I-9)+(S2-6); (I-9)+(S2-7); (I-9)+(S2-8); (I-9)+(S2-9); (I-9)+(S2-10); (I-9)+(S3-1); (I-9)+(S3-2); (I-9)+(S3-3); (I-9)+(S3-4); (I-9)+(S3-5); (I-9)+(S3-6); (I-9)+(S3-7); (I-9)+(S3-8); (I-9)+(S3-9); (I-9)+(S3-10); (I-9)+(S3-11); (I-9)+(S4-1); (I-9)+(S4-2); (I-9)+(S4-3); (I-9)+(S4-4); (I-9)+(S4-5); (I-9)+(S7-1); (I-9)+(S11-1); (I-9)+(S11-2); (I-9)+(S11-3); (I-9)+(S12-1); (I-9)+(S13-1); (I-9)+(S13-2); (I-9)+(S13-3); (I-9)+(S13-4): (I-9)+(S13-5); (I-9)+(S13-6); (I-9)+(S13-7); (I-9)+(S13-8); (I-9)+(S13-9); (I-9)+(S14-1)

(I-10)+(S1-1); (I-10)+(S1-2); (I-10)+(S1-3); (I-10)+(S1-4); (I-10)+(S1-5); (I-10)+(S1-6); (I-10)+(S1-7); (I-10)+(S1-8); (I-10)+(S1-9); (I-10)+(S1-10); (I-10)+(S1-11); (I-10)+(S1-12); (I-10)+(S1-13); (I-10)+(S2-1); (I-10)+(S2-2); (I-10)+(S2-3); (I-10)+(S2-4); (I-10)+(S2-5); (I-10)+(S2-6); (I-10)+(S2-7); (I-10)+(S2-8); (I-10)+(S2-9); (I-10)+(S2-10); (I-10)+(S3-1); (I-10)+(S3-2); (I-10)+(S3-3); (I-10)+(S3-4); (I-10)+(S3-5); (I-10)+(S3-6); (I-10)+(S3-7); (I-10)+(S3-8); (I-10)+(S3-9); (I-10)+(S3-10); (I-10)+(S3-11); (I-10)+(S4-1); (I-10)+(S4-2); (I-10)+(S4-3); (I-10)+(S4-4); (I-10)+(S4-5); (I-10)+(S7-1); (I-10)+(S11-1); (I-10)+(S11-2); (I-10)+(S11-3); (I-10)+(S12-1); (I-10)+(S13-1); (I-10)+(S13-2); (I-10)+(S13-3); (I-10)+(S13-4): (I-10)+(S13-5); (I-10)+(S13-6); (I-10)+(S13-7); (I-10)+(S13-8); (I-10)+(S13-9); (I-10)+(S14-1)

(I-11)+(S1-1); (I-11)+(S1-2); (I-11)+(S1-3); (I-11)+(S1-4); (I-11)+(S1-5); (I-11)+(S1-6); (I-11)+(S1-7); (I-11)+(S1-8); (I-11)+(S1-9); (I-11)+(S1-10); (I-11)+(S1-11); (I-11)+(S1-12); (I-11)+(S1-13); (I-11)+(S2-1); (I-11)+(S2-2); (I-11)+(S2-3); (I-11)+(S2-4); (I-11)+(S2-5); (I-11)+(S2-6); (I-11)+(S2-7); (I-11)+(S2-8); (I-11)+(S2-9); (I-11)+(S2-10); (I-11)+(S3-1); (I-11)+(S3-2); (I-11)+(S3-3); (I-11)+(S3-4); (I-11)+(S3-5); (I-11)+(S3-6); (I-11)+(S3-7); (I-11)+(S3-8); (I-11)+(S3-9); (I-11)+(S3-10); (I-11)+(S3-11); (I-11)+(S4-1); (I-11)+(S4-2); (I-11)+(S4-3); (I-11)+(S4-4); (I-11)+(S4-5); (I-11)+(S7-1); (I-11)+(S11-1); (I-11)+(S11-2); (I-11)+(S11-3); (I-11)+(S12-1); (I-11)+(S13-1); (I-11)+(S13-2); (I-11)+(S13-3); (I-11)+(S13-4): (I-11)+(S13-5); (I-11)+(S13-6); (I-11)+(S13-7); (I-11)+(S13-8); (I-11)+(S13-9); (I-11)+(S14-1)

(I-12)+(S1-1); (I-12)+(S1-2); (I-12)+(S1-3); (I-12)+(S1-4); (I-12)+(S1-5); (I-12)+(S1-6); (I-12)+(S1-7); (I-12)+(S1-8); (I-12)+(S1-9); (I-12)+(S1-10); (I-12)+(S1-11); (I-12)+(S1-12); (I-12)+(S1-13); (I-12)+(S2-1); (I-12)+(S2-2); (I-12)+(S2-3); (I-12)+(S2-4); (I-12)+(S2-5); (I-12)+(S2-6); (I-12)+(S2-7); (I-12)+(S2-8); (I-12)+(S2-9); (I-12)+(S2-10); (I-12)+(S3-1); (I-12)+(S3-2); (I-12)+(S3-3); (I-12)+(S3-4); (I-12)+(S3-5); (I-12)+(S3-6); (I-12)+(S3-7); (I-12)+(S3-8); (I-12)+(S3-9); (I-12)+(S3-10); (I-12)+(S3-11); (I-12)+(S4-1); (I-12)+(S4-2); (I-12)+(S4-3); (I-12)+(S4-4); (I-12)+(S4-5); (I-12)+(S7-1); (I-12)+(S11-1); (I-12)+(S11-2); (I-12)+(S11-3); (I-12)+(S12-1); (I-12)+(S13-1); (I-12)+(S13-2); (I-12)+(S13-3); (I-12)+(S13-4): (I-12)+(S13-5); (I-12)+(S13-6); (I-12)+(S13-7); (I-12)+(S13-8); (I-12)+(S13-9); (I-12)+(S14-1) (I-13)+(S1-1); (I-13)+(S1-2); (I-13)+(S1-3); (I-13)+(S1-4); (I-13)+(S1-5); (I-13)+(S1-6); (I-13)+(S1-7); (I-13)+(S1-8); (I-13)+(S1-9); (I-13)+(S1-10); (I-13)+(S1-11);

(I-13)+(S1-12); (I-13)+(S1-13); (I-13)+(S2-1); (I-13)+(S2-2); (I-13)+(S2-3); (I-13)+(S2-4); (I-13)+(S2-5); (I-13)+(S2-6); (I-13)+(S2-7); (I-13)+(S2-8); (I-13)+(S2-9); (I-13)+(S2-10); (I-13)+(S3-1); (I-13)+(S3-2); (I-13)+(S3-3); (I-13)+(S3-4); (I-13)+(S3-5); (I-13)+(S3-6); (I-13)+(S3-7); (I-13)+(S3-8); (I-13)+(S3-9); (I-13)+(S3-10); (I-13)+(S3-11); (I-13)+(S4-1); (I-13)+(S4-2); (I-13)+(S4-3); (I-13)+(S4-4); (I-13)+(S4-5); (I-13)+(S7-1); (I-13)+(S11-1); (I-13)+(S11-2); (I-13)+(S11-3); (I-13)+(S12-1); (I-13)+(S13-1); (I-13)+(S13-2); (I-13)+(S13-3); (I-13)+(S13-4): (I-13)+(S13-5); (I-13)+(S13-6); (I-13)+(S13-7); (I-13)+(S13-8); (I-13)+(S13-9); (I-13)+(S14-1)

(I-14)+(S1-1); (I-14)+(S1-2); (I-14)+(S1-3); (I-14)+(S1-4); (I-14)+(S1-5); (I-14)+(S1-6); (I-14)+(S1-7); (I-14)+(S1-8); (I-14)+(S1-9); (I-14)+(S1-10); (I-14)+(S1-11); (I-14)+(S1-12); (I-14)+(S1-13); (I-14)+(S2-1); (I-14)+(S2-2); (I-14)+(S2-3); (I-14)+(S2-4); (I-14)+(S2-5); (I-14)+(S2-6); (I-14)+(S2-7); (I-14)+(S2-8); (I-14)+(S2-9); (I-14)+(S2-10); (I-14)+(S3-1); (I-14)+(S3-2); (I-14)+(S3-3); (I-14)+(S3-4); (I-14)+(S3-5); (I-14)+(S3-6); (I-14)+(S3-7); (I-14)+(S3-8); (I-14)+(S3-9); (I-14)+(S3-10); (I-14)+(S3-11); (I-14)+(S4-1); (I-14)+(S4-2); (I-14)+(S4-3); (I-14)+(S4-4); (I-14)+(S4-5); (I-14)+(S7-1); (I-14)+(S11-1); (I-14)+(S11-2); (I-14)+(S11-3); (I-14)+(S12-1); (I-14)+(S13-1); (I-14)+(S13-2); (I-14)+(S13-3); (I-14)+(S13-4): (I-14)+(S13-5); (I-14)+(S13-6); (I-14)+(S13-7); (I-14)+(S13-8); (I-14)+(S13-9); (I-14)+(S14-1)

(I-15)+(S1-1); (I-15)+(S1-2); (I-15)+(S1-3); (I-15)+(S1-4); (I-15)+(S1-5); (I-15)+(S1-6); (I-15)+(S1-7); (I-15)+(S1-8); (I-15)+(S1-9); (I-15)+(S1-10); (I-15)+(S1-11); (I-15)+(S1-12); (I-15)+(S1-13); (I-15)+(S2-1); (I-15)+(S2-2); (I-15)+(S2-3); (I-15)+(S2-4); (I-15)+(S2-5); (I-15)+(S2-6); (I-15)+(S2-7); (I-15)+(S2-8); (I-15)+(S2-9); (I-15)+(S2-10); (I-15)+(S3-1); (I-15)+(S3-2); (I-15)+(S3-3); (I-15)+(S3-4); (I-15)+(S3-5); (I-15)+(S3-6); (I-15)+(S3-7); (I-15)+(S3-8); (I-15)+(S3-9); (I-15)+(S3-10); (I-15)+(S3-11); (I-15)+(S4-1); (I-15)+(S4-2); (I-15)+(S4-3); (I-15)+(S4-4); (I-15)+(S4-5); (I-15)+(S7-1); (I-15)+(S11-1); (I-15)+(S11-2); (I-15)+(S11-3); (I-15)+(S12-1); (I-15)+(S13-1); (I-15)+(S13-2); (I-15)+(S13-3); (I-15)+(S13-4): (I-15)+(S13-5); (I-15)+(S13-6); (I-15)+(S13-7); (I-15)+(S13-8); (I-15)+(S13-9); (I-15)+(S14-1)

(I-16)+(S1-1); (I-16)+(S1-2); (I-16)+(S1-3); (I-16)+(S1-4); (I-16)+(S1-5); (I-16)+(S1-6); (I-16)+(S1-7); (I-16)+(S1-8); (I-16)+(S1-9); (I-16)+(S1-10); (I-16)+(S1-11); (I-16)+(S1-12); (I-16)+(S1-13); (I-16)+(S2-1); (I-16)+(S2-2); (I-16)+(S2-3); (I-16)+(S2-4); (I-16)+(S2-5); (I-16)+(S2-6); (I-16)+(S2-7); (I-16)+(S2-8); (I-16)+(S2-9); (I-16)+(S2-10); (I-16)+(S3-1); (I-16)+(S3-2); (I-16)+(S3-3); (I-16)+(S3-4); (I-16)+(S3-5); (I-16)+(S3-6); (I-16)+(S3-7); (I-16)+(S3-8); (I-16)+(S3-9); (I-16)+(S3-10); (I-16)+(S3-11); (I-16)+(S4-1); (I-16)+(S4-2); (I-16)+(S4-3); (I-16)+(S4-4); (I-16)+(S4-5); (I-16)+(S7-1); (I-16)+(S11-1); (I-16)+(S11-2); (I-16)+(S11-3); (I-16)+(S12-1); (I-16)+(S13-1); (I-16)+(S13-2); (I-16)+(S13-3); (I-16)+(S13-4): (I-16)+(S13-5); (I-16)+(S13-6); (I-16)+(S13-7); (I-16)+(S13-8); (I-16)+(S13-9); (I-16)+(S14-1)

(I-17)+(S1-1); (I-17)+(S1-2); (I-17)+(S1-3); (I-17)+(S1-4); (I-17)+(S1-5); (I-17)+(S1-6); (I-17)+(S1-7); (I-17)+(S1-8); (I-17)+(S1-9); (I-17)+(S1-10); (I-17)+(S1-11); (I-17)+(S1-12); (I-17)+(S1-13); (I-17)+(S2-1); (I-17)+(S2-2); (I-17)+(S2-3); (I-17)+(S2-4); (I-17)+(S2-5); (I-17)+(S2-6); (I-17)+(S2-7); (I-17)+(S2-8); (I-17)+(S2-9); (I-17)+(S2-10); (I-17)+(S3-1); (I-17)+(S3-2); (I-17)+(S3-3); (I-17)+(S3-4); (I-17)+(S3-5); (I-17)+(S3-6); (I-17)+(S3-7); (I-17)+(S3-8); (I-17)+(S3-9); (I-17)+(S3-10); (I-17)+(S3-11); (I-17)+(S4-1); (I-17)+(S4-2); (I-17)+(S4-3); (I-17)+(S4-4); (I-17)+(S4-5); (I-17)+(S7-1); (I-17)+(S11-1); (I-17)+(S11-2); (I-17)+(S11-3); (I-17)+(S12-1); (I-17)+(S13-1); (I-17)+(S13-2); (I-17)+(S13-3); (I-17)+(S13-4): (I-17)+(S13-5); (I-17)+(S13-6); (I-17)+(S13-7); (I-17)+(S13-8); (I-17)+(S13-9); (I-17)+(S14-1)

(I-18)+(S1-1); (I-18)+(S1-2); (I-18)+(S1-3); (I-18)+(S1-4); (I-18)+(S1-5); (I-18)+(S1-6); (I-18)+(S1-7); (I-18)+(S1-8); (I-18)+(S1-9); (I-18)+(S1-10); (I-18)+(S1-11); (I-18)+(S1-12); (I-18)+(S1-13); (I-18)+(S2-1); (I-18)+(S2-2); (I-18)+(S2-3); (I-18)+(S2-4); (I-18)+(S2-5); (I-18)+(S2-6); (I-18)+(S2-7); (I-18)+(S2-8); (I-18)+(S2-9); (I-18)+(S2-10); (I-18)+(S3-1); (I-18)+(S3-2); (I-18)+(S3-3); (I-18)+(S3-4); (I-18)+(S3-5); (I-18)+(S3-6); (I-18)+(S3-7); (I-18)+(S3-8); (I-18)+(S3-9); (I-18)+(S3-10); (I-18)+(S3-11); (I-18)+(S4-1); (I-18)+(S4-2); (I-18)+(S4-3); (I-18)+(S4-4); (I-18)+(S4-5); (I-18)+(S7-1); (I-18)+(S11-1); (I-18)+(S11-2); (I-18)+(S11-3); (I-18)+(S12-1); (I-18)+(S13-1); (I-18)+(S13-2); (I-18)+(S13-3); (I-18)+(S13-4): (I-18)+(S13-5); (I-18)+(S13-6); (I-18)+(S13-7); (I-18)+(S13-8); (I-18)+(S13-9); (I-18)+(S14-1)

(I-19)+(S1-1); (I-19)+(S1-2); (I-19)+(S1-3); (I-19)+(S1-4); (I-19)+(S1-5); (I-19)+(S1-6); (I-19)+(S1-7); (I-19)+(S1-8); (I-19)+(S1-9); (I-19)+(S1-10); (I-19)+(S1-11); (I-19)+(S1-12); (I-19)+(S1-13); (I-19)+(S2-1); (I-19)+(S2-2); (I-19)+(S2-3); (I-19)+(S2-4); (I-19)+(S2-5); (I-19)+(S2-6); (I-19)+(S2-7); (I-19)+(S2-8); (I-19)+(S2-9); (I-19)+(S2-10); (I-19)+(S3-1); (I-19)+(S3-2); (I-19)+(S3-3); (I-19)+(S3-4); (I-19)+(S3-5); (I-19)+(S3-6); (I-19)+(S3-7); (I-19)+(S3-8); (I-19)+(S3-9); (I-19)+(S3-10); (I-19)+(S3-11); (I-19)+(S4-1); (I-19)+(S4-2); (I-19)+(S4-3); (I-19)+(S4-4); (I-19)+(S4-5); (I-19)+(S7-1); (I-19)+(S11-1); (I-19)+(S11-2); (I-19)+(S11-3); (I-19)+(S12-1); (I-19)+(S13-1); (I-19)+(S13-2); (I-19)+(S13-3); (I-19)+(S13-4): (I-19)+(S13-5); (I-19)+(S13-6); (I-19)+(S13-7); (I-19)+(S13-8); (I-19)+(S13-9); (I-19)+(S14-1)

(I-20)+(S1-1); (I-20)+(S1-2); (I-20)+(S1-3); (I-20)+(S1-4); (I-20)+(S1-5); (I-20)+(S1-6); (I-20)+(S1-7); (I-20)+(S1-8); (I-20)+(S1-9); (I-20)+(S1-10); (I-20)+(S1-11); (I-20)+(S1-12); (I-20)+(S1-13); (I-20)+(S2-1); (I-20)+(S2-2); (I-20)+(S2-3); (I-20)+(S2-4); (I-20)+(S2-5); (I-20)+(S2-6); (I-20)+(S2-7); (I-20)+(S2-8); (I-20)+(S2-9); (I-20)+(S2-10); (I-20)+(S3-1); (I-20)+(S3-2); (I-20)+(S3-3); (I-20)+(S3-4); (I-20)+(S3-5); (I-20)+(S3-6); (I-20)+(S3-7); (I-20)+(S3-8); (I-20)+(S3-9); (I-20)+(S3-10); (I-20)+(S3-11); (I-20)+(S4-1); (I-20)+(S4-2); (I-20)+(S4-3); (I-20)+(S4-4); (I-20)+(S4-5); (I-20)+(S7-1); (I-20)+(S11-1); (I-20)+(S11-2); (I-20)+(S11-3); (I-20)+(S12-1); (I-20)+(S13-1); (I-20)+(S13-2); (I-20)+(S13-3); (I-20)+(S13-4): (I-20)+(S13-5); (I-20)+(S13-6); (I-20)+(S13-7); (I-20)+(S13-8); (I-20)+(S13-9); (I-20)+(S14-1)

(I-21)+(S1-1); (I-21)+(S1-2); (I-21)+(S1-3); (I-21)+(S1-4); (I-21)+(S1-5); (I-21)+(S1-6); (I-21)+(S1-7); (I-21)+(S1-8); (I-21)+(S1-9); (I-21)+(S1-10); (I-21)+(S1-11); (I-21)+(S1-12); (I-21)+(S1-13); (I-21)+(S2-1); (I-21)+(S2-2); (I-21)+(S2-3); (I-21)+(S2-4); (I-21)+(S2-5); (I-21)+(S2-6); (I-21)+(S2-7); (I-21)+(S2-8); (I-21)+(S2-9); (I-21)+(S2-10); (I-21)+(S3-1); (I-21)+(S3-2); (I-21)+(S3-3); (I-21)+(S3-4); (I-21)+(S3-5); (I-21)+(S3-6); (I-21)+(S3-7); (I-21)+(S3-8); (I-21)+(S3-9); (I-21)+(S3-10); (I-21)+(S3-11); (I-21)+(S4-1); (I-21)+(S4-2); (I-21)+(S4-3); (I-21)+(S4-4); (I-21)+(S4-5); (I-21)+(S7-1); (I-21)+(S11-1); (I-21)+(S11-2); (I-21)+(S11-3); (I-21)+(S12-1); (I-21)+(S13-1); (I-21)+(S13-2); (I-21)+(S13-3); (I-21)+(S13-4): (I-21)+(S13-5); (I-21)+(S13-6); (I-21)+(S13-7); (I-21)+(S13-8); (I-21)+(S13-9); (I-21)+(S14-1)

(I-22)+(S1-1); (I-22)+(S1-2); (I-22)+(S1-3); (I-22)+(S1-4); (I-22)+(S1-5); (I-22)+(S1-6); (I-22)+(S1-7); (I-22)+(S1-8);

(I-22)+(S1-9); (I-22)+(S1-10); (I-22)+(S1-11); (I-22)+(S1-12); (I-22)+(S1-13); (I-22)+(S2-1); (I-22)+(S2-2); (I-22)+(S2-3); (I-22)+(S2-4); (I-22)+(S2-5); (I-22)+(S2-6); (I-22)+(S2-7); (I-22)+(S2-8); (I-22)+(S2-9); (I-22)+(S2-10); (I-22)+(S3-1); (I-22)+(S3-2); (I-22)+(S3-3); (I-22)+(S3-4); (I-22)+(S3-5); (I-22)+(S3-6); (I-22)+(S3-7); (I-22)+(S3-8); (I-22)+(S3-9); (I-22)+(S3-10); (I-22)+(S3-11); (I-22)+(S4-1); (I-22)+(S4-2); (I-22)+(S4-3); (I-22)+(S4-4); (I-22)+(S4-5); (I-22)+(S7-1); (I-22)+(S11-1); (I-22)+(S11-2); (I-22)+(S11-3); (I-22)+(S12-1); (I-22)+(S13-1); (I-22)+(S13-2); (I-22)+(S13-3); (I-22)+(S13-4): (I-22)+(S13-5); (I-22)+(S13-6); (I-22)+(S13-7); (I-22)+(S13-8); (I-22)+(S13-9); (I-22)+(S14-1)

(I-23)+(S1-1); (I-23)+(S1-2); (I-23)+(S1-3); (I-23)+(S1-4); (I-23)+(S1-5); (I-23)+(S1-6); (I-23)+(S1-7); (I-23)+(S1-8); (I-23)+(S1-9); (I-23)+(S1-10); (I-23)+(S1-11); (I-23)+(S1-12); (I-23)+(S1-13); (I-23)+(S2-1); (I-23)+(S2-2); (I-23)+(S2-3); (I-23)+(S2-4); (I-23)+(S2-5); (I-23)+(S2-6); (I-23)+(S2-7); (I-23)+(S2-8); (I-23)+(S2-9); (I-23)+(S2-10); (I-23)+(S3-1); (I-23)+(S3-2); (I-23)+(S3-3); (I-23)+(S3-4); (I-23)+(S3-5); (I-23)+(S3-6); (I-23)+(S3-7); (I-23)+(S3-8); (I-23)+(S3-9); (I-23)+(S3-10); (I-23)+(S3-11); (I-23)+(S4-1); (I-23)+(S4-2); (I-23)+(S4-3); (I-23)+(S4-4); (I-23)+(S4-5); (I-23)+(S7-1); (I-23)+(S11-1); (I-23)+(S11-2); (I-23)+(S11-3); (I-23)+(S12-1); (I-23)+(S13-1); (I-23)+(S13-2); (I-23)+(S13-3); (I-23)+(S13-4): (I-23)+(S13-5); (I-23)+(S13-6); (I-23)+(S13-7); (I-23)+(S13-8); (I-23)+(S13-9); (I-23)+(S14-1)

(I-24)+(S1-1); (I-24)+(S1-2); (I-24)+(S1-3); (I-24)+(S1-4); (I-24)+(S1-5); (I-24)+(S1-6); (I-24)+(S1-7); (I-24)+(S1-8); (I-24)+(S1-9); (I-24)+(S1-10); (I-24)+(S1-11); (I-24)+(S1-12); (I-24)+(S1-13); (I-24)+(S2-1); (I-24)+(S2-2); (I-24)+(S2-3); (I-24)+(S2-4); (I-24)+(S2-5); (I-24)+(S2-6); (I-24)+(S2-7); (I-24)+(S2-8); (I-24)+(S2-9); (I-24)+(S2-10); (I-24)+(S3-1); (I-24)+(S3-2); (I-24)+(S3-3); (I-24)+(S3-4); (I-24)+(S3-5); (I-24)+(S3-6); (I-24)+(S3-7); (I-24)+(S3-8); (I-24)+(S3-9); (I-24)+(S3-10); (I-24)+(S3-11); (I-24)+(S4-1); (I-24)+(S4-2); (I-24)+(S4-3); (I-24)+(S4-4); (I-24)+(S4-5); (I-24)+(S7-1); (I-24)+(S11-1); (I-24)+(S11-2); (I-24)+(S11-3); (I-24)+(S12-1); (I-24)+(S13-1); (I-24)+(S13-2); (I-24)+(S13-3); (I-24)+(S13-4): (I-24)+(S13-5); (I-24)+(S13-6); (I-24)+(S13-7); (I-24)+(S13-8); (I-24)+(S13-9); (I-24)+(S14-1)

(I-25)+(S1-1); (I-25)+(S1-2); (I-25)+(S1-3); (I-25)+(S1-4); (I-25)+(S1-5); (I-25)+(S1-6); (I-25)+(S1-7); (I-25)+(S1-8); (I-25)+(S1-9); (I-25)+(S1-10); (I-25)+(S1-11); (I-25)+(S1-12); (I-25)+(S1-13); (I-25)+(S2-1); (I-25)+(S2-2); (I-25)+(S2-3); (I-25)+(S2-4); (I-25)+(S2-5); (I-25)+(S2-6); (I-25)+(S2-7); (I-25)+(S2-8); (I-25)+(S2-9); (I-25)+(S2-10); (I-25)+(S3-1); (I-25)+(S3-2); (I-25)+(S3-3); (I-25)+(S3-4); (I-25)+(S3-5); (I-25)+(S3-6); (I-25)+(S3-7); (I-25)+(S3-8); (I-25)+(S3-9); (I-25)+(S3-10); (I-25)+(S3-11); (I-25)+(S4-1); (I-25)+(S4-2); (I-25)+(S4-3); (I-25)+(S4-4); (I-25)+(S4-5); (I-25)+(S7-1); (I-25)+(S11-1); (I-25)+(S11-2); (I-25)+(S11-3); (I-25)+(S12-1); (I-25)+(S13-1); (I-25)+(S13-2); (I-25)+(S13-3); (I-25)+(S13-4); (I-25)+(S13-5); (I-25)+(S13-6); (I-25)+(S13-7); (I-25)+(S13-8); (I-25)+(S13-9); (I-25)+(S14-1)

(I-26)+(S1-1); (I-26)+(S1-2); (I-26)+(S1-3); (I-26)+(S1-4); (I-26)+(S1-5); (I-26)+(S1-6); (I-26)+(S1-7); (I-26)+(S1-8); (I-26)+(S1-9); (I-26)+(S1-10); (I-26)+(S1-11); (I-26)+(S1-12); (I-26)+(S1-13); (I-26)+(S2-1); (I-26)+(S2-2); (I-26)+(S2-3); (I-26)+(S2-4); (I-26)+(S2-5); (I-26)+(S2-6); (I-26)+(S2-7); (I-26)+(S2-8); (I-26)+(S2-9); (I-26)+(S2-10); (I-26)+(S3-1); (I-26)+(S3-2); (I-26)+(S3-3); (I-26)+(S3-4); (I-26)+(S3-5); (I-26)+(S3-6); (I-26)+(S3-7); (I-26)+(S3-8); (I-26)+(S3-9); (I-26)+(S3-10); (I-26)+(S3-11); (I-26)+(S4-1); (I-26)+(S4-2); (I-26)+(S4-3); (I-26)+(S4-4); (I-26)+(S4-5); (I-26)+(S7-1); (I-26)+(S11-1); (I-26)+(S11-2); (I-26)+(S11-3); (I-26)+(S12-1); (I-26)+(S13-1); (I-26)+(S13-2); (I-26)+(S13-3); (I-26)+(S13-4): (I-26)+(S13-5); (I-26)+(S13-6); (I-26)+(S13-7); (I-26)+(S13-8); (I-26)+(S13-9); (I-26)+(S14-1)

(I-27)+(S1-1); (I-27)+(S1-2); (I-27)+(S1-3); (I-27)+(S1-4); (I-27)+(S1-5); (I-27)+(S1-6); (I-27)+(S1-7); (I-27)+(S1-8); (I-27)+(S1-9); (I-27)+(S1-10); (I-27)+(S1-11); (I-27)+(S1-12); (I-27)+(S1-13); (I-27)+(S2-1); (I-27)+(S2-2); (I-27)+(S2-3); (I-27)+(S2-4); (I-27)+(S2-5); (I-27)+(S2-6); (I-27)+(S2-7); (I-27)+(S2-8); (I-27)+(S2-9); (I-27)+(S2-10); (I-27)+(S3-1); (I-27)+(S3-2); (I-27)+(S3-3); (I-27)+(S3-4); (I-27)+(S3-5); (I-27)+(S3-6); (I-27)+(S3-7); (I-27)+(S3-8); (I-27)+(S3-9); (I-27)+(S3-10); (I-27)+(S3-11); (I-27)+(S4-1); (I-27)+(S4-2); (I-27)+(S4-3); (I-27)+(S4-4); (I-27)+(S4-5); (I-27)+(S7-1); (I-27)+(S11-1); (I-27)+(S11-2); (I-27)+(S11-3); (I-27)+(S12-1); (I-27)+(S13-1); (I-27)+(S13-2); (I-27)+(S13-3); (I-27)+(S13-4): (I-27)+(S13-5); (I-27)+(S13-6); (I-27)+(S13-7); (I-27)+(S13-8); (I-27)+(S13-9); (I-27)+(S14-1)

(I-28)+(S1-1); (I-28)+(S1-2); (I-28)+(S1-3); (I-28)+(S1-4); (I-28)+(S1-5); (I-28)+(S1-6); (I-28)+(S1-7); (I-28)+(S1-8); (I-28)+(S1-9); (I-28)+(S1-10); (I-28)+(S1-11); (I-28)+(S1-12); (I-28)+(S1-13); (I-28)+(S2-1); (I-28)+(S2-2); (I-28)+(S2-3); (I-28)+(S2-4); (I-28)+(S2-5); (I-28)+(S2-6); (I-28)+(S2-7); (I-28)+(S2-8); (I-28)+(S2-9); (I-28)+(S2-10); (I-28)+(S3-1); (I-28)+(S3-2); (I-28)+(S3-3); (I-28)+(S3-4); (I-28)+(S3-5); (I-28)+(S3-6); (I-28)+(S3-7); (I-28)+(S3-8); (I-28)+(S3-9); (I-28)+(S3-10); (I-28)+(S3-11); (I-28)+(S4-1); (I-28)+(S4-2); (I-28)+(S4-3); (I-28)+(S4-4); (I-28)+(S4-5); (I-28)+(S7-1); (I-28)+(S11-1); (I-28)+(S11-2); (I-28)+(S11-3); (I-28)+(S12-1); (I-28)+(S13-1); (I-28)+(S13-2); (I-28)+(S13-3); (I-28)+(S13-4): (I-28)+(S13-5); (I-28)+(S13-6); (I-28)+(S13-7); (I-28)+(S13-8); (I-28)+(S13-9); (I-28)+(S14-1)

(I-29)+(S1-1); (I-29)+(S1-2); (I-29)+(S1-3); (I-29)+(S1-4); (I-29)+(S1-5); (I-29)+(S1-6); (I-29)+(S1-7); (I-29)+(S1-8); (I-29)+(S1-9); (I-29)+(S1-10); (I-29)+(S1-11); (I-29)+(S1-12); (I-29)+(S1-13); (I-29)+(S2-1); (I-29)+(S2-2); (I-29)+(S2-3); (I-29)+(S2-4); (I-29)+(S2-5); (I-29)+(S2-6); (I-29)+(S2-7); (I-29)+(S2-8); (I-29)+(S2-9); (I-29)+(S2-10); (I-29)+(S3-1); (I-29)+(S3-2); (I-29)+(S3-3); (I-29)+(S3-4); (I-29)+(S3-5); (I-29)+(S3-6); (I-29)+(S3-7); (I-29)+(S3-8); (I-29)+(S3-9); (I-29)+(S3-10); (I-29)+(S3-11); (I-29)+(S4-1); (I-29)+(S4-2); (I-29)+(S4-3); (I-29)+(S4-4); (I-29)+(S4-5); (I-29)+(S7-1); (I-29)+(S11-1); (I-29)+(S11-2); (I-29)+(S11-3); (I-29)+(S12-1); (I-29)+(S13-1); (I-29)+(S13-2); (I-29)+(S13-3); (I-29)+(S13-4): (I-29)+(S13-5); (I-29)+(S13-6); (I-29)+(S13-7); (I-29)+(S13-8); (I-29)+(S13-9); (I-29)+(S14-1)

(I-30)+(S1-1); (I-30)+(S1-2); (I-30)+(S1-3); (I-30)+(S1-4); (I-30)+(S1-5); (I-30)+(S1-6); (I-30)+(S1-7); (I-30)+(S1-8); (I-30)+(S1-9); (I-30)+(S1-10); (I-30)+(S1-11); (I-30)+(S1-12); (I-30)+(S1-13); (I-30)+(S2-1); (I-30)+(S2-2); (I-30)+(S2-3); (I-30)+(S2-4); (I-30)+(S2-5); (I-30)+(S2-6); (I-30)+(S2-7); (I-30)+(S2-8); (I-30)+(S2-9); (I-30)+(S2-10); (I-30)+(S3-1); (I-30)+(S3-2); (I-30)+(S3-3); (I-30)+(S3-4); (I-30)+(S3-5); (I-30)+(S3-6); (I-30)+(S3-7); (I-30)+(S3-8); (I-30)+(S3-9); (I-30)+(S3-10); (I-30)+(S3-11); (I-30)+(S4-1); (I-30)+(S4-2); (I-30)+(S4-3); (I-30)+(S4-4); (I-30)+(S4-5); (I-30)+(S7-1); (I-30)+(S11-1); (I-30)+(S11-2); (I-30)+(S11-3); (I-30)+(S12-1); (I-30)+(S13-1); (I-30)+(S13-2); (I-30)+(S13-3); (I-30)+(S13-4): (I-30)+(S13-5); (I-30)+(S13-6); (I-30)+(S13-7); (I-30)+(S13-8); (I-30)+(S13-9); (I-30)+(S14-1)

(I-31)+(S1-1); (I-31)+(S1-2); (I-31)+(S1-3); (I-31)+(S1-4); (I-31)+(S1-5); (I-31)+(S1-6); (I-31)+(S1-7); (I-31)+(S1-8); (I-31)+(S1-9); (I-31)+(S1-10); (I-31)+(S1-11); (I-31)+(S1-12); (I-31)+(S1-13); (I-31)+(S2-1); (I-31)+(S2-2); (I-31)+(S2-3); (I-31)+(S2-4); (I-31)+(S2-5); (I-31)+(S2-6); (I-31)+(S2-7); (I-31)+(S2-8); (I-31)+(S2-9); (I-31)+(S2-10); (I-31)+(S3-1); (I-31)+(S3-2); (I-31)+(S3-3); (I-31)+(S3-4); (I-31)+(S3-5); (I-31)+(S3-6); (I-31)+(S3-7); (I-31)+(S3-8); (I-31)+(S3-9); (I-31)+(S3-10); (I-31)+(S3-11); (I-31)+(S4-1); (I-31)+(S4-2); (I-31)+(S4-3); (I-31)+(S4-4); (I-31)+(S4-5); (I-31)+(S7-1); (I-31)+(S11-1); (I-31)+(S11-2); (I-31)+(S11-3); (I-31)+(S12-1); (I-31)+(S13-1); (I-31)+(S13-2); (I-31)+(S13-3); (I-31)+(S13-4): (I-31)+(S13-5); (I-31)+(S13-6); (I-31)+(S13-7); (I-31)+(S13-8); (I-31)+(S13-9); (I-31)+(S14-1)

(I-32)+(S1-1); (I-32)+(S1-2); (I-32)+(S1-3); (I-32)+(S1-4); (I-32)+(S1-5); (I-32)+(S1-6); (I-32)+(S1-7); (I-32)+(S1-8); (I-32)+(S1-9); (I-32)+(S1-10); (I-32)+(S1-11); (I-32)+(S1-12); (I-32)+(S1-13); (I-32)+(S2-1); (I-32)+(S2-2); (I-32)+(S2-3); (I-32)+(S2-4); (I-32)+(S2-5); (I-32)+(S2-6); (I-32)+(S2-7); (I-32)+(S2-8); (I-32)+(S2-9); (I-32)+(S2-10); (I-32)+(S3-1); (I-32)+(S3-2); (I-32)+(S3-3); (I-32)+(S3-4); (I-32)+(S3-5); (I-32)+(S3-6); (I-32)+(S3-7); (I-32)+(S3-8); (I-32)+(S3-9); (I-32)+(S3-10); (I-32)+(S3-11); (I-32)+(S4-1); (I-32)+(S4-2); (I-32)+(S4-3); (I-32)+(S4-4); (I-32)+(S4-5); (I-32)+(S7-1); (I-32)+(S11-1); (I-32)+(S11-2); (I-32)+(S11-3); (I-32)+(S12-1); (I-32)+(S13-1); (I-32)+(S13-2); (I-32)+(S13-3); (I-32)+(S13-4): (I-32)+(S13-5); (I-32)+(S13-6); (I-32)+(S13-7); (I-32)+(S13-8); (I-32)+(S13-9); (I-32)+(S14-1)

(I-33)+(S1-1); (I-33)+(S1-2); (I-33)+(S1-3); (I-33)+(S1-4); (I-33)+(S1-5); (I-33)+(S1-6); (I-33)+(S1-7); (I-33)+(S1-8); (I-33)+(S1-9); (I-33)+(S1-10); (I-33)+(S1-11); (I-33)+(S1-12); (I-33)+(S1-13); (I-33)+(S2-1); (I-33)+(S2-2); (I-33)+(S2-3); (I-33)+(S2-4); (I-33)+(S2-5); (I-33)+(S2-6); (I-33)+(S2-7); (I-33)+(S2-8); (I-33)+(S2-9); (I-33)+(S2-10); (I-33)+(S3-1); (I-33)+(S3-2); (I-33)+(S3-3); (I-33)+(S3-4); (I-33)+(S3-5); (I-33)+(S3-6); (I-33)+(S3-7); (I-33)+(S3-8); (I-33)+(S3-9); (I-33)+(S3-10); (I-33)+(S3-11); (I-33)+(S4-1); (I-33)+(S4-2); (I-33)+(S4-3); (I-33)+(S4-4); (I-33)+(S4-5); (I-33)+(S7-1); (I-33)+(S11-1); (I-33)+(S11-2); (I-33)+(S11-3); (I-33)+(S12-1); (I-33)+(S13-1); (I-33)+(S13-2); (I-33)+(S13-3); (I-33)+(S13-4): (I-33)+(S13-5); (I-33)+(S13-6); (I-33)+(S13-7); (I-33)+(S13-8); (I-33)+(S13-9); (I-33)+(S14-1)

(I-34)+(S1-1); (I-34)+(S1-2); (I-34)+(S1-3); (I-34)+(S1-4); (I-34)+(S1-5); (I-34)+(S1-6); (I-34)+(S1-7); (I-34)+(S1-8); (I-34)+(S1-9); (I-34)+(S1-10); (I-34)+(S1-11); (I-34)+(S1-12); (I-34)+(S1-13); (I-34)+(S2-1); (I-34)+(S2-2); (I-34)+(S2-3); (I-34)+(S2-4); (I-34)+(S2-5); (I-34)+(S2-6); (I-34)+(S2-7); (I-34)+(S2-8); (I-34)+(S2-9); (I-34)+(S2-10); (I-34)+(S3-1); (I-34)+(S3-2); (I-34)+(S3-3); (I-34)+(S3-4); (I-34)+(S3-5); (I-34)+(S3-6); (I-34)+(S3-7); (I-34)+(S3-8); (I-34)+(S3-9); (I-34)+(S3-10); (I-34)+(S3-11); (I-34)+(S4-1); (I-34)+(S4-2); (I-34)+(S4-3); (I-34)+(S4-4); (I-34)+(S4-5); (I-34)+(S7-1); (I-34)+(S11-1); (I-34)+(S11-2); (I-34)+(S11-3); (I-34)+(S12-1); (I-34)+(S13-1); (I-34)+(S13-2); (I-34)+(S13-3); (I-34)+(S13-4): (I-34)+(S13-5); (I-34)+(S13-6); (I-34)+(S13-7); (I-34)+(S13-8); (I-34)+(S13-9); (I-34)+(S14-1)

(I-35)+(S1-1); (I-35)+(S1-2); (I-35)+(S1-3); (I-35)+(S1-4); (I-35)+(S1-5); (I-35)+(S1-6); (I-35)+(S1-7); (I-35)+(S1-8); (I-35)+(S1-9); (I-35)+(S1-10); (I-35)+(S1-11); (I-35)+(S1-12); (I-35)+(S1-13); (I-35)+(S2-1); (I-35)+(S2-2); (I-35)+(S2-3); (I-35)+(S2-4); (I-35)+(S2-5); (I-35)+(S2-6); (I-35)+(S2-7); (I-35)+(S2-8); (I-35)+(S2-9); (I-35)+(S2-10); (I-35)+(S3-1); (I-35)+(S3-2); (I-35)+(S3-3); (I-35)+(S3-4); (I-35)+(S3-5); (I-35)+(S3-6); (I-35)+(S3-7); (I-35)+(S3-8); (I-35)+(S3-9); (I-35)+(S3-10); (I-35)+(S3-11); (I-35)+(S4-1); (I-35)+(S4-2); (I-35)+(S4-3); (I-35)+(S4-4); (I-35)+(S4-5); (I-35)+(S7-1); (I-35)+(S11-1); (I-35)+(S11-2); (I-35)+(S11-3); (I-35)+(S12-1); (I-35)+(S13-1); (I-35)+(S13-2); (I-35)+(S13-3); (I-35)+(S13-4): (I-35)+(S13-5); (I-35)+(S13-6); (I-35)+(S13-7); (I-35)+(S13-8); (I-35)+(S13-9); (I-35)+(S14-1)

(I-36)+(S1-1); (I-36)+(S1-2); (I-36)+(S1-3); (I-36)+(S1-4); (I-36)+(S1-5); (I-36)+(S1-6); (I-36)+(S1-7); (I-36)+(S1-8); (I-36)+(S1-9); (I-36)+(S1-10); (I-36)+(S1-11); (I-36)+(S1-12); (I-36)+(S1-13); (I-36)+(S2-1); (I-36)+(S2-2); (I-36)+(S2-3); (I-36)+(S2-4); (I-36)+(S2-5); (I-36)+(S2-6); (I-36)+(S2-7); (I-36)+(S2-8); (I-36)+(S2-9); (I-36)+(S2-10); (I-36)+(S3-1); (I-36)+(S3-2); (I-36)+(S3-3); (I-36)+(S3-4); (I-36)+(S3-5); (I-36)+(S3-6); (I-36)+(S3-7); (I-36)+(S3-8); (I-36)+(S3-9); (I-36)+(S3-10); (I-36)+(S3-11); (I-36)+(S4-1); (I-36)+(S4-2); (I-36)+(S4-3); (I-36)+(S4-4); (I-36)+(S4-5); (I-36)+(S7-1); (I-36)+(S11-1); (I-36)+(S11-2); (I-36)+(S11-3); (I-36)+(S12-1); (I-36)+(S13-1); (I-36)+(S13-2); (I-36)+(S13-3); (I-36)+(S13-4): (I-36)+(S13-5); (I-36)+(S13-6); (I-36)+(S13-7); (I-36)+(S13-8); (I-36)+(S13-9); (I-36)+(S14-1)

(I-37)+(S1-1); (I-37)+(S1-2); (I-37)+(S1-3); (I-37)+(S1-4); (I-37)+(S1-5); (I-37)+(S1-6); (I-37)+(S1-7); (I-37)+(S1-8); (I-37)+(S1-9); (I-37)+(S1-10); (I-37)+(S1-11); (I-37)+(S1-12); (I-37)+(S1-13); (I-37)+(S2-1); (I-37)+(S2-2); (I-37)+(S2-3); (I-37)+(S2-4); (I-37)+(S2-5); (I-37)+(S2-6); (I-37)+(S2-7); (I-37)+(S2-8); (I-37)+(S2-9); (I-37)+(S2-10); (I-37)+(S3-1); (I-37)+(S3-2); (I-37)+(S3-3); (I-37)+(S3-4); (I-37)+(S3-5); (I-37)+(S3-6); (I-37)+(S3-7); (I-37)+(S3-8); (I-37)+(S3-9); (I-37)+(S3-10); (I-37)+(S3-11); (I-37)+(S4-1); (I-37)+(S4-2); (I-37)+(S4-3); (I-37)+(S4-4); (I-37)+(S4-5); (I-37)+(S7-1); (I-37)+(S11-1); (I-37)+(S11-2); (I-37)+(S11-3); (I-37)+(S12-1); (I-37)+(S13-1); (I-37)+(S13-2); (I-37)+(S13-3); (I-37)+(S13-4): (I-37)+(S13-5); (I-37)+(S13-6); (I-37)+(S13-7); (I-37)+(S13-8); (I-37)+(S13-9); (I-37)+(S14-1)

(I-38)+(S1-1); (I-38)+(S1-2); (I-38)+(S1-3); (I-38)+(S1-4); (I-38)+(S1-5); (I-38)+(S1-6); (I-38)+(S1-7); (I-38)+(S1-8); (I-38)+(S1-9); (I-38)+(S1-10); (I-38)+(S1-11); (I-38)+(S1-12); (I-38)+(S1-13); (I-38)+(S2-1); (I-38)+(S2-2); (I-38)+(S2-3); (I-38)+(S2-4); (I-38)+(S2-5); (I-38)+(S2-6); (I-38)+(S2-7); (I-38)+(S2-8); (I-38)+(S2-9); (I-38)+(S2-10); (I-38)+(S3-1); (I-38)+(S3-2); (I-38)+(S3-3); (I-38)+(S3-4); (I-38)+(S3-5); (I-38)+(S3-6); (I-38)+(S3-7); (I-38)+(S3-8); (I-38)+(S3-9); (I-38)+(S3-10); (I-38)+(S3-11); (I-38)+(S4-1); (I-38)+(S4-2); (I-38)+(S4-3); (I-38)+(S4-4); (I-38)+(S4-5); (I-38)+(S7-1); (I-38)+(S11-1); (I-38)+(S11-2); (I-38)+(S11-3); (I-38)+(S12-1); (I-38)+(S13-1); (I-38)+(S13-2); (I-38)+(S13-3); (I-38)+(S13-4): (I-38)+(S13-5); (I-38)+(S13-6); (I-38)+(S13-7); (I-38)+(S13-8); (I-38)+(S13-9); (I-38)+(S14-1)

(I-39)+(S1-1); (I-39)+(S1-2); (I-39)+(S1-3); (I-39)+(S1-4); (I-39)+(S1-5); (I-39)+(S1-6); (I-39)+(S1-7); (I-39)+(S1-8); (I-39)+(S1-9); (I-39)+(S1-10); (I-39)+(S1-11); (I-39)+(S1-12); (I-39)+(S1-13); (I-39)+(S2-1); (I-39)+(S2-2); (I-39)+(S2-3); (I-39)+(S2-4); (I-39)+(S2-5); (I-39)+(S2-6); (I-39)+(S2-7); (I-39)+(S2-8); (I-39)+(S2-9); (I-39)+(S2-10); (I-39)+(S3-1); (I-39)+(S3-2); (I-39)+(S3-3); (I-39)+(S3-4); (I-39)+(S3-5); (I-39)+(S3-6); (I-39)+(S3-7); (I-39)+(S3-8); (I-39)+(S3-9); (I-39)+(S3-10); (I-39)+(S3-11); (I-39)+(S4-1); (I-39)+(S4-2); (I-39)+(S4-3); (I-39)+(S4-4); (I-39)+(S4-5); (I-39)+(S7-1); (I-39)+(S11-1); (I-39)+(S11-2); (I-39)+(S11-3); (I-39)+(S12-1); (I-39)+(S13-1); (I-39)+(S13-2); (I-39)+

(S13-3); (I-39)+(S13-4): (I-39)+(S13-5); (I-39)+(S13-6); (I-39)+(S13-7); (I-39)+(S13-8); (I-39)+(S13-9); (I-39)+(S14-1)

(I-40)+(S1-1); (I-40)+(S1-2); (I-40)+(S1-3); (I-40)+(S1-4); (I-40)+(S1-5); (I-40)+(S1-6); (I-40)+(S1-7); (I-40)+(S1-8); (I-40)+(S1-9); (I-40)+(S1-10); (I-40)+(S1-11); (I-40)+(S1-12); (I-40)+(S1-13); (I-40)+(S2-1); (I-40)+(S2-2); (I-40)+(S2-3); (I-40)+(S2-4); (I-40)+(S2-5); (I-40)+(S2-6); (I-40)+(S2-7); (I-40)+(S2-8); (I-40)+(S2-9); (I-40)+(S2-10); (I-40)+(S3-1); (I-40)+(S3-2); (I-40)+(S3-3); (I-40)+(S3-4); (I-40)+(S3-5); (I-40)+(S3-6); (I-40)+(S3-7); (I-40)+(S3-8); (I-40)+(S3-9); (I-40)+(S3-10); (I-40)+(S3-11); (I-40)+(S4-1); (I-40)+(S4-2); (I-40)+(S4-3); (I-40)+(S4-4); (I-40)+(S4-5); (I-40)+(S7-1); (I-40)+(S11-1); (I-40)+(S11-2); (I-40)+(S11-3); (I-40)+(S12-1); (I-40)+(S13-1); (I-40)+(S13-2); (I-40)+(S13-3); (I-40)+(S13-4): (I-40)+(S13-5); (I-40)+(S13-6); (I-40)+(S13-7); (I-40)+(S13-8); (I-40)+(S13-9); (I-40)+(S14-1)

(I-41)+(S1-1); (I-41)+(S1-2); (I-41)+(S1-3); (I-41)+(S1-4); (I-41)+(S1-5); (I-41)+(S1-6); (I-41)+(S1-7); (I-41)+(S1-8); (I-41)+(S1-9); (I-41)+(S1-10); (I-41)+(S1-11); (I-41)+(S1-12); (I-41)+(S1-13); (I-41)+(S2-1); (I-41)+(S2-2); (I-41)+(S2-3); (I-41)+(S2-4); (I-41)+(S2-5); (I-41)+(S2-6); (I-41)+(S2-7); (I-41)+(S2-8); (I-41)+(S2-9); (I-41)+(S2-10); (I-41)+(S3-1); (I-41)+(S3-2); (I-41)+(S3-3); (I-41)+(S3-4); (I-41)+(S3-5); (I-41)+(S3-6); (I-41)+(S3-7); (I-41)+(S3-8); (I-41)+(S3-9); (I-41)+(S3-10); (I-41)+(S3-11); (I-41)+(S4-1); (I-41)+(S4-2); (I-41)+(S4-3); (I-41)+(S4-4); (I-41)+(S4-5); (I-41)+(S7-1); (I-41)+(S11-1); (I-41)+(S11-2); (I-41)+(S11-3); (I-41)+(S12-1); (I-41)+(S13-1); (I-41)+(S13-2); (I-41)+(S13-3); (I-41)+(S13-4): (I-41)+(S13-5); (I-41)+(S13-6); (I-41)+(S13-7); (I-41)+(S13-8); (I-41)+(S13-9); (I-41)+(S14-1)

(I-42)+(S1-1); (I-42)+(S1-2); (I-42)+(S1-3); (I-42)+(S1-4); (I-42)+(S1-5); (I-42)+(S1-6); (I-42)+(S1-7); (I-42)+(S1-8); (I-42)+(S1-9); (I-42)+(S1-10); (I-42)+(S1-11); (I-42)+(S1-12); (I-42)+(S1-13); (I-42)+(S2-1); (I-42)+(S2-2); (I-42)+(S2-3); (I-42)+(S2-4); (I-42)+(S2-5); (I-42)+(S2-6); (I-42)+(S2-7); (I-42)+(S2-8); (I-42)+(S2-9); (I-42)+(S2-10); (I-42)+(S3-1); (I-42)+(S3-2); (I-42)+(S3-3); (I-42)+(S3-4); (I-42)+(S3-5); (I-42)+(S3-6); (I-42)+(S3-7); (I-42)+(S3-8); (I-42)+(S3-9); (I-42)+(S3-10); (I-42)+(S3-11); (I-42)+(S4-1); (I-42)+(S4-2); (I-42)+(S4-3); (I-42)+(S4-4); (I-42)+(S4-5); (I-42)+(S7-1); (I-42)+(S11-1); (I-42)+(S11-2); (I-42)+(S11-3); (I-42)+(S12-1); (I-42)+(S13-1); (I-42)+(S13-2); (I-42)+(S13-3); (I-42)+(S13-4): (I-42)+(S13-5); (I-42)+(S13-6); (I-42)+(S13-7); (I-42)+(S13-8); (I-42)+(S13-9); (I-42)+(S14-1)

(I-43)+(S1-1); (I-43)+(S1-2); (I-43)+(S1-3); (I-43)+(S1-4); (I-43)+(S1-5); (I-43)+(S1-6); (I-43)+(S1-7); (I-43)+(S1-8); (I-43)+(S1-9); (I-43)+(S1-10); (I-43)+(S1-11); (I-43)+(S1-12); (I-43)+(S1-13); (I-43)+(S2-1); (I-43)+(S2-2); (I-43)+(S2-3); (I-43)+(S2-4); (I-43)+(S2-5); (I-43)+(S2-6); (I-43)+(S2-7); (I-43)+(S2-8); (I-43)+(S2-9); (I-43)+(S2-10); (I-43)+(S3-1); (I-43)+(S3-2); (I-43)+(S3-3); (I-43)+(S3-4); (I-43)+(S3-5); (I-43)+(S3-6); (I-43)+(S3-7); (I-43)+(S3-8); (I-43)+(S3-9); (I-43)+(S3-10); (I-43)+(S3-11); (I-43)+(S4-1); (I-43)+(S4-2); (I-43)+(S4-3); (I-43)+(S4-4); (I-43)+(S4-5); (I-43)+(S7-1); (I-43)+(S11-1); (I-43)+(S11-2); (I-43)+(S11-3); (I-43)+(S12-1); (I-43)+(S13-1); (I-43)+(S13-2); (I-43)+(S13-3); (I-43)+(S13-4); (I-43)+(S13-5); (I-43)+(S13-6); (I-43)+(S13-7); (I-43)+(S13-8); (I-43)+(S13-9); (I-43)+(S14-1)

(I-44)+(S1-1); (I-44)+(S1-2); (I-44)+(S1-3); (I-44)+(S1-4); (I-44)+(S1-5); (I-44)+(S1-6); (I-44)+(S1-7); (I-44)+(S1-8); (I-44)+(S1-9); (I-44)+(S1-10); (I-44)+(S1-11); (I-44)+(S1-12); (I-44)+(S1-13); (I-44)+(S2-1); (I-44)+(S2-2); (I-44)+(S2-3); (I-44)+(S2-4); (I-44)+(S2-5); (I-44)+(S2-6); (I-44)+(S2-7); (I-44)+(S2-8); (I-44)+(S2-9); (I-44)+(S2-10); (I-44)+(S3-1); (I-44)+(S3-2); (I-44)+(S3-3); (I-44)+(S3-4); (I-44)+(S3-5); (I-44)+(S3-6); (I-44)+(S3-7); (I-44)+(S3-8); (I-44)+(S3-9); (I-44)+(S3-10); (I-44)+(S3-11); (I-44)+(S4-1); (I-44)+(S4-2); (I-44)+(S4-3); (I-44)+(S4-4); (I-44)+(S4-5); (I-44)+(S7-1); (I-44)+(S11-1); (I-44)+(S11-2); (I-44)+(S11-3); (I-44)+(S12-1); (I-44)+(S13-1); (I-44)+(S13-2); (I-44)+(S13-3); (I-44)+(S13-4): (I-44)+(S13-5); (I-44)+(S13-6); (I-44)+(S13-7); (I-44)+(S13-8); (I-44)+(S13-9); (I-44)+(S14-1)

(I-45)+(S1-1); (I-45)+(S1-2); (I-45)+(S1-3); (I-45)+(S1-4); (I-45)+(S1-5); (I-45)+(S1-6); (I-45)+(S1-7); (I-45)+(S1-8); (I-45)+(S1-9); (I-45)+(S1-10); (I-45)+(S1-11); (I-45)+(S1-12); (I-45)+(S1-13); (I-45)+(S2-1); (I-45)+(S2-2); (I-45)+(S2-3); (I-45)+(S2-4); (I-45)+(S2-5); (I-45)+(S2-6); (I-45)+(S2-7); (I-45)+(S2-8); (I-45)+(S2-9); (I-45)+(S2-10); (I-45)+(S3-1); (I-45)+(S3-2); (I-45)+(S3-3); (I-45)+(S3-4); (I-45)+(S3-5); (I-45)+(S3-6); (I-45)+(S3-7); (I-45)+(S3-8); (I-45)+(S3-9); (I-45)+(S3-10); (I-45)+(S3-11); (I-45)+(S4-1); (I-45)+(S4-2); (I-45)+(S4-3); (I-45)+(S4-4); (I-45)+(S4-5); (I-45)+(S7-1); (I-45)+(S11-1); (I-45)+(S11-2); (I-45)+(S11-3); (I-45)+(S12-1); (I-45)+(S13-1); (I-45)+(S13-2); (I-45)+(S13-3); (I-45)+(S13-4): (I-45)+(S13-5); (I-45)+(S13-6); (I-45)+(S13-7); (I-45)+(S13-8); (I-45)+(S13-9); (I-45)+(S14-1)

(I-46)+(S1-1); (I-46)+(S1-2); (I-46)+(S1-3); (I-46)+(S1-4); (I-46)+(S1-5); (I-46)+(S1-6); (I-46)+(S1-7); (I-46)+(S1-8); (I-46)+(S1-9); (I-46)+(S1-10); (I-46)+(S1-11); (I-46)+(S1-12); (I-46)+(S1-13); (I-46)+(S2-1); (I-46)+(S2-2); (I-46)+(S2-3); (I-46)+(S2-4); (I-46)+(S2-5); (I-46)+(S2-6); (I-46)+(S2-7); (I-46)+(S2-8); (I-46)+(S2-9); (I-46)+(S2-10); (I-46)+(S3-1); (I-46)+(S3-2); (I-46)+(S3-3); (I-46)+(S3-4); (I-46)+(S3-5); (I-46)+(S3-6); (I-46)+(S3-7); (I-46)+(S3-8); (I-46)+(S3-9); (I-46)+(S3-10); (I-46)+(S3-11); (I-46)+(S4-1); (I-46)+(S4-2); (I-46)+(S4-3); (I-46)+(S4-4); (I-46)+(S4-5); (I-46)+(S7-1); (I-46)+(S11-1); (I-46)+(S11-2); (I-46)+(S11-3); (I-46)+(S12-1); (I-46)+(S13-1); (I-46)+(S13-2); (I-46)+(S13-3); (I-46)+(S13-4): (I-46)+(S13-5); (I-46)+(S13-6); (I-46)+(S13-7); (I-46)+(S13-8); (I-46)+(S13-9); (I-46)+(S14-1)

(I-47)+(S1-1); (I-47)+(S1-2); (I-47)+(S1-3); (I-47)+(S1-4); (I-47)+(S1-5); (I-47)+(S1-6); (I-47)+(S1-7); (I-47)+(S1-8); (I-47)+(S1-9); (I-47)+(S1-10); (I-47)+(S1-11); (I-47)+(S1-12); (I-47)+(S1-13); (I-47)+(S2-1); (I-47)+(S2-2); (I-47)+(S2-3); (I-47)+(S2-4); (I-47)+(S2-5); (I-47)+(S2-6); (I-47)+(S2-7); (I-47)+(S2-8); (I-47)+(S2-9); (I-47)+(S2-10); (I-47)+(S3-1); (I-47)+(S3-2); (I-47)+(S3-3); (I-47)+(S3-4); (I-47)+(S3-5); (I-47)+(S3-6); (I-47)+(S3-7); (I-47)+(S3-8); (I-47)+(S3-9); (I-47)+(S3-10); (I-47)+(S3-11); (I-47)+(S4-1); (I-47)+(S4-2); (I-47)+(S4-3); (I-47)+(S4-4); (I-47)+(S4-5); (I-47)+(S7-1); (I-47)+(S11-1); (I-47)+(S11-2); (I-47)+(S11-3); (I-47)+(S12-1); (I-47)+(S13-1); (I-47)+(S13-2); (I-47)+(S13-3); (I-47)+(S13-4): (I-47)+(S13-5); (I-47)+(S13-6); (I-47)+(S13-7); (I-47)+(S13-8); (I-47)+(S13-9); (I-47)+(S14-1)

(I-48)+(S1-1); (I-48)+(S1-2); (I-48)+(S1-3); (I-48)+(S1-4); (I-48)+(S1-5); (I-48)+(S1-6); (I-48)+(S1-7); (I-48)+(S1-8); (I-48)+(S1-9); (I-48)+(S1-10); (I-48)+(S1-11); (I-48)+(S1-12); (I-48)+(S1-13); (I-48)+(S2-1); (I-48)+(S2-2); (I-48)+(S2-3); (I-48)+(S2-4); (I-48)+(S2-5); (I-48)+(S2-6); (I-48)+(S2-7); (I-48)+(S2-8); (I-48)+(S2-9); (I-48)+(S2-10); (I-48)+(S3-1); (I-48)+(S3-2); (I-48)+(S3-3); (I-48)+(S3-4); (I-48)+(S3-5); (I-48)+(S3-6); (I-48)+(S3-7); (I-48)+(S3-8); (I-48)+(S3-9); (I-48)+(S3-10); (I-48)+(S3-11); (I-48)+(S4-1); (I-48)+(S4-2); (I-48)+(S4-3); (I-48)+(S4-4); (I-48)+(S4-5); (I-48)+(S7-1); (I-48)+(S11-1); (I-48)+(S11-2); (I-48)+(S11-

3); (I-48)+(S12-1); (I-48)+(S13-1); (I-48)+(S13-2); (I-48)+(S13-3); (I-48)+(S13-4): (I-48)+(S13-5); (I-48)+(S13-6); (I-48)+(S13-7); (I-48)+(S13-8); (I-48)+(S13-9); (I-48)+(S14-1)

(I-49)+(S1-1); (I-49)+(S1-2); (I-49)+(S1-3); (I-49)+(S1-4); (I-49)+(S1-5); (I-49)+(S1-6); (I-49)+(S1-7); (I-49)+(S1-8); (I-49)+(S1-9); (I-49)+(S1-10); (I-49)+(S1-11); (I-49)+(S1-12); (I-49)+(S1-13); (I-49)+(S2-1); (I-49)+(S2-2); (I-49)+(S2-3); (I-49)+(S2-4); (I-49)+(S2-5); (I-49)+(S2-6); (I-49)+(S2-7); (I-49)+(S2-8); (I-49)+(S2-9); (I-49)+(S2-10); (I-49)+(S3-1); (I-49)+(S3-2); (I-49)+(S3-3); (I-49)+(S3-4); (I-49)+(S3-5); (I-49)+(S3-6); (I-49)+(S3-7); (I-49)+(S3-8); (I-49)+(S3-9); (I-49)+(S3-10); (I-49)+(S3-11); (I-49)+(S4-1); (I-49)+(S4-2); (I-49)+(S4-3); (I-49)+(S4-4); (I-49)+(S4-5); (I-49)+(S7-1); (I-49)+(S11-1); (I-49)+(S11-2); (I-49)+(S11-3); (I-49)+(S12-1); (I-49)+(S13-1); (I-49)+(S13-2); (I-49)+(S13-3); (I-49)+(S13-4): (I-49)+(S13-5); (I-49)+(S13-6); (I-49)+(S13-7); (I-49)+(S13-8); (I-49)+(S13-9); (I-49)+(S14-1)

(I-50)+(S1-1); (I-50)+(S1-2); (I-50)+(S1-3); (I-50)+(S1-4); (I-50)+(S1-5); (I-50)+(S1-6); (I-50)+(S1-7); (I-50)+(S1-8); (I-50)+(S1-9); (I-50)+(S1-10); (I-50)+(S1-11); (I-50)+(S1-12); (I-50)+(S1-13); (I-50)+(S2-1); (I-50)+(S2-2); (I-50)+(S2-3); (I-50)+(S2-4); (I-50)+(S2-5); (I-50)+(S2-6); (I-50)+(S2-7); (I-50)+(S2-8); (I-50)+(S2-9); (I-50)+(S2-10); (I-50)+(S3-1); (I-50)+(S3-2); (I-50)+(S3-3); (I-50)+(S3-4); (I-50)+(S3-5); (I-50)+(S3-6); (I-50)+(S3-7); (I-50)+(S3-8); (I-50)+(S3-9); (I-50)+(S3-10); (I-50)+(S3-11); (I-50)+(S4-1); (I-50)+(S4-2); (I-50)+(S4-3); (I-50)+(S4-4); (I-50)+(S4-5); (I-50)+(S7-1); (I-50)+(S11-1); (I-50)+(S11-2); (I-50)+(S11-3); (I-50)+(S12-1); (I-50)+(S13-1); (I-50)+(S13-2); (I-50)+(S13-3); (I-50)+(S13-4): (I-50)+(S13-5); (I-50)+(S13-6); (I-50)+(S13-7); (I-50)+(S13-8); (I-50)+(S13-9); (I-50)+(S14-1)

(I-51)+(S1-1); (I-51)+(S1-2); (I-51)+(S1-3); (I-51)+(S1-4); (I-51)+(S1-5); (I-51)+(S1-6); (I-51)+(S1-7); (I-51)+(S1-8); (I-51)+(S1-9); (I-51)+(S1-10); (I-51)+(S1-11); (I-51)+(S1-12); (I-51)+(S1-13); (I-51)+(S2-1); (I-51)+(S2-2); (I-51)+(S2-3); (I-51)+(S2-4); (I-51)+(S2-5); (I-51)+(S2-6); (I-51)+(S2-7); (I-51)+(S2-8); (I-51)+(S2-9); (I-51)+(S2-10); (I-51)+(S3-1); (I-51)+(S3-2); (I-51)+(S3-3); (I-51)+(S3-4); (I-51)+(S3-5); (I-51)+(S3-6); (I-51)+(S3-7); (I-51)+(S3-8); (I-51)+(S3-9); (I-51)+(S3-10); (I-51)+(S3-11); (I-51)+(S4-1); (I-51)+(S4-2); (I-51)+(S4-3); (I-51)+(S4-4); (I-51)+(S4-5); (I-51)+(S7-1); (I-51)+(S11-1); (I-51)+(S11-2); (I-51)+(S11-3); (I-51)+(S12-1); (I-51)+(S13-1); (I-51)+(S13-2); (I-51)+(S13-3); (I-51)+(S13-4): (I-51)+(S13-5); (I-51)+(S13-6); (I-51)+(S13-7); (I-51)+(S13-8); (I-51)+(S13-9); (I-51)+(S14-1)

(I-52)+(S1-1); (I-52)+(S1-2); (I-52)+(S1-3); (I-52)+(S1-4); (I-52)+(S1-5); (I-52)+(S1-6); (I-52)+(S1-7); (I-52)+(S1-8); (I-52)+(S1-9); (I-52)+(S1-10); (I-52)+(S1-11); (I-52)+(S1-12); (I-52)+(S1-13); (I-52)+(S2-1); (I-52)+(S2-2); (I-52)+(S2-3); (I-52)+(S2-4); (I-52)+(S2-5); (I-52)+(S2-6); (I-52)+(S2-7); (I-52)+(S2-8); (I-52)+(S2-9); (I-52)+(S2-10); (I-52)+(S3-1); (I-52)+(S3-2); (I-52)+(S3-3); (I-52)+(S3-4); (I-52)+(S3-5); (I-52)+(S3-6); (I-52)+(S3-7); (I-52)+(S3-8); (I-52)+(S3-9); (I-52)+(S3-10); (I-52)+(S3-11); (I-52)+(S4-1); (I-52)+(S4-2); (I-52)+(S4-3); (I-52)+(S4-4); (I-52)+(S4-5); (I-52)+(S7-1); (I-52)+(S11-1); (I-52)+(S11-2); (I-52)+(S11-3); (I-52)+(S12-1); (I-52)+(S13-1); (I-52)+(S13-2); (I-52)+(S13-3); (I-52)+(S13-4); (I-52)+(S13-5); (I-52)+(S13-6); (I-52)+(S13-7); (I-52)+(S13-8); (I-52)+(S13-9); (I-52)+(S14-1)

(I-53)+(S1-1); (I-53)+(S1-2); (I-53)+(S1-3); (I-53)+(S1-4); (I-53)+(S1-5); (I-53)+(S1-6); (I-53)+(S1-7); (I-53)+(S1-8); (I-53)+(S1-9); (I-53)+(S1-10); (I-53)+(S1-11); (I-53)+(S1-12); (I-53)+(S1-13); (I-53)+(S2-1); (I-53)+(S2-2); (I-53)+(S2-3); (I-53)+(S2-4); (I-53)+(S2-5); (I-53)+(S2-6); (I-53)+(S2-7); (I-53)+(S2-8); (I-53)+(S2-9); (I-53)+(S2-10); (I-53)+(S3-1); (I-53)+(S3-2); (I-53)+(S3-3); (I-53)+(S3-4); (I-53)+(S3-5); (I-53)+(S3-6); (I-53)+(S3-7); (I-53)+(S3-8); (I-53)+(S3-9); (I-53)+(S3-10); (I-53)+(S3-11); (I-53)+(S4-1); (I-53)+(S4-2); (I-53)+(S4-3); (I-53)+(S4-4); (I-53)+(S4-5); (I-53)+(S7-1); (I-53)+(S11-1); (I-53)+(S11-2); (I-53)+(S11-3); (I-53)+(S12-1); (I-53)+(S13-1); (I-53)+(S13-2); (I-53)+(S13-3); (I-53)+(S13-4): (I-53)+(S13-5); (I-53)+(S13-6); (I-53)+(S13-7); (I-53)+(S13-8); (I-53)+(S13-9); (I-53)+(S14-1)

(I-54)+(S1-1); (I-54)+(S1-2); (I-54)+(S1-3); (I-54)+(S1-4); (I-54)+(S1-5); (I-54)+(S1-6); (I-54)+(S1-7); (I-54)+(S1-8); (I-54)+(S1-9); (I-54)+(S1-10); (I-54)+(S1-11); (I-54)+(S1-12); (I-54)+(S1-13); (I-54)+(S2-1); (I-54)+(S2-2); (I-54)+(S2-3); (I-54)+(S2-4); (I-54)+(S2-5); (I-54)+(S2-6); (I-54)+(S2-7); (I-54)+(S2-8); (I-54)+(S2-9); (I-54)+(S2-10); (I-54)+(S3-1); (I-54)+(S3-2); (I-54)+(S3-3); (I-54)+(S3-4); (I-54)+(S3-5); (I-54)+(S3-6); (I-54)+(S3-7); (I-54)+(S3-8); (I-54)+(S3-9); (I-54)+(S3-10); (I-54)+(S3-11); (I-54)+(S4-1); (I-54)+(S4-2); (I-54)+(S4-3); (I-54)+(S4-4); (I-54)+(S4-5); (I-54)+(S7-1); (I-54)+(S11-1); (I-54)+(S11-2); (I-54)+(S11-3); (I-54)+(S12-1); (I-54)+(S13-1); (I-54)+(S13-2); (I-54)+(S13-3); (I-54)+(S13-4): (I-54)+(S13-5); (I-54)+(S13-6); (I-54)+(S13-7); (I-54)+(S13-8); (I-54)+(S13-9); (I-54)+(S14-1)

(I-55)+(S1-1); (I-55)+(S1-2); (I-55)+(S1-3); (I-55)+(S1-4); (I-55)+(S1-5); (I-55)+(S1-6); (I-55)+(S1-7); (I-55)+(S1-8); (I-55)+(S1-9); (I-55)+(S1-10); (I-55)+(S1-11); (I-55)+(S1-12); (I-55)+(S1-13); (I-55)+(S2-1); (I-55)+(S2-2); (I-55)+(S2-3); (I-55)+(S2-4); (I-55)+(S2-5); (I-55)+(S2-6); (I-55)+(S2-7); (I-55)+(S2-8); (I-55)+(S2-9); (I-55)+(S2-10); (I-55)+(S3-1); (I-55)+(S3-2); (I-55)+(S3-3); (I-55)+(S3-4); (I-55)+(S3-5); (I-55)+(S3-6); (I-55)+(S3-7); (I-55)+(S3-8); (I-55)+(S3-9); (I-55)+(S3-10); (I-55)+(S3-11); (I-55)+(S4-1); (I-55)+(S4-2); (I-55)+(S4-3); (I-55)+(S4-4); (I-55)+(S4-5); (I-55)+(S7-1); (I-55)+(S11-1); (I-55)+(S11-2); (I-55)+(S11-3); (I-55)+(S12-1); (I-55)+(S13-1); (I-55)+(S13-2); (I-55)+(S13-3); (I-55)+(S13-4): (I-55)+(S13-5); (I-55)+(S13-6); (I-55)+(S13-7); (I-55)+(S13-8); (I-55)+(S13-9); (I-55)+(S14-1)

(I-56)+(S1-1); (I-56)+(S1-2); (I-56)+(S1-3); (I-56)+(S1-4); (I-56)+(S1-5); (I-56)+(S1-6); (I-56)+(S1-7); (I-56)+(S1-8); (I-56)+(S1-9); (I-56)+(S1-10); (I-56)+(S1-11); (I-56)+(S1-12); (I-56)+(S1-13); (I-56)+(S2-1); (I-56)+(S2-2); (I-56)+(S2-3); (I-56)+(S2-4); (I-56)+(S2-5); (I-56)+(S2-6); (I-56)+(S2-7); (I-56)+(S2-8); (I-56)+(S2-9); (I-56)+(S2-10); (I-56)+(S3-1); (I-56)+(S3-2); (I-56)+(S3-3); (I-56)+(S3-4); (I-56)+(S3-5); (I-56)+(S3-6); (I-56)+(S3-7); (I-56)+(S3-8); (I-56)+(S3-9); (I-56)+(S3-10); (I-56)+(S3-11); (I-56)+(S4-1); (I-56)+(S4-2); (I-56)+(S4-3); (I-56)+(S4-4); (I-56)+(S4-5); (I-56)+(S7-1); (I-56)+(S11-1); (I-56)+(S11-2); (I-56)+(S11-3); (I-56)+(S12-1); (I-56)+(S13-1); (I-56)+(S13-2); (I-56)+(S13-3); (I-56)+(S13-4): (I-56)+(S13-5); (I-56)+(S13-6); (I-56)+(S13-7); (I-56)+(S13-8); (I-56)+(S13-9); (I-56)+(S14-1)

(I-57)+(S1-1); (I-57)+(S1-2); (I-57)+(S1-3); (I-57)+(S1-4); (I-57)+(S1-5); (I-57)+(S1-6); (I-57)+(S1-7); (I-57)+(S1-8); (I-57)+(S1-9); (I-57)+(S1-10); (I-57)+(S1-11); (I-57)+(S1-12); (I-57)+(S1-13); (I-57)+(S2-1); (I-57)+(S2-2); (I-57)+(S2-3); (I-57)+(S2-4); (I-57)+(S2-5); (I-57)+(S2-6); (I-57)+(S2-7); (I-57)+(S2-8); (I-57)+(S2-9); (I-57)+(S2-10); (I-57)+(S3-1); (I-57)+(S3-2); (I-57)+(S3-3); (I-57)+(S3-4); (I-57)+(S3-5); (I-57)+(S3-6); (I-57)+(S3-7); (I-57)+(S3-8); (I-57)+(S3-9); (I-57)+(S3-10); (I-57)+(S3-11); (I-57)+(S4-1); (I-57)+(S4-2); (I-57)+(S4-3); (I-57)+(S4-4); (I-57)+(S4-5);

(I-57)+(S7-1); (I-57)+(S11-1); (I-57)+(S11-2); (I-57)+(S11-3); (I-57)+(S12-1); (I-57)+(S13-1); (I-57)+(S13-2); (I-57)+(S13-3); (I-57)+(S13-4): (I-57)+(S13-5); (I-57)+(S13-6); (I-57)+(S13-7); (I-57)+(S13-8); (I-57)+(S13-9); (I-57)+(S14-1)

(I-58)+(S1-1); (I-58)+(S1-2); (I-58)+(S1-3); (I-58)+(S1-4); (I-58)+(S1-5); (I-58)+(S1-6); (I-58)+(S1-7); (I-58)+(S1-8); (I-58)+(S1-9); (I-58)+(S1-10); (I-58)+(S1-11); (I-58)+(S1-12); (I-58)+(S1-13); (I-58)+(S2-1); (I-58)+(S2-2); (I-58)+(S2-3); (I-58)+(S2-4); (I-58)+(S2-5); (I-58)+(S2-6); (I-58)+(S2-7); (I-58)+(S2-8); (I-58)+(S2-9); (I-58)+(S2-10); (I-58)+(S3-1); (I-58)+(S3-2); (I-58)+(S3-3); (I-58)+(S3-4); (I-58)+(S3-5); (I-58)+(S3-6); (I-58)+(S3-7); (I-58)+(S3-8); (I-58)+(S3-9); (I-58)+(S3-10); (I-58)+(S3-11); (I-58)+(S4-1); (I-58)+(S4-2); (I-58)+(S4-3); (I-58)+(S4-4); (I-58)+(S4-5); (I-58)+(S7-1); (I-58)+(S11-1); (I-58)+(S11-2); (I-58)+(S11-3); (I-58)+(S12-1); (I-58)+(S13-1); (I-58)+(S13-2); (I-58)+(S13-3); (I-58)+(S13-4): (I-58)+(S13-5); (I-58)+(S13-6); (I-58)+(S13-7); (I-58)+(S13-8); (I-58)+(S13-9); (I-58)+(S14-1)

(I-59)+(S1-1); (I-59)+(S1-2); (I-59)+(S1-3); (I-59)+(S1-4); (I-59)+(S1-5); (I-59)+(S1-6); (I-59)+(S1-7); (I-59)+(S1-8); (I-59)+(S1-9); (I-59)+(S1-10); (I-59)+(S1-11); (I-59)+(S1-12); (I-59)+(S1-13); (I-59)+(S2-1); (I-59)+(S2-2); (I-59)+(S2-3); (I-59)+(S2-4); (I-59)+(S2-5); (I-59)+(S2-6); (I-59)+(S2-7); (I-59)+(S2-8); (I-59)+(S2-9); (I-59)+(S2-10); (I-59)+(S3-1); (I-59)+(S3-2); (I-59)+(S3-3); (I-59)+(S3-4); (I-59)+(S3-5); (I-59)+(S3-6); (I-59)+(S3-7); (I-59)+(S3-8); (I-59)+(S3-9); (I-59)+(S3-10); (I-59)+(S3-11); (I-59)+(S4-1); (I-59)+(S4-2); (I-59)+(S4-3); (I-59)+(S4-4); (I-59)+(S4-5); (I-59)+(S7-1); (I-59)+(S11-1); (I-59)+(S11-2); (I-59)+(S11-3); (I-59)+(S12-1); (I-59)+(S13-1); (I-59)+(S13-2); (I-59)+(S13-3); (I-59)+(S13-4): (I-59)+(S13-5); (I-59)+(S13-6); (I-59)+(S13-7); (I-59)+(S13-8); (I-59)+(S13-9); (I-59)+(S14-1)

(I-60)+(S1-1); (I-60)+(S1-2); (I-60)+(S1-3); (I-60)+(S1-4); (I-60)+(S1-5); (I-60)+(S1-6); (I-60)+(S1-7); (I-60)+(S1-8); (I-60)+(S1-9); (I-60)+(S1-10); (I-60)+(S1-11); (I-60)+(S1-12); (I-60)+(S1-13); (I-60)+(S2-1); (I-60)+(S2-2); (I-60)+(S2-3); (I-60)+(S2-4); (I-60)+(S2-5); (I-60)+(S2-6); (I-60)+(S2-7); (I-60)+(S2-8); (I-60)+(S2-9); (I-60)+(S2-10); (I-60)+(S3-1); (I-60)+(S3-2); (I-60)+(S3-3); (I-60)+(S3-4); (I-60)+(S3-5); (I-60)+(S3-6); (I-60)+(S3-7); (I-60)+(S3-8); (I-60)+(S3-9); (I-60)+(S3-10); (I-60)+(S3-11); (I-60)+(S4-1); (I-60)+(S4-2); (I-60)+(S4-3); (I-60)+(S4-4); (I-60)+(S4-5); (I-60)+(S7-1); (I-60)+(S11-1); (I-60)+(S11-2); (I-60)+(S11-3); (I-60)+(S12-1); (I-60)+(S13-1); (I-60)+(S13-2); (I-60)+(S13-3); (I-60)+(S13-4): (I-60)+(S13-5); (I-60)+(S13-6); (I-60)+(S13-7); (I-60)+(S13-8); (I-60)+(S13-9); (I-60)+(S14-1)

(I-61)+(S1-1); (I-61)+(S1-2); (I-61)+(S1-3); (I-61)+(S1-4); (I-61)+(S1-5); (I-61)+(S1-6); (I-61)+(S1-7); (I-61)+(S1-8); (I-61)+(S1-9); (I-61)+(S1-10); (I-61)+(S1-11); (I-61)+(S1-12); (I-61)+(S1-13); (I-61)+(S2-1); (I-61)+(S2-2); (I-61)+(S2-3); (I-61)+(S2-4); (I-61)+(S2-5); (I-61)+(S2-6); (I-61)+(S2-7); (I-61)+(S2-8); (I-61)+(S2-9); (I-61)+(S2-10); (I-61)+(S3-1); (I-61)+(S3-2); (I-61)+(S3-3); (I-61)+(S3-4); (I-61)+(S3-5); (I-61)+(S3-6); (I-61)+(S3-7); (I-61)+(S3-8); (I-61)+(S3-9); (I-61)+(S3-10); (I-61)+(S3-11); (I-61)+(S4-1); (I-61)+(S4-2); (I-61)+(S4-3); (I-61)+(S4-4); (I-61)+(S4-5); (I-61)+(S7-1); (I-61)+(S11-1); (I-61)+(S11-2); (I-61)+(S11-3); (I-61)+(S12-1); (I-61)+(S13-1); (I-61)+(S13-2); (I-61)+(S13-3); (I-61)+(S13-4): (I-61)+(S13-5); (I-61)+(S13-6); (I-61)+(S13-7); (I-61)+(S13-8); (I-61)+(S13-9); (I-61)+(S14-1)

(I-62)+(S1-1); (I-62)+(S1-2); (I-62)+(S1-3); (I-62)+(S1-4); (I-62)+(S1-5); (I-62)+(S1-6); (I-62)+(S1-7); (I-62)+(S1-8); (I-62)+(S1-9); (I-62)+(S1-10); (I-62)+(S1-11); (I-62)+(S1-12); (I-62)+(S1-13); (I-62)+(S2-1); (I-62)+(S2-2); (I-62)+(S2-3); (I-62)+(S2-4); (I-62)+(S2-5); (I-62)+(S2-6); (I-62)+(S2-7); (I-62)+(S2-8); (I-62)+(S2-9); (I-62)+(S2-10); (I-62)+(S3-1); (I-62)+(S3-2); (I-62)+(S3-3); (I-62)+(S3-4); (I-62)+(S3-5); (I-62)+(S3-6); (I-62)+(S3-7); (I-62)+(S3-8); (I-62)+(S3-9); (I-62)+(S3-10); (I-62)+(S3-11); (I-62)+(S4-1); (I-62)+(S4-2); (I-62)+(S4-3); (I-62)+(S4-4); (I-62)+(S4-5); (I-62)+(S7-1); (I-62)+(S11-1); (I-62)+(S11-2); (I-62)+(S11-3); (I-62)+(S12-1); (I-62)+(S13-1); (I-62)+(S13-2); (I-62)+(S13-3); (I-62)+(S13-4): (I-62)+(S13-5); (I-62)+(S13-6); (I-62)+(S13-7); (I-62)+(S13-8); (I-62)+(S13-9); (I-62)+(S14-1)

(I-63)+(S1-1); (I-63)+(S1-2); (I-63)+(S1-3); (I-63)+(S1-4); (I-63)+(S1-5); (I-63)+(S1-6); (I-63)+(S1-7); (I-63)+(S1-8); (I-63)+(S1-9); (I-63)+(S1-10); (I-63)+(S1-11); (I-63)+(S1-12); (I-63)+(S1-13); (I-63)+(S2-1); (I-63)+(S2-2); (I-63)+(S2-3); (I-63)+(S2-4); (I-63)+(S2-5); (I-63)+(S2-6); (I-63)+(S2-7); (I-63)+(S2-8); (I-63)+(S2-9); (I-63)+(S2-10); (I-63)+(S3-1); (I-63)+(S3-2); (I-63)+(S3-3); (I-63)+(S3-4); (I-63)+(S3-5); (I-63)+(S3-6); (I-63)+(S3-7); (I-63)+(S3-8); (I-63)+(S3-9); (I-63)+(S3-10); (I-63)+(S3-11); (I-63)+(S4-1); (I-63)+(S4-2); (I-63)+(S4-3); (I-63)+(S4-4); (I-63)+(S4-5); (I-63)+(S7-1); (I-63)+(S11-1); (I-63)+(S11-2); (I-63)+(S11-3); (I-63)+(S12-1); (I-63)+(S13-1); (I-63)+(S13-2); (I-63)+(S13-3); (I-63)+(S13-4): (I-63)+(S13-5); (I-63)+(S13-6); (I-63)+(S13-7); (I-63)+(S13-8); (I-63)+(S13-9); (I-63)+(S14-1)

(I-64)+(S1-1); (I-64)+(S1-2); (I-64)+(S1-3); (I-64)+(S1-4); (I-64)+(S1-5); (I-64)+(S1-6); (I-64)+(S1-7); (I-64)+(S1-8); (I-64)+(S1-9); (I-64)+(S1-10); (I-64)+(S1-11); (I-64)+(S1-12); (I-64)+(S1-13); (I-64)+(S2-1); (I-64)+(S2-2); (I-64)+(S2-3); (I-64)+(S2-4); (I-64)+(S2-5); (I-64)+(S2-6); (I-64)+(S2-7); (I-64)+(S2-8); (I-64)+(S2-9); (I-64)+(S2-10); (I-64)+(S3-1); (I-64)+(S3-2); (I-64)+(S3-3); (I-64)+(S3-4); (I-64)+(S3-5); (I-64)+(S3-6); (I-64)+(S3-7); (I-64)+(S3-8); (I-64)+(S3-9); (I-64)+(S3-10); (I-64)+(S3-11); (I-64)+(S4-1); (I-64)+(S4-2); (I-64)+(S4-3); (I-64)+(S4-4); (I-64)+(S4-5); (I-64)+(S7-1); (I-64)+(S11-1); (I-64)+(S11-2); (I-64)+(S11-3); (I-64)+(S12-1); (I-64)+(S13-1); (I-64)+(S13-2); (I-64)+(S13-3); (I-64)+(S13-4): (I-64)+(S13-5); (I-64)+(S13-6); (I-64)+(S13-7); (I-64)+(S13-8); (I-64)+(S13-9); (I-64)+(S14-1)

(I-65)+(S1-1); (I-65)+(S1-2); (I-65)+(S1-3); (I-65)+(S1-4); (I-65)+(S1-5); (I-65)+(S1-6); (I-65)+(S1-7); (I-65)+(S1-8); (I-65)+(S1-9); (I-65)+(S1-10); (I-65)+(S1-11); (I-65)+(S1-12); (I-65)+(S1-13); (I-65)+(S2-1); (I-65)+(S2-2); (I-65)+(S2-3); (I-65)+(S2-4); (I-65)+(S2-5); (I-65)+(S2-6); (I-65)+(S2-7); (I-65)+(S2-8); (I-65)+(S2-9); (I-65)+(S2-10); (I-65)+(S3-1); (I-65)+(S3-2); (I-65)+(S3-3); (I-65)+(S3-4); (I-65)+(S3-5); (I-65)+(S3-6); (I-65)+(S3-7); (I-65)+(S3-8); (I-65)+(S3-9); (I-65)+(S3-10); (I-65)+(S3-11); (I-65)+(S4-1); (I-65)+(S4-2); (I-65)+(S4-3); (I-65)+(S4-4); (I-65)+(S4-5); (I-65)+(S7-1); (I-65)+(S11-1); (I-65)+(S11-2); (I-65)+(S11-3); (I-65)+(S12-1); (I-65)+(S13-1); (I-65)+(S13-2); (I-65)+(S13-3); (I-65)+(S13-4): (I-65)+(S13-5); (I-65)+(S13-6); (I-65)+(S13-7); (I-65)+(S13-8); (I-65)+(S13-9); (I-65)+(S14-1)

(I-66)+(S1-1); (I-66)+(S1-2); (I-66)+(S1-3); (I-66)+(S1-4); (I-66)+(S1-5); (I-66)+(S1-6); (I-66)+(S1-7); (I-66)+(S1-8); (I-66)+(S1-9); (I-66)+(S1-10); (I-66)+(S1-11); (I-66)+(S1-12); (I-66)+(S1-13); (I-66)+(S2-1); (I-66)+(S2-2); (I-66)+(S2-3); (I-66)+(S2-4); (I-66)+(S2-5); (I-66)+(S2-6); (I-66)+(S2-7); (I-66)+(S2-8); (I-66)+(S2-9); (I-66)+(S2-10); (I-66)+(S3-1); (I-66)+(S3-2); (I-66)+(S3-3); (I-66)+(S3-4); (I-66)+(S3-5); (I-66)+(S3-6); (I-66)+(S3-7); (I-66)+(S3-8); (I-66)+(S3-9); (I-66)+(S3-10); (I-66)+(S3-11); (I-66)+(S4-1);

(I-66)+(S4-2); (I-66)+(S4-3); (I-66)+(S4-4); (I-66)+(S4-5); (I-66)+(S7-1); (I-66)+(S11-1); (I-66)+(S11-2); (I-66)+(S11-3); (I-66)+(S12-1); (I-66)+(S13-1); (I-66)+(S13-2); (I-66)+(S13-3); (I-66)+(S13-4): (I-66)+(S13-5); (I-66)+(S13-6); (I-66)+(S13-7); (I-66)+(S13-8); (I-66)+(S13-9); (I-66)+(S14-1)

(I-67)+(S1-1); (I-67)+(S1-2); (I-67)+(S1-3); (I-67)+(S1-4); (I-67)+(S1-5); (I-67)+(S1-6); (I-67)+(S1-7); (I-67)+(S1-8); (I-67)+(S1-9); (I-67)+(S1-10); (I-67)+(S1-11); (I-67)+(S1-12); (I-67)+(S1-13); (I-67)+(S2-1); (I-67)+(S2-2); (I-67)+(S2-3); (I-67)+(S2-4); (I-67)+(S2-5); (I-67)+(S2-6); (I-67)+(S2-7); (I-67)+(S2-8); (I-67)+(S2-9); (I-67)+(S2-10); (I-67)+(S3-1); (I-67)+(S3-2); (I-67)+(S3-3); (I-67)+(S3-4); (I-67)+(S3-5); (I-67)+(S3-6); (I-67)+(S3-7); (I-67)+(S3-8); (I-67)+(S3-9); (I-67)+(S3-10); (I-67)+(S3-11); (I-67)+(S4-1); (I-67)+(S4-2); (I-67)+(S4-3); (I-67)+(S4-4); (I-67)+(S4-5); (I-67)+(S7-1); (I-67)+(S11-1); (I-67)+(S11-2); (I-67)+(S11-3); (I-67)+(S12-1); (I-67)+(S13-1); (I-67)+(S13-2); (I-67)+(S13-3); (I-67)+(S13-4): (I-67)+(S13-5); (I-67)+(S13-6); (I-67)+(S13-7); (I-67)+(S13-8); (I-67)+(S13-9); (I-67)+(S14-1)

(I-68)+(S1-1); (I-68)+(S1-2); (I-68)+(S1-3); (I-68)+(S1-4); (I-68)+(S1-5); (I-68)+(S1-6); (I-68)+(S1-7); (I-68)+(S1-8); (I-68)+(S1-9); (I-68)+(S1-10); (I-68)+(S1-11); (I-68)+(S1-12); (I-68)+(S1-13); (I-68)+(S2-1); (I-68)+(S2-2); (I-68)+(S2-3); (I-68)+(S2-4); (I-68)+(S2-5); (I-68)+(S2-6); (I-68)+(S2-7); (I-68)+(S2-8); (I-68)+(S2-9); (I-68)+(S2-10); (I-68)+(S3-1); (I-68)+(S3-2); (I-68)+(S3-3); (I-68)+(S3-4); (I-68)+(S3-5); (I-68)+(S3-6); (I-68)+(S3-7); (I-68)+(S3-8); (I-68)+(S3-9); (I-68)+(S3-10); (I-68)+(S3-11); (I-68)+(S4-1); (I-68)+(S4-2); (I-68)+(S4-3); (I-68)+(S4-4); (I-68)+(S4-5); (I-68)+(S7-1); (I-68)+(S11-1); (I-68)+(S11-2); (I-68)+(S11-3); (I-68)+(S12-1); (I-68)+(S13-1); (I-68)+(S13-2); (I-68)+(S13-3); (I-68)+(S13-4): (I-68)+(S13-5); (I-68)+(S13-6); (I-68)+(S13-7); (I-68)+(S13-8); (I-68)+(S13-9); (I-68)+(S14-1)

(I-69)+(S1-1); (I-69)+(S1-2); (I-69)+(S1-3); (I-69)+(S1-4); (I-69)+(S1-5); (I-69)+(S1-6); (I-69)+(S1-7); (I-69)+(S1-8); (I-69)+(S1-9); (I-69)+(S1-10); (I-69)+(S1-11); (I-69)+(S1-12); (I-69)+(S1-13); (I-69)+(S2-1); (I-69)+(S2-2); (I-69)+(S2-3); (I-69)+(S2-4); (I-69)+(S2-5); (I-69)+(S2-6); (I-69)+(S2-7); (I-69)+(S2-8); (I-69)+(S2-9); (I-69)+(S2-10); (I-69)+(S3-1); (I-69)+(S3-2); (I-69)+(S3-3); (I-69)+(S3-4); (I-69)+(S3-5); (I-69)+(S3-6); (I-69)+(S3-7); (I-69)+(S3-8); (I-69)+(S3-9); (I-69)+(S3-10); (I-69)+(S3-11); (I-69)+(S4-1); (I-69)+(S4-2); (I-69)+(S4-3); (I-69)+(S4-4); (I-69)+(S4-5); (I-69)+(S7-1); (I-69)+(S11-1); (I-69)+(S11-2); (I-69)+(S11-3); (I-69)+(S12-1); (I-69)+(S13-1); (I-69)+(S13-2); (I-69)+(S13-3); (I-69)+(S13-4): (I-69)+(S13-5); (I-69)+(S13-6); (I-69)+(S13-7); (I-69)+(S13-8); (I-69)+(S13-9); (I-69)+(S14-1)

(I-70)+(S1-1); (I-70)+(S1-2); (I-70)+(S1-3); (I-70)+(S1-4); (I-70)+(S1-5); (I-70)+(S1-6); (I-70)+(S1-7); (I-70)+(S1-8); (I-70)+(S1-9); (I-70)+(S1-10); (I-70)+(S1-11); (I-70)+(S1-12); (I-70)+(S1-13); (I-70)+(S2-1); (I-70)+(S2-2); (I-70)+(S2-3); (I-70)+(S2-4); (I-70)+(S2-5); (I-70)+(S2-6); (I-70)+(S2-7); (I-70)+(S2-8); (I-70)+(S2-9); (I-70)+(S2-10); (I-70)+(S3-1); (I-70)+(S3-2); (I-70)+(S3-3); (I-70)+(S3-4); (I-70)+(S3-5); (I-70)+(S3-6); (I-70)+(S3-7); (I-70)+(S3-8); (I-70)+(S3-9); (I-70)+(S3-10); (I-70)+(S3-11); (I-70)+(S4-1); (I-70)+(S4-2); (I-70)+(S4-3); (I-70)+(S4-4); (I-70)+(S4-5); (I-70)+(S7-1); (I-70)+(S11-1); (I-70)+(S11-2); (I-70)+(S11-3); (I-70)+(S12-1); (I-70)+(S13-1); (I-70)+(S13-2); (I-70)+(S13-3); (I-70)+(S13-4): (I-70)+(S13-5); (I-70)+(S13-6); (I-70)+(S13-7); (I-70)+(S13-8); (I-70)+(S13-9); (I-70)+(S14-1)

(I-71)+(S1-1); (I-71)+(S1-2); (I-71)+(S1-3); (I-71)+(S1-4); (I-71)+(S1-5); (I-71)+(S1-6); (I-71)+(S1-7); (I-71)+(S1-8); (I-71)+(S1-9); (I-71)+(S1-10); (I-71)+(S1-11); (I-71)+(S1-12); (I-71)+(S1-13); (I-71)+(S2-1); (I-71)+(S2-2); (I-71)+(S2-3); (I-71)+(S2-4); (I-71)+(S2-5); (I-71)+(S2-6); (I-71)+(S2-7); (I-71)+(S2-8); (I-71)+(S2-9); (I-71)+(S2-10); (I-71)+(S3-1); (I-71)+(S3-2); (I-71)+(S3-3); (I-71)+(S3-4); (I-71)+(S3-5); (I-71)+(S3-6); (I-71)+(S3-7); (I-71)+(S3-8); (I-71)+(S3-9); (I-71)+(S3-10); (I-71)+(S3-11); (I-71)+(S4-1); (I-71)+(S4-2); (I-71)+(S4-3); (I-71)+(S4-4); (I-71)+(S4-5); (I-71)+(S7-1); (I-71)+(S11-1); (I-71)+(S11-2); (I-71)+(S11-3); (I-71)+(S12-1); (I-71)+(S13-1); (I-71)+(S13-2); (I-71)+(S13-3); (I-71)+(S13-4): (I-71)+(S13-5); (I-71)+(S13-6); (I-71)+(S13-7); (I-71)+(S13-8); (I-71)+(S13-9); (I-71)+(S14-1)

(I-72)+(S1-1); (I-72)+(S1-2); (I-72)+(S1-3); (I-72)+(S1-4); (I-72)+(S1-5); (I-72)+(S1-6); (I-72)+(S1-7); (I-72)+(S1-8); (I-72)+(S1-9); (I-72)+(S1-10); (I-72)+(S1-11); (I-72)+(S1-12); (I-72)+(S1-13); (I-72)+(S2-1); (I-72)+(S2-2); (I-72)+(S2-3); (I-72)+(S2-4); (I-72)+(S2-5); (I-72)+(S2-6); (I-72)+(S2-7); (I-72)+(S2-8); (I-72)+(S2-9); (I-72)+(S2-10); (I-72)+(S3-1); (I-72)+(S3-2); (I-72)+(S3-3); (I-72)+(S3-4); (I-72)+(S3-5); (I-72)+(S3-6); (I-72)+(S3-7); (I-72)+(S3-8); (I-72)+(S3-9); (I-72)+(S3-10); (I-72)+(S3-11); (I-72)+(S4-1); (I-72)+(S4-2); (I-72)+(S4-3); (I-72)+(S4-4); (I-72)+(S4-5); (I-72)+(S7-1); (I-72)+(S11-1); (I-72)+(S11-2); (I-72)+(S11-3); (I-72)+(S12-1); (I-72)+(S13-1); (I-72)+(S13-2); (I-72)+(S13-3); (I-72)+(S13-4): (I-72)+(S13-5); (I-72)+(S13-6); (I-72)+(S13-7); (I-72)+(S13-8); (I-72)+(S13-9); (I-72)+(S14-1)

(I-73)+(S1-1); (I-73)+(S1-2); (I-73)+(S1-3); (I-73)+(S1-4); (I-73)+(S1-5); (I-73)+(S1-6); (I-73)+(S1-7); (I-73)+(S1-8); (I-73)+(S1-9); (I-73)+(S1-10); (I-73)+(S1-11); (I-73)+(S1-12); (I-73)+(S1-13); (I-73)+(S2-1); (I-73)+(S2-2); (I-73)+(S2-3); (I-73)+(S2-4); (I-73)+(S2-5); (I-73)+(S2-6); (I-73)+(S2-7); (I-73)+(S2-8); (I-73)+(S2-9); (I-73)+(S2-10); (I-73)+(S3-1); (I-73)+(S3-2); (I-73)+(S3-3); (I-73)+(S3-4); (I-73)+(S3-5); (I-73)+(S3-6); (I-73)+(S3-7); (I-73)+(S3-8); (I-73)+(S3-9); (I-73)+(S3-10); (I-73)+(S3-11); (I-73)+(S4-1); (I-73)+(S4-2); (I-73)+(S4-3); (I-73)+(S4-4); (I-73)+(S4-5); (I-73)+(S7-1); (I-73)+(S11-1); (I-73)+(S11-2); (I-73)+(S11-3); (I-73)+(S12-1); (I-73)+(S13-1); (I-73)+(S13-2); (I-73)+(S13-3); (I-73)+(S13-4): (I-73)+(S13-5); (I-73)+(S13-6); (I-73)+(S13-7); (I-73)+(S13-8); (I-73)+(S13-9); (I-73)+(S14-1)

(I-74)+(S1-1); (I-74)+(S1-2); (I-74)+(S1-3); (I-74)+(S1-4); (I-74)+(S1-5); (I-74)+(S1-6); (I-74)+(S1-7); (I-74)+(S1-8); (I-74)+(S1-9); (I-74)+(S1-10); (I-74)+(S1-11); (I-74)+(S1-12); (I-74)+(S1-13); (I-74)+(S2-1); (I-74)+(S2-2); (I-74)+(S2-3); (I-74)+(S2-4); (I-74)+(S2-5); (I-74)+(S2-6); (I-74)+(S2-7); (I-74)+(S2-8); (I-74)+(S2-9); (I-74)+(S2-10); (I-74)+(S3-1); (I-74)+(S3-2); (I-74)+(S3-3); (I-74)+(S3-4); (I-74)+(S3-5); (I-74)+(S3-6); (I-74)+(S3-7); (I-74)+(S3-8); (I-74)+(S3-9); (I-74)+(S3-10); (I-74)+(S3-11); (I-74)+(S4-1); (I-74)+(S4-2); (I-74)+(S4-3); (I-74)+(S4-4); (I-74)+(S4-5); (I-74)+(S7-1); (I-74)+(S11-1); (I-74)+(S11-2); (I-74)+(S11-3); (I-74)+(S12-1); (I-74)+(S13-1); (I-74)+(S13-2); (I-74)+(S13-3); (I-74)+(S13-4): (I-74)+(S13-5); (I-74)+(S13-6); (I-74)+(S13-7); (I-74)+(S13-8); (I-74)+(S13-9); (I-74)+(S14-1)

(I-75)+(S1-1); (I-75)+(S1-2); (I-75)+(S1-3); (I-75)+(S1-4); (I-75)+(S1-5); (I-75)+(S1-6); (I-75)+(S1-7); (I-75)+(S1-8); (I-75)+(S1-9); (I-75)+(S1-10); (I-75)+(S1-11); (I-75)+(S1-12); (I-75)+(S1-13); (I-75)+(S2-1); (I-75)+(S2-2); (I-75)+(S2-3); (I-75)+(S2-4); (I-75)+(S2-5); (I-75)+(S2-6); (I-75)+(S2-7); (I-75)+(S2-8); (I-75)+(S2-9); (I-75)+(S2-10); (I-75)+(S3-1); (I-75)+(S3-2); (I-75)+(S3-3); (I-75)+(S3-4); (I-75)+

(S3-5); (I-75)+(S3-6); (I-75)+(S3-7); (I-75)+(S3-8); (I-75)+(S3-9); (I-75)+(S3-10); (I-75)+(S3-11); (I-75)+(S4-1); (I-75)+(S4-2); (I-75)+(S4-3); (I-75)+(S4-4); (I-75)+(S4-5); (I-75)+(S7-1); (I-75)+(S11-1); (I-75)+(S11-2); (I-75)+(S11-3); (I-75)+(S12-1); (I-75)+(S13-1); (I-75)+(S13-2); (I-75)+(S13-3); (I-75)+(S13-4): (I-75)+(S13-5); (I-75)+(S13-6); (I-75)+(S13-7); (I-75)+(S13-8); (I-75)+(S13-9); (I-75)+(S14-1)

(I-76)+(S1-1); (I-76)+(S1-2); (I-76)+(S1-3); (I-76)+(S1-4); (I-76)+(S1-5); (I-76)+(S1-6); (I-76)+(S1-7); (I-76)+(S1-8); (I-76)+(S1-9); (I-76)+(S1-10); (I-76)+(S1-11); (I-76)+(S1-12); (I-76)+(S1-13); (I-76)+(S2-1); (I-76)+(S2-2); (I-76)+(S2-3); (I-76)+(S2-4); (I-76)+(S2-5); (I-76)+(S2-6); (I-76)+(S2-7); (I-76)+(S2-8); (I-76)+(S2-9); (I-76)+(S2-10); (I-76)+(S3-1); (I-76)+(S3-2); (I-76)+(S3-3); (I-76)+(S3-4); (I-76)+(S3-5); (I-76)+(S3-6); (I-76)+(S3-7); (I-76)+(S3-8); (I-76)+(S3-9); (I-76)+(S3-10); (I-76)+(S3-11); (I-76)+(S4-1); (I-76)+(S4-2); (I-76)+(S4-3); (I-76)+(S4-4); (I-76)+(S4-5); (I-76)+(S7-1); (I-76)+(S11-1); (I-76)+(S11-2); (I-76)+(S11-3); (I-76)+(S12-1); (I-76)+(S13-1); (I-76)+(S13-2); (I-76)+(S13-3); (I-76)+(S13-4): (I-76)+(S13-5); (I-76)+(S13-6); (I-76)+(S13-7); (I-76)+(S13-8); (I-76)+(S13-9); (I-76)+(S14-1)

(I-77)+(S1-1); (I-77)+(S1-2); (I-77)+(S1-3); (I-77)+(S1-4); (I-77)+(S1-5); (I-77)+(S1-6); (I-77)+(S1-7); (I-77)+(S1-8); (I-77)+(S1-9); (I-77)+(S1-10); (I-77)+(S1-11); (I-77)+(S1-12); (I-77)+(S1-13); (I-77)+(S2-1); (I-77)+(S2-2); (I-77)+(S2-3); (I-77)+(S2-4); (I-77)+(S2-5); (I-77)+(S2-6); (I-77)+(S2-7); (I-77)+(S2-8); (I-77)+(S2-9); (I-77)+(S2-10); (I-77)+(S3-1); (I-77)+(S3-2); (I-77)+(S3-3); (I-77)+(S3-4); (I-77)+(S3-5); (I-77)+(S3-6); (I-77)+(S3-7); (I-77)+(S3-8); (I-77)+(S3-9); (I-77)+(S3-10); (I-77)+(S3-11); (I-77)+(S4-1); (I-77)+(S4-2); (I-77)+(S4-3); (I-77)+(S4-4); (I-77)+(S4-5); (I-77)+(S7-1); (I-77)+(S11-1); (I-77)+(S11-2); (I-77)+(S11-3); (I-77)+(S12-1); (I-77)+(S13-1); (I-77)+(S13-2); (I-77)+(S13-3); (I-77)+(S13-4): (I-77)+(S13-5); (I-77)+(S13-6); (I-77)+(S13-7); (I-77)+(S13-8); (I-77)+(S13-9); (I-77)+(S14-1)

(I-78)+(S1-1); (I-78)+(S1-2); (I-78)+(S1-3); (I-78)+(S1-4); (I-78)+(S1-5); (I-78)+(S1-6); (I-78)+(S1-7); (I-78)+(S1-8); (I-78)+(S1-9); (I-78)+(S1-10); (I-78)+(S1-11); (I-78)+(S1-12); (I-78)+(S1-13); (I-78)+(S2-1); (I-78)+(S2-2); (I-78)+(S2-3); (I-78)+(S2-4); (I-78)+(S2-5); (I-78)+(S2-6); (I-78)+(S2-7); (I-78)+(S2-8); (I-78)+(S2-9); (I-78)+(S2-10); (I-78)+(S3-1); (I-78)+(S3-2); (I-78)+(S3-3); (I-78)+(S3-4); (I-78)+(S3-5); (I-78)+(S3-6); (I-78)+(S3-7); (I-78)+(S3-8); (I-78)+(S3-9); (I-78)+(S3-10); (I-78)+(S3-11); (I-78)+(S4-1); (I-78)+(S4-2); (I-78)+(S4-3); (I-78)+(S4-4); (I-78)+(S4-5); (I-78)+(S7-1); (I-78)+(S11-1); (I-78)+(S11-2); (I-78)+(S11-3); (I-78)+(S12-1); (I-78)+(S13-1); (I-78)+(S13-2); (I-78)+(S13-3); (I-78)+(S13-4): (I-78)+(S13-5); (I-78)+(S13-6); (I-78)+(S13-7); (I-78)+(S13-8); (I-78)+(S13-9); (I-78)+(S14-1)

(I-79)+(S1-1); (I-79)+(S1-2); (I-79)+(S1-3); (I-79)+(S1-4); (I-79)+(S1-5); (I-79)+(S1-6); (I-79)+(S1-7); (I-79)+(S1-8); (I-79)+(S1-9); (I-79)+(S1-10); (I-79)+(S1-11); (I-79)+(S1-12); (I-79)+(S1-13); (I-79)+(S2-1); (I-79)+(S2-2); (I-79)+(S2-3); (I-79)+(S2-4); (I-79)+(S2-5); (I-79)+(S2-6); (I-79)+(S2-7); (I-79)+(S2-8); (I-79)+(S2-9); (I-79)+(S2-10); (I-79)+(S3-1); (I-79)+(S3-2); (I-79)+(S3-3); (I-79)+(S3-4); (I-79)+(S3-5); (I-79)+(S3-6); (I-79)+(S3-7); (I-79)+(S3-8); (I-79)+(S3-9); (I-79)+(S3-10); (I-79)+(S3-11); (I-79)+(S4-1); (I-79)+(S4-2); (I-79)+(S4-3); (I-79)+(S4-4); (I-79)+(S4-5); (I-79)+(S7-1); (I-79)+(S11-1); (I-79)+(S11-2); (I-79)+(S11-3); (I-79)+(S12-1); (I-79)+(S13-1); (I-79)+(S13-2); (I-79)+(S13-3); (I-79)+(S13-4): (I-79)+(S13-5); (I-79)+(S13-6); (I-79)+(S13-7); (I-79)+(S13-8); (I-79)+(S13-9); (I-79)+(S14-1)

(I-80)+(S1-1); (I-80)+(S1-2); (I-80)+(S1-3); (I-80)+(S1-4); (I-80)+(S1-5); (I-80)+(S1-6); (I-80)+(S1-7); (I-80)+(S1-8); (I-80)+(S1-9); (I-80)+(S1-10); (I-80)+(S1-11); (I-80)+(S1-12); (I-80)+(S1-13); (I-80)+(S2-1); (I-80)+(S2-2); (I-80)+(S2-3); (I-80)+(S2-4); (I-80)+(S2-5); (I-80)+(S2-6); (I-80)+(S2-7); (I-80)+(S2-8); (I-80)+(S2-9); (I-80)+(S2-10); (I-80)+(S3-1); (I-80)+(S3-2); (I-80)+(S3-3); (I-80)+(S3-4); (I-80)+(S3-5); (I-80)+(S3-6); (I-80)+(S3-7); (I-80)+(S3-8); (I-80)+(S3-9); (I-80)+(S3-10); (I-80)+(S3-11); (I-80)+(S4-1); (I-80)+(S4-2); (I-80)+(S4-3); (I-80)+(S4-4); (I-80)+(S4-5); (I-80)+(S7-1); (I-80)+(S11-1); (I-80)+(S11-2); (I-80)+(S11-3); (I-80)+(S12-1); (I-80)+(S13-1); (I-80)+(S13-2); (I-80)+(S13-3); (I-80)+(S13-4): (I-80)+(S13-5); (I-80)+(S13-6); (I-80)+(S13-7); (I-80)+(S13-8); (I-80)+(S13-9); (I-80)+(S14-1)

(I-81)+(S1-1); (I-81)+(S1-2); (I-81)+(S1-3); (I-81)+(S1-4); (I-81)+(S1-5); (I-81)+(S1-6); (I-81)+(S1-7); (I-81)+(S1-8); (I-81)+(S1-9); (I-81)+(S1-10); (I-81)+(S1-11); (I-81)+(S1-12); (I-81)+(S1-13); (I-81)+(S2-1); (I-81)+(S2-2); (I-81)+(S2-3); (I-81)+(S2-4); (I-81)+(S2-5); (I-81)+(S2-6); (I-81)+(S2-7); (I-81)+(S2-8); (I-81)+(S2-9); (I-81)+(S2-10); (I-81)+(S3-1); (I-81)+(S3-2); (I-81)+(S3-3); (I-81)+(S3-4); (I-81)+(S3-5); (I-81)+(S3-6); (I-81)+(S3-7); (I-81)+(S3-8); (I-81)+(S3-9); (I-81)+(S3-10); (I-81)+(S3-11); (I-81)+(S4-1); (I-81)+(S4-2); (I-81)+(S4-3); (I-81)+(S4-4); (I-81)+(S4-5); (I-81)+(S7-1); (I-81)+(S11-1); (I-81)+(S11-2); (I-81)+(S11-3); (I-81)+(S12-1); (I-81)+(S13-1); (I-81)+(S13-2); (I-81)+(S13-3); (I-81)+(S13-4): (I-81)+(S13-5); (I-81)+(S13-6); (I-81)+(S13-7); (I-81)+(S13-8); (I-81)+(S13-9); (I-81)+(S14-1)

(I-82)+(S1-1); (I-82)+(S1-2); (I-82)+(S1-3); (I-82)+(S1-4); (I-82)+(S1-5); (I-82)+(S1-6); (I-82)+(S1-7); (I-82)+(S1-8); (I-82)+(S1-9); (I-82)+(S1-10); (I-82)+(S1-11); (I-82)+(S1-12); (I-82)+(S1-13); (I-82)+(S2-1); (I-82)+(S2-2); (I-82)+(S2-3); (I-82)+(S2-4); (I-82)+(S2-5); (I-82)+(S2-6); (I-82)+(S2-7); (I-82)+(S2-8); (I-82)+(S2-9); (I-82)+(S2-10); (I-82)+(S3-1); (I-82)+(S3-2); (I-82)+(S3-3); (I-82)+(S3-4); (I-82)+(S3-5); (I-82)+(S3-6); (I-82)+(S3-7); (I-82)+(S3-8); (I-82)+(S3-9); (I-82)+(S3-10); (I-82)+(S3-11); (I-82)+(S4-1); (I-82)+(S4-2); (I-82)+(S4-3); (I-82)+(S4-4); (I-82)+(S4-5); (I-82)+(S7-1); (I-82)+(S11-1); (I-82)+(S11-2); (I-82)+(S11-3); (I-82)+(S12-1); (I-82)+(S13-1); (I-82)+(S13-2); (I-82)+(S13-3); (I-82)+(S13-4): (I-82)+(S13-5); (I-82)+(S13-6); (I-82)+(S13-7); (I-82)+(S13-8); (I-82)+(S13-9); (I-82)+(S14-1)

(I-83)+(S1-1); (I-83)+(S1-2); (I-83)+(S1-3); (I-83)+(S1-4); (I-83)+(S1-5); (I-83)+(S1-6); (I-83)+(S1-7); (I-83)+(S1-8); (I-83)+(S1-9); (I-83)+(S1-10); (I-83)+(S1-11); (I-83)+(S1-12); (I-83)+(S1-13); (I-83)+(S2-1); (I-83)+(S2-2); (I-83)+(S2-3); (I-83)+(S2-4); (I-83)+(S2-5); (I-83)+(S2-6); (I-83)+(S2-7); (I-83)+(S2-8); (I-83)+(S2-9); (I-83)+(S2-10); (I-83)+(S3-1); (I-83)+(S3-2); (I-83)+(S3-3); (I-83)+(S3-4); (I-83)+(S3-5); (I-83)+(S3-6); (I-83)+(S3-7); (I-83)+(S3-8); (I-83)+(S3-9); (I-83)+(S3-10); (I-83)+(S3-11); (I-83)+(S4-1); (I-83)+(S4-2); (I-83)+(S4-3); (I-83)+(S4-4); (I-83)+(S4-5); (I-83)+(S7-1); (I-83)+(S11-1); (I-83)+(S11-2); (I-83)+(S11-3); (I-83)+(S12-1); (I-83)+(S13-1); (I-83)+(S13-2); (I-83)+(S13-3); (I-83)+(S13-4): (I-83)+(S13-5); (I-83)+(S13-6); (I-83)+(S13-7); (I-83)+(S13-8); (I-83)+(S13-9); (I-83)+(S14-1)

(I-84)+(S1-1); (I-84)+(S1-2); (I-84)+(S1-3); (I-84)+(S1-4); (I-84)+(S1-5); (I-84)+(S1-6); (I-84)+(S1-7); (I-84)+(S1-8); (I-84)+(S1-9); (I-84)+(S1-10); (I-84)+(S1-11); (I-84)+(S1-12); (I-84)+(S1-13); (I-84)+(S2-1); (I-84)+(S2-2); (I-84)+

(S2-3); (I-84)+(S2-4); (I-84)+(S2-5); (I-84)+(S2-6); (I-84)+(S2-7); (I-84)+(S2-8); (I-84)+(S2-9); (I-84)+(S2-10); (I-84)+(S3-1); (I-84)+(S3-2); (I-84)+(S3-3); (I-84)+(S3-4); (I-84)+(S3-5); (I-84)+(S3-6); (I-84)+(S3-7); (I-84)+(S3-8); (I-84)+(S3-9); (I-84)+(S3-10); (I-84)+(S3-11); (I-84)+(S4-1); (I-84)+(S4-2); (I-84)+(S4-3); (I-84)+(S4-4); (I-84)+(S4-5); (I-84)+(S7-1); (I-84)+(S11-1); (I-84)+(S11-2); (I-84)+(S11-3); (I-84)+(S12-1); (I-84)+(S13-1); (I-84)+(S13-2); (I-84)+(S13-3); (I-84)+(S13-4): (I-84)+(S13-5); (I-84)+(S13-6); (I-84)+(S13-7); (I-84)+(S13-8); (I-84)+(S13-9); (I-84)+(S14-1)

(I-85)+(S1-1); (I-85)+(S1-2); (I-85)+(S1-3); (I-85)+(S1-4); (I-85)+(S1-5); (I-85)+(S1-6); (I-85)+(S1-7); (I-85)+(S1-8); (I-85)+(S1-9); (I-85)+(S1-10); (I-85)+(S1-11); (I-85)+(S1-12); (I-85)+(S1-13); (I-85)+(S2-1); (I-85)+(S2-2); (I-85)+(S2-3); (I-85)+(S2-4); (I-85)+(S2-5); (I-85)+(S2-6); (I-85)+(S2-7); (I-85)+(S2-8); (I-85)+(S2-9); (I-85)+(S2-10); (I-85)+(S3-1); (I-85)+(S3-2); (I-85)+(S3-3); (I-85)+(S3-4); (I-85)+(S3-5); (I-85)+(S3-6); (I-85)+(S3-7); (I-85)+(S3-8); (I-85)+(S3-9); (I-85)+(S3-10); (I-85)+(S3-11); (I-85)+(S4-1); (I-85)+(S4-2); (I-85)+(S4-3); (I-85)+(S4-4); (I-85)+(S4-5); (I-85)+(S7-1); (I-85)+(S11-1); (I-85)+(S11-2); (I-85)+(S11-3); (I-85)+(S12-1); (I-85)+(S13-1); (I-85)+(S13-2); (I-85)+(S13-3); (I-85)+(S13-4): (I-85)+(S13-5); (I-85)+(S13-6); (I-85)+(S13-7); (I-85)+(S13-8); (I-85)+(S13-9); (I-85)+(S14-1)

(I-86)+(S1-1); (I-86)+(S1-2); (I-86)+(S1-3); (I-86)+(S1-4); (I-86)+(S1-5); (I-86)+(S1-6); (I-86)+(S1-7); (I-86)+(S1-8); (I-86)+(S1-9); (I-86)+(S1-10); (I-86)+(S1-11); (I-86)+(S1-12); (I-86)+(S1-13); (I-86)+(S2-1); (I-86)+(S2-2); (I-86)+(S2-3); (I-86)+(S2-4); (I-86)+(S2-5); (I-86)+(S2-6); (I-86)+(S2-7); (I-86)+(S2-8); (I-86)+(S2-9); (I-86)+(S2-10); (I-86)+(S3-1); (I-86)+(S3-2); (I-86)+(S3-3); (I-86)+(S3-4); (I-86)+(S3-5); (I-86)+(S3-6); (I-86)+(S3-7); (I-86)+(S3-8); (I-86)+(S3-9); (I-86)+(S3-10); (I-86)+(S3-11); (I-86)+(S4-1); (I-86)+(S4-2); (I-86)+(S4-3); (I-86)+(S4-4); (I-86)+(S4-5); (I-86)+(S7-1); (I-86)+(S11-1); (I-86)+(S11-2); (I-86)+(S11-3); (I-86)+(S12-1); (I-86)+(S13-1); (I-86)+(S13-2); (I-86)+(S13-3); (I-86)+(S13-4): (I-86)+(S13-5); (I-86)+(S13-6); (I-86)+(S13-7); (I-86)+(S13-8); (I-86)+(S13-9); (I-86)+(S14-1)

(I-87)+(S1-1); (I-87)+(S1-2); (I-87)+(S1-3); (I-87)+(S1-4); (I-87)+(S1-5); (I-87)+(S1-6); (I-87)+(S1-7); (I-87)+(S1-8); (I-87)+(S1-9); (I-87)+(S1-10); (I-87)+(S1-11); (I-87)+(S1-12); (I-87)+(S1-13); (I-87)+(S2-1); (I-87)+(S2-2); (I-87)+(S2-3); (I-87)+(S2-4); (I-87)+(S2-5); (I-87)+(S2-6); (I-87)+(S2-7); (I-87)+(S2-8); (I-87)+(S2-9); (I-87)+(S2-10); (I-87)+(S3-1); (I-87)+(S3-2); (I-87)+(S3-3); (I-87)+(S3-4); (I-87)+(S3-5); (I-87)+(S3-6); (I-87)+(S3-7); (I-87)+(S3-8); (I-87)+(S3-9); (I-87)+(S3-10); (I-87)+(S3-11); (I-87)+(S4-1); (I-87)+(S4-2); (I-87)+(S4-3); (I-87)+(S4-4); (I-87)+(S4-5); (I-87)+(S7-1); (I-87)+(S11-1); (I-87)+(S11-2); (I-87)+(S11-3); (I-87)+(S12-1); (I-87)+(S13-1); (I-87)+(S13-2); (I-87)+(S13-3); (I-87)+(S13-4): (I-87)+(S13-5); (I-87)+(S13-6); (I-87)+(S13-7); (I-87)+(S13-8); (I-87)+(S13-9); (I-87)+(S14-1)

(I-88)+(S1-1); (I-88)+(S1-2); (I-88)+(S1-3); (I-88)+(S1-4); (I-88)+(S1-5); (I-88)+(S1-6); (I-88)+(S1-7); (I-88)+(S1-8); (I-88)+(S1-9); (I-88)+(S1-10); (I-88)+(S1-11); (I-88)+(S1-12); (I-88)+(S1-13); (I-88)+(S2-1); (I-88)+(S2-2); (I-88)+(S2-3); (I-88)+(S2-4); (I-88)+(S2-5); (I-88)+(S2-6); (I-88)+(S2-7); (I-88)+(S2-8); (I-88)+(S2-9); (I-88)+(S2-10); (I-88)+(S3-1); (I-88)+(S3-2); (I-88)+(S3-3); (I-88)+(S3-4); (I-88)+(S3-5); (I-88)+(S3-6); (I-88)+(S3-7); (I-88)+(S3-8); (I-88)+(S3-9); (I-88)+(S3-10); (I-88)+(S3-11); (I-88)+(S4-1); (I-88)+(S4-2); (I-88)+(S4-3); (I-88)+(S4-4); (I-88)+(S4-5); (I-88)+(S7-1); (I-88)+(S11-1); (I-88)+(S11-2); (I-88)+(S11-3); (I-88)+(S12-1); (I-88)+(S13-1); (I-88)+(S13-2); (I-88)+(S13-3); (I-88)+(S13-4): (I-88)+(S13-5); (I-88)+(S13-6); (I-88)+(S13-7); (I-88)+(S13-8); (I-88)+(S13-9); (I-88)+(S14-1)

(I-89)+(S1-1); (I-89)+(S1-2); (I-89)+(S1-3); (I-89)+(S1-4); (I-89)+(S1-5); (I-89)+(S1-6); (I-89)+(S1-7); (I-89)+(S1-8); (I-89)+(S1-9); (I-89)+(S1-10); (I-89)+(S1-11); (I-89)+(S1-12); (I-89)+(S1-13); (I-89)+(S2-1); (I-89)+(S2-2); (I-89)+(S2-3); (I-89)+(S2-4); (I-89)+(S2-5); (I-89)+(S2-6); (I-89)+(S2-7); (I-89)+(S2-8); (I-89)+(S2-9); (I-89)+(S2-10); (I-89)+(S3-1); (I-89)+(S3-2); (I-89)+(S3-3); (I-89)+(S3-4); (I-89)+(S3-5); (I-89)+(S3-6); (I-89)+(S3-7); (I-89)+(S3-8); (I-89)+(S3-9); (I-89)+(S3-10); (I-89)+(S3-11); (I-89)+(S4-1); (I-89)+(S4-2); (I-89)+(S4-3); (I-89)+(S4-4); (I-89)+(S4-5); (I-89)+(S7-1); (I-89)+(S11-1); (I-89)+(S11-2); (I-89)+(S11-3); (I-89)+(S12-1); (I-89)+(S13-1); (I-89)+(S13-2); (I-89)+(S13-3); (I-89)+(S13-4): (I-89)+(S13-5); (I-89)+(S13-6); (I-89)+(S13-7); (I-89)+(S13-8); (I-89)+(S13-9); (I-89)+(S14-1)

(I-90)+(S1-1); (I-90)+(S1-2); (I-90)+(S1-3); (I-90)+(S1-4); (I-90)+(S1-5); (I-90)+(S1-6); (I-90)+(S1-7); (I-90)+(S1-8); (I-90)+(S1-9); (I-90)+(S1-10); (I-90)+(S1-11); (I-90)+(S1-12); (I-90)+(S1-13); (I-90)+(S2-1); (I-90)+(S2-2); (I-90)+(S2-3); (I-90)+(S2-4); (I-90)+(S2-5); (I-90)+(S2-6); (I-90)+(S2-7); (I-90)+(S2-8); (I-90)+(S2-9); (I-90)+(S2-10); (I-90)+(S3-1); (I-90)+(S3-2); (I-90)+(S3-3); (I-90)+(S3-4); (I-90)+(S3-5); (I-90)+(S3-6); (I-90)+(S3-7); (I-90)+(S3-8); (I-90)+(S3-9); (I-90)+(S3-10); (I-90)+(S3-11); (I-90)+(S4-1); (I-90)+(S4-2); (I-90)+(S4-3); (I-90)+(S4-4); (I-90)+(S4-5); (I-90)+(S7-1); (I-90)+(S11-1); (I-90)+(S11-2); (I-90)+(S11-3); (I-90)+(S12-1); (I-90)+(S13-1); (I-90)+(S13-2); (I-90)+(S13-3); (I-90)+(S13-4): (I-90)+(S13-5); (I-90)+(S13-6); (I-90)+(S13-7); (I-90)+(S13-8); (I-90)+(S13-9); (I-90)+(S14-1)

(I-91)+(S1-1); (I-91)+(S1-2); (I-91)+(S1-3); (I-91)+(S1-4); (I-91)+(S1-5); (I-91)+(S1-6); (I-91)+(S1-7); (I-91)+(S1-8); (I-91)+(S1-9); (I-91)+(S1-10); (I-91)+(S1-11); (I-91)+(S1-12); (I-91)+(S1-13); (I-91)+(S2-1); (I-91)+(S2-2); (I-91)+(S2-3); (I-91)+(S2-4); (I-91)+(S2-5); (I-91)+(S2-6); (I-91)+(S2-7); (I-91)+(S2-8); (I-91)+(S2-9); (I-91)+(S2-10); (I-91)+(S3-1); (I-91)+(S3-2); (I-91)+(S3-3); (I-91)+(S3-4); (I-91)+(S3-5); (I-91)+(S3-6); (I-91)+(S3-7); (I-91)+(S3-8); (I-91)+(S3-9); (I-91)+(S3-10); (I-91)+(S3-11); (I-91)+(S4-1); (I-91)+(S4-2); (I-91)+(S4-3); (I-91)+(S4-4); (I-91)+(S4-5); (I-91)+(S7-1); (I-91)+(S11-1); (I-91)+(S11-2); (I-91)+(S11-3); (I-91)+(S12-1); (I-91)+(S13-1); (I-91)+(S13-2); (I-91)+(S13-3); (I-91)+(S13-4): (I-91)+(S13-5); (I-91)+(S13-6); (I-91)+(S13-7); (I-91)+(S13-8); (I-91)+(S13-9); (I-91)+(S14-1)

(I-92)+(S1-1); (I-92)+(S1-2); (I-92)+(S1-3); (I-92)+(S1-4); (I-92)+(S1-5); (I-92)+(S1-6); (I-92)+(S1-7); (I-92)+(S1-8); (I-92)+(S1-9); (I-92)+(S1-10); (I-92)+(S1-11); (I-92)+(S1-12); (I-92)+(S1-13); (I-92)+(S2-1); (I-92)+(S2-2); (I-92)+(S2-3); (I-92)+(S2-4); (I-92)+(S2-5); (I-92)+(S2-6); (I-92)+(S2-7); (I-92)+(S2-8); (I-92)+(S2-9); (I-92)+(S2-10); (I-92)+(S3-1); (I-92)+(S3-2); (I-92)+(S3-3); (I-92)+(S3-4); (I-92)+(S3-5); (I-92)+(S3-6); (I-92)+(S3-7); (I-92)+(S3-8); (I-92)+(S3-9); (I-92)+(S3-10); (I-92)+(S3-11); (I-92)+(S4-1); (I-92)+(S4-2); (I-92)+(S4-3); (I-92)+(S4-4); (I-92)+(S4-5); (I-92)+(S7-1); (I-92)+(S11-1); (I-92)+(S11-2); (I-92)+(S11-3); (I-92)+(S12-1); (I-92)+(S13-1); (I-92)+(S13-2); (I-92)+(S13-3); (I-92)+(S13-4): (I-92)+(S13-5); (I-92)+(S13-6); (I-92)+(S13-7); (I-92)+(S13-8); (I-92)+(S13-9); (I-92)+(S14-1)

(I-93)+(S1-1); (I-93)+(S1-2); (I-93)+(S1-3); (I-93)+(S1-4); (I-93)+(S1-5); (I-93)+(S1-6); (I-93)+(S1-7); (I-93)+(S1-8); (I-93)+(S1-9); (I-93)+(S1-10); (I-93)+(S1-11); (I-93)+(S1-

12); (I-93)+(S1-13); (I-93)+(S2-1); (I-93)+(S2-2); (I-93)+(S2-3); (I-93)+(S2-4); (I-93)+(S2-5); (I-93)+(S2-6); (I-93)+(S2-7); (I-93)+(S2-8); (I-93)+(S2-9); (I-93)+(S2-10); (I-93)+(S3-1); (I-93)+(S3-2); (I-93)+(S3-3); (I-93)+(S3-4); (I-93)+(S3-5); (I-93)+(S3-6); (I-93)+(S3-7); (I-93)+(S3-8); (I-93)+(S3-9); (I-93)+(S3-10); (I-93)+(S3-11); (I-93)+(S4-1); (I-93)+(S4-2); (I-93)+(S4-3); (I-93)+(S4-4); (I-93)+(S4-5); (I-93)+(S7-1); (I-93)+(S11-1); (I-93)+(S11-2); (I-93)+(S11-3); (I-93)+(S12-1); (I-93)+(S13-1); (I-93)+(S13-2); (I-93)+(S13-3); (I-93)+(S13-4): (I-93)+(S13-5); (I-93)+(S13-6); (I-93)+(S13-7); (I-93)+(S13-8); (I-93)+(S13-9); (I-93)+(S14-1)

(I-94)+(S1-1); (I-94)+(S1-2); (I-94)+(S1-3); (I-94)+(S1-4); (I-94)+(S1-5); (I-94)+(S1-6); (I-94)+(S1-7); (I-94)+(S1-8); (I-94)+(S1-9); (I-94)+(S1-10); (I-94)+(S1-11); (I-94)+(S1-12); (I-94)+(S1-13); (I-94)+(S2-1); (I-94)+(S2-2); (I-94)+(S2-3); (I-94)+(S2-4); (I-94)+(S2-5); (I-94)+(S2-6); (I-94)+(S2-7); (I-94)+(S2-8); (I-94)+(S2-9); (I-94)+(S2-10); (I-94)+(S3-1); (I-94)+(S3-2); (I-94)+(S3-3); (I-94)+(S3-4); (I-94)+(S3-5); (I-94)+(S3-6); (I-94)+(S3-7); (I-94)+(S3-8); (I-94)+(S3-9); (I-94)+(S3-10); (I-94)+(S3-11); (I-94)+(S4-1); (I-94)+(S4-2); (I-94)+(S4-3); (I-94)+(S4-4); (I-94)+(S4-5); (I-94)+(S7-1); (I-94)+(S11-1); (I-94)+(S11-2); (I-94)+(S11-3); (I-94)+(S12-1); (I-94)+(S13-1); (I-94)+(S13-2); (I-94)+(S13-3); (I-94)+(S13-4): (I-94)+(S13-5); (I-94)+(S13-6); (I-94)+(S13-7); (I-94)+(S13-8); (I-94)+(S13-9); (I-94)+(S14-1)

(I-95)+(S1-1); (I-95)+(S1-2); (I-95)+(S1-3); (I-95)+(S1-4); (I-95)+(S1-5); (I-95)+(S1-6); (I-95)+(S1-7); (I-95)+(S1-8); (I-95)+(S1-9); (I-95)+(S1-10); (I-95)+(S1-11); (I-95)+(S1-12); (I-95)+(S1-13); (I-95)+(S2-1); (I-95)+(S2-2); (I-95)+(S2-3); (I-95)+(S2-4); (I-95)+(S2-5); (I-95)+(S2-6); (I-95)+(S2-7); (I-95)+(S2-8); (I-95)+(S2-9); (I-95)+(S2-10); (I-95)+(S3-1); (I-95)+(S3-2); (I-95)+(S3-3); (I-95)+(S3-4); (I-95)+(S3-5); (I-95)+(S3-6); (I-95)+(S3-7); (I-95)+(S3-8); (I-95)+(S3-9); (I-95)+(S3-10); (I-95)+(S3-11); (I-95)+(S4-1); (I-95)+(S4-2); (I-95)+(S4-3); (I-95)+(S4-4); (I-95)+(S4-5); (I-95)+(S7-1); (I-95)+(S11-1); (I-95)+(S11-2); (I-95)+(S11-3); (I-95)+(S12-1); (I-95)+(S13-1); (I-95)+(S13-2); (I-95)+(S13-3); (I-95)+(S13-4): (I-95)+(S13-5); (I-95)+(S13-6); (I-95)+(S13-7); (I-95)+(S13-8); (I-95)+(S13-9); (I-95)+(S14-1)

(I-96)+(S1-1); (I-96)+(S1-2); (I-96)+(S1-3); (I-96)+(S1-4); (I-96)+(S1-5); (I-96)+(S1-6); (I-96)+(S1-7); (I-96)+(S1-8); (I-96)+(S1-9); (I-96)+(S1-10); (I-96)+(S1-11); (I-96)+(S1-12); (I-96)+(S1-13); (I-96)+(S2-1); (I-96)+(S2-2); (I-96)+(S2-3); (I-96)+(S2-4); (I-96)+(S2-5); (I-96)+(S2-6); (I-96)+(S2-7); (I-96)+(S2-8); (I-96)+(S2-9); (I-96)+(S2-10); (I-96)+(S3-1); (I-96)+(S3-2); (I-96)+(S3-3); (I-96)+(S3-4); (I-96)+(S3-5); (I-96)+(S3-6); (I-96)+(S3-7); (I-96)+(S3-8); (I-96)+(S3-9); (I-96)+(S3-10); (I-96)+(S3-11); (I-96)+(S4-1); (I-96)+(S4-2); (I-96)+(S4-3); (I-96)+(S4-4); (I-96)+(S4-5); (I-96)+(S7-1); (I-96)+(S11-1); (I-96)+(S11-2); (I-96)+(S11-3); (I-96)+(S12-1); (I-96)+(S13-1); (I-96)+(S13-2); (I-96)+(S13-3); (I-96)+(S13-4): (I-96)+(S13-5); (I-96)+(S13-6); (I-96)+(S13-7); (I-96)+(S13-8); (I-96)+(S13-9); (I-96)+(S14-1)

(I-97)+(S1-1); (I-97)+(S1-2); (I-97)+(S1-3); (I-97)+(S1-4); (I-97)+(S1-5); (I-97)+(S1-6); (I-97)+(S1-7); (I-97)+(S1-8); (I-97)+(S1-9); (I-97)+(S1-10); (I-97)+(S1-11); (I-97)+(S1-12); (I-97)+(S1-13); (I-97)+(S2-1); (I-97)+(S2-2); (I-97)+(S2-3); (I-97)+(S2-4); (I-97)+(S2-5); (I-97)+(S2-6); (I-97)+(S2-7); (I-97)+(S2-8); (I-97)+(S2-9); (I-97)+(S2-10); (I-97)+(S3-1); (I-97)+(S3-2); (I-97)+(S3-3); (I-97)+(S3-4); (I-97)+(S3-5); (I-97)+(S3-6); (I-97)+(S3-7); (I-97)+(S3-8); (I-97)+(S3-9); (I-97)+(S3-10); (I-97)+(S3-11); (I-97)+(S4-1); (I-97)+(S4-2); (I-97)+(S4-3); (I-97)+(S4-4); (I-97)+(S4-5); (I-97)+(S7-1); (I-97)+(S11-1); (I-97)+(S11-2); (I-97)+(S11-3); (I-97)+(S12-1); (I-97)+(S13-1); (I-97)+(S13-2); (I-97)+(S13-3); (I-97)+(S13-4): (I-97)+(S13-5); (I-97)+(S13-6); (I-97)+(S13-7); (I-97)+(S13-8); (I-97)+(S13-9); (I-97)+(S14-1)

(I-98)+(S1-1); (I-98)+(S1-2); (I-98)+(S1-3); (I-98)+(S1-4); (I-98)+(S1-5); (I-98)+(S1-6); (I-98)+(S1-7); (I-98)+(S1-8); (I-98)+(S1-9); (I-98)+(S1-10); (I-98)+(S1-11); (I-98)+(S1-12); (I-98)+(S1-13); (I-98)+(S2-1); (I-98)+(S2-2); (I-98)+(S2-3); (I-98)+(S2-4); (I-98)+(S2-5); (I-98)+(S2-6); (I-98)+(S2-7); (I-98)+(S2-8); (I-98)+(S2-9); (I-98)+(S2-10); (I-98)+(S3-1); (I-98)+(S3-2); (I-98)+(S3-3); (I-98)+(S3-4); (I-98)+(S3-5); (I-98)+(S3-6); (I-98)+(S3-7); (I-98)+(S3-8); (I-98)+(S3-9); (I-98)+(S3-10); (I-98)+(S3-11); (I-98)+(S4-1); (I-98)+(S4-2); (I-98)+(S4-3); (I-98)+(S4-4); (I-98)+(S4-5); (I-98)+(S7-1); (I-98)+(S11-1); (I-98)+(S11-2); (I-98)+(S11-3); (I-98)+(S12-1); (I-98)+(S13-1); (I-98)+(S13-2); (I-98)+(S13-3); (I-98)+(S13-4): (I-98)+(S13-5); (I-98)+(S13-6); (I-98)+(S13-7); (I-98)+(S13-8); (I-98)+(S13-9); (I-98)+(S14-1)

(I-99)+(S1-1); (I-99)+(S1-2); (I-99)+(S1-3); (I-99)+(S1-4); (I-99)+(S1-5); (I-99)+(S1-6); (I-99)+(S1-7); (I-99)+(S1-8); (I-99)+(S1-9); (I-99)+(S1-10); (I-99)+(S1-11); (I-99)+(S1-12); (I-99)+(S1-13); (I-99)+(S2-1); (I-99)+(S2-2); (I-99)+(S2-3); (I-99)+(S2-4); (I-99)+(S2-5); (I-99)+(S2-6); (I-99)+(S2-7); (I-99)+(S2-8); (I-99)+(S2-9); (I-99)+(S2-10); (I-99)+(S3-1); (I-99)+(S3-2); (I-99)+(S3-3); (I-99)+(S3-4); (I-99)+(S3-5); (I-99)+(S3-6); (I-99)+(S3-7); (I-99)+(S3-8); (I-99)+(S3-9); (I-99)+(S3-10); (I-99)+(S3-11); (I-99)+(S4-1); (I-99)+(S4-2); (I-99)+(S4-3); (I-99)+(S4-4); (I-99)+(S4-5); (I-99)+(S7-1); (I-99)+(S11-1); (I-99)+(S11-2); (I-99)+(S11-3); (I-99)+(S12-1); (I-99)+(S13-1); (I-99)+(S13-2); (I-99)+(S13-3); (I-99)+(S13-4): (I-99)+(S13-5); (I-99)+(S13-6); (I-99)+(S13-7); (I-99)+(S13-8); (I-99)+(S13-9); (I-99)+(S14-1)

(I-100)+(S1-1); (I-100)+(S1-2); (I-100)+(S1-3); (I-100)+(S1-4); (I-100)+(S1-5); (I-100)+(S1-6); (I-100)+(S1-7); (I-100)+(S1-8); (I-100)+(S1-9); (I-100)+(S1-10); (I-100)+(S1-11); (I-100)+(S1-12); (I-100)+(S1-13); (I-100)+(S2-1); (I-100)+(S2-2); (I-100)+(S2-3); (I-100)+(S2-4); (I-100)+(S2-5); (I-100)+(S2-6); (I-100)+(S2-7); (I-100)+(S2-8); (I-100)+(S2-9); (I-100)+(S2-10); (I-100)+(S3-1); (I-100)+(S3-2); (I-100)+(S3-3); (I-100)+(S3-4); (I-100)+(S3-5); (I-100)+(S3-6); (I-100)+(S3-7); (I-100)+(S3-8); (I-100)+(S3-9); (I-100)+(S3-10); (I-100)+(S3-11); (I-100)+(S4-1); (I-100)+(S4-2); (I-100)+(S4-3); (I-100)+(S4-4); (I-100)+(S4-5); (I-100)+(S7-1); (I-100)+(S11-1); (I-100)+(S11-2); (I-100)+(S11-3); (I-100)+(S12-1); (I-100)+(S13-1); (I-100)+(S13-2); (I-100)+(S13-3); (I-100)+(S13-4): (I-100)+(S13-5); (I-100)+(S13-6); (I-100)+(S13-7); (I-100)+(S13-8); (I-100)+(S13-9); (I-100)+(S14-1)

(I-101)+(S1-1); (I-101)+(S1-2); (I-101)+(S1-3); (I-101)+(S1-4); (I-101)+(S1-5); (I-101)+(S1-6); (I-101)+(S1-7); (I-101)+(S1-8); (I-101)+(S1-9); (I-101)+(S1-10); (I-101)+(S1-11); (I-101)+(S1-12); (I-101)+(S1-13); (I-101)+(S2-1); (I-101)+(S2-2); (I-101)+(S2-3); (I-101)+(S2-4); (I-101)+(S2-5); (I-101)+(S2-6); (I-101)+(S2-7); (I-101)+(S2-8); (I-101)+(S2-9); (I-101)+(S2-10); (I-101)+(S3-1); (I-101)+(S3-2); (I-101)+(S3-3); (I-101)+(S3-4); (I-101)+(S3-5); (I-101)+(S3-6); (I-101)+(S3-7); (I-101)+(S3-8); (I-101)+(S3-9); (I-101)+(S3-10); (I-101)+(S3-11); (I-101)+(S4-1); (I-101)+(S4-2); (I-101)+(S4-3); (I-101)+(S4-4); (I-101)+(S4-5); (I-101)+(S7-1); (I-101)+(S11-1); (I-101)+(S11-2); (I-101)+(S11-3); (I-101)+(S12-1); (I-101)+(S13-1); (I-101)+(S13-2); (I-101)+(S13-3); (I-101)+(S13-4): (I-101)+(S13-5); (I-101)+(S13-6); (I-101)+(S13-7); (I-101)+(S13-8); (I-101)+(S13-9); (I-101)+(S14-1)

(I-102)+(S1-1); (I-102)+(S1-2); (I-102)+(S1-3); (I-102)+(S1-4); (I-102)+(S1-5); (I-102)+(S1-6); (I-102)+(S1-7); (I-102)+(S1-8); (I-102)+(S1-9); (I-102)+(S1-10); (I-102)+(S1-11); (I-102)+(S1-12); (I-102)+(S1-13); (I-102)+(S2-1); (I-102)+(S2-2); (I-102)+(S2-3); (I-102)+(S2-4); (I-102)+(S2-5); (I-102)+(S2-6); (I-102)+(S2-7); (I-102)+(S2-8); (I-102)+(S2-9); (I-102)+(S2-10); (I-102)+(S3-1); (I-102)+(S3-2); (I-102)+(S3-3); (I-102)+(S3-4); (I-102)+(S3-5); (I-102)+(S3-6); (I-102)+(S3-7); (I-102)+(S3-8); (I-102)+(S3-9); (I-102)+(S3-10); (I-102)+(S3-11); (I-102)+(S4-1); (I-102)+(S4-2); (I-102)+(S4-3); (I-102)+(S4-4); (I-102)+(S4-5); (I-102)+(S7-1); (I-102)+(S11-1); (I-102)+(S11-2); (I-102)+(S11-3); (I-102)+(S12-1); (I-102)+(S13-1); (I-102)+(S13-2); (I-102)+(S13-3); (I-102)+(S13-4): (I-102)+(S13-5); (I-102)+(S13-6); (I-102)+(S13-7); (I-102)+(S13-8); (I-102)+(S13-9); (I-102)+(S14-1)

(I-103)+(S1-1); (I-103)+(S1-2); (I-103)+(S1-3); (I-103)+(S1-4); (I-103)+(S1-5); (I-103)+(S1-6); (I-103)+(S1-7); (I-103)+(S1-8); (I-103)+(S1-9); (I-103)+(S1-10); (I-103)+(S1-11); (I-103)+(S1-12); (I-103)+(S1-13); (I-103)+(S2-1); (I-103)+(S2-2); (I-103)+(S2-3); (I-103)+(S2-4); (I-103)+(S2-5); (I-103)+(S2-6); (I-103)+(S2-7); (I-103)+(S2-8); (I-103)+(S2-9); (I-103)+(S2-10); (I-103)+(S3-1); (I-103)+(S3-2); (I-103)+(S3-3); (I-103)+(S3-4); (I-103)+(S3-5); (I-103)+(S3-6); (I-103)+(S3-7); (I-103)+(S3-8); (I-103)+(S3-9); (I-103)+(S3-10); (I-103)+(S3-11); (I-103)+(S4-1); (I-103)+(S4-2); (I-103)+(S4-3); (I-103)+(S4-4); (I-103)+(S4-5); (I-103)+(S7-1); (I-103)+(S11-1); (I-103)+(S11-2); (I-103)+(S11-3); (I-103)+(S12-1); (I-103)+(S13-1); (I-103)+(S13-2); (I-103)+(S13-3); (I-103)+(S13-4): (I-103)+(S13-5); (I-103)+(S13-6); (I-103)+(S13-7); (I-103)+(S13-8); (I-103)+(S13-9); (I-103)+(S14-1)

(I-104)+(S1-1); (I-104)+(S1-2); (I-104)+(S1-3); (I-104)+(S1-4); (I-104)+(S1-5); (I-104)+(S1-6); (I-104)+(S1-7); (I-104)+(S1-8); (I-104)+(S1-9); (I-104)+(S1-10); (I-104)+(S1-11); (I-104)+(S1-12); (I-104)+(S1-13); (I-104)+(S2-1); (I-104)+(S2-2); (I-104)+(S2-3); (I-104)+(S2-4); (I-104)+(S2-5); (I-104)+(S2-6); (I-104)+(S2-7); (I-104)+(S2-8); (I-104)+(S2-9); (I-104)+(S2-10); (I-104)+(S3-1); (I-104)+(S3-2); (I-104)+(S3-3); (I-104)+(S3-4); (I-104)+(S3-5); (I-104)+(S3-6); (I-104)+(S3-7); (I-104)+(S3-8); (I-104)+(S3-9); (I-104)+(S3-10); (I-104)+(S3-11); (I-104)+(S4-1); (I-104)+(S4-2); (I-104)+(S4-3); (I-104)+(S4-4); (I-104)+(S4-5); (I-104)+(S7-1); (I-104)+(S11-1); (I-104)+(S11-2); (I-104)+(S11-3); (I-104)+(S12-1); (I-104)+(S13-1); (I-104)+(S13-2); (I-104)+(S13-3); (I-104)+(S13-4): (I-104)+(S13-5); (I-104)+(S13-6); (I-104)+(S13-7); (I-104)+(S13-8); (I-104)+(S13-9); (I-104)+(S14-1)

(I-105)+(S1-1); (I-105)+(S1-2); (I-105)+(S1-3); (I-105)+(S1-4); (I-105)+(S1-5); (I-105)+(S1-6); (I-105)+(S1-7); (I-105)+(S1-8); (I-105)+(S1-9); (I-105)+(S1-10); (I-105)+(S1-11); (I-105)+(S1-12); (I-105)+(S1-13); (I-105)+(S2-1); (I-105)+(S2-2); (I-105)+(S2-3); (I-105)+(S2-4); (I-105)+(S2-5); (I-105)+(S2-6); (I-105)+(S2-7); (I-105)+(S2-8); (I-105)+(S2-9); (I-105)+(S2-10); (I-105)+(S3-1); (I-105)+(S3-2); (I-105)+(S3-3); (I-105)+(S3-4); (I-105)+(S3-5); (I-105)+(S3-6); (I-105)+(S3-7); (I-105)+(S3-8); (I-105)+(S3-9); (I-105)+(S3-10); (I-105)+(S3-11); (I-105)+(S4-1); (I-105)+(S4-2); (I-105)+(S4-3); (I-105)+(S4-4); (I-105)+(S4-5); (I-105)+(S7-1); (I-105)+(S11-1); (I-105)+(S11-2); (I-105)+(S11-3); (I-105)+(S12-1); (I-105)+(S13-1); (I-105)+(S13-2); (I-105)+(S13-3); (I-105)+(S13-4): (I-105)+(S13-5); (I-105)+(S13-6); (I-105)+(S13-7); (I-105)+(S13-8); (I-105)+(S13-9); (I-105)+(S14-1)

(I-106)+(S1-1); (I-106)+(S1-2); (I-106)+(S1-3); (I-106)+(S1-4); (I-106)+(S1-5); (I-106)+(S1-6); (I-106)+(S1-7); (I-106)+(S1-8); (I-106)+(S1-9); (I-106)+(S1-10); (I-106)+(S1-11); (I-106)+(S1-12); (I-106)+(S1-13); (I-106)+(S2-1); (I-106)+(S2-2); (I-106)+(S2-3); (I-106)+(S2-4); (I-106)+(S2-5); (I-106)+(S2-6); (I-106)+(S2-7); (I-106)+(S2-8); (I-106)+(S2-9); (I-106)+(S2-10); (I-106)+(S3-1); (I-106)+(S3-2); (I-106)+(S3-3); (I-106)+(S3-4); (I-106)+(S3-5); (I-106)+(S3-6); (I-106)+(S3-7); (I-106)+(S3-8); (I-106)+(S3-9); (I-106)+(S3-10); (I-106)+(S3-11); (I-106)+(S4-1); (I-106)+(S4-2); (I-106)+(S4-3); (I-106)+(S4-4); (I-106)+(S4-5); (I-106)+(S7-1); (I-106)+(S11-1); (I-106)+(S11-2); (I-106)+(S11-3); (I-106)+(S12-1); (I-106)+(S13-1); (I-106)+(S13-2); (I-106)+(S13-3); (I-106)+(S13-4): (I-106)+(S13-5); (I-106)+(S13-6); (I-106)+(S13-7); (I-106)+(S13-8); (I-106)+(S13-9); (I-106)+(S14-1)

(I-107)+(S1-1); (I-107)+(S1-2); (I-107)+(S1-3); (I-107)+(S1-4); (I-107)+(S1-5); (I-107)+(S1-6); (I-107)+(S1-7); (I-107)+(S1-8); (I-107)+(S1-9); (I-107)+(S1-10); (I-107)+(S1-11); (I-107)+(S1-12); (I-107)+(S1-13); (I-107)+(S2-1); (I-107)+(S2-2); (I-107)+(S2-3); (I-107)+(S2-4); (I-107)+(S2-5); (I-107)+(S2-6); (I-107)+(S2-7); (I-107)+(S2-8); (I-107)+(S2-9); (I-107)+(S2-10); (I-107)+(S3-1); (I-107)+(S3-2); (I-107)+(S3-3); (I-107)+(S3-4); (I-107)+(S3-5); (I-107)+(S3-6); (I-107)+(S3-7); (I-107)+(S3-8); (I-107)+(S3-9); (I-107)+(S3-10); (I-107)+(S3-11); (I-107)+(S4-1); (I-107)+(S4-2); (I-107)+(S4-3); (I-107)+(S4-4); (I-107)+(S4-5); (I-107)+(S7-1); (I-107)+(S11-1); (I-107)+(S11-2); (I-107)+(S11-3); (I-107)+(S12-1); (I-107)+(S13-1); (I-107)+(S13-2); (I-107)+(S13-3); (I-107)+(S13-4): (I-107)+(S13-5); (I-107)+(S13-6); (I-107)+(S13-7); (I-107)+(S13-8); (I-107)+(S13-9); (I-107)+(S14-1)

(I-108)+(S1-1); (I-108)+(S1-2); (I-108)+(S1-3); (I-108)+(S1-4); (I-108)+(S1-5); (I-108)+(S1-6); (I-108)+(S1-7); (I-108)+(S1-8); (I-108)+(S1-9); (I-108)+(S1-10); (I-108)+(S1-11); (I-108)+(S1-12); (I-108)+(S1-13); (I-108)+(S2-1); (I-108)+(S2-2); (I-108)+(S2-3); (I-108)+(S2-4); (I-108)+(S2-5); (I-108)+(S2-6); (I-108)+(S2-7); (I-108)+(S2-8); (I-108)+(S2-9); (I-108)+(S2-10); (I-108)+(S3-1); (I-108)+(S3-2); (I-108)+(S3-3); (I-108)+(S3-4); (I-108)+(S3-5); (I-108)+(S3-6); (I-108)+(S3-7); (I-108)+(S3-8); (I-108)+(S3-9); (I-108)+(S3-10); (I-108)+(S3-11); (I-108)+(S4-1); (I-108)+(S4-2); (I-108)+(S4-3); (I-108)+(S4-4); (I-108)+(S4-5); (I-108)+(S7-1); (I-108)+(S11-1); (I-108)+(S11-2); (I-108)+(S11-3); (I-108)+(S12-1); (I-108)+(S13-1); (I-108)+(S13-2); (I-108)+(S13-3); (I-108)+(S13-4): (I-108)+(S13-5); (I-108)+(S13-6); (I-108)+(S13-7); (I-108)+(S13-8); (I-108)+(S13-9); (I-108)+(S14-1)

(I-109)+(S1-1); (I-109)+(S1-2); (I-109)+(S1-3); (I-109)+(S1-4); (I-109)+(S1-5); (I-109)+(S1-6); (I-109)+(S1-7); (I-109)+(S1-8); (I-109)+(S1-9); (I-109)+(S1-10); (I-109)+(S1-11); (I-109)+(S1-12); (I-109)+(S1-13); (I-109)+(S2-1); (I-109)+(S2-2); (I-109)+(S2-3); (I-109)+(S2-4); (I-109)+(S2-5); (I-109)+(S2-6); (I-109)+(S2-7); (I-109)+(S2-8); (I-109)+(S2-9); (I-109)+(S2-10); (I-109)+(S3-1); (I-109)+(S3-2); (I-109)+(S3-3); (I-109)+(S3-4); (I-109)+(S3-5); (I-109)+(S3-6); (I-109)+(S3-7); (I-109)+(S3-8); (I-109)+(S3-9); (I-109)+(S3-10); (I-109)+(S3-11); (I-109)+(S4-1); (I-109)+(S4-2); (I-109)+(S4-3); (I-109)+(S4-4); (I-109)+(S4-5); (I-109)+(S7-1); (I-109)+(S11-1); (I-109)+(S11-2); (I-109)+(S11-3); (I-109)+(S12-1); (I-109)+(S13-1); (I-109)+(S13-2); (I-109)+(S13-3); (I-109)+(S13-4): (I-109)+(S13-5); (I-109)+(S13-6); (I-109)+(S13-7); (I-109)+(S13-8); (I-109)+(S13-9); (I-109)+(S14-1)

(I-110)+(S1-1); (I-110)+(S1-2); (I-110)+(S1-3); (I-110)+(S1-4); (I-110)+(S1-5); (I-110)+(S1-6); (I-110)+(S1-7); (I-110)+(S1-8); (I-110)+(S1-9); (I-110)+(S1-10); (I-110)+(S1-11); (I-110)+(S1-12); (I-110)+(S1-13); (I-110)+(S2-1); (I-110)+(S2-2); (I-110)+(S2-3); (I-110)+(S2-4); (I-110)+(S2-5); (I-110)+(S2-6); (I-110)+(S2-7); (I-110)+(S2-8);

(I-110)+(S2-9); (I-110)+(S2-10); (I-110)+(S3-1); (I-110)+(S3-2); (I-110)+(S3-3); (I-110)+(S3-4); (I-110)+(S3-5); (I-110)+(S3-6); (I-110)+(S3-7); (I-110)+(S3-8); (I-110)+(S3-9); (I-110)+(S3-10); (I-110)+(S3-11); (I-110)+(S4-1); (I-110)+(S4-2); (I-110)+(S4-3); (I-110)+(S4-4); (I-110)+(S4-5); (I-110)+(S7-1); (I-110)+(S11-1); (I-110)+(S11-2); (I-110)+(S11-3); (I-110)+(S12-1); (I-110)+(S13-1); (I-110)+(S13-2); (I-110)+(S13-3); (I-110)+(S13-4): (I-110)+(S13-5); (I-110)+(S13-6); (I-110)+(S13-7); (I-110)+(S13-8); (I-110)+(S13-9); (I-110)+(S14-1)

(I-111)+(S1-1); (I-111)+(S1-2); (I-111)+(S1-3); (I-111)+(S1-4); (I-111)+(S1-5); (I-111)+(S1-6); (I-111)+(S1-7); (I-111)+(S1-8); (I-111)+(S1-9); (I-111)+(S1-10); (I-111)+(S1-11); (I-111)+(S1-12); (I-111)+(S1-13); (I-111)+(S2-1); (I-111)+(S2-2); (I-111)+(S2-3); (I-111)+(S2-4); (I-111)+(S2-5); (I-111)+(S2-6); (I-111)+(S2-7); (I-111)+(S2-8); (I-111)+(S2-9); (I-111)+(S2-10); (I-111)+(S3-1); (I-111)+(S3-2); (I-111)+(S3-3); (I-111)+(S3-4); (I-111)+(S3-5); (I-111)+(S3-6); (I-111)+(S3-7); (I-111)+(S3-8); (I-111)+(S3-9); (I-111)+(S3-10); (I-111)+(S3-11); (I-111)+(S4-1); (I-111)+(S4-2); (I-111)+(S4-3); (I-111)+(S4-4); (I-111)+(S4-5); (I-111)+(S7-1); (I-111)+(S11-1); (I-111)+(S11-2); (I-111)+(S11-3); (I-111)+(S12-1); (I-111)+(S13-1); (I-111)+(S13-2); (I-111)+(S13-3); (I-111)+(S13-4): (I-111)+(S13-5); (I-111)+(S13-6); (I-111)+(S13-7); (I-111)+(S13-8); (I-111)+(S13-9); (I-111)+(S14-1)

(I-112)+(S1-1); (I-112)+(S1-2); (I-112)+(S1-3); (I-112)+(S1-4); (I-112)+(S1-5); (I-112)+(S1-6); (I-112)+(S1-7); (I-112)+(S1-8); (I-112)+(S1-9); (I-112)+(S1-10); (I-112)+(S1-11); (I-112)+(S1-12); (I-112)+(S1-13); (I-112)+(S2-1); (I-112)+(S2-2); (I-112)+(S2-3); (I-112)+(S2-4); (I-112)+(S2-5); (I-112)+(S2-6); (I-112)+(S2-7); (I-112)+(S2-8); (I-112)+(S2-9); (I-112)+(S2-10); (I-112)+(S3-1); (I-112)+(S3-2); (I-112)+(S3-3); (I-112)+(S3-4); (I-112)+(S3-5); (I-112)+(S3-6); (I-112)+(S3-7); (I-112)+(S3-8); (I-112)+(S3-9); (I-112)+(S3-10); (I-112)+(S3-11); (I-112)+(S4-1); (I-112)+(S4-2); (I-112)+(S4-3); (I-112)+(S4-4); (I-112)+(S4-5); (I-112)+(S7-1); (I-112)+(S11-1); (I-112)+(S11-2); (I-112)+(S11-3); (I-112)+(S12-1); (I-112)+(S13-1); (I-112)+(S13-2); (I-112)+(S13-3); (I-112)+(S13-4): (I-112)+(S13-5); (I-112)+(S13-6); (I-112)+(S13-7); (I-112)+(S13-8); (I-112)+(S13-9); (I-112)+(S14-1)

(I-113)+(S1-1); (I-113)+(S1-2); (I-113)+(S1-3); (I-113)+(S1-4); (I-113)+(S1-5); (I-113)+(S1-6); (I-113)+(S1-7); (I-113)+(S1-8); (I-113)+(S1-9); (I-113)+(S1-10); (I-113)+(S1-11); (I-113)+(S1-12); (I-113)+(S1-13); (I-113)+(S2-1); (I-113)+(S2-2); (I-113)+(S2-3); (I-113)+(S2-4); (I-113)+(S2-5); (I-113)+(S2-6); (I-113)+(S2-7); (I-113)+(S2-8); (I-113)+(S2-9); (I-113)+(S2-10); (I-113)+(S3-1); (I-113)+(S3-2); (I-113)+(S3-3); (I-113)+(S3-4); (I-113)+(S3-5); (I-113)+(S3-6); (I-113)+(S3-7); (I-113)+(S3-8); (I-113)+(S3-9); (I-113)+(S3-10); (I-113)+(S3-11); (I-113)+(S4-1); (I-113)+(S4-2); (I-113)+(S4-3); (I-113)+(S4-4); (I-113)+(S4-5); (I-113)+(S7-1); (I-113)+(S11-1); (I-113)+(S11-2); (I-113)+(S11-3); (I-113)+(S12-1); (I-113)+(S13-1); (I-113)+(S13-2); (I-113)+(S13-3); (I-113)+(S13-4): (I-113)+(S13-5); (I-113)+(S13-6); (I-113)+(S13-7); (I-113)+(S13-8); (I-113)+(S13-9); (I-113)+(S14-1)

(I-114)+(S1-1); (I-114)+(S1-2); (I-114)+(S1-3); (I-114)+(S1-4); (I-114)+(S1-5); (I-114)+(S1-6); (I-114)+(S1-7); (I-114)+(S1-8); (I-114)+(S1-9); (I-114)+(S1-10); (I-114)+(S1-11); (I-114)+(S1-12); (I-114)+(S1-13); (I-114)+(S2-1); (I-114)+(S2-2); (I-114)+(S2-3); (I-114)+(S2-4); (I-114)+(S2-5); (I-114)+(S2-6); (I-114)+(S2-7); (I-114)+(S2-8); (I-114)+(S2-9); (I-114)+(S2-10); (I-114)+(S3-1); (I-114)+(S3-2); (I-114)+(S3-3); (I-114)+(S3-4); (I-114)+(S3-5); (I-114)+(S3-6); (I-114)+(S3-7); (I-114)+(S3-8); (I-114)+(S3-9); (I-114)+(S3-10); (I-114)+(S3-11); (I-114)+(S4-1); (I-114)+(S4-2); (I-114)+(S4-3); (I-114)+(S4-4); (I-114)+(S4-5); (I-114)+(S7-1); (I-114)+(S11-1); (I-114)+(S11-2); (I-114)+(S11-3); (I-114)+(S12-1); (I-114)+(S13-1); (I-114)+(S13-2); (I-114)+(S13-3); (I-114)+(S13-4): (I-114)+(S13-5); (I-114)+(S13-6); (I-114)+(S13-7); (I-114)+(S13-8); (I-114)+(S13-9); (I-114)+(S14-1)

(I-115)+(S1-1); (I-115)+(S1-2); (I-115)+(S1-3); (I-115)+(S1-4); (I-115)+(S1-5); (I-115)+(S1-6); (I-115)+(S1-7); (I-115)+(S1-8); (I-115)+(S1-9); (I-115)+(S1-10); (I-115)+(S1-11); (I-115)+(S1-12); (I-115)+(S1-13); (I-115)+(S2-1); (I-115)+(S2-2); (I-115)+(S2-3); (I-115)+(S2-4); (I-115)+(S2-5); (I-115)+(S2-6); (I-115)+(S2-7); (I-115)+(S2-8); (I-115)+(S2-9); (I-115)+(S2-10); (I-115)+(S3-1); (I-115)+(S3-2); (I-115)+(S3-3); (I-115)+(S3-4); (I-115)+(S3-5); (I-115)+(S3-6); (I-115)+(S3-7); (I-115)+(S3-8); (I-115)+(S3-9); (I-115)+(S3-10); (I-115)+(S3-11); (I-115)+(S4-1); (I-115)+(S4-2); (I-115)+(S4-3); (I-115)+(S4-4); (I-115)+(S4-5); (I-115)+(S7-1); (I-115)+(S11-1); (I-115)+(S11-2); (I-115)+(S11-3); (I-115)+(S12-1); (I-115)+(S13-1); (I-115)+(S13-2); (I-115)+(S13-3); (I-115)+(S13-4): (I-115)+(S13-5); (I-115)+(S13-6); (I-115)+(S13-7); (I-115)+(S13-8); (I-115)+(S13-9); (I-115)+(S14-1)

(I-116)+(S1-1); (I-116)+(S1-2); (I-116)+(S1-3); (I-116)+(S1-4); (I-116)+(S1-5); (I-116)+(S1-6); (I-116)+(S1-7); (I-116)+(S1-8); (I-116)+(S1-9); (I-116)+(S1-10); (I-116)+(S1-11); (I-116)+(S1-12); (I-116)+(S1-13); (I-116)+(S2-1); (I-116)+(S2-2); (I-116)+(S2-3); (I-116)+(S2-4); (I-116)+(S2-5); (I-116)+(S2-6); (I-116)+(S2-7); (I-116)+(S2-8); (I-116)+(S2-9); (I-116)+(S2-10); (I-116)+(S3-1); (I-116)+(S3-2); (I-116)+(S3-3); (I-116)+(S3-4); (I-116)+(S3-5); (I-116)+(S3-6); (I-116)+(S3-7); (I-116)+(S3-8); (I-116)+(S3-9); (I-116)+(S3-10); (I-116)+(S3-11); (I-116)+(S4-1); (I-116)+(S4-2); (I-116)+(S4-3); (I-116)+(S4-4); (I-116)+(S4-5); (I-116)+(S7-1); (I-116)+(S11-1); (I-116)+(S11-2); (I-116)+(S11-3); (I-116)+(S12-1); (I-116)+(S13-1); (I-116)+(S13-2); (I-116)+(S13-3); (I-116)+(S13-4): (I-116)+(S13-5); (I-116)+(S13-6); (I-116)+(S13-7); (I-116)+(S13-8); (I-116)+(S13-9); (I-116)+(S14-1)

(I-117)+(S1-1); (I-117)+(S1-2); (I-117)+(S1-3); (I-117)+(S1-4); (I-117)+(S1-5); (I-117)+(S1-6); (I-117)+(S1-7); (I-117)+(S1-8); (I-117)+(S1-9); (I-117)+(S1-10); (I-117)+(S1-11); (I-117)+(S1-12); (I-117)+(S1-13); (I-117)+(S2-1); (I-117)+(S2-2); (I-117)+(S2-3); (I-117)+(S2-4); (I-117)+(S2-5); (I-117)+(S2-6); (I-117)+(S2-7); (I-117)+(S2-8); (I-117)+(S2-9); (I-117)+(S2-10); (I-117)+(S3-1); (I-117)+(S3-2); (I-117)+(S3-3); (I-117)+(S3-4); (I-117)+(S3-5); (I-117)+(S3-6); (I-117)+(S3-7); (I-117)+(S3-8); (I-117)+(S3-9); (I-117)+(S3-10); (I-117)+(S3-11); (I-117)+(S4-1); (I-117)+(S4-2); (I-117)+(S4-3); (I-117)+(S4-4); (I-117)+(S4-5); (I-117)+(S7-1); (I-117)+(S11-1); (I-117)+(S11-2); (I-117)+(S11-3); (I-117)+(S12-1); (I-117)+(S13-1); (I-117)+(S13-2); (I-117)+(S13-3); (I-117)+(S13-4): (I-117)+(S13-5); (I-117)+(S13-6); (I-117)+(S13-7); (I-117)+(S13-8); (I-117)+(S13-9); (I-117)+(S14-1)

(I-118)+(S1-1); (I-118)+(S1-2); (I-118)+(S1-3); (I-118)+(S1-4); (I-118)+(S1-5); (I-118)+(S1-6); (I-118)+(S1-7); (I-118)+(S1-8); (I-118)+(S1-9); (I-118)+(S1-10); (I-118)+(S1-11); (I-118)+(S1-12); (I-118)+(S1-13); (I-118)+(S2-1); (I-118)+(S2-2); (I-118)+(S2-3); (I-118)+(S2-4); (I-118)+(S2-5); (I-118)+(S2-6); (I-118)+(S2-7); (I-118)+(S2-8); (I-118)+(S2-9); (I-118)+(S2-10); (I-118)+(S3-1); (I-118)+(S3-2); (I-118)+(S3-3); (I-118)+(S3-4); (I-118)+(S3-5); (I-118)+(S3-6); (I-118)+(S3-7); (I-118)+(S3-8); (I-118)+(S3-9); (I-118)+(S3-10); (I-118)+(S3-11); (I-118)+(S4-1); (I-118)+(S4-2); (I-118)+(S4-3); (I-118)+(S4-4); (I-118)+(S4-5); (I-118)+(S7-1); (I-118)+(S11-1); (I-118)+(S11-2);

(I-118)+(S11-3); (I-118)+(S12-1); (I-118)+(S13-1); (I-118)+(S13-2); (I-118)+(S13-3); (I-118)+(S13-4): (I-118)+(S13-5); (I-118)+(S13-6); (I-118)+(S13-7); (I-118)+(S13-8); (I-118)+(S13-9); (I-118)+(S14-1)

(I-119)+(S1-1); (I-119)+(S1-2); (I-119)+(S1-3); (I-119)+(S1-4); (I-119)+(S1-5); (I-119)+(S1-6); (I-119)+(S1-7); (I-119)+(S1-8); (I-119)+(S1-9); (I-119)+(S1-10); (I-119)+(S1-11); (I-119)+(S1-12); (I-119)+(S1-13); (I-119)+(S2-1); (I-119)+(S2-2); (I-119)+(S2-3); (I-119)+(S2-4); (I-119)+(S2-5); (I-119)+(S2-6); (I-119)+(S2-7); (I-119)+(S2-8); (I-119)+(S2-9); (I-119)+(S2-10); (I-119)+(S3-1); (I-119)+(S3-2); (I-119)+(S3-3); (I-119)+(S3-4); (I-119)+(S3-5); (I-119)+(S3-6); (I-119)+(S3-7); (I-119)+(S3-8); (I-119)+(S3-9); (I-119)+(S3-10); (I-119)+(S3-11); (I-119)+(S4-1); (I-119)+(S4-2); (I-119)+(S4-3); (I-119)+(S4-4); (I-119)+(S4-5); (I-119)+(S7-1); (I-119)+(S11-1); (I-119)+(S11-2); (I-119)+(S11-3); (I-119)+(S12-1); (I-119)+(S13-1); (I-119)+(S13-2); (I-119)+(S13-3); (I-119)+(S13-4): (I-119)+(S13-5); (I-119)+(S13-6); (I-119)+(S13-7); (I-119)+(S13-8); (I-119)+(S13-9); (I-119)+(S14-1)

(I-120)+(S1-1); (I-120)+(S1-2); (I-120)+(S1-3); (I-120)+(S1-4); (I-120)+(S1-5); (I-120)+(S1-6); (I-120)+(S1-7); (I-120)+(S1-8); (I-120)+(S1-9); (I-120)+(S1-10); (I-120)+(S1-11); (I-120)+(S1-12); (I-120)+(S1-13); (I-120)+(S2-1); (I-120)+(S2-2); (I-120)+(S2-3); (I-120)+(S2-4); (I-120)+(S2-5); (I-120)+(S2-6); (I-120)+(S2-7); (I-120)+(S2-8); (I-120)+(S2-9); (I-120)+(S2-10); (I-120)+(S3-1); (I-120)+(S3-2); (I-120)+(S3-3); (I-120)+(S3-4); (I-120)+(S3-5); (I-120)+(S3-6); (I-120)+(S3-7); (I-120)+(S3-8); (I-120)+(S3-9); (I-120)+(S3-10); (I-120)+(S3-11); (I-120)+(S4-1); (I-120)+(S4-2); (I-120)+(S4-3); (I-120)+(S4-4); (I-120)+(S4-5); (I-120)+(S7-1); (I-120)+(S11-1); (I-120)+(S11-2); (I-120)+(S11-3); (I-120)+(S12-1); (I-120)+(S13-1); (I-120)+(S13-2); (I-120)+(S13-3); (I-120)+(S13-4): (I-120)+(S13-5); (I-120)+(S13-6); (I-120)+(S13-7); (I-120)+(S13-8); (I-120)+(S13-9); (I-120)+(S14-1)

(I-121)+(S1-1); (I-121)+(S1-2); (I-121)+(S1-3); (I-121)+(S1-4); (I-121)+(S1-5); (I-121)+(S1-6); (I-121)+(S1-7); (I-121)+(S1-8); (I-121)+(S1-9); (I-121)+(S1-10); (I-121)+(S1-11); (I-121)+(S1-12); (I-121)+(S1-13); (I-121)+(S2-1); (I-121)+(S2-2); (I-121)+(S2-3); (I-121)+(S2-4); (I-121)+(S2-5); (I-121)+(S2-6); (I-121)+(S2-7); (I-121)+(S2-8); (I-121)+(S2-9); (I-121)+(S2-10); (I-121)+(S3-1); (I-121)+(S3-2); (I-121)+(S3-3); (I-121)+(S3-4); (I-121)+(S3-5); (I-121)+(S3-6); (I-121)+(S3-7); (I-121)+(S3-8); (I-121)+(S3-9); (I-121)+(S3-10); (I-121)+(S3-11); (I-121)+(S4-1); (I-121)+(S4-2); (I-121)+(S4-3); (I-121)+(S4-4); (I-121)+(S4-5); (I-121)+(S7-1); (I-121)+(S11-1); (I-121)+(S11-2); (I-121)+(S11-3); (I-121)+(S12-1); (I-121)+(S13-1); (I-121)+(S13-2); (I-121)+(S13-3); (I-121)+(S13-4): (I-121)+(S13-5); (I-121)+(S13-6); (I-121)+(S13-7); (I-121)+(S13-8); (I-121)+(S13-9); (I-121)+(S14-1)

(I-122)+(S1-1); (I-122)+(S1-2); (I-122)+(S1-3); (I-122)+(S1-4); (I-122)+(S1-5); (I-122)+(S1-6); (I-122)+(S1-7); (I-122)+(S1-8); (I-122)+(S1-9); (I-122)+(S1-10); (I-122)+(S1-11); (I-122)+(S1-12); (I-122)+(S1-13); (I-122)+(S2-1); (I-122)+(S2-2); (I-122)+(S2-3); (I-122)+(S2-4); (I-122)+(S2-5); (I-122)+(S2-6); (I-122)+(S2-7); (I-122)+(S2-8); (I-122)+(S2-9); (I-122)+(S2-10); (I-122)+(S3-1); (I-122)+(S3-2); (I-122)+(S3-3); (I-122)+(S3-4); (I-122)+(S3-5); (I-122)+(S3-6); (I-122)+(S3-7); (I-122)+(S3-8); (I-122)+(S3-9); (I-122)+(S3-10); (I-122)+(S3-11); (I-122)+(S4-1); (I-122)+(S4-2); (I-122)+(S4-3); (I-122)+(S4-4); (I-122)+(S4-5); (I-122)+(S7-1); (I-122)+(S11-1); (I-122)+(S11-2); (I-122)+(S11-3); (I-122)+(S12-1); (I-122)+(S13-1); (I-122)+(S13-2); (I-122)+(S13-3); (I-122)+(S13-4): (I-122)+(S13-5); (I-122)+(S13-6); (I-122)+(S13-7); (I-122)+(S13-8); (I-122)+(S13-9); (I-122)+(S14-1)

(I-123)+(S1-1); (I-123)+(S1-2); (I-123)+(S1-3); (I-123)+(S1-4); (I-123)+(S1-5); (I-123)+(S1-6); (I-123)+(S1-7); (I-123)+(S1-8); (I-123)+(S1-9); (I-123)+(S1-10); (I-123)+(S1-11); (I-123)+(S1-12); (I-123)+(S1-13); (I-123)+(S2-1); (I-123)+(S2-2); (I-123)+(S2-3); (I-123)+(S2-4); (I-123)+(S2-5); (I-123)+(S2-6); (I-123)+(S2-7); (I-123)+(S2-8); (I-123)+(S2-9); (I-123)+(S2-10); (I-123)+(S3-1); (I-123)+(S3-2); (I-123)+(S3-3); (I-123)+(S3-4); (I-123)+(S3-5); (I-123)+(S3-6); (I-123)+(S3-7); (I-123)+(S3-8); (I-123)+(S3-9); (I-123)+(S3-10); (I-123)+(S3-11); (I-123)+(S4-1); (I-123)+(S4-2); (I-123)+(S4-3); (I-123)+(S4-4); (I-123)+(S4-5); (I-123)+(S7-1); (I-123)+(S11-1); (I-123)+(S11-2); (I-123)+(S11-3); (I-123)+(S12-1); (I-123)+(S13-1); (I-123)+(S13-2); (I-123)+(S13-3); (I-123)+(S13-4): (I-123)+(S13-5); (I-123)+(S13-6); (I-123)+(S13-7); (I-123)+(S13-8); (I-123)+(S13-9); (I-123)+(S14-1)

(I-124)+(S1-1); (I-124)+(S1-2); (I-124)+(S1-3); (I-124)+(S1-4); (I-124)+(S1-5); (I-124)+(S1-6); (I-124)+(S1-7); (I-124)+(S1-8); (I-124)+(S1-9); (I-124)+(S1-10); (I-124)+(S1-11); (I-124)+(S1-12); (I-124)+(S1-13); (I-124)+(S2-1); (I-124)+(S2-2); (I-124)+(S2-3); (I-124)+(S2-4); (I-124)+(S2-5); (I-124)+(S2-6); (I-124)+(S2-7); (I-124)+(S2-8); (I-124)+(S2-9); (I-124)+(S2-10); (I-124)+(S3-1); (I-124)+(S3-2); (I-124)+(S3-3); (I-124)+(S3-4); (I-124)+(S3-5); (I-124)+(S3-6); (I-124)+(S3-7); (I-124)+(S3-8); (I-124)+(S3-9); (I-124)+(S3-10); (I-124)+(S3-11); (I-124)+(S4-1); (I-124)+(S4-2); (I-124)+(S4-3); (I-124)+(S4-4); (I-124)+(S4-5); (I-124)+(S7-1); (I-124)+(S11-1); (I-124)+(S11-2); (I-124)+(S11-3); (I-124)+(S12-1); (I-124)+(S13-1); (I-124)+(S13-2); (I-124)+(S13-3); (I-124)+(S13-4): (I-124)+(S13-5); (I-124)+(S13-6); (I-124)+(S13-7); (I-124)+(S13-8); (I-124)+(S13-9); (I-124)+(S14-1)

(I-125)+(S1-1); (I-125)+(S1-2); (I-125)+(S1-3); (I-125)+(S1-4); (I-125)+(S1-5); (I-125)+(S1-6); (I-125)+(S1-7); (I-125)+(S1-8); (I-125)+(S1-9); (I-125)+(S1-10); (I-125)+(S1-11); (I-125)+(S1-12); (I-125)+(S1-13); (I-125)+(S2-1); (I-125)+(S2-2); (I-125)+(S2-3); (I-125)+(S2-4); (I-125)+(S2-5); (I-125)+(S2-6); (I-125)+(S2-7); (I-125)+(S2-8); (I-125)+(S2-9); (I-125)+(S2-10); (I-125)+(S3-1); (I-125)+(S3-2); (I-125)+(S3-3); (I-125)+(S3-4); (I-125)+(S3-5); (I-125)+(S3-6); (I-125)+(S3-7); (I-125)+(S3-8); (I-125)+(S3-9); (I-125)+(S3-10); (I-125)+(S3-11); (I-125)+(S4-1); (I-125)+(S4-2); (I-125)+(S4-3); (I-125)+(S4-4); (I-125)+(S4-5); (I-125)+(S7-1); (I-125)+(S11-1); (I-125)+(S11-2); (I-125)+(S11-3); (I-125)+(S12-1); (I-125)+(S13-1); (I-125)+(S13-2); (I-125)+(S13-3); (I-125)+(S13-4): (I-125)+(S13-5); (I-125)+(S13-6); (I-125)+(S13-7); (I-125)+(S13-8); (I-125)+(S13-9); (I-125)+(S14-1)

(I-126)+(S1-1); (I-126)+(S1-2); (I-126)+(S1-3); (I-126)+(S1-4); (I-126)+(S1-5); (I-126)+(S1-6); (I-126)+(S1-7); (I-126)+(S1-8); (I-126)+(S1-9); (I-126)+(S1-10); (I-126)+(S1-11); (I-126)+(S1-12); (I-126)+(S1-13); (I-126)+(S2-1); (I-126)+(S2-2); (I-126)+(S2-3); (I-126)+(S2-4); (I-126)+(S2-5); (I-126)+(S2-6); (I-126)+(S2-7); (I-126)+(S2-8); (I-126)+(S2-9); (I-126)+(S2-10); (I-126)+(S3-1); (I-126)+(S3-2); (I-126)+(S3-3); (I-126)+(S3-4); (I-126)+(S3-5); (I-126)+(S3-6); (I-126)+(S3-7); (I-126)+(S3-8); (I-126)+(S3-9); (I-126)+(S3-10); (I-126)+(S3-11); (I-126)+(S4-1); (I-126)+(S4-2); (I-126)+(S4-3); (I-126)+(S4-4); (I-126)+(S4-5); (I-126)+(S7-1); (I-126)+(S11-1); (I-126)+(S11-2); (I-126)+(S11-3); (I-126)+(S12-1); (I-126)+(S13-1); (I-126)+(S13-2); (I-126)+(S13-3); (I-126)+(S13-4): (I-126)+(S13-5); (I-126)+(S13-6); (I-126)+(S13-7); (I-126)+(S13-8); (I-126)+(S13-9); (I-126)+(S14-1)

(I-127)+(S1-1); (I-127)+(S1-2); (I-127)+(S1-3); (I-127)+(S1-4); (I-127)+(S1-5); (I-127)+(S1-6); (I-127)+(S1-7); (I-127)+(S1-8); (I-127)+(S1-9); (I-127)+(S1-10); (I-127)+(S1-11); (I-127)+(S1-12); (I-127)+(S1-13); (I-127)+(S2-1); (I-127)+(S2-2); (I-127)+(S2-3); (I-127)+(S2-4); (I-127)+(S2-5); (I-127)+(S2-6); (I-127)+(S2-7); (I-127)+(S2-8); (I-127)+(S2-9); (I-127)+(S2-10); (I-127)+(S3-1); (I-127)+(S3-2); (I-127)+(S3-3); (I-127)+(S3-4); (I-127)+(S3-5); (I-127)+(S3-6); (I-127)+(S3-7); (I-127)+(S3-8); (I-127)+(S3-9); (I-127)+(S3-10); (I-127)+(S3-11); (I-127)+(S4-1); (I-127)+(S4-2); (I-127)+(S4-3); (I-127)+(S4-4); (I-127)+(S4-5); (I-127)+(S7-1); (I-127)+(S11-1); (I-127)+(S11-2); (I-127)+(S11-3); (I-127)+(S12-1); (I-127)+(S13-1); (I-127)+(S13-2); (I-127)+(S13-3); (I-127)+(S13-4): (I-127)+(S13-5); (I-127)+(S13-6); (I-127)+(S13-7); (I-127)+(S13-8); (I-127)+(S13-9); (I-127)+(S14-1)

(I-128)+(S1-1); (I-128)+(S1-2); (I-128)+(S1-3); (I-128)+(S1-4); (I-128)+(S1-5); (I-128)+(S1-6); (I-128)+(S1-7); (I-128)+(S1-8); (I-128)+(S1-9); (I-128)+(S1-10); (I-128)+(S1-11); (I-128)+(S1-12); (I-128)+(S1-13); (I-128)+(S2-1); (I-128)+(S2-2); (I-128)+(S2-3); (I-128)+(S2-4); (I-128)+(S2-5); (I-128)+(S2-6); (I-128)+(S2-7); (I-128)+(S2-8); (I-128)+(S2-9); (I-128)+(S2-10); (I-128)+(S3-1); (I-128)+(S3-2); (I-128)+(S3-3); (I-128)+(S3-4); (I-128)+(S3-5); (I-128)+(S3-6); (I-128)+(S3-7); (I-128)+(S3-8); (I-128)+(S3-9); (I-128)+(S3-10); (I-128)+(S3-11); (I-128)+(S4-1); (I-128)+(S4-2); (I-128)+(S4-3); (I-128)+(S4-4); (I-128)+(S4-5); (I-128)+(S7-1); (I-128)+(S11-1); (I-128)+(S11-2); (I-128)+(S11-3); (I-128)+(S12-1); (I-128)+(S13-1); (I-128)+(S13-2); (I-128)+(S13-3); (I-128)+(S13-4): (I-128)+(S13-5); (I-128)+(S13-6); (I-128)+(S13-7); (I-128)+(S13-8); (I-128)+(S13-9); (I-128)+(S14-1)

(I-129)+(S1-1); (I-129)+(S1-2); (I-129)+(S1-3); (I-129)+(S1-4); (I-129)+(S1-5); (I-129)+(S1-6); (I-129)+(S1-7); (I-129)+(S1-8); (I-129)+(S1-9); (I-129)+(S1-10); (I-129)+(S1-11); (I-129)+(S1-12); (I-129)+(S1-13); (I-129)+(S2-1); (I-129)+(S2-2); (I-129)+(S2-3); (I-129)+(S2-4); (I-129)+(S2-5); (I-129)+(S2-6); (I-129)+(S2-7); (I-129)+(S2-8); (I-129)+(S2-9); (I-129)+(S2-10); (I-129)+(S3-1); (I-129)+(S3-2); (I-129)+(S3-3); (I-129)+(S3-4); (I-129)+(S3-5); (I-129)+(S3-6); (I-129)+(S3-7); (I-129)+(S3-8); (I-129)+(S3-9); (I-129)+(S3-10); (I-129)+(S3-11); (I-129)+(S4-1); (I-129)+(S4-2); (I-129)+(S4-3); (I-129)+(S4-4); (I-129)+(S4-5); (I-129)+(S7-1); (I-129)+(S11-1); (I-129)+(S11-2); (I-129)+(S11-3); (I-129)+(S12-1); (I-129)+(S13-1); (I-129)+(S13-2); (I-129)+(S13-3); (I-129)+(S13-4): (I-129)+(S13-5); (I-129)+(S13-6); (I-129)+(S13-7); (I-129)+(S13-8); (I-129)+(S13-9); (I-129)+(S14-1)

(I-130)+(S1-1); (I-130)+(S1-2); (I-130)+(S1-3); (I-130)+(S1-4); (I-130)+(S1-5); (I-130)+(S1-6); (I-130)+(S1-7); (I-130)+(S1-8); (I-130)+(S1-9); (I-130)+(S1-10); (I-130)+(S1-11); (I-130)+(S1-12); (I-130)+(S1-13); (I-130)+(S2-1); (I-130)+(S2-2); (I-130)+(S2-3); (I-130)+(S2-4); (I-130)+(S2-5); (I-130)+(S2-6); (I-130)+(S2-7); (I-130)+(S2-8); (I-130)+(S2-9); (I-130)+(S2-10); (I-130)+(S3-1); (I-130)+(S3-2); (I-130)+(S3-3); (I-130)+(S3-4); (I-130)+(S3-5); (I-130)+(S3-6); (I-130)+(S3-7); (I-130)+(S3-8); (I-130)+(S3-9); (I-130)+(S3-10); (I-130)+(S3-11); (I-130)+(S4-1); (I-130)+(S4-2); (I-130)+(S4-3); (I-130)+(S4-4); (I-130)+(S4-5); (I-130)+(S7-1); (I-130)+(S11-1); (I-130)+(S11-2); (I-130)+(S11-3); (I-130)+(S12-1); (I-130)+(S13-1); (I-130)+(S13-2); (I-130)+(S13-3); (I-130)+(S13-4): (I-130)+(S13-5); (I-130)+(S13-6); (I-130)+(S13-7); (I-130)+(S13-8); (I-130)+(S13-9); (I-130)+(S14-1)

(I-131)+(S1-1); (I-131)+(S1-2); (I-131)+(S1-3); (I-131)+(S1-4); (I-131)+(S1-5); (I-131)+(S1-6); (I-131)+(S1-7); (I-131)+(S1-8); (I-131)+(S1-9); (I-131)+(S1-10); (I-131)+(S1-11); (I-131)+(S1-12); (I-131)+(S1-13); (I-131)+(S2-1); (I-131)+(S2-2); (I-131)+(S2-3); (I-131)+(S2-4); (I-131)+(S2-5); (I-131)+(S2-6); (I-131)+(S2-7); (I-131)+(S2-8); (I-131)+(S2-9); (I-131)+(S2-10); (I-131)+(S3-1); (I-131)+(S3-2); (I-131)+(S3-3); (I-131)+(S3-4); (I-131)+(S3-5); (I-131)+(S3-6); (I-131)+(S3-7); (I-131)+(S3-8); (I-131)+(S3-9); (I-131)+(S3-10); (I-131)+(S3-11); (I-131)+(S4-1); (I-131)+(S4-2); (I-131)+(S4-3); (I-131)+(S4-4); (I-131)+(S4-5); (I-131)+(S7-1); (I-131)+(S11-1); (I-131)+(S11-2); (I-131)+(S11-3); (I-131)+(S12-1); (I-131)+(S13-1); (I-131)+(S13-2); (I-131)+(S13-3); (I-131)+(S13-4): (I-131)+(S13-5); (I-131)+(S13-6); (I-131)+(S13-7); (I-131)+(S13-8); (I-131)+(S13-9); (I-131)+(S14-1)

(I-132)+(S1-1); (I-132)+(S1-2); (I-132)+(S1-3); (I-132)+(S1-4); (I-132)+(S1-5); (I-132)+(S1-6); (I-132)+(S1-7); (I-132)+(S1-8); (I-132)+(S1-9); (I-132)+(S1-10); (I-132)+(S1-11); (I-132)+(S1-12); (I-132)+(S1-13); (I-132)+(S2-1); (I-132)+(S2-2); (I-132)+(S2-3); (I-132)+(S2-4); (I-132)+(S2-5); (I-132)+(S2-6); (I-132)+(S2-7); (I-132)+(S2-8); (I-132)+(S2-9); (I-132)+(S2-10); (I-132)+(S3-1); (I-132)+(S3-2); (I-132)+(S3-3); (I-132)+(S3-4); (I-132)+(S3-5); (I-132)+(S3-6); (I-132)+(S3-7); (I-132)+(S3-8); (I-132)+(S3-9); (I-132)+(S3-10); (I-132)+(S3-11); (I-132)+(S4-1); (I-132)+(S4-2); (I-132)+(S4-3); (I-132)+(S4-4); (I-132)+(S4-5); (I-132)+(S7-1); (I-132)+(S11-1); (I-132)+(S11-2); (I-132)+(S11-3); (I-132)+(S12-1); (I-132)+(S13-1); (I-132)+(S13-2); (I-132)+(S13-3); (I-132)+(S13-4): (I-132)+(S13-5); (I-132)+(S13-6); (I-132)+(S13-7); (I-132)+(S13-8); (I-132)+(S13-9); (I-132)+(S14-1)

(I-133)+(S1-1); (I-133)+(S1-2); (I-133)+(S1-3); (I-133)+(S1-4); (I-133)+(S1-5); (I-133)+(S1-6); (I-133)+(S1-7); (I-133)+(S1-8); (I-133)+(S1-9); (I-133)+(S1-10); (I-133)+(S1-11); (I-133)+(S1-12); (I-133)+(S1-13); (I-133)+(S2-1); (I-133)+(S2-2); (I-133)+(S2-3); (I-133)+(S2-4); (I-133)+(S2-5); (I-133)+(S2-6); (I-133)+(S2-7); (I-133)+(S2-8); (I-133)+(S2-9); (I-133)+(S2-10); (I-133)+(S3-1); (I-133)+(S3-2); (I-133)+(S3-3); (I-133)+(S3-4); (I-133)+(S3-5); (I-133)+(S3-6); (I-133)+(S3-7); (I-133)+(S3-8); (I-133)+(S3-9); (I-133)+(S3-10); (I-133)+(S3-11); (I-133)+(S4-1); (I-133)+(S4-2); (I-133)+(S4-3); (I-133)+(S4-4); (I-133)+(S4-5); (I-133)+(S7-1); (I-133)+(S11-1); (I-133)+(S11-2); (I-133)+(S11-3); (I-133)+(S12-1); (I-133)+(S13-1); (I-133)+(S13-2); (I-133)+(S13-3); (I-133)+(S13-4): (I-133)+(S13-5); (I-133)+(S13-6); (I-133)+(S13-7); (I-133)+(S13-8); (I-133)+(S13-9); (I-133)+(S14-1)

(I-134)+(S1-1); (I-134)+(S1-2); (I-134)+(S1-3); (I-134)+(S1-4); (I-134)+(S1-5); (I-134)+(S1-6); (I-134)+(S1-7); (I-134)+(S1-8); (I-134)+(S1-9); (I-134)+(S1-10); (I-134)+(S1-11); (I-134)+(S1-12); (I-134)+(S1-13); (I-134)+(S2-1); (I-134)+(S2-2); (I-134)+(S2-3); (I-134)+(S2-4); (I-134)+(S2-5); (I-134)+(S2-6); (I-134)+(S2-7); (I-134)+(S2-8); (I-134)+(S2-9); (I-134)+(S2-10); (I-134)+(S3-1); (I-134)+(S3-2); (I-134)+(S3-3); (I-134)+(S3-4); (I-134)+(S3-5); (I-134)+(S3-6); (I-134)+(S3-7); (I-134)+(S3-8); (I-134)+(S3-9); (I-134)+(S3-10); (I-134)+(S3-11); (I-134)+(S4-1); (I-134)+(S4-2); (I-134)+(S4-3); (I-134)+(S4-4); (I-134)+(S4-5); (I-134)+(S7-1); (I-134)+(S11-1); (I-134)+(S11-2); (I-134)+(S11-3); (I-134)+(S12-1); (I-134)+(S13-1); (I-134)+(S13-2); (I-134)+(S13-3); (I-134)+(S13-4): (I-134)+(S13-5); (I-134)+(S13-6); (I-134)+(S13-7); (I-134)+(S13-8); (I-134)+(S13-9); (I-134)+(S14-1)

(I-135)+(S1-1); (I-135)+(S1-2); (I-135)+(S1-3); (I-135)+(S1-4); (I-135)+(S1-5); (I-135)+(S1-6); (I-135)+(S1-7); (I-135)+(S1-8); (I-135)+(S1-9); (I-135)+(S1-10); (I-135)+(S1-11); (I-135)+(S1-12); (I-135)+(S1-13); (I-135)+(S2-1); (I-135)+(S2-2); (I-135)+(S2-3); (I-135)+(S2-4); (I-135)+(S2-5); (I-135)+(S2-6); (I-135)+(S2-7); (I-135)+(S2-8);

(I-135)+(S2-9); (I-135)+(S2-10); (I-135)+(S3-1); (I-135)+(S3-2); (I-135)+(S3-3); (I-135)+(S3-4); (I-135)+(S3-5); (I-135)+(S3-6); (I-135)+(S3-7); (I-135)+(S3-8); (I-135)+(S3-9); (I-135)+(S3-10); (I-135)+(S3-11); (I-135)+(S4-1); (I-135)+(S4-2); (I-135)+(S4-3); (I-135)+(S4-4); (I-135)+(S4-5); (I-135)+(S7-1); (I-135)+(S11-1); (I-135)+(S11-2); (I-135)+(S11-3); (I-135)+(S12-1); (I-135)+(S13-1); (I-135)+(S13-2); (I-135)+(S13-3); (I-135)+(S13-4): (I-135)+(S13-5); (I-135)+(S13-6); (I-135)+(S13-7); (I-135)+(S13-8); (I-135)+(S13-9); (I-135)+(S14-1)

(I-136)+(S1-1); (I-136)+(S1-2); (I-136)+(S1-3); (I-136)+(S1-4); (I-136)+(S1-5); (I-136)+(S1-6); (I-136)+(S1-7); (I-136)+(S1-8); (I-136)+(S1-9); (I-136)+(S1-10); (I-136)+(S1-11); (I-136)+(S1-12); (I-136)+(S1-13); (I-136)+(S2-1); (I-136)+(S2-2); (I-136)+(S2-3); (I-136)+(S2-4); (I-136)+(S2-5); (I-136)+(S2-6); (I-136)+(S2-7); (I-136)+(S2-8); (I-136)+(S2-9); (I-136)+(S2-10); (I-136)+(S3-1); (I-136)+(S3-2); (I-136)+(S3-3); (I-136)+(S3-4); (I-136)+(S3-5); (I-136)+(S3-6); (I-136)+(S3-7); (I-136)+(S3-8); (I-136)+(S3-9); (I-136)+(S3-10); (I-136)+(S3-11); (I-136)+(S4-1); (I-136)+(S4-2); (I-136)+(S4-3); (I-136)+(S4-4); (I-136)+(S4-5); (I-136)+(S7-1); (I-136)+(S11-1); (I-136)+(S11-2); (I-136)+(S11-3); (I-136)+(S12-1); (I-136)+(S13-1); (I-136)+(S13-2); (I-136)+(S13-3); (I-136)+(S13-4): (I-136)+(S13-5); (I-136)+(S13-6); (I-136)+(S13-7); (I-136)+(S13-8); (I-136)+(S13-9); (I-136)+(S14-1)

(I-137)+(S1-1); (I-137)+(S1-2); (I-137)+(S1-3); (I-137)+(S1-4); (I-137)+(S1-5); (I-137)+(S1-6); (I-137)+(S1-7); (I-137)+(S1-8); (I-137)+(S1-9); (I-137)+(S1-10); (I-137)+(S1-11); (I-137)+(S1-12); (I-137)+(S1-13); (I-137)+(S2-1); (I-137)+(S2-2); (I-137)+(S2-3); (I-137)+(S2-4); (I-137)+(S2-5); (I-137)+(S2-6); (I-137)+(S2-7); (I-137)+(S2-8); (I-137)+(S2-9); (I-137)+(S2-10); (I-137)+(S3-1); (I-137)+(S3-2); (I-137)+(S3-3); (I-137)+(S3-4); (I-137)+(S3-5); (I-137)+(S3-6); (I-137)+(S3-7); (I-137)+(S3-8); (I-137)+(S3-9); (I-137)+(S3-10); (I-137)+(S3-11); (I-137)+(S4-1); (I-137)+(S4-2); (I-137)+(S4-3); (I-137)+(S4-4); (I-137)+(S4-5); (I-137)+(S7-1); (I-137)+(S11-1); (I-137)+(S11-2); (I-137)+(S11-3); (I-137)+(S12-1); (I-137)+(S13-1); (I-137)+(S13-2); (I-137)+(S13-3); (I-137)+(S13-4): (I-137)+(S13-5); (I-137)+(S13-6); (I-137)+(S13-7); (I-137)+(S13-8); (I-137)+(S13-9); (I-137)+(S14-1)

(I-138)+(S1-1); (I-138)+(S1-2); (I-138)+(S1-3); (I-138)+(S1-4); (I-138)+(S1-5); (I-138)+(S1-6); (I-138)+(S1-7); (I-138)+(S1-8); (I-138)+(S1-9); (I-138)+(S1-10); (I-138)+(S1-11); (I-138)+(S1-12); (I-138)+(S1-13); (I-138)+(S2-1); (I-138)+(S2-2); (I-138)+(S2-3); (I-138)+(S2-4); (I-138)+(S2-5); (I-138)+(S2-6); (I-138)+(S2-7); (I-138)+(S2-8); (I-138)+(S2-9); (I-138)+(S2-10); (I-138)+(S3-1); (I-138)+(S3-2); (I-138)+(S3-3); (I-138)+(S3-4); (I-138)+(S3-5); (I-138)+(S3-6); (I-138)+(S3-7); (I-138)+(S3-8); (I-138)+(S3-9); (I-138)+(S3-10); (I-138)+(S3-11); (I-138)+(S4-1); (I-138)+(S4-2); (I-138)+(S4-3); (I-138)+(S4-4); (I-138)+(S4-5); (I-138)+(S7-1); (I-138)+(S11-1); (I-138)+(S11-2); (I-138)+(S11-3); (I-138)+(S12-1); (I-138)+(S13-1); (I-138)+(S13-2); (I-138)+(S13-3); (I-138)+(S13-4): (I-138)+(S13-5); (I-138)+(S13-6); (I-138)+(S13-7); (I-138)+(S13-8); (I-138)+(S13-9); (I-138)+(S14-1)

(I-139)+(S1-1); (I-139)+(S1-2); (I-139)+(S1-3); (I-139)+(S1-4); (I-139)+(S1-5); (I-139)+(S1-6); (I-139)+(S1-7); (I-139)+(S1-8); (I-139)+(S1-9); (I-139)+(S1-10); (I-139)+(S1-11); (I-139)+(S1-12); (I-139)+(S1-13); (I-139)+(S2-1); (I-139)+(S2-2); (I-139)+(S2-3); (I-139)+(S2-4); (I-139)+(S2-5); (I-139)+(S2-6); (I-139)+(S2-7); (I-139)+(S2-8); (I-139)+(S2-9); (I-139)+(S2-10); (I-139)+(S3-1); (I-139)+(S3-2); (I-139)+(S3-3); (I-139)+(S3-4); (I-139)+(S3-5); (I-139)+(S3-6); (I-139)+(S3-7); (I-139)+(S3-8); (I-139)+(S3-9); (I-139)+(S3-10); (I-139)+(S3-11); (I-139)+(S4-1); (I-139)+(S4-2); (I-139)+(S4-3); (I-139)+(S4-4); (I-139)+(S4-5); (I-139)+(S7-1); (I-139)+(S11-1); (I-139)+(S11-2); (I-139)+(S11-3); (I-139)+(S12-1); (I-139)+(S13-1); (I-139)+(S13-2); (I-139)+(S13-3); (I-139)+(S13-4): (I-139)+(S13-5); (I-139)+(S13-6); (I-139)+(S13-7); (I-139)+(S13-8); (I-139)+(S13-9); (I-139)+(S14-1)

(I-140)+(S1-1); (I-140)+(S1-2); (I-140)+(S1-3); (I-140)+(S1-4); (I-140)+(S1-5); (I-140)+(S1-6); (I-140)+(S1-7); (I-140)+(S1-8); (I-140)+(S1-9); (I-140)+(S1-10); (I-140)+(S1-11); (I-140)+(S1-12); (I-140)+(S1-13); (I-140)+(S2-1); (I-140)+(S2-2); (I-140)+(S2-3); (I-140)+(S2-4); (I-140)+(S2-5); (I-140)+(S2-6); (I-140)+(S2-7); (I-140)+(S2-8); (I-140)+(S2-9); (I-140)+(S2-10); (I-140)+(S3-1); (I-140)+(S3-2); (I-140)+(S3-3); (I-140)+(S3-4); (I-140)+(S3-5); (I-140)+(S3-6); (I-140)+(S3-7); (I-140)+(S3-8); (I-140)+(S3-9); (I-140)+(S3-10); (I-140)+(S3-11); (I-140)+(S4-1); (I-140)+(S4-2); (I-140)+(S4-3); (I-140)+(S4-4); (I-140)+(S4-5); (I-140)+(S7-1); (I-140)+(S11-1); (I-140)+(S11-2); (I-140)+(S11-3); (I-140)+(S12-1); (I-140)+(S13-1); (I-140)+(S13-2); (I-140)+(S13-3); (I-140)+(S13-4): (I-140)+(S13-5); (I-140)+(S13-6); (I-140)+(S13-7); (I-140)+(S13-8); (I-140)+(S13-9); (I-140)+(S14-1)

(I-141)+(S1-1); (I-141)+(S1-2); (I-141)+(S1-3); (I-141)+(S1-4); (I-141)+(S1-5); (I-141)+(S1-6); (I-141)+(S1-7); (I-141)+(S1-8); (I-141)+(S1-9); (I-141)+(S1-10); (I-141)+(S1-11); (I-141)+(S1-12); (I-141)+(S1-13); (I-141)+(S2-1); (I-141)+(S2-2); (I-141)+(S2-3); (I-141)+(S2-4); (I-141)+(S2-5); (I-141)+(S2-6); (I-141)+(S2-7); (I-141)+(S2-8); (I-141)+(S2-9); (I-141)+(S2-10); (I-141)+(S3-1); (I-141)+(S3-2); (I-141)+(S3-3); (I-141)+(S3-4); (I-141)+(S3-5); (I-141)+(S3-6); (I-141)+(S3-7); (I-141)+(S3-8); (I-141)+(S3-9); (I-141)+(S3-10); (I-141)+(S3-11); (I-141)+(S4-1); (I-141)+(S4-2); (I-141)+(S4-3); (I-141)+(S4-4); (I-141)+(S4-5); (I-141)+(S7-1); (I-141)+(S11-1); (I-141)+(S11-2); (I-141)+(S11-3); (I-141)+(S12-1); (I-141)+(S13-1); (I-141)+(S13-2); (I-141)+(S13-3); (I-141)+(S13-4): (I-141)+(S13-5); (I-141)+(S13-6); (I-141)+(S13-7); (I-141)+(S13-8); (I-141)+(S13-9); (I-141)+(S14-1)

(I-142)+(S1-1); (I-142)+(S1-2); (I-142)+(S1-3); (I-142)+(S1-4); (I-142)+(S1-5); (I-142)+(S1-6); (I-142)+(S1-7); (I-142)+(S1-8); (I-142)+(S1-9); (I-142)+(S1-10); (I-142)+(S1-11); (I-142)+(S1-12); (I-142)+(S1-13); (I-142)+(S2-1); (I-142)+(S2-2); (I-142)+(S2-3); (I-142)+(S2-4); (I-142)+(S2-5); (I-142)+(S2-6); (I-142)+(S2-7); (I-142)+(S2-8); (I-142)+(S2-9); (I-142)+(S2-10); (I-142)+(S3-1); (I-142)+(S3-2); (I-142)+(S3-3); (I-142)+(S3-4); (I-142)+(S3-5); (I-142)+(S3-6); (I-142)+(S3-7); (I-142)+(S3-8); (I-142)+(S3-9); (I-142)+(S3-10); (I-142)+(S3-11); (I-142)+(S4-1); (I-142)+(S4-2); (I-142)+(S4-3); (I-142)+(S4-4); (I-142)+(S4-5); (I-142)+(S7-1); (I-142)+(S11-1); (I-142)+(S11-2); (I-142)+(S11-3); (I-142)+(S12-1); (I-142)+(S13-1); (I-142)+(S13-2); (I-142)+(S13-3); (I-142)+(S13-4): (I-142)+(S13-5); (I-142)+(S13-6); (I-142)+(S13-7); (I-142)+(S13-8); (I-142)+(S13-9); (I-142)+(S14-1)

(I-143)+(S1-1); (I-143)+(S1-2); (I-143)+(S1-3); (I-143)+(S1-4); (I-143)+(S1-5); (I-143)+(S1-6); (I-143)+(S1-7); (I-143)+(S1-8); (I-143)+(S1-9); (I-143)+(S1-10); (I-143)+(S1-11); (I-143)+(S1-12); (I-143)+(S1-13); (I-143)+(S2-1); (I-143)+(S2-2); (I-143)+(S2-3); (I-143)+(S2-4); (I-143)+(S2-5); (I-143)+(S2-6); (I-143)+(S2-7); (I-143)+(S2-8); (I-143)+(S2-9); (I-143)+(S2-10); (I-143)+(S3-1); (I-143)+(S3-2); (I-143)+(S3-3); (I-143)+(S3-4); (I-143)+(S3-5); (I-143)+(S3-6); (I-143)+(S3-7); (I-143)+(S3-8); (I-143)+(S3-9); (I-143)+(S3-10); (I-143)+(S3-11); (I-143)+(S4-1); (I-143)+(S4-2); (I-143)+(S4-3); (I-143)+(S4-4); (I-143)+(S4-5); (I-143)+(S7-1); (I-143)+(S11-1); (I-143)+(S11-2);

(I-143)+(S11-3); (I-143)+(S12-1); (I-143)+(S13-1); (I-143)+(S13-2); (I-143)+(S13-3); (I-143)+(S13-4): (I-143)+(S13-5); (I-143)+(S13-6); (I-143)+(S13-7); (I-143)+(S13-8); (I-143)+(S13-9); (I-143)+(S14-1)

(I-144)+(S1-1); (I-144)+(S1-2); (I-144)+(S1-3); (I-144)+(S1-4); (I-144)+(S1-5); (I-144)+(S1-6); (I-144)+(S1-7); (I-144)+(S1-8); (I-144)+(S1-9); (I-144)+(S1-10); (I-144)+(S1-11); (I-144)+(S1-12); (I-144)+(S1-13); (I-144)+(S2-1); (I-144)+(S2-2); (I-144)+(S2-3); (I-144)+(S2-4); (I-144)+(S2-5); (I-144)+(S2-6); (I-144)+(S2-7); (I-144)+(S2-8); (I-144)+(S2-9); (I-144)+(S2-10); (I-144)+(S3-1); (I-144)+(S3-2); (I-144)+(S3-3); (I-144)+(S3-4); (I-144)+(S3-5); (I-144)+(S3-6); (I-144)+(S3-7); (I-144)+(S3-8); (I-144)+(S3-9); (I-144)+(S3-10); (I-144)+(S3-11); (I-144)+(S4-1); (I-144)+(S4-2); (I-144)+(S4-3); (I-144)+(S4-4); (I-144)+(S4-5); (I-144)+(S7-1); (I-144)+(S11-1); (I-144)+(S11-2); (I-144)+(S11-3); (I-144)+(S12-1); (I-144)+(S13-1); (I-144)+(S13-2); (I-144)+(S13-3); (I-144)+(S13-4): (I-144)+(S13-5); (I-144)+(S13-6); (I-144)+(S13-7); (I-144)+(S13-8); (I-144)+(S13-9); (I-144)+(S14-1)

(I-145)+(S1-1); (I-145)+(S1-2); (I-145)+(S1-3); (I-145)+(S1-4); (I-145)+(S1-5); (I-145)+(S1-6); (I-145)+(S1-7); (I-145)+(S1-8); (I-145)+(S1-9); (I-145)+(S1-10); (I-145)+(S1-11); (I-145)+(S1-12); (I-145)+(S1-13); (I-145)+(S2-1); (I-145)+(S2-2); (I-145)+(S2-3); (I-145)+(S2-4); (I-145)+(S2-5); (I-145)+(S2-6); (I-145)+(S2-7); (I-145)+(S2-8); (I-145)+(S2-9); (I-145)+(S2-10); (I-145)+(S3-1); (I-145)+(S3-2); (I-145)+(S3-3); (I-145)+(S3-4); (I-145)+(S3-5); (I-145)+(S3-6); (I-145)+(S3-7); (I-145)+(S3-8); (I-145)+(S3-9); (I-145)+(S3-10); (I-145)+(S3-11); (I-145)+(S4-1); (I-145)+(S4-2); (I-145)+(S4-3); (I-145)+(S4-4); (I-145)+(S4-5); (I-145)+(S7-1); (I-145)+(S11-1); (I-145)+(S11-2); (I-145)+(S11-3); (I-145)+(S12-1); (I-145)+(S13-1); (I-145)+(S13-2); (I-145)+(S13-3); (I-145)+(S13-4): (I-145)+(S13-5); (I-145)+(S13-6); (I-145)+(S13-7); (I-145)+(S13-8); (I-145)+(S13-9); (I-145)+(S14-1)

(I-146)+(S1-1); (I-146)+(S1-2); (I-146)+(S1-3); (I-146)+(S1-4); (I-146)+(S1-5); (I-146)+(S1-6); (I-146)+(S1-7); (I-146)+(S1-8); (I-146)+(S1-9); (I-146)+(S1-10); (I-146)+(S1-11); (I-146)+(S1-12); (I-146)+(S1-13); (I-146)+(S2-1); (I-146)+(S2-2); (I-146)+(S2-3); (I-146)+(S2-4); (I-146)+(S2-5); (I-146)+(S2-6); (I-146)+(S2-7); (I-146)+(S2-8); (I-146)+(S2-9); (I-146)+(S2-10); (I-146)+(S3-1); (I-146)+(S3-2); (I-146)+(S3-3); (I-146)+(S3-4); (I-146)+(S3-5); (I-146)+(S3-6); (I-146)+(S3-7); (I-146)+(S3-8); (I-146)+(S3-9); (I-146)+(S3-10); (I-146)+(S3-11); (I-146)+(S4-1); (I-146)+(S4-2); (I-146)+(S4-3); (I-146)+(S4-4); (I-146)+(S4-5); (I-146)+(S7-1); (I-146)+(S11-1); (I-146)+(S11-2); (I-146)+(S11-3); (I-146)+(S12-1); (I-146)+(S13-1); (I-146)+(S13-2); (I-146)+(S13-3); (I-146)+(S13-4): (I-146)+(S13-5); (I-146)+(S13-6); (I-146)+(S13-7); (I-146)+(S13-8); (I-146)+(S13-9); (I-146)+(S14-1)

(I-147)+(S1-1); (I-147)+(S1-2); (I-147)+(S1-3); (I-147)+(S1-4); (I-147)+(S1-5); (I-147)+(S1-6); (I-147)+(S1-7); (I-147)+(S1-8); (I-147)+(S1-9); (I-147)+(S1-10); (I-147)+(S1-11); (I-147)+(S1-12); (I-147)+(S1-13); (I-147)+(S2-1); (I-147)+(S2-2); (I-147)+(S2-3); (I-147)+(S2-4); (I-147)+(S2-5); (I-147)+(S2-6); (I-147)+(S2-7); (I-147)+(S2-8); (I-147)+(S2-9); (I-147)+(S2-10); (I-147)+(S3-1); (I-147)+(S3-2); (I-147)+(S3-3); (I-147)+(S3-4); (I-147)+(S3-5); (I-147)+(S3-6); (I-147)+(S3-7); (I-147)+(S3-8); (I-147)+(S3-9); (I-147)+(S3-10); (I-147)+(S3-11); (I-147)+(S4-1); (I-147)+(S4-2); (I-147)+(S4-3); (I-147)+(S4-4); (I-147)+(S4-5); (I-147)+(S7-1); (I-147)+(S11-1); (I-147)+(S11-2); (I-147)+(S11-3); (I-147)+(S12-1); (I-147)+(S13-1); (I-147)+(S13-2); (I-147)+(S13-3); (I-147)+(S13-4): (I-147)+(S13-5); (I-147)+(S13-6); (I-147)+(S13-7); (I-147)+(S13-8); (I-147)+(S13-9); (I-147)+(S14-1)

(I-148)+(S1-1); (I-148)+(S1-2); (I-148)+(S1-3); (I-148)+(S1-4); (I-148)+(S1-5); (I-148)+(S1-6); (I-148)+(S1-7); (I-148)+(S1-8); (I-148)+(S1-9); (I-148)+(S1-10); (I-148)+(S1-11); (I-148)+(S1-12); (I-148)+(S1-13); (I-148)+(S2-1); (I-148)+(S2-2); (I-148)+(S2-3); (I-148)+(S2-4); (I-148)+(S2-5); (I-148)+(S2-6); (I-148)+(S2-7); (I-148)+(S2-8); (I-148)+(S2-9); (I-148)+(S2-10); (I-148)+(S3-1); (I-148)+(S3-2); (I-148)+(S3-3); (I-148)+(S3-4); (I-148)+(S3-5); (I-148)+(S3-6); (I-148)+(S3-7); (I-148)+(S3-8); (I-148)+(S3-9); (I-148)+(S3-10); (I-148)+(S3-11); (I-148)+(S4-1); (I-148)+(S4-2); (I-148)+(S4-3); (I-148)+(S4-4); (I-148)+(S4-5); (I-148)+(S7-1); (I-148)+(S11-1); (I-148)+(S11-2); (I-148)+(S11-3); (I-148)+(S12-1); (I-148)+(S13-1); (I-148)+(S13-2); (I-148)+(S13-3); (I-148)+(S13-4): (I-148)+(S13-5); (I-148)+(S13-6); (I-148)+(S13-7); (I-148)+(S13-8); (I-148)+(S13-9); (I-148)+(S14-1)

(I-149)+(S1-1); (I-149)+(S1-2); (I-149)+(S1-3); (I-149)+(S1-4); (I-149)+(S1-5); (I-149)+(S1-6); (I-149)+(S1-7); (I-149)+(S1-8); (I-149)+(S1-9); (I-149)+(S1-10); (I-149)+(S1-11); (I-149)+(S1-12); (I-149)+(S1-13); (I-149)+(S2-1); (I-149)+(S2-2); (I-149)+(S2-3); (I-149)+(S2-4); (I-149)+(S2-5); (I-149)+(S2-6); (I-149)+(S2-7); (I-149)+(S2-8); (I-149)+(S2-9); (I-149)+(S2-10); (I-149)+(S3-1); (I-149)+(S3-2); (I-149)+(S3-3); (I-149)+(S3-4); (I-149)+(S3-5); (I-149)+(S3-6); (I-149)+(S3-7); (I-149)+(S3-8); (I-149)+(S3-9); (I-149)+(S3-10); (I-149)+(S3-11); (I-149)+(S4-1); (I-149)+(S4-2); (I-149)+(S4-3); (I-149)+(S4-4); (I-149)+(S4-5); (I-149)+(S7-1); (I-149)+(S11-1); (I-149)+(S11-2); (I-149)+(S11-3); (I-149)+(S12-1); (I-149)+(S13-1); (I-149)+(S13-2); (I-149)+(S13-3); (I-149)+(S13-4): (I-149)+(S13-5); (I-149)+(S13-6); (I-149)+(S13-7); (I-149)+(S13-8); (I-149)+(S13-9); (I-149)+(S14-1)

(I-150)+(S1-1); (I-150)+(S1-2); (I-150)+(S1-3); (I-150)+(S1-4); (I-150)+(S1-5); (I-150)+(S1-6); (I-150)+(S1-7); (I-150)+(S1-8); (I-150)+(S1-9); (I-150)+(S1-10); (I-150)+(S1-11); (I-150)+(S1-12); (I-150)+(S1-13); (I-150)+(S2-1); (I-150)+(S2-2); (I-150)+(S2-3); (I-150)+(S2-4); (I-150)+(S2-5); (I-150)+(S2-6); (I-150)+(S2-7); (I-150)+(S2-8); (I-150)+(S2-9); (I-150)+(S2-10); (I-150)+(S3-1); (I-150)+(S3-2); (I-150)+(S3-3); (I-150)+(S3-4); (I-150)+(S3-5); (I-150)+(S3-6); (I-150)+(S3-7); (I-150)+(S3-8); (I-150)+(S3-9); (I-150)+(S3-10); (I-150)+(S3-11); (I-150)+(S4-1); (I-150)+(S4-2); (I-150)+(S4-3); (I-150)+(S4-4); (I-150)+(S4-5); (I-150)+(S7-1); (I-150)+(S11-1); (I-150)+(S11-2); (I-150)+(S11-3); (I-150)+(S12-1); (I-150)+(S13-1); (I-150)+(S13-2); (I-150)+(S13-3); (I-150)+(S13-4): (I-150)+(S13-5); (I-150)+(S13-6); (I-150)+(S13-7); (I-150)+(S13-8); (I-150)+(S13-9); (I-150)+(S14-1)

(I-151)+(S1-1); (I-151)+(S1-2); (I-151)+(S1-3); (I-151)+(S1-4); (I-151)+(S1-5); (I-151)+(S1-6); (I-151)+(S1-7); (I-151)+(S1-8); (I-151)+(S1-9); (I-151)+(S1-10); (I-151)+(S1-11); (I-151)+(S1-12); (I-151)+(S1-13); (I-151)+(S2-1); (I-151)+(S2-2); (I-151)+(S2-3); (I-151)+(S2-4); (I-151)+(S2-5); (I-151)+(S2-6); (I-151)+(S2-7); (I-151)+(S2-8); (I-151)+(S2-9); (I-151)+(S2-10); (I-151)+(S3-1); (I-151)+(S3-2); (I-151)+(S3-3); (I-151)+(S3-4); (I-151)+(S3-5); (I-151)+(S3-6); (I-151)+(S3-7); (I-151)+(S3-8); (I-151)+(S3-9); (I-151)+(S3-10); (I-151)+(S3-11); (I-151)+(S4-1); (I-151)+(S4-2); (I-151)+(S4-3); (I-151)+(S4-4); (I-151)+(S4-5); (I-151)+(S7-1); (I-151)+(S11-1); (I-151)+(S11-2); (I-151)+(S11-3); (I-151)+(S12-1); (I-151)+(S13-1); (I-151)+(S13-2); (I-151)+(S13-3); (I-151)+(S13-4): (I-151)+(S13-5); (I-151)+(S13-6); (I-151)+(S13-7); (I-151)+(S13-8); (I-151)+(S13-9); (I-151)+(S14-1)

(I-152)+(S1-1); (I-152)+(S1-2); (I-152)+(S1-3); (I-152)+(S1-4); (I-152)+(S1-5); (I-152)+(S1-6); (I-152)+(S1-7); (I-152)+(S1-8); (I-152)+(S1-9); (I-152)+(S1-10); (I-152)+(S1-11); (I-152)+(S1-12); (I-152)+(S1-13); (I-152)+(S2-1); (I-152)+(S2-2); (I-152)+(S2-3); (I-152)+(S2-4); (I-152)+(S2-5); (I-152)+(S2-6); (I-152)+(S2-7); (I-152)+(S2-8); (I-152)+(S2-9); (I-152)+(S2-10); (I-152)+(S3-1); (I-152)+(S3-2); (I-152)+(S3-3); (I-152)+(S3-4); (I-152)+(S3-5); (I-152)+(S3-6); (I-152)+(S3-7); (I-152)+(S3-8); (I-152)+(S3-9); (I-152)+(S3-10); (I-152)+(S3-11); (I-152)+(S4-1); (I-152)+(S4-2); (I-152)+(S4-3); (I-152)+(S4-4); (I-152)+(S4-5); (I-152)+(S7-1); (I-152)+(S11-1); (I-152)+(S11-2); (I-152)+(S11-3); (I-152)+(S12-1); (I-152)+(S13-1); (I-152)+(S13-2); (I-152)+(S13-3); (I-152)+(S13-4): (I-152)+(S13-5); (I-152)+(S13-6); (I-152)+(S13-7); (I-152)+(S13-8); (I-152)+(S13-9); (I-152)+(S14-1)

(I-153)+(S1-1); (I-153)+(S1-2); (I-153)+(S1-3); (I-153)+(S1-4); (I-153)+(S1-5); (I-153)+(S1-6); (I-153)+(S1-7); (I-153)+(S1-8); (I-153)+(S1-9); (I-153)+(S1-10); (I-153)+(S1-11); (I-153)+(S1-12); (I-153)+(S1-13); (I-153)+(S2-1); (I-153)+(S2-2); (I-153)+(S2-3); (I-153)+(S2-4); (I-153)+(S2-5); (I-153)+(S2-6); (I-153)+(S2-7); (I-153)+(S2-8); (I-153)+(S2-9); (I-153)+(S2-10); (I-153)+(S3-1); (I-153)+(S3-2); (I-153)+(S3-3); (I-153)+(S3-4); (I-153)+(S3-5); (I-153)+(S3-6); (I-153)+(S3-7); (I-153)+(S3-8); (I-153)+(S3-9); (I-153)+(S3-10); (I-153)+(S3-11); (I-153)+(S4-1); (I-153)+(S4-2); (I-153)+(S4-3); (I-153)+(S4-4); (I-153)+(S4-5); (I-153)+(S7-1); (I-153)+(S11-1); (I-153)+(S11-2); (I-153)+(S11-3); (I-153)+(S12-1); (I-153)+(S13-1); (I-153)+(S13-2); (I-153)+(S13-3); (I-153)+(S13-4): (I-153)+(S13-5); (I-153)+(S13-6); (I-153)+(S13-7); (I-153)+(S13-8); (I-153)+(S13-9); (I-153)+(S14-1)

(I-154)+(S1-1); (I-154)+(S1-2); (I-154)+(S1-3); (I-154)+(S1-4); (I-154)+(S1-5); (I-154)+(S1-6); (I-154)+(S1-7); (I-154)+(S1-8); (I-154)+(S1-9); (I-154)+(S1-10); (I-154)+(S1-11); (I-154)+(S1-12); (I-154)+(S1-13); (I-154)+(S2-1); (I-154)+(S2-2); (I-154)+(S2-3); (I-154)+(S2-4); (I-154)+(S2-5); (I-154)+(S2-6); (I-154)+(S2-7); (I-154)+(S2-8); (I-154)+(S2-9); (I-154)+(S2-10); (I-154)+(S3-1); (I-154)+(S3-2); (I-154)+(S3-3); (I-154)+(S3-4); (I-154)+(S3-5); (I-154)+(S3-6); (I-154)+(S3-7); (I-154)+(S3-8); (I-154)+(S3-9); (I-154)+(S3-10); (I-154)+(S3-11); (I-154)+(S4-1); (I-154)+(S4-2); (I-154)+(S4-3); (I-154)+(S4-4); (I-154)+(S4-5); (I-154)+(S7-1); (I-154)+(S11-1); (I-154)+(S11-2); (I-154)+(S11-3); (I-154)+(S12-1); (I-154)+(S13-1); (I-154)+(S13-2); (I-154)+(S13-3); (I-154)+(S13-4): (I-154)+(S13-5); (I-154)+(S13-6); (I-154)+(S13-7); (I-154)+(S13-8); (I-154)+(S13-9); (I-154)+(S14-1)

(I-155)+(S1-1); (I-155)+(S1-2); (I-155)+(S1-3); (I-155)+(S1-4); (I-155)+(S1-5); (I-155)+(S1-6); (I-155)+(S1-7); (I-155)+(S1-8); (I-155)+(S1-9); (I-155)+(S1-10); (I-155)+(S1-11); (I-155)+(S1-12); (I-155)+(S1-13); (I-155)+(S2-1); (I-155)+(S2-2); (I-155)+(S2-3); (I-155)+(S2-4); (I-155)+(S2-5); (I-155)+(S2-6); (I-155)+(S2-7); (I-155)+(S2-8); (I-155)+(S2-9); (I-155)+(S2-10); (I-155)+(S3-1); (I-155)+(S3-2); (I-155)+(S3-3); (I-155)+(S3-4); (I-155)+(S3-5); (I-155)+(S3-6); (I-155)+(S3-7); (I-155)+(S3-8); (I-155)+(S3-9); (I-155)+(S3-10); (I-155)+(S3-11); (I-155)+(S4-1); (I-155)+(S4-2); (I-155)+(S4-3); (I-155)+(S4-4); (I-155)+(S4-5); (I-155)+(S7-1); (I-155)+(S11-1); (I-155)+(S11-2); (I-155)+(S11-3); (I-155)+(S12-1); (I-155)+(S13-1); (I-155)+(S13-2); (I-155)+(S13-3); (I-155)+(S13-4): (I-155)+(S13-5); (I-155)+(S13-6); (I-155)+(S13-7); (I-155)+(S13-8); (I-155)+(S13-9); (I-155)+(S14-1)

(I-156)+(S1-1); (I-156)+(S1-2); (I-156)+(S1-3); (I-156)+(S1-4); (I-156)+(S1-5); (I-156)+(S1-6); (I-156)+(S1-7); (I-156)+(S1-8); (I-156)+(S1-9); (I-156)+(S1-10); (I-156)+(S1-11); (I-156)+(S1-12); (I-156)+(S1-13); (I-156)+(S2-1); (I-156)+(S2-2); (I-156)+(S2-3); (I-156)+(S2-4); (I-156)+(S2-5); (I-156)+(S2-6); (I-156)+(S2-7); (I-156)+(S2-8); (I-156)+(S2-9); (I-156)+(S2-10); (I-156)+(S3-1); (I-156)+(S3-2); (I-156)+(S3-3); (I-156)+(S3-4); (I-156)+(S3-5); (I-156)+(S3-6); (I-156)+(S3-7); (I-156)+(S3-8); (I-156)+(S3-9); (I-156)+(S3-10); (I-156)+(S3-11); (I-156)+(S4-1); (I-156)+(S4-2); (I-156)+(S4-3); (I-156)+(S4-4); (I-156)+(S4-5); (I-156)+(S7-1); (I-156)+(S11-1); (I-156)+(S11-2); (I-156)+(S11-3); (I-156)+(S12-1); (I-156)+(S13-1); (I-156)+(S13-2); (I-156)+(S13-3); (I-156)+(S13-4): (I-156)+(S13-5); (I-156)+(S13-6); (I-156)+(S13-7); (I-156)+(S13-8); (I-156)+(S13-9); (I-156)+(S14-1)

(I-157)+(S1-1); (I-157)+(S1-2); (I-157)+(S1-3); (I-157)+(S1-4); (I-157)+(S1-5); (I-157)+(S1-6); (I-157)+(S1-7); (I-157)+(S1-8); (I-157)+(S1-9); (I-157)+(S1-10); (I-157)+(S1-11); (I-157)+(S1-12); (I-157)+(S1-13); (I-157)+(S2-1); (I-157)+(S2-2); (I-157)+(S2-3); (I-157)+(S2-4); (I-157)+(S2-5); (I-157)+(S2-6); (I-157)+(S2-7); (I-157)+(S2-8); (I-157)+(S2-9); (I-157)+(S2-10); (I-157)+(S3-1); (I-157)+(S3-2); (I-157)+(S3-3); (I-157)+(S3-4); (I-157)+(S3-5); (I-157)+(S3-6); (I-157)+(S3-7); (I-157)+(S3-8); (I-157)+(S3-9); (I-157)+(S3-10); (I-157)+(S3-11); (I-157)+(S4-1); (I-157)+(S4-2); (I-157)+(S4-3); (I-157)+(S4-4); (I-157)+(S4-5); (I-157)+(S7-1); (I-157)+(S11-1); (I-157)+(S11-2); (I-157)+(S11-3); (I-157)+(S12-1); (I-157)+(S13-1); (I-157)+(S13-2); (I-157)+(S13-3); (I-157)+(S13-4): (I-157)+(S13-5); (I-157)+(S13-6); (I-157)+(S13-7); (I-157)+(S13-8); (I-157)+(S13-9); (I-157)+(S14-1)

(I-158)+(S1-1); (I-158)+(S1-2); (I-158)+(S1-3); (I-158)+(S1-4); (I-158)+(S1-5); (I-158)+(S1-6); (I-158)+(S1-7); (I-158)+(S1-8); (I-158)+(S1-9); (I-158)+(S1-10); (I-158)+(S1-11); (I-158)+(S1-12); (I-158)+(S1-13); (I-158)+(S2-1); (I-158)+(S2-2); (I-158)+(S2-3); (I-158)+(S2-4); (I-158)+(S2-5); (I-158)+(S2-6); (I-158)+(S2-7); (I-158)+(S2-8); (I-158)+(S2-9); (I-158)+(S2-10); (I-158)+(S3-1); (I-158)+(S3-2); (I-158)+(S3-3); (I-158)+(S3-4); (I-158)+(S3-5); (I-158)+(S3-6); (I-158)+(S3-7); (I-158)+(S3-8); (I-158)+(S3-9); (I-158)+(S3-10); (I-158)+(S3-11); (I-158)+(S4-1); (I-158)+(S4-2); (I-158)+(S4-3); (I-158)+(S4-4); (I-158)+(S4-5); (I-158)+(S7-1); (I-158)+(S11-1); (I-158)+(S11-2); (I-158)+(S11-3); (I-158)+(S12-1); (I-158)+(S13-1); (I-158)+(S13-2); (I-158)+(S13-3); (I-158)+(S13-4): (I-158)+(S13-5); (I-158)+(S13-6); (I-158)+(S13-7); (I-158)+(S13-8); (I-158)+(S13-9); (I-158)+(S14-1)

(I-159)+(S1-1); (I-159)+(S1-2); (I-159)+(S1-3); (I-159)+(S1-4); (I-159)+(S1-5); (I-159)+(S1-6); (I-159)+(S1-7); (I-159)+(S1-8); (I-159)+(S1-9); (I-159)+(S1-10); (I-159)+(S1-11); (I-159)+(S1-12); (I-159)+(S1-13); (I-159)+(S2-1); (I-159)+(S2-2); (I-159)+(S2-3); (I-159)+(S2-4); (I-159)+(S2-5); (I-159)+(S2-6); (I-159)+(S2-7); (I-159)+(S2-8); (I-159)+(S2-9); (I-159)+(S2-10); (I-159)+(S3-1); (I-159)+(S3-2); (I-159)+(S3-3); (I-159)+(S3-4); (I-159)+(S3-5); (I-159)+(S3-6); (I-159)+(S3-7); (I-159)+(S3-8); (I-159)+(S3-9); (I-159)+(S3-10); (I-159)+(S3-11); (I-159)+(S4-1); (I-159)+(S4-2); (I-159)+(S4-3); (I-159)+(S4-4); (I-159)+(S4-5); (I-159)+(S7-1); (I-159)+(S11-1); (I-159)+(S11-2); (I-159)+(S11-3); (I-159)+(S12-1); (I-159)+(S13-1); (I-159)+(S13-2); (I-159)+(S13-3); (I-159)+(S13-4): (I-159)+(S13-5); (I-159)+(S13-6); (I-159)+(S13-7); (I-159)+(S13-8); (I-159)+(S13-9); (I-159)+(S14-1)

(I-160)+(S1-1); (I-160)+(S1-2); (I-160)+(S1-3); (I-160)+(S1-4); (I-160)+(S1-5); (I-160)+(S1-6); (I-160)+(S1-7); (I-160)+(S1-8); (I-160)+(S1-9); (I-160)+(S1-10); (I-160)+(S1-11); (I-160)+(S1-12); (I-160)+(S1-13); (I-160)+(S2-1); (I-160)+(S2-2); (I-160)+(S2-3); (I-160)+(S2-4); (I-160)+(S2-5); (I-160)+(S2-6); (I-160)+(S2-7); (I-160)+(S2-8);

(I-160)+(S2-9); (I-160)+(S2-10); (I-160)+(S3-1); (I-160)+(S3-2); (I-160)+(S3-3); (I-160)+(S3-4); (I-160)+(S3-5); (I-160)+(S3-6); (I-160)+(S3-7); (I-160)+(S3-8); (I-160)+(S3-9); (I-160)+(S3-10); (I-160)+(S3-11); (I-160)+(S4-1); (I-160)+(S4-2); (I-160)+(S4-3); (I-160)+(S4-4); (I-160)+(S4-5); (I-160)+(S7-1); (I-160)+(S11-1); (I-160)+(S11-2); (I-160)+(S11-3); (I-160)+(S12-1); (I-160)+(S13-1); (I-160)+(S13-2); (I-160)+(S13-3); (I-160)+(S13-4): (I-160)+(S13-5); (I-160)+(S13-6); (I-160)+(S13-7); (I-160)+(S13-8); (I-160)+(S13-9); (I-160)+(S14-1)

(I-161)+(S1-1); (I-161)+(S1-2); (I-161)+(S1-3); (I-161)+(S1-4); (I-161)+(S1-5); (I-161)+(S1-6); (I-161)+(S1-7); (I-161)+(S1-8); (I-161)+(S1-9); (I-161)+(S1-10); (I-161)+(S1-11); (I-161)+(S1-12); (I-161)+(S1-13); (I-161)+(S2-1); (I-161)+(S2-2); (I-161)+(S2-3); (I-161)+(S2-4); (I-161)+(S2-5); (I-161)+(S2-6); (I-161)+(S2-7); (I-161)+(S2-8); (I-161)+(S2-9); (I-161)+(S2-10); (I-161)+(S3-1); (I-161)+(S3-2); (I-161)+(S3-3); (I-161)+(S3-4); (I-161)+(S3-5); (I-161)+(S3-6); (I-161)+(S3-7); (I-161)+(S3-8); (I-161)+(S3-9); (I-161)+(S3-10); (I-161)+(S3-11); (I-161)+(S4-1); (I-161)+(S4-2); (I-161)+(S4-3); (I-161)+(S4-4); (I-161)+(S4-5); (I-161)+(S7-1); (I-161)+(S11-1); (I-161)+(S11-2); (I-161)+(S11-3); (I-161)+(S12-1); (I-161)+(S13-1); (I-161)+(S13-2); (I-161)+(S13-3); (I-161)+(S13-4): (I-161)+(S13-5); (I-161)+(S13-6); (I-161)+(S13-7); (I-161)+(S13-8); (I-161)+(S13-9); (I-161)+(S14-1)

(I-162)+(S1-1); (I-162)+(S1-2); (I-162)+(S1-3); (I-162)+(S1-4); (I-162)+(S1-5); (I-162)+(S1-6); (I-162)+(S1-7); (I-162)+(S1-8); (I-162)+(S1-9); (I-162)+(S1-10); (I-162)+(S1-11); (I-162)+(S1-12); (I-162)+(S1-13); (I-162)+(S2-1); (I-162)+(S2-2); (I-162)+(S2-3); (I-162)+(S2-4); (I-162)+(S2-5); (I-162)+(S2-6); (I-162)+(S2-7); (I-162)+(S2-8); (I-162)+(S2-9); (I-162)+(S2-10); (I-162)+(S3-1); (I-162)+(S3-2); (I-162)+(S3-3); (I-162)+(S3-4); (I-162)+(S3-5); (I-162)+(S3-6); (I-162)+(S3-7); (I-162)+(S3-8); (I-162)+(S3-9); (I-162)+(S3-10); (I-162)+(S3-11); (I-162)+(S4-1); (I-162)+(S4-2); (I-162)+(S4-3); (I-162)+(S4-4); (I-162)+(S4-5); (I-162)+(S7-1); (I-162)+(S11-1); (I-162)+(S11-2); (I-162)+(S11-3); (I-162)+(S12-1); (I-162)+(S13-1); (I-162)+(S13-2); (I-162)+(S13-3); (I-162)+(S13-4): (I-162)+(S13-5); (I-162)+(S13-6); (I-162)+(S13-7); (I-162)+(S13-8); (I-162)+(S13-9); (I-162)+(S14-1)

(I-163)+(S1-1); (I-163)+(S1-2); (I-163)+(S1-3); (I-163)+(S1-4); (I-163)+(S1-5); (I-163)+(S1-6); (I-163)+(S1-7); (I-163)+(S1-8); (I-163)+(S1-9); (I-163)+(S1-10); (I-163)+(S1-11); (I-163)+(S1-12); (I-163)+(S1-13); (I-163)+(S2-1); (I-163)+(S2-2); (I-163)+(S2-3); (I-163)+(S2-4); (I-163)+(S2-5); (I-163)+(S2-6); (I-163)+(S2-7); (I-163)+(S2-8); (I-163)+(S2-9); (I-163)+(S2-10); (I-163)+(S3-1); (I-163)+(S3-2); (I-163)+(S3-3); (I-163)+(S3-4); (I-163)+(S3-5); (I-163)+(S3-6); (I-163)+(S3-7); (I-163)+(S3-8); (I-163)+(S3-9); (I-163)+(S3-10); (I-163)+(S3-11); (I-163)+(S4-1); (I-163)+(S4-2); (I-163)+(S4-3); (I-163)+(S4-4); (I-163)+(S4-5); (I-163)+(S7-1); (I-163)+(S11-1); (I-163)+(S11-2); (I-163)+(S11-3); (I-163)+(S12-1); (I-163)+(S13-1); (I-163)+(S13-2); (I-163)+(S13-3); (I-163)+(S13-4): (I-163)+(S13-5); (I-163)+(S13-6); (I-163)+(S13-7); (I-163)+(S13-8); (I-163)+(S13-9); (I-163)+(S14-1)

(I-164)+(S1-1); (I-164)+(S1-2); (I-164)+(S1-3); (I-164)+(S1-4); (I-164)+(S1-5); (I-164)+(S1-6); (I-164)+(S1-7); (I-164)+(S1-8); (I-164)+(S1-9); (I-164)+(S1-10); (I-164)+(S1-11); (I-164)+(S1-12); (I-164)+(S1-13); (I-164)+(S2-1); (I-164)+(S2-2); (I-164)+(S2-3); (I-164)+(S2-4); (I-164)+(S2-5); (I-164)+(S2-6); (I-164)+(S2-7); (I-164)+(S2-8); (I-164)+(S2-9); (I-164)+(S2-10); (I-164)+(S3-1); (I-164)+(S3-2); (I-164)+(S3-3); (I-164)+(S3-4); (I-164)+(S3-5); (I-164)+(S3-6); (I-164)+(S3-7); (I-164)+(S3-8); (I-164)+(S3-9); (I-164)+(S3-10); (I-164)+(S3-11); (I-164)+(S4-1); (I-164)+(S4-2); (I-164)+(S4-3); (I-164)+(S4-4); (I-164)+(S4-5); (I-164)+(S7-1); (I-164)+(S11-1); (I-164)+(S11-2); (I-164)+(S11-3); (I-164)+(S12-1); (I-164)+(S13-1); (I-164)+(S13-2); (I-164)+(S13-3); (I-164)+(S13-4): (I-164)+(S13-5); (I-164)+(S13-6); (I-164)+(S13-7); (I-164)+(S13-8); (I-164)+(S13-9); (I-164)+(S14-1)

(I-165)+(S1-1); (I-165)+(S1-2); (I-165)+(S1-3); (I-165)+(S1-4); (I-165)+(S1-5); (I-165)+(S1-6); (I-165)+(S1-7); (I-165)+(S1-8); (I-165)+(S1-9); (I-165)+(S1-10); (I-165)+(S1-11); (I-165)+(S1-12); (I-165)+(S1-13); (I-165)+(S2-1); (I-165)+(S2-2); (I-165)+(S2-3); (I-165)+(S2-4); (I-165)+(S2-5); (I-165)+(S2-6); (I-165)+(S2-7); (I-165)+(S2-8); (I-165)+(S2-9); (I-165)+(S2-10); (I-165)+(S3-1); (I-165)+(S3-2); (I-165)+(S3-3); (I-165)+(S3-4); (I-165)+(S3-5); (I-165)+(S3-6); (I-165)+(S3-7); (I-165)+(S3-8); (I-165)+(S3-9); (I-165)+(S3-10); (I-165)+(S3-11); (I-165)+(S4-1); (I-165)+(S4-2); (I-165)+(S4-3); (I-165)+(S4-4); (I-165)+(S4-5); (I-165)+(S7-1); (I-165)+(S11-1); (I-165)+(S11-2); (I-165)+(S11-3); (I-165)+(S12-1); (I-165)+(S13-1); (I-165)+(S13-2); (I-165)+(S13-3); (I-165)+(S13-4): (I-165)+(S13-5); (I-165)+(S13-6); (I-165)+(S13-7); (I-165)+(S13-8); (I-165)+(S13-9); (I-165)+(S14-1)

(I-166)+(S1-1); (I-166)+(S1-2); (I-166)+(S1-3); (I-166)+(S1-4); (I-166)+(S1-5); (I-166)+(S1-6); (I-166)+(S1-7); (I-166)+(S1-8); (I-166)+(S1-9); (I-166)+(S1-10); (I-166)+(S1-11); (I-166)+(S1-12); (I-166)+(S1-13); (I-166)+(S2-1); (I-166)+(S2-2); (I-166)+(S2-3); (I-166)+(S2-4); (I-166)+(S2-5); (I-166)+(S2-6); (I-166)+(S2-7); (I-166)+(S2-8); (I-166)+(S2-9); (I-166)+(S2-10); (I-166)+(S3-1); (I-166)+(S3-2); (I-166)+(S3-3); (I-166)+(S3-4); (I-166)+(S3-5); (I-166)+(S3-6); (I-166)+(S3-7); (I-166)+(S3-8); (I-166)+(S3-9); (I-166)+(S3-10); (I-166)+(S3-11); (I-166)+(S4-1); (I-166)+(S4-2); (I-166)+(S4-3); (I-166)+(S4-4); (I-166)+(S4-5); (I-166)+(S7-1); (I-166)+(S11-1); (I-166)+(S11-2); (I-166)+(S11-3); (I-166)+(S12-1); (I-166)+(S13-1); (I-166)+(S13-2); (I-166)+(S13-3); (I-166)+(S13-4): (I-166)+(S13-5); (I-166)+(S13-6); (I-166)+(S13-7); (I-166)+(S13-8); (I-166)+(S13-9); (I-166)+(S14-1)

(I-167)+(S1-1); (I-167)+(S1-2); (I-167)+(S1-3); (I-167)+(S1-4); (I-167)+(S1-5); (I-167)+(S1-6); (I-167)+(S1-7); (I-167)+(S1-8); (I-167)+(S1-9); (I-167)+(S1-10); (I-167)+(S1-11); (I-167)+(S1-12); (I-167)+(S1-13); (I-167)+(S2-1); (I-167)+(S2-2); (I-167)+(S2-3); (I-167)+(S2-4); (I-167)+(S2-5); (I-167)+(S2-6); (I-167)+(S2-7); (I-167)+(S2-8); (I-167)+(S2-9); (I-167)+(S2-10); (I-167)+(S3-1); (I-167)+(S3-2); (I-167)+(S3-3); (I-167)+(S3-4); (I-167)+(S3-5); (I-167)+(S3-6); (I-167)+(S3-7); (I-167)+(S3-8); (I-167)+(S3-9); (I-167)+(S3-10); (I-167)+(S3-11); (I-167)+(S4-1); (I-167)+(S4-2); (I-167)+(S4-3); (I-167)+(S4-4); (I-167)+(S4-5); (I-167)+(S7-1); (I-167)+(S11-1); (I-167)+(S11-2); (I-167)+(S11-3); (I-167)+(S12-1); (I-167)+(S13-1); (I-167)+(S13-2); (I-167)+(S13-3); (I-167)+(S13-4): (I-167)+(S13-5); (I-167)+(S13-6); (I-167)+(S13-7); (I-167)+(S13-8); (I-167)+(S13-9); (I-167)+(S14-1)

(I-168)+(S1-1); (I-168)+(S1-2); (I-168)+(S1-3); (I-168)+(S1-4); (I-168)+(S1-5); (I-168)+(S1-6); (I-168)+(S1-7); (I-168)+(S1-8); (I-168)+(S1-9); (I-168)+(S1-10); (I-168)+(S1-11); (I-168)+(S1-12); (I-168)+(S1-13); (I-168)+(S2-1); (I-168)+(S2-2); (I-168)+(S2-3); (I-168)+(S2-4); (I-168)+(S2-5); (I-168)+(S2-6); (I-168)+(S2-7); (I-168)+(S2-8); (I-168)+(S2-9); (I-168)+(S2-10); (I-168)+(S3-1); (I-168)+(S3-2); (I-168)+(S3-3); (I-168)+(S3-4); (I-168)+(S3-5); (I-168)+(S3-6); (I-168)+(S3-7); (I-168)+(S3-8); (I-168)+(S3-9); (I-168)+(S3-10); (I-168)+(S3-11); (I-168)+(S4-1); (I-168)+(S4-2); (I-168)+(S4-3); (I-168)+(S4-4); (I-168)+(S4-5); (I-168)+(S7-1); (I-168)+(S11-1); (I-168)+(S11-2);

(I-168)+(S11-3); (I-168)+(S12-1); (I-168)+(S13-1); (I-168)+(S13-2); (I-168)+(S13-3); (I-168)+(S13-4): (I-168)+(S13-5); (I-168)+(S13-6); (I-168)+(S13-7); (I-168)+(S13-8); (I-168)+(S13-9); (I-168)+(S14-1)

(I-169)+(S1-1); (I-169)+(S1-2); (I-169)+(S1-3); (I-169)+(S1-4); (I-169)+(S1-5); (I-169)+(S1-6); (I-169)+(S1-7); (I-169)+(S1-8); (I-169)+(S1-9); (I-169)+(S1-10); (I-169)+(S1-11); (I-169)+(S1-12); (I-169)+(S1-13); (I-169)+(S2-1); (I-169)+(S2-2); (I-169)+(S2-3); (I-169)+(S2-4); (I-169)+(S2-5); (I-169)+(S2-6); (I-169)+(S2-7); (I-169)+(S2-8); (I-169)+(S2-9); (I-169)+(S2-10); (I-169)+(S3-1); (I-169)+(S3-2); (I-169)+(S3-3); (I-169)+(S3-4); (I-169)+(S3-5); (I-169)+(S3-6); (I-169)+(S3-7); (I-169)+(S3-8); (I-169)+(S3-9); (I-169)+(S3-10); (I-169)+(S3-11); (I-169)+(S4-1); (I-169)+(S4-2); (I-169)+(S4-3); (I-169)+(S4-4); (I-169)+(S4-5); (I-169)+(S7-1); (I-169)+(S11-1); (I-169)+(S11-2); (I-169)+(S11-3); (I-169)+(S12-1); (I-169)+(S13-1); (I-169)+(S13-2); (I-169)+(S13-3); (I-169)+(S13-4): (I-169)+(S13-5); (I-169)+(S13-6); (I-169)+(S13-7); (I-169)+(S13-8); (I-169)+(S13-9); (I-169)+(S14-1)

(I-170)+(S1-1); (I-170)+(S1-2); (I-170)+(S1-3); (I-170)+(S1-4); (I-170)+(S1-5); (I-170)+(S1-6); (I-170)+(S1-7); (I-170)+(S1-8); (I-170)+(S1-9); (I-170)+(S1-10); (I-170)+(S1-11); (I-170)+(S1-12); (I-170)+(S1-13); (I-170)+(S2-1); (I-170)+(S2-2); (I-170)+(S2-3); (I-170)+(S2-4); (I-170)+(S2-5); (I-170)+(S2-6); (I-170)+(S2-7); (I-170)+(S2-8); (I-170)+(S2-9); (I-170)+(S2-10); (I-170)+(S3-1); (I-170)+(S3-2); (I-170)+(S3-3); (I-170)+(S3-4); (I-170)+(S3-5); (I-170)+(S3-6); (I-170)+(S3-7); (I-170)+(S3-8); (I-170)+(S3-9); (I-170)+(S3-10); (I-170)+(S3-11); (I-170)+(S4-1); (I-170)+(S4-2); (I-170)+(S4-3); (I-170)+(S4-4); (I-170)+(S4-5); (I-170)+(S7-1); (I-170)+(S11-1); (I-170)+(S11-2); (I-170)+(S11-3); (I-170)+(S12-1); (I-170)+(S13-1); (I-170)+(S13-2); (I-170)+(S13-3); (I-170)+(S13-4): (I-170)+(S13-5); (I-170)+(S13-6); (I-170)+(S13-7); (I-170)+(S13-8); (I-170)+(S13-9); (I-170)+(S14-1)

(I-171)+(S1-1); (I-171)+(S1-2); (I-171)+(S1-3); (I-171)+(S1-4); (I-171)+(S1-5); (I-171)+(S1-6); (I-171)+(S1-7); (I-171)+(S1-8); (I-171)+(S1-9); (I-171)+(S1-10); (I-171)+(S1-11); (I-171)+(S1-12); (I-171)+(S1-13); (I-171)+(S2-1); (I-171)+(S2-2); (I-171)+(S2-3); (I-171)+(S2-4); (I-171)+(S2-5); (I-171)+(S2-6); (I-171)+(S2-7); (I-171)+(S2-8); (I-171)+(S2-9); (I-171)+(S2-10); (I-171)+(S3-1); (I-171)+(S3-2); (I-171)+(S3-3); (I-171)+(S3-4); (I-171)+(S3-5); (I-171)+(S3-6); (I-171)+(S3-7); (I-171)+(S3-8); (I-171)+(S3-9); (I-171)+(S3-10); (I-171)+(S3-11); (I-171)+(S4-1); (I-171)+(S4-2); (I-171)+(S4-3); (I-171)+(S4-4); (I-171)+(S4-5); (I-171)+(S7-1); (I-171)+(S11-1); (I-171)+(S11-2); (I-171)+(S11-3); (I-171)+(S12-1); (I-171)+(S13-1); (I-171)+(S13-2); (I-171)+(S13-3); (I-171)+(S13-4): (I-171)+(S13-5); (I-171)+(S13-6); (I-171)+(S13-7); (I-171)+(S13-8); (I-171)+(S13-9); (I-171)+(S14-1)

(I-172)+(S1-1); (I-172)+(S1-2); (I-172)+(S1-3); (I-172)+(S1-4); (I-172)+(S1-5); (I-172)+(S1-6); (I-172)+(S1-7); (I-172)+(S1-8); (I-172)+(S1-9); (I-172)+(S1-10); (I-172)+(S1-11); (I-172)+(S1-12); (I-172)+(S1-13); (I-172)+(S2-1); (I-172)+(S2-2); (I-172)+(S2-3); (I-172)+(S2-4); (I-172)+(S2-5); (I-172)+(S2-6); (I-172)+(S2-7); (I-172)+(S2-8); (I-172)+(S2-9); (I-172)+(S2-10); (I-172)+(S3-1); (I-172)+(S3-2); (I-172)+(S3-3); (I-172)+(S3-4); (I-172)+(S3-5); (I-172)+(S3-6); (I-172)+(S3-7); (I-172)+(S3-8); (I-172)+(S3-9); (I-172)+(S3-10); (I-172)+(S3-11); (I-172)+(S4-1); (I-172)+(S4-2); (I-172)+(S4-3); (I-172)+(S4-4); (I-172)+(S4-5); (I-172)+(S7-1); (I-172)+(S11-1); (I-172)+(S11-2); (I-172)+(S11-3); (I-172)+(S12-1); (I-172)+(S13-1); (I-172)+(S13-2); (I-172)+(S13-3); (I-172)+(S13-4): (I-172)+(S13-5); (I-172)+(S13-6); (I-172)+(S13-7); (I-172)+(S13-8); (I-172)+(S13-9); (I-172)+(S14-1)

(I-173)+(S1-1); (I-173)+(S1-2); (I-173)+(S1-3); (I-173)+(S1-4); (I-173)+(S1-5); (I-173)+(S1-6); (I-173)+(S1-7); (I-173)+(S1-8); (I-173)+(S1-9); (I-173)+(S1-10); (I-173)+(S1-11); (I-173)+(S1-12); (I-173)+(S1-13); (I-173)+(S2-1); (I-173)+(S2-2); (I-173)+(S2-3); (I-173)+(S2-4); (I-173)+(S2-5); (I-173)+(S2-6); (I-173)+(S2-7); (I-173)+(S2-8); (I-173)+(S2-9); (I-173)+(S2-10); (I-173)+(S3-1); (I-173)+(S3-2); (I-173)+(S3-3); (I-173)+(S3-4); (I-173)+(S3-5); (I-173)+(S3-6); (I-173)+(S3-7); (I-173)+(S3-8); (I-173)+(S3-9); (I-173)+(S3-10); (I-173)+(S3-11); (I-173)+(S4-1); (I-173)+(S4-2); (I-173)+(S4-3); (I-173)+(S4-4); (I-173)+(S4-5); (I-173)+(S7-1); (I-173)+(S11-1); (I-173)+(S11-2); (I-173)+(S11-3); (I-173)+(S12-1); (I-173)+(S13-1); (I-173)+(S13-2); (I-173)+(S13-3); (I-173)+(S13-4): (I-173)+(S13-5); (I-173)+(S13-6); (I-173)+(S13-7); (I-173)+(S13-8); (I-173)+(S13-9); (I-173)+(S14-1)

(I-174)+(S1-1); (I-174)+(S1-2); (I-174)+(S1-3); (I-174)+(S1-4); (I-174)+(S1-5); (I-174)+(S1-6); (I-174)+(S1-7); (I-174)+(S1-8); (I-174)+(S1-9); (I-174)+(S1-10); (I-174)+(S1-11); (I-174)+(S1-12); (I-174)+(S1-13); (I-174)+(S2-1); (I-174)+(S2-2); (I-174)+(S2-3); (I-174)+(S2-4); (I-174)+(S2-5); (I-174)+(S2-6); (I-174)+(S2-7); (I-174)+(S2-8); (I-174)+(S2-9); (I-174)+(S2-10); (I-174)+(S3-1); (I-174)+(S3-2); (I-174)+(S3-3); (I-174)+(S3-4); (I-174)+(S3-5); (I-174)+(S3-6); (I-174)+(S3-7); (I-174)+(S3-8); (I-174)+(S3-9); (I-174)+(S3-10); (I-174)+(S3-11); (I-174)+(S4-1); (I-174)+(S4-2); (I-174)+(S4-3); (I-174)+(S4-4); (I-174)+(S4-5); (I-174)+(S7-1); (I-174)+(S11-1); (I-174)+(S11-2); (I-174)+(S11-3); (I-174)+(S12-1); (I-174)+(S13-1); (I-174)+(S13-2); (I-174)+(S13-3); (I-174)+(S13-4): (I-174)+(S13-5); (I-174)+(S13-6); (I-174)+(S13-7); (I-174)+(S13-8); (I-174)+(S13-9); (I-174)+(S14-1)

(I-175)+(S1-1); (I-175)+(S1-2); (I-175)+(S1-3); (I-175)+(S1-4); (I-175)+(S1-5); (I-175)+(S1-6); (I-175)+(S1-7); (I-175)+(S1-8); (I-175)+(S1-9); (I-175)+(S1-10); (I-175)+(S1-11); (I-175)+(S1-12); (I-175)+(S1-13); (I-175)+(S2-1); (I-175)+(S2-2); (I-175)+(S2-3); (I-175)+(S2-4); (I-175)+(S2-5); (I-175)+(S2-6); (I-175)+(S2-7); (I-175)+(S2-8); (I-175)+(S2-9); (I-175)+(S2-10); (I-175)+(S3-1); (I-175)+(S3-2); (I-175)+(S3-3); (I-175)+(S3-4); (I-175)+(S3-5); (I-175)+(S3-6); (I-175)+(S3-7); (I-175)+(S3-8); (I-175)+(S3-9); (I-175)+(S3-10); (I-175)+(S3-11); (I-175)+(S4-1); (I-175)+(S4-2); (I-175)+(S4-3); (I-175)+(S4-4); (I-175)+(S4-5); (I-175)+(S7-1); (I-175)+(S11-1); (I-175)+(S11-2); (I-175)+(S11-3); (I-175)+(S12-1); (I-175)+(S13-1); (I-175)+(S13-2); (I-175)+(S13-3); (I-175)+(S13-4): (I-175)+(S13-5); (I-175)+(S13-6); (I-175)+(S13-7); (I-175)+(S13-8); (I-175)+(S13-9); (I-175)+(S14-1)

(I-176)+(S1-1); (I-176)+(S1-2); (I-176)+(S1-3); (I-176)+(S1-4); (I-176)+(S1-5); (I-176)+(S1-6); (I-176)+(S1-7); (I-176)+(S1-8); (I-176)+(S1-9); (I-176)+(S1-10); (I-176)+(S1-11); (I-176)+(S1-12); (I-176)+(S1-13); (I-176)+(S2-1); (I-176)+(S2-2); (I-176)+(S2-3); (I-176)+(S2-4); (I-176)+(S2-5); (I-176)+(S2-6); (I-176)+(S2-7); (I-176)+(S2-8); (I-176)+(S2-9); (I-176)+(S2-10); (I-176)+(S3-1); (I-176)+(S3-2); (I-176)+(S3-3); (I-176)+(S3-4); (I-176)+(S3-5); (I-176)+(S3-6); (I-176)+(S3-7); (I-176)+(S3-8); (I-176)+(S3-9); (I-176)+(S3-10); (I-176)+(S3-11); (I-176)+(S4-1); (I-176)+(S4-2); (I-176)+(S4-3); (I-176)+(S4-4); (I-176)+(S4-5); (I-176)+(S7-1); (I-176)+(S11-1); (I-176)+(S11-2); (I-176)+(S11-3); (I-176)+(S12-1); (I-176)+(S13-1); (I-176)+(S13-2); (I-176)+(S13-3); (I-176)+(S13-4): (I-176)+(S13-5); (I-176)+(S13-6); (I-176)+(S13-7); (I-176)+(S13-8); (I-176)+(S13-9); (I-176)+(S14-1)

(I-177)+(S1-1); (I-177)+(S1-2); (I-177)+(S1-3); (I-177)+(S1-4); (I-177)+(S1-5); (I-177)+(S1-6); (I-177)+(S1-7); (I-177)+(S1-8); (I-177)+(S1-9); (I-177)+(S1-10); (I-177)+(S1-11); (I-177)+(S1-12); (I-177)+(S1-13); (I-177)+(S2-1); (I-177)+(S2-2); (I-177)+(S2-3); (I-177)+(S2-4); (I-177)+(S2-5); (I-177)+(S2-6); (I-177)+(S2-7); (I-177)+(S2-8); (I-177)+(S2-9); (I-177)+(S2-10); (I-177)+(S3-1); (I-177)+(S3-2); (I-177)+(S3-3); (I-177)+(S3-4); (I-177)+(S3-5); (I-177)+(S3-6); (I-177)+(S3-7); (I-177)+(S3-8); (I-177)+(S3-9); (I-177)+(S3-10); (I-177)+(S3-11); (I-177)+(S4-1); (I-177)+(S4-2); (I-177)+(S4-3); (I-177)+(S4-4); (I-177)+(S4-5); (I-177)+(S7-1); (I-177)+(S11-1); (I-177)+(S11-2); (I-177)+(S11-3); (I-177)+(S12-1); (I-177)+(S13-1); (I-177)+(S13-2); (I-177)+(S13-3); (I-177)+(S13-4): (I-177)+(S13-5); (I-177)+(S13-6); (I-177)+(S13-7); (I-177)+(S13-8); (I-177)+(S13-9); (I-177)+(S14-1)

(I-178)+(S1-1); (I-178)+(S1-2); (I-178)+(S1-3); (I-178)+(S1-4); (I-178)+(S1-5); (I-178)+(S1-6); (I-178)+(S1-7); (I-178)+(S1-8); (I-178)+(S1-9); (I-178)+(S1-10); (I-178)+(S1-11); (I-178)+(S1-12); (I-178)+(S1-13); (I-178)+(S2-1); (I-178)+(S2-2); (I-178)+(S2-3); (I-178)+(S2-4); (I-178)+(S2-5); (I-178)+(S2-6); (I-178)+(S2-7); (I-178)+(S2-8); (I-178)+(S2-9); (I-178)+(S2-10); (I-178)+(S3-1); (I-178)+(S3-2); (I-178)+(S3-3); (I-178)+(S3-4); (I-178)+(S3-5); (I-178)+(S3-6); (I-178)+(S3-7); (I-178)+(S3-8); (I-178)+(S3-9); (I-178)+(S3-10); (I-178)+(S3-11); (I-178)+(S4-1); (I-178)+(S4-2); (I-178)+(S4-3); (I-178)+(S4-4); (I-178)+(S4-5); (I-178)+(S7-1); (I-178)+(S11-1); (I-178)+(S11-2); (I-178)+(S11-3); (I-178)+(S12-1); (I-178)+(S13-1); (I-178)+(S13-2); (I-178)+(S13-3); (I-178)+(S13-4): (I-178)+(S13-5); (I-178)+(S13-6); (I-178)+(S13-7); (I-178)+(S13-8); (I-178)+(S13-9); (I-178)+(S14-1)

(I-179)+(S1-1); (I-179)+(S1-2); (I-179)+(S1-3); (I-179)+(S1-4); (I-179)+(S1-5); (I-179)+(S1-6); (I-179)+(S1-7); (I-179)+(S1-8); (I-179)+(S1-9); (I-179)+(S1-10); (I-179)+(S1-11); (I-179)+(S1-12); (I-179)+(S1-13); (I-179)+(S2-1); (I-179)+(S2-2); (I-179)+(S2-3); (I-179)+(S2-4); (I-179)+(S2-5); (I-179)+(S2-6); (I-179)+(S2-7); (I-179)+(S2-8); (I-179)+(S2-9); (I-179)+(S2-10); (I-179)+(S3-1); (I-179)+(S3-2); (I-179)+(S3-3); (I-179)+(S3-4); (I-179)+(S3-5); (I-179)+(S3-6); (I-179)+(S3-7); (I-179)+(S3-8); (I-179)+(S3-9); (I-179)+(S3-10); (I-179)+(S3-11); (I-179)+(S4-1); (I-179)+(S4-2); (I-179)+(S4-3); (I-179)+(S4-4); (I-179)+(S4-5); (I-179)+(S7-1); (I-179)+(S11-1); (I-179)+(S11-2); (I-179)+(S11-3); (I-179)+(S12-1); (I-179)+(S13-1); (I-179)+(S13-2); (I-179)+(S13-3); (I-179)+(S13-4): (I-179)+(S13-5); (I-179)+(S13-6); (I-179)+(S13-7); (I-179)+(S13-8); (I-179)+(S13-9); (I-179)+(S14-1)

(I-180)+(S1-1); (I-180)+(S1-2); (I-180)+(S1-3); (I-180)+(S1-4); (I-180)+(S1-5); (I-180)+(S1-6); (I-180)+(S1-7); (I-180)+(S1-8); (I-180)+(S1-9); (I-180)+(S1-10); (I-180)+(S1-11); (I-180)+(S1-12); (I-180)+(S1-13); (I-180)+(S2-1); (I-180)+(S2-2); (I-180)+(S2-3); (I-180)+(S2-4); (I-180)+(S2-5); (I-180)+(S2-6); (I-180)+(S2-7); (I-180)+(S2-8); (I-180)+(S2-9); (I-180)+(S2-10); (I-180)+(S3-1); (I-180)+(S3-2); (I-180)+(S3-3); (I-180)+(S3-4); (I-180)+(S3-5); (I-180)+(S3-6); (I-180)+(S3-7); (I-180)+(S3-8); (I-180)+(S3-9); (I-180)+(S3-10); (I-180)+(S3-11); (I-180)+(S4-1); (I-180)+(S4-2); (I-180)+(S4-3); (I-180)+(S4-4); (I-180)+(S4-5); (I-180)+(S7-1); (I-180)+(S11-1); (I-180)+(S11-2); (I-180)+(S11-3); (I-180)+(S12-1); (I-180)+(S13-1); (I-180)+(S13-2); (I-180)+(S13-3); (I-180)+(S13-4): (I-180)+(S13-5); (I-180)+(S13-6); (I-180)+(S13-7); (I-180)+(S13-8); (I-180)+(S13-9); (I-180)+(S14-1)

(I-181)+(S1-1); (I-181)+(S1-2); (I-181)+(S1-3); (I-181)+(S1-4); (I-181)+(S1-5); (I-181)+(S1-6); (I-181)+(S1-7); (I-181)+(S1-8); (I-181)+(S1-9); (I-181)+(S1-10); (I-181)+(S1-11); (I-181)+(S1-12); (I-181)+(S1-13); (I-181)+(S2-1); (I-181)+(S2-2); (I-181)+(S2-3); (I-181)+(S2-4); (I-181)+(S2-5); (I-181)+(S2-6); (I-181)+(S2-7); (I-181)+(S2-8); (I-181)+(S2-9); (I-181)+(S2-10); (I-181)+(S3-1); (I-181)+(S3-2); (I-181)+(S3-3); (I-181)+(S3-4); (I-181)+(S3-5); (I-181)+(S3-6); (I-181)+(S3-7); (I-181)+(S3-8); (I-181)+(S3-9); (I-181)+(S3-10); (I-181)+(S3-11); (I-181)+(S4-1); (I-181)+(S4-2); (I-181)+(S4-3); (I-181)+(S4-4); (I-181)+(S4-5); (I-181)+(S7-1); (I-181)+(S11-1); (I-181)+(S11-2); (I-181)+(S11-3); (I-181)+(S12-1); (I-181)+(S13-1); (I-181)+(S13-2); (I-181)+(S13-3); (I-181)+(S13-4): (I-181)+(S13-5); (I-181)+(S13-6); (I-181)+(S13-7); (I-181)+(S13-8); (I-181)+(S13-9); (I-181)+(S14-1)

(I-182)+(S1-1); (I-182)+(S1-2); (I-182)+(S1-3); (I-182)+(S1-4); (I-182)+(S1-5); (I-182)+(S1-6); (I-182)+(S1-7); (I-182)+(S1-8); (I-182)+(S1-9); (I-182)+(S1-10); (I-182)+(S1-11); (I-182)+(S1-12); (I-182)+(S1-13); (I-182)+(S2-1); (I-182)+(S2-2); (I-182)+(S2-3); (I-182)+(S2-4); (I-182)+(S2-5); (I-182)+(S2-6); (I-182)+(S2-7); (I-182)+(S2-8); (I-182)+(S2-9); (I-182)+(S2-10); (I-182)+(S3-1); (I-182)+(S3-2); (I-182)+(S3-3); (I-182)+(S3-4); (I-182)+(S3-5); (I-182)+(S3-6); (I-182)+(S3-7); (I-182)+(S3-8); (I-182)+(S3-9); (I-182)+(S3-10); (I-182)+(S3-11); (I-182)+(S4-1); (I-182)+(S4-2); (I-182)+(S4-3); (I-182)+(S4-4); (I-182)+(S4-5); (I-182)+(S7-1); (I-182)+(S11-1); (I-182)+(S11-2); (I-182)+(S11-3); (I-182)+(S12-1); (I-182)+(S13-1); (I-182)+(S13-2); (I-182)+(S13-3); (I-182)+(S13-4): (I-182)+(S13-5); (I-182)+(S13-6); (I-182)+(S13-7); (I-182)+(S13-8); (I-182)+(S13-9); (I-182)+(S14-1)

(I-183)+(S1-1); (I-183)+(S1-2); (I-183)+(S1-3); (I-183)+(S1-4); (I-183)+(S1-5); (I-183)+(S1-6); (I-183)+(S1-7); (I-183)+(S1-8); (I-183)+(S1-9); (I-183)+(S1-10); (I-183)+(S1-11); (I-183)+(S1-12); (I-183)+(S1-13); (I-183)+(S2-1); (I-183)+(S2-2); (I-183)+(S2-3); (I-183)+(S2-4); (I-183)+(S2-5); (I-183)+(S2-6); (I-183)+(S2-7); (I-183)+(S2-8); (I-183)+(S2-9); (I-183)+(S2-10); (I-183)+(S3-1); (I-183)+(S3-2); (I-183)+(S3-3); (I-183)+(S3-4); (I-183)+(S3-5); (I-183)+(S3-6); (I-183)+(S3-7); (I-183)+(S3-8); (I-183)+(S3-9); (I-183)+(S3-10); (I-183)+(S3-11); (I-183)+(S4-1); (I-183)+(S4-2); (I-183)+(S4-3); (I-183)+(S4-4); (I-183)+(S4-5); (I-183)+(S7-1); (I-183)+(S11-1); (I-183)+(S11-2); (I-183)+(S11-3); (I-183)+(S12-1); (I-183)+(S13-1); (I-183)+(S13-2); (I-183)+(S13-3); (I-183)+(S13-4): (I-183)+(S13-5); (I-183)+(S13-6); (I-183)+(S13-7); (I-183)+(S13-8); (I-183)+(S13-9); (I-183)+(S14-1)

(I-184)+(S1-1); (I-184)+(S1-2); (I-184)+(S1-3); (I-184)+(S1-4); (I-184)+(S1-5); (I-184)+(S1-6); (I-184)+(S1-7); (I-184)+(S1-8); (I-184)+(S1-9); (I-184)+(S1-10); (I-184)+(S1-11); (I-184)+(S1-12); (I-184)+(S1-13); (I-184)+(S2-1); (I-184)+(S2-2); (I-184)+(S2-3); (I-184)+(S2-4); (I-184)+(S2-5); (I-184)+(S2-6); (I-184)+(S2-7); (I-184)+(S2-8); (I-184)+(S2-9); (I-184)+(S2-10); (I-184)+(S3-1); (I-184)+(S3-2); (I-184)+(S3-3); (I-184)+(S3-4); (I-184)+(S3-5); (I-184)+(S3-6); (I-184)+(S3-7); (I-184)+(S3-8); (I-184)+(S3-9); (I-184)+(S3-10); (I-184)+(S3-11); (I-184)+(S4-1); (I-184)+(S4-2); (I-184)+(S4-3); (I-184)+(S4-4); (I-184)+(S4-5); (I-184)+(S7-1); (I-184)+(S11-1); (I-184)+(S11-2); (I-184)+(S11-3); (I-184)+(S12-1); (I-184)+(S13-1); (I-184)+(S13-2); (I-184)+(S13-3); (I-184)+(S13-4): (I-184)+(S13-5); (I-184)+(S13-6); (I-184)+(S13-7); (I-184)+(S13-8); (I-184)+(S13-9); (I-184)+(S14-1)

(I-185)+(S1-1); (I-185)+(S1-2); (I-185)+(S1-3); (I-185)+(S1-4); (I-185)+(S1-5); (I-185)+(S1-6); (I-185)+(S1-7); (I-185)+(S1-8); (I-185)+(S1-9); (I-185)+(S1-10); (I-185)+(S1-11); (I-185)+(S1-12); (I-185)+(S1-13); (I-185)+(S2-1); (I-185)+(S2-2); (I-185)+(S2-3); (I-185)+(S2-4); (I-185)+(S2-5); (I-185)+(S2-6); (I-185)+(S2-7); (I-185)+(S2-8);

(I-185)+(S2-9); (I-185)+(S2-10); (I-185)+(S3-1); (I-185)+(S3-2); (I-185)+(S3-3); (I-185)+(S3-4); (I-185)+(S3-5); (I-185)+(S3-6); (I-185)+(S3-7); (I-185)+(S3-8); (I-185)+(S3-9); (I-185)+(S3-10); (I-185)+(S3-11); (I-185)+(S4-1); (I-185)+(S4-2); (I-185)+(S4-3); (I-185)+(S4-4); (I-185)+(S4-5); (I-185)+(S7-1); (I-185)+(S11-1); (I-185)+(S11-2); (I-185)+(S11-3); (I-185)+(S12-1); (I-185)+(S13-1); (I-185)+(S13-2); (I-185)+(S13-3); (I-185)+(S13-4): (I-185)+(S13-5); (I-185)+(S13-6); (I-185)+(S13-7); (I-185)+(S13-8); (I-185)+(S13-9); (I-185)+(S14-1)

(I-186)+(S1-1); (I-186)+(S1-2); (I-186)+(S1-3); (I-186)+(S1-4); (I-186)+(S1-5); (I-186)+(S1-6); (I-186)+(S1-7); (I-186)+(S1-8); (I-186)+(S1-9); (I-186)+(S1-10); (I-186)+(S1-11); (I-186)+(S1-12); (I-186)+(S1-13); (I-186)+(S2-1); (I-186)+(S2-2); (I-186)+(S2-3); (I-186)+(S2-4); (I-186)+(S2-5); (I-186)+(S2-6); (I-186)+(S2-7); (I-186)+(S2-8); (I-186)+(S2-9); (I-186)+(S2-10); (I-186)+(S3-1); (I-186)+(S3-2); (I-186)+(S3-3); (I-186)+(S3-4); (I-186)+(S3-5); (I-186)+(S3-6); (I-186)+(S3-7); (I-186)+(S3-8); (I-186)+(S3-9); (I-186)+(S3-10); (I-186)+(S3-11); (I-186)+(S4-1); (I-186)+(S4-2); (I-186)+(S4-3); (I-186)+(S4-4); (I-186)+(S4-5); (I-186)+(S7-1); (I-186)+(S11-1); (I-186)+(S11-2); (I-186)+(S11-3); (I-186)+(S12-1); (I-186)+(S13-1); (I-186)+(S13-2); (I-186)+(S13-3); (I-186)+(S13-4): (I-186)+(S13-5); (I-186)+(S13-6); (I-186)+(S13-7); (I-186)+(S13-8); (I-186)+(S13-9); (I-186)+(S14-1)

(I-187)+(S1-1); (I-187)+(S1-2); (I-187)+(S1-3); (I-187)+(S1-4); (I-187)+(S1-5); (I-187)+(S1-6); (I-187)+(S1-7); (I-187)+(S1-8); (I-187)+(S1-9); (I-187)+(S1-10); (I-187)+(S1-11); (I-187)+(S1-12); (I-187)+(S1-13); (I-187)+(S2-1); (I-187)+(S2-2); (I-187)+(S2-3); (I-187)+(S2-4); (I-187)+(S2-5); (I-187)+(S2-6); (I-187)+(S2-7); (I-187)+(S2-8); (I-187)+(S2-9); (I-187)+(S2-10); (I-187)+(S3-1); (I-187)+(S3-2); (I-187)+(S3-3); (I-187)+(S3-4); (I-187)+(S3-5); (I-187)+(S3-6); (I-187)+(S3-7); (I-187)+(S3-8); (I-187)+(S3-9); (I-187)+(S3-10); (I-187)+(S3-11); (I-187)+(S4-1); (I-187)+(S4-2); (I-187)+(S4-3); (I-187)+(S4-4); (I-187)+(S4-5); (I-187)+(S7-1); (I-187)+(S11-1); (I-187)+(S11-2); (I-187)+(S11-3); (I-187)+(S12-1); (I-187)+(S13-1); (I-187)+(S13-2); (I-187)+(S13-3); (I-187)+(S13-4): (I-187)+(S13-5); (I-187)+(S13-6); (I-187)+(S13-7); (I-187)+(S13-8); (I-187)+(S13-9); (I-187)+(S14-1)

(I-188)+(S1-1); (I-188)+(S1-2); (I-188)+(S1-3); (I-188)+(S1-4); (I-188)+(S1-5); (I-188)+(S1-6); (I-188)+(S1-7); (I-188)+(S1-8); (I-188)+(S1-9); (I-188)+(S1-10); (I-188)+(S1-11); (I-188)+(S1-12); (I-188)+(S1-13); (I-188)+(S2-1); (I-188)+(S2-2); (I-188)+(S2-3); (I-188)+(S2-4); (I-188)+(S2-5); (I-188)+(S2-6); (I-188)+(S2-7); (I-188)+(S2-8); (I-188)+(S2-9); (I-188)+(S2-10); (I-188)+(S3-1); (I-188)+(S3-2); (I-188)+(S3-3); (I-188)+(S3-4); (I-188)+(S3-5); (I-188)+(S3-6); (I-188)+(S3-7); (I-188)+(S3-8); (I-188)+(S3-9); (I-188)+(S3-10); (I-188)+(S3-11); (I-188)+(S4-1); (I-188)+(S4-2); (I-188)+(S4-3); (I-188)+(S4-4); (I-188)+(S4-5); (I-188)+(S7-1); (I-188)+(S11-1); (I-188)+(S11-2); (I-188)+(S11-3); (I-188)+(S12-1); (I-188)+(S13-1); (I-188)+(S13-2); (I-188)+(S13-3); (I-188)+(S13-4): (I-188)+(S13-5); (I-188)+(S13-6); (I-188)+(S13-7); (I-188)+(S13-8); (I-188)+(S13-9); (I-188)+(S14-1)

(I-189)+(S1-1); (I-189)+(S1-2); (I-189)+(S1-3); (I-189)+(S1-4); (I-189)+(S1-5); (I-189)+(S1-6); (I-189)+(S1-7); (I-189)+(S1-8); (I-189)+(S1-9); (I-189)+(S1-10); (I-189)+(S1-11); (I-189)+(S1-12); (I-189)+(S1-13); (I-189)+(S2-1); (I-189)+(S2-2); (I-189)+(S2-3); (I-189)+(S2-4); (I-189)+(S2-5); (I-189)+(S2-6); (I-189)+(S2-7); (I-189)+(S2-8); (I-189)+(S2-9); (I-189)+(S2-10); (I-189)+(S3-1); (I-189)+(S3-2); (I-189)+(S3-3); (I-189)+(S3-4); (I-189)+(S3-5); (I-189)+(S3-6); (I-189)+(S3-7); (I-189)+(S3-8); (I-189)+(S3-9); (I-189)+(S3-10); (I-189)+(S3-11); (I-189)+(S4-1); (I-189)+(S4-2); (I-189)+(S4-3); (I-189)+(S4-4); (I-189)+(S4-5); (I-189)+(S7-1); (I-189)+(S11-1); (I-189)+(S11-2); (I-189)+(S11-3); (I-189)+(S12-1); (I-189)+(S13-1); (I-189)+(S13-2); (I-189)+(S13-3); (I-189)+(S13-4): (I-189)+(S13-5); (I-189)+(S13-6); (I-189)+(S13-7); (I-189)+(S13-8); (I-189)+(S13-9); (I-189)+(S14-1)

(I-190)+(S1-1); (I-190)+(S1-2); (I-190)+(S1-3); (I-190)+(S1-4); (I-190)+(S1-5); (I-190)+(S1-6); (I-190)+(S1-7); (I-190)+(S1-8); (I-190)+(S1-9); (I-190)+(S1-10); (I-190)+(S1-11); (I-190)+(S1-12); (I-190)+(S1-13); (I-190)+(S2-1); (I-190)+(S2-2); (I-190)+(S2-3); (I-190)+(S2-4); (I-190)+(S2-5); (I-190)+(S2-6); (I-190)+(S2-7); (I-190)+(S2-8); (I-190)+(S2-9); (I-190)+(S2-10); (I-190)+(S3-1); (I-190)+(S3-2); (I-190)+(S3-3); (I-190)+(S3-4); (I-190)+(S3-5); (I-190)+(S3-6); (I-190)+(S3-7); (I-190)+(S3-8); (I-190)+(S3-9); (I-190)+(S3-10); (I-190)+(S3-11); (I-190)+(S4-1); (I-190)+(S4-2); (I-190)+(S4-3); (I-190)+(S4-4); (I-190)+(S4-5); (I-190)+(S7-1); (I-190)+(S11-1); (I-190)+(S11-2); (I-190)+(S11-3); (I-190)+(S12-1); (I-190)+(S13-1); (I-190)+(S13-2); (I-190)+(S13-3); (I-190)+(S13-4): (I-190)+(S13-5); (I-190)+(S13-6); (I-190)+(S13-7); (I-190)+(S13-8); (I-190)+(S13-9); (I-190)+(S14-1)

(I-191)+(S1-1); (I-191)+(S1-2); (I-191)+(S1-3); (I-191)+(S1-4); (I-191)+(S1-5); (I-191)+(S1-6); (I-191)+(S1-7); (I-191)+(S1-8); (I-191)+(S1-9); (I-191)+(S1-10); (I-191)+(S1-11); (I-191)+(S1-12); (I-191)+(S1-13); (I-191)+(S2-1); (I-191)+(S2-2); (I-191)+(S2-3); (I-191)+(S2-4); (I-191)+(S2-5); (I-191)+(S2-6); (I-191)+(S2-7); (I-191)+(S2-8); (I-191)+(S2-9); (I-191)+(S2-10); (I-191)+(S3-1); (I-191)+(S3-2); (I-191)+(S3-3); (I-191)+(S3-4); (I-191)+(S3-5); (I-191)+(S3-6); (I-191)+(S3-7); (I-191)+(S3-8); (I-191)+(S3-9); (I-191)+(S3-10); (I-191)+(S3-11); (I-191)+(S4-1); (I-191)+(S4-2); (I-191)+(S4-3); (I-191)+(S4-4); (I-191)+(S4-5); (I-191)+(S7-1); (I-191)+(S11-1); (I-191)+(S11-2); (I-191)+(S11-3); (I-191)+(S12-1); (I-191)+(S13-1); (I-191)+(S13-2); (I-191)+(S13-3); (I-191)+(S13-4): (I-191)+(S13-5); (I-191)+(S13-6); (I-191)+(S13-7); (I-191)+(S13-8); (I-191)+(S13-9); (I-191)+(S14-1)

(I-192)+(S1-1); (I-192)+(S1-2); (I-192)+(S1-3); (I-192)+(S1-4); (I-192)+(S1-5); (I-192)+(S1-6); (I-192)+(S1-7); (I-192)+(S1-8); (I-192)+(S1-9); (I-192)+(S1-10); (I-192)+(S1-11); (I-192)+(S1-12); (I-192)+(S1-13); (I-192)+(S2-1); (I-192)+(S2-2); (I-192)+(S2-3); (I-192)+(S2-4); (I-192)+(S2-5); (I-192)+(S2-6); (I-192)+(S2-7); (I-192)+(S2-8); (I-192)+(S2-9); (I-192)+(S2-10); (I-192)+(S3-1); (I-192)+(S3-2); (I-192)+(S3-3); (I-192)+(S3-4); (I-192)+(S3-5); (I-192)+(S3-6); (I-192)+(S3-7); (I-192)+(S3-8); (I-192)+(S3-9); (I-192)+(S3-10); (I-192)+(S3-11); (I-192)+(S4-1); (I-192)+(S4-2); (I-192)+(S4-3); (I-192)+(S4-4); (I-192)+(S4-5); (I-192)+(S7-1); (I-192)+(S11-1); (I-192)+(S11-2); (I-192)+(S11-3); (I-192)+(S12-1); (I-192)+(S13-1); (I-192)+(S13-2); (I-192)+(S13-3); (I-192)+(S13-4): (I-192)+(S13-5); (I-192)+(S13-6); (I-192)+(S13-7); (I-192)+(S13-8); (I-192)+(S13-9); (I-192)+(S14-1)

(I-193)+(S1-1); (I-193)+(S1-2); (I-193)+(S1-3); (I-193)+(S1-4); (I-193)+(S1-5); (I-193)+(S1-6); (I-193)+(S1-7); (I-193)+(S1-8); (I-193)+(S1-9); (I-193)+(S1-10); (I-193)+(S1-11); (I-193)+(S1-12); (I-193)+(S1-13); (I-193)+(S2-1); (I-193)+(S2-2); (I-193)+(S2-3); (I-193)+(S2-4); (I-193)+(S2-5); (I-193)+(S2-6); (I-193)+(S2-7); (I-193)+(S2-8); (I-193)+(S2-9); (I-193)+(S2-10); (I-193)+(S3-1); (I-193)+(S3-2); (I-193)+(S3-3); (I-193)+(S3-4); (I-193)+(S3-5); (I-193)+(S3-6); (I-193)+(S3-7); (I-193)+(S3-8); (I-193)+(S3-9); (I-193)+(S3-10); (I-193)+(S3-11); (I-193)+(S4-1); (I-193)+(S4-2); (I-193)+(S4-3); (I-193)+(S4-4); (I-193)+(S4-5); (I-193)+(S7-1); (I-193)+(S11-1); (I-193)+(S11-2);

(I-193)+(S11-3); (I-193)+(S12-1); (I-193)+(S13-1); (I-193)+(S13-2); (I-193)+(S13-3); (I-193)+(S13-4): (I-193)+(S13-5); (I-193)+(S13-6); (I-193)+(S13-7); (I-193)+(S13-8); (I-193)+(S13-9); (I-193)+(S14-1)

(I-194)+(S1-1); (I-194)+(S1-2); (I-194)+(S1-3); (I-194)+(S1-4); (I-194)+(S1-5); (I-194)+(S1-6); (I-194)+(S1-7); (I-194)+(S1-8); (I-194)+(S1-9); (I-194)+(S1-10); (I-194)+(S1-11); (I-194)+(S1-12); (I-194)+(S1-13); (I-194)+(S2-1); (I-194)+(S2-2); (I-194)+(S2-3); (I-194)+(S2-4); (I-194)+(S2-5); (I-194)+(S2-6); (I-194)+(S2-7); (I-194)+(S2-8); (I-194)+(S2-9); (I-194)+(S2-10); (I-194)+(S3-1); (I-194)+(S3-2); (I-194)+(S3-3); (I-194)+(S3-4); (I-194)+(S3-5); (I-194)+(S3-6); (I-194)+(S3-7); (I-194)+(S3-8); (I-194)+(S3-9); (I-194)+(S3-10); (I-194)+(S3-11); (I-194)+(S4-1); (I-194)+(S4-2); (I-194)+(S4-3); (I-194)+(S4-4); (I-194)+(S4-5); (I-194)+(S7-1); (I-194)+(S11-1); (I-194)+(S11-2); (I-194)+(S11-3); (I-194)+(S12-1); (I-194)+(S13-1); (I-194)+(S13-2); (I-194)+(S13-3); (I-194)+(S13-4): (I-194)+(S13-5); (I-194)+(S13-6); (I-194)+(S13-7); (I-194)+(S13-8); (I-194)+(S13-9); (I-194)+(S14-1)

(I-195)+(S1-1); (I-195)+(S1-2); (I-195)+(S1-3); (I-195)+(S1-4); (I-195)+(S1-5); (I-195)+(S1-6); (I-195)+(S1-7); (I-195)+(S1-8); (I-195)+(S1-9); (I-195)+(S1-10); (I-195)+(S1-11); (I-195)+(S1-12); (I-195)+(S1-13); (I-195)+(S2-1); (I-195)+(S2-2); (I-195)+(S2-3); (I-195)+(S2-4); (I-195)+(S2-5); (I-195)+(S2-6); (I-195)+(S2-7); (I-195)+(S2-8); (I-195)+(S2-9); (I-195)+(S2-10); (I-195)+(S3-1); (I-195)+(S3-2); (I-195)+(S3-3); (I-195)+(S3-4); (I-195)+(S3-5); (I-195)+(S3-6); (I-195)+(S3-7); (I-195)+(S3-8); (I-195)+(S3-9); (I-195)+(S3-10); (I-195)+(S3-11); (I-195)+(S4-1); (I-195)+(S4-2); (I-195)+(S4-3); (I-195)+(S4-4); (I-195)+(S4-5); (I-195)+(S7-1); (I-195)+(S11-1); (I-195)+(S11-2); (I-195)+(S11-3); (I-195)+(S12-1); (I-195)+(S13-1); (I-195)+(S13-2); (I-195)+(S13-3); (I-195)+(S13-4): (I-195)+(S13-5); (I-195)+(S13-6); (I-195)+(S13-7); (I-195)+(S13-8); (I-195)+(S13-9); (I-195)+(S14-1)

(I-196)+(S1-1); (I-196)+(S1-2); (I-196)+(S1-3); (I-196)+(S1-4); (I-196)+(S1-5); (I-196)+(S1-6); (I-196)+(S1-7); (I-196)+(S1-8); (I-196)+(S1-9); (I-196)+(S1-10); (I-196)+(S1-11); (I-196)+(S1-12); (I-196)+(S1-13); (I-196)+(S2-1); (I-196)+(S2-2); (I-196)+(S2-3); (I-196)+(S2-4); (I-196)+(S2-5); (I-196)+(S2-6); (I-196)+(S2-7); (I-196)+(S2-8); (I-196)+(S2-9); (I-196)+(S2-10); (I-196)+(S3-1); (I-196)+(S3-2); (I-196)+(S3-3); (I-196)+(S3-4); (I-196)+(S3-5); (I-196)+(S3-6); (I-196)+(S3-7); (I-196)+(S3-8); (I-196)+(S3-9); (I-196)+(S3-10); (I-196)+(S3-11); (I-196)+(S4-1); (I-196)+(S4-2); (I-196)+(S4-3); (I-196)+(S4-4); (I-196)+(S4-5); (I-196)+(S7-1); (I-196)+(S11-1); (I-196)+(S11-2); (I-196)+(S11-3); (I-196)+(S12-1); (I-196)+(S13-1); (I-196)+(S13-2); (I-196)+(S13-3); (I-196)+(S13-4): (I-196)+(S13-5); (I-196)+(S13-6); (I-196)+(S13-7); (I-196)+(S13-8); (I-196)+(S13-9); (I-196)+(S14-1)

(I-197)+(S1-1); (I-197)+(S1-2); (I-197)+(S1-3); (I-197)+(S1-4); (I-197)+(S1-5); (I-197)+(S1-6); (I-197)+(S1-7); (I-197)+(S1-8); (I-197)+(S1-9); (I-197)+(S1-10); (I-197)+(S1-11); (I-197)+(S1-12); (I-197)+(S1-13); (I-197)+(S2-1); (I-197)+(S2-2); (I-197)+(S2-3); (I-197)+(S2-4); (I-197)+(S2-5); (I-197)+(S2-6); (I-197)+(S2-7); (I-197)+(S2-8); (I-197)+(S2-9); (I-197)+(S2-10); (I-197)+(S3-1); (I-197)+(S3-2); (I-197)+(S3-3); (I-197)+(S3-4); (I-197)+(S3-5); (I-197)+(S3-6); (I-197)+(S3-7); (I-197)+(S3-8); (I-197)+(S3-9); (I-197)+(S3-10); (I-197)+(S3-11); (I-197)+(S4-1); (I-197)+(S4-2); (I-197)+(S4-3); (I-197)+(S4-4); (I-197)+(S4-5); (I-197)+(S7-1); (I-197)+(S11-1); (I-197)+(S11-2); (I-197)+(S11-3); (I-197)+(S12-1); (I-197)+(S13-1); (I-197)+(S13-2); (I-197)+(S13-3); (I-197)+(S13-4): (I-197)+(S13-5); (I-197)+(S13-6); (I-197)+(S13-7); (I-197)+(S13-8); (I-197)+(S13-9); (I-197)+(S14-1)

(I-198)+(S1-1); (I-198)+(S1-2); (I-198)+(S1-3); (I-198)+(S1-4); (I-198)+(S1-5); (I-198)+(S1-6); (I-198)+(S1-7); (I-198)+(S1-8); (I-198)+(S1-9); (I-198)+(S1-10); (I-198)+(S1-11); (I-198)+(S1-12); (I-198)+(S1-13); (I-198)+(S2-1); (I-198)+(S2-2); (I-198)+(S2-3); (I-198)+(S2-4); (I-198)+(S2-5); (I-198)+(S2-6); (I-198)+(S2-7); (I-198)+(S2-8); (I-198)+(S2-9); (I-198)+(S2-10); (I-198)+(S3-1); (I-198)+(S3-2); (I-198)+(S3-3); (I-198)+(S3-4); (I-198)+(S3-5); (I-198)+(S3-6); (I-198)+(S3-7); (I-198)+(S3-8); (I-198)+(S3-9); (I-198)+(S3-10); (I-198)+(S3-11); (I-198)+(S4-1); (I-198)+(S4-2); (I-198)+(S4-3); (I-198)+(S4-4); (I-198)+(S4-5); (I-198)+(S7-1); (I-198)+(S11-1); (I-198)+(S11-2); (I-198)+(S11-3); (I-198)+(S12-1); (I-198)+(S13-1); (I-198)+(S13-2); (I-198)+(S13-3); (I-198)+(S13-4): (I-198)+(S13-5); (I-198)+(S13-6); (I-198)+(S13-7); (I-198)+(S13-8); (I-198)+(S13-9); (I-198)+(S14-1)

(I-199)+(S1-1); (I-199)+(S1-2); (I-199)+(S1-3); (I-199)+(S1-4); (I-199)+(S1-5); (I-199)+(S1-6); (I-199)+(S1-7); (I-199)+(S1-8); (I-199)+(S1-9); (I-199)+(S1-10); (I-199)+(S1-11); (I-199)+(S1-12); (I-199)+(S1-13); (I-199)+(S2-1); (I-199)+(S2-2); (I-199)+(S2-3); (I-199)+(S2-4); (I-199)+(S2-5); (I-199)+(S2-6); (I-199)+(S2-7); (I-199)+(S2-8); (I-199)+(S2-9); (I-199)+(S2-10); (I-199)+(S3-1); (I-199)+(S3-2); (I-199)+(S3-3); (I-199)+(S3-4); (I-199)+(S3-5); (I-199)+(S3-6); (I-199)+(S3-7); (I-199)+(S3-8); (I-199)+(S3-9); (I-199)+(S3-10); (I-199)+(S3-11); (I-199)+(S4-1); (I-199)+(S4-2); (I-199)+(S4-3); (I-199)+(S4-4); (I-199)+(S4-5); (I-199)+(S7-1); (I-199)+(S11-1); (I-199)+(S11-2); (I-199)+(S11-3); (I-199)+(S12-1); (I-199)+(S13-1); (I-199)+(S13-2); (I-199)+(S13-3); (I-199)+(S13-4): (I-199)+(S13-5); (I-199)+(S13-6); (I-199)+(S13-7); (I-199)+(S13-8); (I-199)+(S13-9); (I-199)+(S14-1)

(I-200)+(S1-1); (I-200)+(S1-2); (I-200)+(S1-3); (I-200)+(S1-4); (I-200)+(S1-5); (I-200)+(S1-6); (I-200)+(S1-7); (I-200)+(S1-8); (I-200)+(S1-9); (I-200)+(S1-10); (I-200)+(S1-11); (I-200)+(S1-12); (I-200)+(S1-13); (I-200)+(S2-1); (I-200)+(S2-2); (I-200)+(S2-3); (I-200)+(S2-4); (I-200)+(S2-5); (I-200)+(S2-6); (I-200)+(S2-7); (I-200)+(S2-8); (I-200)+(S2-9); (I-200)+(S2-10); (I-200)+(S3-1); (I-200)+(S3-2); (I-200)+(S3-3); (I-200)+(S3-4); (I-200)+(S3-5); (I-200)+(S3-6); (I-200)+(S3-7); (I-200)+(S3-8); (I-200)+(S3-9); (I-200)+(S3-10); (I-200)+(S3-11); (I-200)+(S4-1); (I-200)+(S4-2); (I-200)+(S4-3); (I-200)+(S4-4); (I-200)+(S4-5); (I-200)+(S7-1); (I-200)+(S11-1); (I-200)+(S11-2); (I-200)+(S11-3); (I-200)+(S12-1); (I-200)+(S13-1); (I-200)+(S13-2); (I-200)+(S13-3); (I-200)+(S13-4): (I-200)+(S13-5); (I-200)+(S13-6); (I-200)+(S13-7); (I-200)+(S13-8); (I-200)+(S13-9); (I-200)+(S14-1)

(I-201)+(S1-1); (I-201)+(S1-2); (I-201)+(S1-3); (I-201)+(S1-4); (I-201)+(S1-5); (I-201)+(S1-6); (I-201)+(S1-7); (I-201)+(S1-8); (I-201)+(S1-9); (I-201)+(S1-10); (I-201)+(S1-11); (I-201)+(S1-12); (I-201)+(S1-13); (I-201)+(S2-1); (I-201)+(S2-2); (I-201)+(S2-3); (I-201)+(S2-4); (I-201)+(S2-5); (I-201)+(S2-6); (I-201)+(S2-7); (I-201)+(S2-8); (I-201)+(S2-9); (I-201)+(S2-10); (I-201)+(S3-1); (I-201)+(S3-2); (I-201)+(S3-3); (I-201)+(S3-4); (I-201)+(S3-5); (I-201)+(S3-6); (I-201)+(S3-7); (I-201)+(S3-8); (I-201)+(S3-9); (I-201)+(S3-10); (I-201)+(S3-11); (I-201)+(S4-1); (I-201)+(S4-2); (I-201)+(S4-3); (I-201)+(S4-4); (I-201)+(S4-5); (I-201)+(S7-1); (I-201)+(S11-1); (I-201)+(S11-2); (I-201)+(S11-3); (I-201)+(S12-1); (I-201)+(S13-1); (I-201)+(S13-2); (I-201)+(S13-3); (I-201)+(S13-4): (I-201)+(S13-5); (I-201)+(S13-6); (I-201)+(S13-7); (I-201)+(S13-8); (I-201)+(S13-9); (I-201)+(S14-1)

(I-202)+(S1-1); (I-202)+(S1-2); (I-202)+(S1-3); (I-202)+(S1-4); (I-202)+(S1-5); (I-202)+(S1-6); (I-202)+(S1-7); (I-202)+(S1-8); (I-202)+(S1-9); (I-202)+(S1-10); (I-202)+(S1-11); (I-202)+(S1-12); (I-202)+(S1-13); (I-202)+(S2-1); (I-202)+(S2-2); (I-202)+(S2-3); (I-202)+(S2-4); (I-202)+(S2-5); (I-202)+(S2-6); (I-202)+(S2-7); (I-202)+(S2-8); (I-202)+(S2-9); (I-202)+(S2-10); (I-202)+(S3-1); (I-202)+(S3-2); (I-202)+(S3-3); (I-202)+(S3-4); (I-202)+(S3-5); (I-202)+(S3-6); (I-202)+(S3-7); (I-202)+(S3-8); (I-202)+(S3-9); (I-202)+(S3-10); (I-202)+(S3-11); (I-202)+(S4-1); (I-202)+(S4-2); (I-202)+(S4-3); (I-202)+(S4-4); (I-202)+(S4-5); (I-202)+(S7-1); (I-202)+(S11-1); (I-202)+(S11-2); (I-202)+(S11-3); (I-202)+(S12-1); (I-202)+(S13-1); (I-202)+(S13-2); (I-202)+(S13-3); (I-202)+(S13-4): (I-202)+(S13-5); (I-202)+(S13-6); (I-202)+(S13-7); (I-202)+(S13-8); (I-202)+(S13-9); (I-202)+(S14-1)

(I-203)+(S1-1); (I-203)+(S1-2); (I-203)+(S1-3); (I-203)+(S1-4); (I-203)+(S1-5); (I-203)+(S1-6); (I-203)+(S1-7); (I-203)+(S1-8); (I-203)+(S1-9); (I-203)+(S1-10); (I-203)+(S1-11); (I-203)+(S1-12); (I-203)+(S1-13); (I-203)+(S2-1); (I-203)+(S2-2); (I-203)+(S2-3); (I-203)+(S2-4); (I-203)+(S2-5); (I-203)+(S2-6); (I-203)+(S2-7); (I-203)+(S2-8); (I-203)+(S2-9); (I-203)+(S2-10); (I-203)+(S3-1); (I-203)+(S3-2); (I-203)+(S3-3); (I-203)+(S3-4); (I-203)+(S3-5); (I-203)+(S3-6); (I-203)+(S3-7); (I-203)+(S3-8); (I-203)+(S3-9); (I-203)+(S3-10); (I-203)+(S3-11); (I-203)+(S4-1); (I-203)+(S4-2); (I-203)+(S4-3); (I-203)+(S4-4); (I-203)+(S4-5); (I-203)+(S7-1); (I-203)+(S11-1); (I-203)+(S11-2); (I-203)+(S11-3); (I-203)+(S12-1); (I-203)+(S13-1); (I-203)+(S13-2); (I-203)+(S13-3); (I-203)+(S13-4): (I-203)+(S13-5); (I-203)+(S13-6); (I-203)+(S13-7); (I-203)+(S13-8); (I-203)+(S13-9); (I-203)+(S14-1)

(I-204)+(S1-1); (I-204)+(S1-2); (I-204)+(S1-3); (I-204)+(S1-4); (I-204)+(S1-5); (I-204)+(S1-6); (I-204)+(S1-7); (I-204)+(S1-8); (I-204)+(S1-9); (I-204)+(S1-10); (I-204)+(S1-11); (I-204)+(S1-12); (I-204)+(S1-13); (I-204)+(S2-1); (I-204)+(S2-2); (I-204)+(S2-3); (I-204)+(S2-4); (I-204)+(S2-5); (I-204)+(S2-6); (I-204)+(S2-7); (I-204)+(S2-8); (I-204)+(S2-9); (I-204)+(S2-10); (I-204)+(S3-1); (I-204)+(S3-2); (I-204)+(S3-3); (I-204)+(S3-4); (I-204)+(S3-5); (I-204)+(S3-6); (I-204)+(S3-7); (I-204)+(S3-8); (I-204)+(S3-9); (I-204)+(S3-10); (I-204)+(S3-11); (I-204)+(S4-1); (I-204)+(S4-2); (I-204)+(S4-3); (I-204)+(S4-4); (I-204)+(S4-5); (I-204)+(S7-1); (I-204)+(S11-1); (I-204)+(S11-2); (I-204)+(S11-3); (I-204)+(S12-1); (I-204)+(S13-1); (I-204)+(S13-2); (I-204)+(S13-3); (I-204)+(S13-4): (I-204)+(S13-5); (I-204)+(S13-6); (I-204)+(S13-7); (I-204)+(S13-8); (I-204)+(S13-9); (I-204)+(S14-1)

(I-205)+(S1-1); (I-205)+(S1-2); (I-205)+(S1-3); (I-205)+(S1-4); (I-205)+(S1-5); (I-205)+(S1-6); (I-205)+(S1-7); (I-205)+(S1-8); (I-205)+(S1-9); (I-205)+(S1-10); (I-205)+(S1-11); (I-205)+(S1-12); (I-205)+(S1-13); (I-205)+(S2-1); (I-205)+(S2-2); (I-205)+(S2-3); (I-205)+(S2-4); (I-205)+(S2-5); (I-205)+(S2-6); (I-205)+(S2-7); (I-205)+(S2-8); (I-205)+(S2-9); (I-205)+(S2-10); (I-205)+(S3-1); (I-205)+(S3-2); (I-205)+(S3-3); (I-205)+(S3-4); (I-205)+(S3-5); (I-205)+(S3-6); (I-205)+(S3-7); (I-205)+(S3-8); (I-205)+(S3-9); (I-205)+(S3-10); (I-205)+(S3-11); (I-205)+(S4-1); (I-205)+(S4-2); (I-205)+(S4-3); (I-205)+(S4-4); (I-205)+(S4-5); (I-205)+(S7-1); (I-205)+(S11-1); (I-205)+(S11-2); (I-205)+(S11-3); (I-205)+(S12-1); (I-205)+(S13-1); (I-205)+(S13-2); (I-205)+(S13-3); (I-205)+(S13-4): (I-205)+(S13-5); (I-205)+(S13-6); (I-205)+(S13-7); (I-205)+(S13-8); (I-205)+(S13-9); (I-205)+(S14-1)

(I-206)+(S1-1); (I-206)+(S1-2); (I-206)+(S1-3); (I-206)+(S1-4); (I-206)+(S1-5); (I-206)+(S1-6); (I-206)+(S1-7); (I-206)+(S1-8); (I-206)+(S1-9); (I-206)+(S1-10); (I-206)+(S1-11); (I-206)+(S1-12); (I-206)+(S1-13); (I-206)+(S2-1); (I-206)+(S2-2); (I-206)+(S2-3); (I-206)+(S2-4); (I-206)+(S2-5); (I-206)+(S2-6); (I-206)+(S2-7); (I-206)+(S2-8); (I-206)+(S2-9); (I-206)+(S2-10); (I-206)+(S3-1); (I-206)+(S3-2); (I-206)+(S3-3); (I-206)+(S3-4); (I-206)+(S3-5); (I-206)+(S3-6); (I-206)+(S3-7); (I-206)+(S3-8); (I-206)+(S3-9); (I-206)+(S3-10); (I-206)+(S3-11); (I-206)+(S4-1); (I-206)+(S4-2); (I-206)+(S4-3); (I-206)+(S4-4); (I-206)+(S4-5); (I-206)+(S7-1); (I-206)+(S11-1); (I-206)+(S11-2); (I-206)+(S11-3); (I-206)+(S12-1); (I-206)+(S13-1); (I-206)+(S13-2); (I-206)+(S13-3); (I-206)+(S13-4): (I-206)+(S13-5); (I-206)+(S13-6); (I-206)+(S13-7); (I-206)+(S13-8); (I-206)+(S13-9); (I-206)+(S14-1)

(I-207)+(S1-1); (I-207)+(S1-2); (I-207)+(S1-3); (I-207)+(S1-4); (I-207)+(S1-5); (I-207)+(S1-6); (I-207)+(S1-7); (I-207)+(S1-8); (I-207)+(S1-9); (I-207)+(S1-10); (I-207)+(S1-11); (I-207)+(S1-12); (I-207)+(S1-13); (I-207)+(S2-1); (I-207)+(S2-2); (I-207)+(S2-3); (I-207)+(S2-4); (I-207)+(S2-5); (I-207)+(S2-6); (I-207)+(S2-7); (I-207)+(S2-8); (I-207)+(S2-9); (I-207)+(S2-10); (I-207)+(S3-1); (I-207)+(S3-2); (I-207)+(S3-3); (I-207)+(S3-4); (I-207)+(S3-5); (I-207)+(S3-6); (I-207)+(S3-7); (I-207)+(S3-8); (I-207)+(S3-9); (I-207)+(S3-10); (I-207)+(S3-11); (I-207)+(S4-1); (I-207)+(S4-2); (I-207)+(S4-3); (I-207)+(S4-4); (I-207)+(S4-5); (I-207)+(S7-1); (I-207)+(S11-1); (I-207)+(S11-2); (I-207)+(S11-3); (I-207)+(S12-1); (I-207)+(S13-1); (I-207)+(S13-2); (I-207)+(S13-3); (I-207)+(S13-4): (I-207)+(S13-5); (I-207)+(S13-6); (I-207)+(S13-7); (I-207)+(S13-8); (I-207)+(S13-9); (I-207)+(S14-1)

(I-208)+(S1-1); (I-208)+(S1-2); (I-208)+(S1-3); (I-208)+(S1-4); (I-208)+(S1-5); (I-208)+(S1-6); (I-208)+(S1-7); (I-208)+(S1-8); (I-208)+(S1-9); (I-208)+(S1-10); (I-208)+(S1-11); (I-208)+(S1-12); (I-208)+(S1-13); (I-208)+(S2-1); (I-208)+(S2-2); (I-208)+(S2-3); (I-208)+(S2-4); (I-208)+(S2-5); (I-208)+(S2-6); (I-208)+(S2-7); (I-208)+(S2-8); (I-208)+(S2-9); (I-208)+(S2-10); (I-208)+(S3-1); (I-208)+(S3-2); (I-208)+(S3-3); (I-208)+(S3-4); (I-208)+(S3-5); (I-208)+(S3-6); (I-208)+(S3-7); (I-208)+(S3-8); (I-208)+(S3-9); (I-208)+(S3-10); (I-208)+(S3-11); (I-208)+(S4-1); (I-208)+(S4-2); (I-208)+(S4-3); (I-208)+(S4-4); (I-208)+(S4-5); (I-208)+(S7-1); (I-208)+(S11-1); (I-208)+(S11-2); (I-208)+(S11-3); (I-208)+(S12-1); (I-208)+(S13-1); (I-208)+(S13-2); (I-208)+(S13-3); (I-208)+(S13-4): (I-208)+(S13-5); (I-208)+(S13-6); (I-208)+(S13-7); (I-208)+(S13-8); (I-208)+(S13-9); (I-208)+(S14-1)

(I-209)+(S1-1); (I-209)+(S1-2); (I-209)+(S1-3); (I-209)+(S1-4); (I-209)+(S1-5); (I-209)+(S1-6); (I-209)+(S1-7); (I-209)+(S1-8); (I-209)+(S1-9); (I-209)+(S1-10); (I-209)+(S1-11); (I-209)+(S1-12); (I-209)+(S1-13); (I-209)+(S2-1); (I-209)+(S2-2); (I-209)+(S2-3); (I-209)+(S2-4); (I-209)+(S2-5); (I-209)+(S2-6); (I-209)+(S2-7); (I-209)+(S2-8); (I-209)+(S2-9); (I-209)+(S2-10); (I-209)+(S3-1); (I-209)+(S3-2); (I-209)+(S3-3); (I-209)+(S3-4); (I-209)+(S3-5); (I-209)+(S3-6); (I-209)+(S3-7); (I-209)+(S3-8); (I-209)+(S3-9); (I-209)+(S3-10); (I-209)+(S3-11); (I-209)+(S4-1); (I-209)+(S4-2); (I-209)+(S4-3); (I-209)+(S4-4); (I-209)+(S4-5); (I-209)+(S7-1); (I-209)+(S11-1); (I-209)+(S11-2); (I-209)+(S11-3); (I-209)+(S12-1); (I-209)+(S13-1); (I-209)+(S13-2); (I-209)+(S13-3); (I-209)+(S13-4): (I-209)+(S13-5); (I-209)+(S13-6); (I-209)+(S13-7); (I-209)+(S13-8); (I-209)+(S13-9); (I-209)+(S14-1)

(I-210)+(S1-1); (I-210)+(S1-2); (I-210)+(S1-3); (I-210)+(S1-4); (I-210)+(S1-5); (I-210)+(S1-6); (I-210)+(S1-7); (I-210)+(S1-8); (I-210)+(S1-9); (I-210)+(S1-10); (I-210)+(S1-11); (I-210)+(S1-12); (I-210)+(S1-13); (I-210)+(S2-1); (I-210)+(S2-2); (I-210)+(S2-3); (I-210)+(S2-4); (I-210)+(S2-5); (I-210)+(S2-6); (I-210)+(S2-7); (I-210)+(S2-8);

(I-210)+(S2-9); (I-210)+(S2-10); (I-210)+(S3-1); (I-210)+(S3-2); (I-210)+(S3-3); (I-210)+(S3-4); (I-210)+(S3-5); (I-210)+(S3-6); (I-210)+(S3-7); (I-210)+(S3-8); (I-210)+(S3-9); (I-210)+(S3-10); (I-210)+(S3-11); (I-210)+(S4-1); (I-210)+(S4-2); (I-210)+(S4-3); (I-210)+(S4-4); (I-210)+(S4-5); (I-210)+(S7-1); (I-210)+(S11-1); (I-210)+(S11-2); (I-210)+(S11-3); (I-210)+(S12-1); (I-210)+(S13-1); (I-210)+(S13-2); (I-210)+(S13-3); (I-210)+(S13-4): (I-210)+(S13-5); (I-210)+(S13-6); (I-210)+(S13-7); (I-210)+(S13-8); (I-210)+(S13-9); (I-210)+(S14-1)

(I-211)+(S1-1); (I-211)+(S1-2); (I-211)+(S1-3); (I-211)+(S1-4); (I-211)+(S1-5); (I-211)+(S1-6); (I-211)+(S1-7); (I-211)+(S1-8); (I-211)+(S1-9); (I-211)+(S1-10); (I-211)+(S1-11); (I-211)+(S1-12); (I-211)+(S1-13); (I-211)+(S2-1); (I-211)+(S2-2); (I-211)+(S2-3); (I-211)+(S2-4); (I-211)+(S2-5); (I-211)+(S2-6); (I-211)+(S2-7); (I-211)+(S2-8); (I-211)+(S2-9); (I-211)+(S2-10); (I-211)+(S3-1); (I-211)+(S3-2); (I-211)+(S3-3); (I-211)+(S3-4); (I-211)+(S3-5); (I-211)+(S3-6); (I-211)+(S3-7); (I-211)+(S3-8); (I-211)+(S3-9); (I-211)+(S3-10); (I-211)+(S3-11); (I-211)+(S4-1); (I-211)+(S4-2); (I-211)+(S4-3); (I-211)+(S4-4); (I-211)+(S4-5); (I-211)+(S7-1); (I-211)+(S11-1); (I-211)+(S11-2); (I-211)+(S11-3); (I-211)+(S12-1); (I-211)+(S13-1); (I-211)+(S13-2); (I-211)+(S13-3); (I-211)+(S13-4): (I-211)+(S13-5); (I-211)+(S13-6); (I-211)+(S13-7); (I-211)+(S13-8); (I-211)+(S13-9); (I-211)+(S14-1)

(I-212)+(S1-1); (I-212)+(S1-2); (I-212)+(S1-3); (I-212)+(S1-4); (I-212)+(S1-5); (I-212)+(S1-6); (I-212)+(S1-7); (I-212)+(S1-8); (I-212)+(S1-9); (I-212)+(S1-10); (I-212)+(S1-11); (I-212)+(S1-12); (I-212)+(S1-13); (I-212)+(S2-1); (I-212)+(S2-2); (I-212)+(S2-3); (I-212)+(S2-4); (I-212)+(S2-5); (I-212)+(S2-6); (I-212)+(S2-7); (I-212)+(S2-8); (I-212)+(S2-9); (I-212)+(S2-10); (I-212)+(S3-1); (I-212)+(S3-2); (I-212)+(S3-3); (I-212)+(S3-4); (I-212)+(S3-5); (I-212)+(S3-6); (I-212)+(S3-7); (I-212)+(S3-8); (I-212)+(S3-9); (I-212)+(S3-10); (I-212)+(S3-11); (I-212)+(S4-1); (I-212)+(S4-2); (I-212)+(S4-3); (I-212)+(S4-4); (I-212)+(S4-5); (I-212)+(S7-1); (I-212)+(S11-1); (I-212)+(S11-2); (I-212)+(S11-3); (I-212)+(S12-1); (I-212)+(S13-1); (I-212)+(S13-2); (I-212)+(S13-3); (I-212)+(S13-4): (I-212)+(S13-5); (I-212)+(S13-6); (I-212)+(S13-7); (I-212)+(S13-8); (I-212)+(S13-9); (I-212)+(S14-1)

(I-213)+(S1-1); (I-213)+(S1-2); (I-213)+(S1-3); (I-213)+(S1-4); (I-213)+(S1-5); (I-213)+(S1-6); (I-213)+(S1-7); (I-213)+(S1-8); (I-213)+(S1-9); (I-213)+(S1-10); (I-213)+(S1-11); (I-213)+(S1-12); (I-213)+(S1-13); (I-213)+(S2-1); (I-213)+(S2-2); (I-213)+(S2-3); (I-213)+(S2-4); (I-213)+(S2-5); (I-213)+(S2-6); (I-213)+(S2-7); (I-213)+(S2-8); (I-213)+(S2-9); (I-213)+(S2-10); (I-213)+(S3-1); (I-213)+(S3-2); (I-213)+(S3-3); (I-213)+(S3-4); (I-213)+(S3-5); (I-213)+(S3-6); (I-213)+(S3-7); (I-213)+(S3-8); (I-213)+(S3-9); (I-213)+(S3-10); (I-213)+(S3-11); (I-213)+(S4-1); (I-213)+(S4-2); (I-213)+(S4-3); (I-213)+(S4-4); (I-213)+(S4-5); (I-213)+(S7-1); (I-213)+(S11-1); (I-213)+(S11-2); (I-213)+(S11-3); (I-213)+(S12-1); (I-213)+(S13-1); (I-213)+(S13-2); (I-213)+(S13-3); (I-213)+(S13-4): (I-213)+(S13-5); (I-213)+(S13-6); (I-213)+(S13-7); (I-213)+(S13-8); (I-213)+(S13-9); (I-213)+(S14-1)

(I-214)+(S1-1); (I-214)+(S1-2); (I-214)+(S1-3); (I-214)+(S1-4); (I-214)+(S1-5); (I-214)+(S1-6); (I-214)+(S1-7); (I-214)+(S1-8); (I-214)+(S1-9); (I-214)+(S1-10); (I-214)+(S1-11); (I-214)+(S1-12); (I-214)+(S1-13); (I-214)+(S2-1); (I-214)+(S2-2); (I-214)+(S2-3); (I-214)+(S2-4); (I-214)+(S2-5); (I-214)+(S2-6); (I-214)+(S2-7); (I-214)+(S2-8); (I-214)+(S2-9); (I-214)+(S2-10); (I-214)+(S3-1); (I-214)+(S3-2); (I-214)+(S3-3); (I-214)+(S3-4); (I-214)+(S3-5); (I-214)+(S3-6); (I-214)+(S3-7); (I-214)+(S3-8); (I-214)+(S3-9); (I-214)+(S3-10); (I-214)+(S3-11); (I-214)+(S4-1); (I-214)+(S4-2); (I-214)+(S4-3); (I-214)+(S4-4); (I-214)+(S4-5); (I-214)+(S7-1); (I-214)+(S11-1); (I-214)+(S11-2); (I-214)+(S11-3); (I-214)+(S12-1); (I-214)+(S13-1); (I-214)+(S13-2); (I-214)+(S13-3); (I-214)+(S13-4): (I-214)+(S13-5); (I-214)+(S13-6); (I-214)+(S13-7); (I-214)+(S13-8); (I-214)+(S13-9); (I-214)+(S14-1)

(I-215)+(S1-1); (I-215)+(S1-2); (I-215)+(S1-3); (I-215)+(S1-4); (I-215)+(S1-5); (I-215)+(S1-6); (I-215)+(S1-7); (I-215)+(S1-8); (I-215)+(S1-9); (I-215)+(S1-10); (I-215)+(S1-11); (I-215)+(S1-12); (I-215)+(S1-13); (I-215)+(S2-1); (I-215)+(S2-2); (I-215)+(S2-3); (I-215)+(S2-4); (I-215)+(S2-5); (I-215)+(S2-6); (I-215)+(S2-7); (I-215)+(S2-8); (I-215)+(S2-9); (I-215)+(S2-10); (I-215)+(S3-1); (I-215)+(S3-2); (I-215)+(S3-3); (I-215)+(S3-4); (I-215)+(S3-5); (I-215)+(S3-6); (I-215)+(S3-7); (I-215)+(S3-8); (I-215)+(S3-9); (I-215)+(S3-10); (I-215)+(S3-11); (I-215)+(S4-1); (I-215)+(S4-2); (I-215)+(S4-3); (I-215)+(S4-4); (I-215)+(S4-5); (I-215)+(S7-1); (I-215)+(S11-1); (I-215)+(S11-2); (I-215)+(S11-3); (I-215)+(S12-1); (I-215)+(S13-1); (I-215)+(S13-2); (I-215)+(S13-3); (I-215)+(S13-4): (I-215)+(S13-5); (I-215)+(S13-6); (I-215)+(S13-7); (I-215)+(S13-8); (I-215)+(S13-9); (I-215)+(S14-1)

(I-216)+(S1-1); (I-216)+(S1-2); (I-216)+(S1-3); (I-216)+(S1-4); (I-216)+(S1-5); (I-216)+(S1-6); (I-216)+(S1-7); (I-216)+(S1-8); (I-216)+(S1-9); (I-216)+(S1-10); (I-216)+(S1-11); (I-216)+(S1-12); (I-216)+(S1-13); (I-216)+(S2-1); (I-216)+(S2-2); (I-216)+(S2-3); (I-216)+(S2-4); (I-216)+(S2-5); (I-216)+(S2-6); (I-216)+(S2-7); (I-216)+(S2-8); (I-216)+(S2-9); (I-216)+(S2-10); (I-216)+(S3-1); (I-216)+(S3-2); (I-216)+(S3-3); (I-216)+(S3-4); (I-216)+(S3-5); (I-216)+(S3-6); (I-216)+(S3-7); (I-216)+(S3-8); (I-216)+(S3-9); (I-216)+(S3-10); (I-216)+(S3-11); (I-216)+(S4-1); (I-216)+(S4-2); (I-216)+(S4-3); (I-216)+(S4-4); (I-216)+(S4-5); (I-216)+(S7-1); (I-216)+(S11-1); (I-216)+(S11-2); (I-216)+(S11-3); (I-216)+(S12-1); (I-216)+(S13-1); (I-216)+(S13-2); (I-216)+(S13-3); (I-216)+(S13-4): (I-216)+(S13-5); (I-216)+(S13-6); (I-216)+(S13-7); (I-216)+(S13-8); (I-216)+(S13-9); (I-216)+(S14-1)

(I-217)+(S1-1); (I-217)+(S1-2); (I-217)+(S1-3); (I-217)+(S1-4); (I-217)+(S1-5); (I-217)+(S1-6); (I-217)+(S1-7); (I-217)+(S1-8); (I-217)+(S1-9); (I-217)+(S1-10); (I-217)+(S1-11); (I-217)+(S1-12); (I-217)+(S1-13); (I-217)+(S2-1); (I-217)+(S2-2); (I-217)+(S2-3); (I-217)+(S2-4); (I-217)+(S2-5); (I-217)+(S2-6); (I-217)+(S2-7); (I-217)+(S2-8); (I-217)+(S2-9); (I-217)+(S2-10); (I-217)+(S3-1); (I-217)+(S3-2); (I-217)+(S3-3); (I-217)+(S3-4); (I-217)+(S3-5); (I-217)+(S3-6); (I-217)+(S3-7); (I-217)+(S3-8); (I-217)+(S3-9); (I-217)+(S3-10); (I-217)+(S3-11); (I-217)+(S4-1); (I-217)+(S4-2); (I-217)+(S4-3); (I-217)+(S4-4); (I-217)+(S4-5); (I-217)+(S7-1); (I-217)+(S11-1); (I-217)+(S11-2); (I-217)+(S11-3); (I-217)+(S12-1); (I-217)+(S13-1); (I-217)+(S13-2); (I-217)+(S13-3); (I-217)+(S13-4): (I-217)+(S13-5); (I-217)+(S13-6); (I-217)+(S13-7); (I-217)+(S13-8); (I-217)+(S13-9); (I-217)+(S14-1)

(I-218)+(S1-1); (I-218)+(S1-2); (I-218)+(S1-3); (I-218)+(S1-4); (I-218)+(S1-5); (I-218)+(S1-6); (I-218)+(S1-7); (I-218)+(S1-8); (I-218)+(S1-9); (I-218)+(S1-10); (I-218)+(S1-11); (I-218)+(S1-12); (I-218)+(S1-13); (I-218)+(S2-1); (I-218)+(S2-2); (I-218)+(S2-3); (I-218)+(S2-4); (I-218)+(S2-5); (I-218)+(S2-6); (I-218)+(S2-7); (I-218)+(S2-8); (I-218)+(S2-9); (I-218)+(S2-10); (I-218)+(S3-1); (I-218)+(S3-2); (I-218)+(S3-3); (I-218)+(S3-4); (I-218)+(S3-5); (I-218)+(S3-6); (I-218)+(S3-7); (I-218)+(S3-8); (I-218)+(S3-9); (I-218)+(S3-10); (I-218)+(S3-11); (I-218)+(S4-1); (I-218)+(S4-2); (I-218)+(S4-3); (I-218)+(S4-4); (I-218)+(S4-5); (I-218)+(S7-1); (I-218)+(S11-1); (I-218)+(S11-2);

(I-218)+(S11-3); (I-218)+(S12-1); (I-218)+(S13-1); (I-218)+(S13-2); (I-218)+(S13-3); (I-218)+(S13-4): (I-218)+(S13-5); (I-218)+(S13-6); (I-218)+(S13-7); (I-218)+(S13-8); (I-218)+(S13-9); (I-218)+(S14-1)

(I-219)+(S1-1); (I-219)+(S1-2); (I-219)+(S1-3); (I-219)+(S1-4); (I-219)+(S1-5); (I-219)+(S1-6); (I-219)+(S1-7); (I-219)+(S1-8); (I-219)+(S1-9); (I-219)+(S1-10); (I-219)+(S1-11); (I-219)+(S1-12); (I-219)+(S1-13); (I-219)+(S2-1); (I-219)+(S2-2); (I-219)+(S2-3); (I-219)+(S2-4); (I-219)+(S2-5); (I-219)+(S2-6); (I-219)+(S2-7); (I-219)+(S2-8); (I-219)+(S2-9); (I-219)+(S2-10); (I-219)+(S3-1); (I-219)+(S3-2); (I-219)+(S3-3); (I-219)+(S3-4); (I-219)+(S3-5); (I-219)+(S3-6); (I-219)+(S3-7); (I-219)+(S3-8); (I-219)+(S3-9); (I-219)+(S3-10); (I-219)+(S3-11); (I-219)+(S4-1); (I-219)+(S4-2); (I-219)+(S4-3); (I-219)+(S4-4); (I-219)+(S4-5); (I-219)+(S7-1); (I-219)+(S11-1); (I-219)+(S11-2); (I-219)+(S11-3); (I-219)+(S12-1); (I-219)+(S13-1); (I-219)+(S13-2); (I-219)+(S13-3); (I-219)+(S13-4): (I-219)+(S13-5); (I-219)+(S13-6); (I-219)+(S13-7); (I-219)+(S13-8); (I-219)+(S13-9); (I-219)+(S14-1)

(I-220)+(S1-1); (I-220)+(S1-2); (I-220)+(S1-3); (I-220)+(S1-4); (I-220)+(S1-5); (I-220)+(S1-6); (I-220)+(S1-7); (I-220)+(S1-8); (I-220)+(S1-9); (I-220)+(S1-10); (I-220)+(S1-11); (I-220)+(S1-12); (I-220)+(S1-13); (I-220)+(S2-1); (I-220)+(S2-2); (I-220)+(S2-3); (I-220)+(S2-4); (I-220)+(S2-5); (I-220)+(S2-6); (I-220)+(S2-7); (I-220)+(S2-8); (I-220)+(S2-9); (I-220)+(S2-10); (I-220)+(S3-1); (I-220)+(S3-2); (I-220)+(S3-3); (I-220)+(S3-4); (I-220)+(S3-5); (I-220)+(S3-6); (I-220)+(S3-7); (I-220)+(S3-8); (I-220)+(S3-9); (I-220)+(S3-10); (I-220)+(S3-11); (I-220)+(S4-1); (I-220)+(S4-2); (I-220)+(S4-3); (I-220)+(S4-4); (I-220)+(S4-5); (I-220)+(S7-1); (I-220)+(S11-1); (I-220)+(S11-2); (I-220)+(S11-3); (I-220)+(S12-1); (I-220)+(S13-1); (I-220)+(S13-2); (I-220)+(S13-3); (I-220)+(S13-4): (I-220)+(S13-5); (I-220)+(S13-6); (I-220)+(S13-7); (I-220)+(S13-8); (I-220)+(S13-9); (I-220)+(S14-1)

(I-221)+(S1-1); (I-221)+(S1-2); (I-221)+(S1-3); (I-221)+(S1-4); (I-221)+(S1-5); (I-221)+(S1-6); (I-221)+(S1-7); (I-221)+(S1-8); (I-221)+(S1-9); (I-221)+(S1-10); (I-221)+(S1-11); (I-221)+(S1-12); (I-221)+(S1-13); (I-221)+(S2-1); (I-221)+(S2-2); (I-221)+(S2-3); (I-221)+(S2-4); (I-221)+(S2-5); (I-221)+(S2-6); (I-221)+(S2-7); (I-221)+(S2-8); (I-221)+(S2-9); (I-221)+(S2-10); (I-221)+(S3-1); (I-221)+(S3-2); (I-221)+(S3-3); (I-221)+(S3-4); (I-221)+(S3-5); (I-221)+(S3-6); (I-221)+(S3-7); (I-221)+(S3-8); (I-221)+(S3-9); (I-221)+(S3-10); (I-221)+(S3-11); (I-221)+(S4-1); (I-221)+(S4-2); (I-221)+(S4-3); (I-221)+(S4-4); (I-221)+(S4-5); (I-221)+(S7-1); (I-221)+(S11-1); (I-221)+(S11-2); (I-221)+(S11-3); (I-221)+(S12-1); (I-221)+(S13-1); (I-221)+(S13-2); (I-221)+(S13-3); (I-221)+(S13-4): (I-221)+(S13-5); (I-221)+(S13-6); (I-221)+(S13-7); (I-221)+(S13-8); (I-221)+(S13-9); (I-221)+(S14-1)

(I-222)+(S1-1); (I-222)+(S1-2); (I-222)+(S1-3); (I-222)+(S1-4); (I-222)+(S1-5); (I-222)+(S1-6); (I-222)+(S1-7); (I-222)+(S1-8); (I-222)+(S1-9); (I-222)+(S1-10); (I-222)+(S1-11); (I-222)+(S1-12); (I-222)+(S1-13); (I-222)+(S2-1); (I-222)+(S2-2); (I-222)+(S2-3); (I-222)+(S2-4); (I-222)+(S2-5); (I-222)+(S2-6); (I-222)+(S2-7); (I-222)+(S2-8); (I-222)+(S2-9); (I-222)+(S2-10); (I-222)+(S3-1); (I-222)+(S3-2); (I-222)+(S3-3); (I-222)+(S3-4); (I-222)+(S3-5); (I-222)+(S3-6); (I-222)+(S3-7); (I-222)+(S3-8); (I-222)+(S3-9); (I-222)+(S3-10); (I-222)+(S3-11); (I-222)+(S4-1); (I-222)+(S4-2); (I-222)+(S4-3); (I-222)+(S4-4); (I-222)+(S4-5); (I-222)+(S7-1); (I-222)+(S11-1); (I-222)+(S11-2); (I-222)+(S11-3); (I-222)+(S12-1); (I-222)+(S13-1); (I-222)+(S13-2); (I-222)+(S13-3); (I-222)+(S13-4): (I-222)+(S13-5); (I-222)+(S13-6); (I-222)+(S13-7); (I-222)+(S13-8); (I-222)+(S13-9); (I-222)+(S14-1)

(I-223)+(S1-1); (I-223)+(S1-2); (I-223)+(S1-3); (I-223)+(S1-4); (I-223)+(S1-5); (I-223)+(S1-6); (I-223)+(S1-7); (I-223)+(S1-8); (I-223)+(S1-9); (I-223)+(S1-10); (I-223)+(S1-11); (I-223)+(S1-12); (I-223)+(S1-13); (I-223)+(S2-1); (I-223)+(S2-2); (I-223)+(S2-3); (I-223)+(S2-4); (I-223)+(S2-5); (I-223)+(S2-6); (I-223)+(S2-7); (I-223)+(S2-8); (I-223)+(S2-9); (I-223)+(S2-10); (I-223)+(S3-1); (I-223)+(S3-2); (I-223)+(S3-3); (I-223)+(S3-4); (I-223)+(S3-5); (I-223)+(S3-6); (I-223)+(S3-7); (I-223)+(S3-8); (I-223)+(S3-9); (I-223)+(S3-10); (I-223)+(S3-11); (I-223)+(S4-1); (I-223)+(S4-2); (I-223)+(S4-3); (I-223)+(S4-4); (I-223)+(S4-5); (I-223)+(S7-1); (I-223)+(S11-1); (I-223)+(S11-2); (I-223)+(S11-3); (I-223)+(S12-1); (I-223)+(S13-1); (I-223)+(S13-2); (I-223)+(S13-3); (I-223)+(S13-4): (I-223)+(S13-5); (I-223)+(S13-6); (I-223)+(S13-7); (I-223)+(S13-8); (I-223)+(S13-9); (I-223)+(S14-1)

(I-224)+(S1-1); (I-224)+(S1-2); (I-224)+(S1-3); (I-224)+(S1-4); (I-224)+(S1-5); (I-224)+(S1-6); (I-224)+(S1-7); (I-224)+(S1-8); (I-224)+(S1-9); (I-224)+(S1-10); (I-224)+(S1-11); (I-224)+(S1-12); (I-224)+(S1-13); (I-224)+(S2-1); (I-224)+(S2-2); (I-224)+(S2-3); (I-224)+(S2-4); (I-224)+(S2-5); (I-224)+(S2-6); (I-224)+(S2-7); (I-224)+(S2-8); (I-224)+(S2-9); (I-224)+(S2-10); (I-224)+(S3-1); (I-224)+(S3-2); (I-224)+(S3-3); (I-224)+(S3-4); (I-224)+(S3-5); (I-224)+(S3-6); (I-224)+(S3-7); (I-224)+(S3-8); (I-224)+(S3-9); (I-224)+(S3-10); (I-224)+(S3-11); (I-224)+(S4-1); (I-224)+(S4-2); (I-224)+(S4-3); (I-224)+(S4-4); (I-224)+(S4-5); (I-224)+(S7-1); (I-224)+(S11-1); (I-224)+(S11-2); (I-224)+(S11-3); (I-224)+(S12-1); (I-224)+(S13-1); (I-224)+(S13-2); (I-224)+(S13-3); (I-224)+(S13-4): (I-224)+(S13-5); (I-224)+(S13-6); (I-224)+(S13-7); (I-224)+(S13-8); (I-224)+(S13-9); (I-224)+(S14-1)

(I-225)+(S1-1); (I-225)+(S1-2); (I-225)+(S1-3); (I-225)+(S1-4); (I-225)+(S1-5); (I-225)+(S1-6); (I-225)+(S1-7); (I-225)+(S1-8); (I-225)+(S1-9); (I-225)+(S1-10); (I-225)+(S1-11); (I-225)+(S1-12); (I-225)+(S1-13); (I-225)+(S2-1); (I-225)+(S2-2); (I-225)+(S2-3); (I-225)+(S2-4); (I-225)+(S2-5); (I-225)+(S2-6); (I-225)+(S2-7); (I-225)+(S2-8); (I-225)+(S2-9); (I-225)+(S2-10); (I-225)+(S3-1); (I-225)+(S3-2); (I-225)+(S3-3); (I-225)+(S3-4); (I-225)+(S3-5); (I-225)+(S3-6); (I-225)+(S3-7); (I-225)+(S3-8); (I-225)+(S3-9); (I-225)+(S3-10); (I-225)+(S3-11); (I-225)+(S4-1); (I-225)+(S4-2); (I-225)+(S4-3); (I-225)+(S4-4); (I-225)+(S4-5); (I-225)+(S7-1); (I-225)+(S11-1); (I-225)+(S11-2); (I-225)+(S11-3); (I-225)+(S12-1); (I-225)+(S13-1); (I-225)+(S13-2); (I-225)+(S13-3); (I-225)+(S13-4): (I-225)+(S13-5); (I-225)+(S13-6); (I-225)+(S13-7); (I-225)+(S13-8); (I-225)+(S13-9); (I-225)+(S14-1)

(I-226)+(S1-1); (I-226)+(S1-2); (I-226)+(S1-3); (I-226)+(S1-4); (I-226)+(S1-5); (I-226)+(S1-6); (I-226)+(S1-7); (I-226)+(S1-8); (I-226)+(S1-9); (I-226)+(S1-10); (I-226)+(S1-11); (I-226)+(S1-12); (I-226)+(S1-13); (I-226)+(S2-1); (I-226)+(S2-2); (I-226)+(S2-3); (I-226)+(S2-4); (I-226)+(S2-5); (I-226)+(S2-6); (I-226)+(S2-7); (I-226)+(S2-8); (I-226)+(S2-9); (I-226)+(S2-10); (I-226)+(S3-1); (I-226)+(S3-2); (I-226)+(S3-3); (I-226)+(S3-4); (I-226)+(S3-5); (I-226)+(S3-6); (I-226)+(S3-7); (I-226)+(S3-8); (I-226)+(S3-9); (I-226)+(S3-10); (I-226)+(S3-11); (I-226)+(S4-1); (I-226)+(S4-2); (I-226)+(S4-3); (I-226)+(S4-4); (I-226)+(S4-5); (I-226)+(S7-1); (I-226)+(S11-1); (I-226)+(S11-2); (I-226)+(S11-3); (I-226)+(S12-1); (I-226)+(S13-1); (I-226)+(S13-2); (I-226)+(S13-3); (I-226)+(S13-4): (I-226)+(S13-5); (I-226)+(S13-6); (I-226)+(S13-7); (I-226)+(S13-8); (I-226)+(S13-9); (I-226)+(S14-1)

(I-227)+(S1-1); (I-227)+(S1-2); (I-227)+(S1-3); (I-227)+(S1-4); (I-227)+(S1-5); (I-227)+(S1-6); (I-227)+(S1-7); (I-227)+(S1-8); (I-227)+(S1-9); (I-227)+(S1-10); (I-227)+(S1-11); (I-227)+(S1-12); (I-227)+(S1-13); (I-227)+(S2-1); (I-227)+(S2-2); (I-227)+(S2-3); (I-227)+(S2-4); (I-227)+(S2-5); (I-227)+(S2-6); (I-227)+(S2-7); (I-227)+(S2-8); (I-227)+(S2-9); (I-227)+(S2-10); (I-227)+(S3-1); (I-227)+(S3-2); (I-227)+(S3-3); (I-227)+(S3-4); (I-227)+(S3-5); (I-227)+(S3-6); (I-227)+(S3-7); (I-227)+(S3-8); (I-227)+(S3-9); (I-227)+(S3-10); (I-227)+(S3-11); (I-227)+(S4-1); (I-227)+(S4-2); (I-227)+(S4-3); (I-227)+(S4-4); (I-227)+(S4-5); (I-227)+(S7-1); (I-227)+(S11-1); (I-227)+(S11-2); (I-227)+(S11-3); (I-227)+(S12-1); (I-227)+(S13-1); (I-227)+(S13-2); (I-227)+(S13-3); (I-227)+(S13-4): (I-227)+(S13-5); (I-227)+(S13-6); (I-227)+(S13-7); (I-227)+(S13-8); (I-227)+(S13-9); (I-227)+(S14-1)

(I-228)+(S1-1); (I-228)+(S1-2); (I-228)+(S1-3); (I-228)+(S1-4); (I-228)+(S1-5); (I-228)+(S1-6); (I-228)+(S1-7); (I-228)+(S1-8); (I-228)+(S1-9); (I-228)+(S1-10); (I-228)+(S1-11); (I-228)+(S1-12); (I-228)+(S1-13); (I-228)+(S2-1); (I-228)+(S2-2); (I-228)+(S2-3); (I-228)+(S2-4); (I-228)+(S2-5); (I-228)+(S2-6); (I-228)+(S2-7); (I-228)+(S2-8); (I-228)+(S2-9); (I-228)+(S2-10); (I-228)+(S3-1); (I-228)+(S3-2); (I-228)+(S3-3); (I-228)+(S3-4); (I-228)+(S3-5); (I-228)+(S3-6); (I-228)+(S3-7); (I-228)+(S3-8); (I-228)+(S3-9); (I-228)+(S3-10); (I-228)+(S3-11); (I-228)+(S4-1); (I-228)+(S4-2); (I-228)+(S4-3); (I-228)+(S4-4); (I-228)+(S4-5); (I-228)+(S7-1); (I-228)+(S11-1); (I-228)+(S11-2); (I-228)+(S11-3); (I-228)+(S12-1); (I-228)+(S13-1); (I-228)+(S13-2); (I-228)+(S13-3); (I-228)+(S13-4): (I-228)+(S13-5); (I-228)+(S13-6); (I-228)+(S13-7); (I-228)+(S13-8); (I-228)+(S13-9); (I-228)+(S14-1)

(I-229)+(S1-1); (I-229)+(S1-2); (I-229)+(S1-3); (I-229)+(S1-4); (I-229)+(S1-5); (I-229)+(S1-6); (I-229)+(S1-7); (I-229)+(S1-8); (I-229)+(S1-9); (I-229)+(S1-10); (I-229)+(S1-11); (I-229)+(S1-12); (I-229)+(S1-13); (I-229)+(S2-1); (I-229)+(S2-2); (I-229)+(S2-3); (I-229)+(S2-4); (I-229)+(S2-5); (I-229)+(S2-6); (I-229)+(S2-7); (I-229)+(S2-8); (I-229)+(S2-9); (I-229)+(S2-10); (I-229)+(S3-1); (I-229)+(S3-2); (I-229)+(S3-3); (I-229)+(S3-4); (I-229)+(S3-5); (I-229)+(S3-6); (I-229)+(S3-7); (I-229)+(S3-8); (I-229)+(S3-9); (I-229)+(S3-10); (I-229)+(S3-11); (I-229)+(S4-1); (I-229)+(S4-2); (I-229)+(S4-3); (I-229)+(S4-4); (I-229)+(S4-5); (I-229)+(S7-1); (I-229)+(S11-1); (I-229)+(S11-2); (I-229)+(S11-3); (I-229)+(S12-1); (I-229)+(S13-1); (I-229)+(S13-2); (I-229)+(S13-3); (I-229)+(S13-4): (I-229)+(S13-5); (I-229)+(S13-6); (I-229)+(S13-7); (I-229)+(S13-8); (I-229)+(S13-9); (I-229)+(S14-1)

(I-230)+(S1-1); (I-230)+(S1-2); (I-230)+(S1-3); (I-230)+(S1-4); (I-230)+(S1-5); (I-230)+(S1-6); (I-230)+(S1-7); (I-230)+(S1-8); (I-230)+(S1-9); (I-230)+(S1-10); (I-230)+(S1-11); (I-230)+(S1-12); (I-230)+(S1-13); (I-230)+(S2-1); (I-230)+(S2-2); (I-230)+(S2-3); (I-230)+(S2-4); (I-230)+(S2-5); (I-230)+(S2-6); (I-230)+(S2-7); (I-230)+(S2-8); (I-230)+(S2-9); (I-230)+(S2-10); (I-230)+(S3-1); (I-230)+(S3-2); (I-230)+(S3-3); (I-230)+(S3-4); (I-230)+(S3-5); (I-230)+(S3-6); (I-230)+(S3-7); (I-230)+(S3-8); (I-230)+(S3-9); (I-230)+(S3-10); (I-230)+(S3-11); (I-230)+(S4-1); (I-230)+(S4-2); (I-230)+(S4-3); (I-230)+(S4-4); (I-230)+(S4-5); (I-230)+(S7-1); (I-230)+(S11-1); (I-230)+(S11-2); (I-230)+(S11-3); (I-230)+(S12-1); (I-230)+(S13-1); (I-230)+(S13-2); (I-230)+(S13-3); (I-230)+(S13-4): (I-230)+(S13-5); (I-230)+(S13-6); (I-230)+(S13-7); (I-230)+(S13-8); (I-230)+(S13-9); (I-230)+(S14-1)

(I-231)+(S1-1); (I-231)+(S1-2); (I-231)+(S1-3); (I-231)+(S1-4); (I-231)+(S1-5); (I-231)+(S1-6); (I-231)+(S1-7); (I-231)+(S1-8); (I-231)+(S1-9); (I-231)+(S1-10); (I-231)+(S1-11); (I-231)+(S1-12); (I-231)+(S1-13); (I-231)+(S2-1); (I-231)+(S2-2); (I-231)+(S2-3); (I-231)+(S2-4); (I-231)+(S2-5); (I-231)+(S2-6); (I-231)+(S2-7); (I-231)+(S2-8); (I-231)+(S2-9); (I-231)+(S2-10); (I-231)+(S3-1); (I-231)+(S3-2); (I-231)+(S3-3); (I-231)+(S3-4); (I-231)+(S3-5); (I-231)+(S3-6); (I-231)+(S3-7); (I-231)+(S3-8); (I-231)+(S3-9); (I-231)+(S3-10); (I-231)+(S3-11); (I-231)+(S4-1); (I-231)+(S4-2); (I-231)+(S4-3); (I-231)+(S4-4); (I-231)+(S4-5); (I-231)+(S7-1); (I-231)+(S11-1); (I-231)+(S11-2); (I-231)+(S11-3); (I-231)+(S12-1); (I-231)+(S13-1); (I-231)+(S13-2); (I-231)+(S13-3); (I-231)+(S13-4): (I-231)+(S13-5); (I-231)+(S13-6); (I-231)+(S13-7); (I-231)+(S13-8); (I-231)+(S13-9); (I-231)+(S14-1)

(I-232)+(S1-1); (I-232)+(S1-2); (I-232)+(S1-3); (I-232)+(S1-4); (I-232)+(S1-5); (I-232)+(S1-6); (I-232)+(S1-7); (I-232)+(S1-8); (I-232)+(S1-9); (I-232)+(S1-10); (I-232)+(S1-11); (I-232)+(S1-12); (I-232)+(S1-13); (I-232)+(S2-1); (I-232)+(S2-2); (I-232)+(S2-3); (I-232)+(S2-4); (I-232)+(S2-5); (I-232)+(S2-6); (I-232)+(S2-7); (I-232)+(S2-8); (I-232)+(S2-9); (I-232)+(S2-10); (I-232)+(S3-1); (I-232)+(S3-2); (I-232)+(S3-3); (I-232)+(S3-4); (I-232)+(S3-5); (I-232)+(S3-6); (I-232)+(S3-7); (I-232)+(S3-8); (I-232)+(S3-9); (I-232)+(S3-10); (I-232)+(S3-11); (I-232)+(S4-1); (I-232)+(S4-2); (I-232)+(S4-3); (I-232)+(S4-4); (I-232)+(S4-5); (I-232)+(S7-1); (I-232)+(S11-1); (I-232)+(S11-2); (I-232)+(S11-3); (I-232)+(S12-1); (I-232)+(S13-1); (I-232)+(S13-2); (I-232)+(S13-3); (I-232)+(S13-4): (I-232)+(S13-5); (I-232)+(S13-6); (I-232)+(S13-7); (I-232)+(S13-8); (I-232)+(S13-9); (I-232)+(S14-1)

(I-233)+(S1-1); (I-233)+(S1-2); (I-233)+(S1-3); (I-233)+(S1-4); (I-233)+(S1-5); (I-233)+(S1-6); (I-233)+(S1-7); (I-233)+(S1-8); (I-233)+(S1-9); (I-233)+(S1-10); (I-233)+(S1-11); (I-233)+(S1-12); (I-233)+(S1-13); (I-233)+(S2-1); (I-233)+(S2-2); (I-233)+(S2-3); (I-233)+(S2-4); (I-233)+(S2-5); (I-233)+(S2-6); (I-233)+(S2-7); (I-233)+(S2-8); (I-233)+(S2-9); (I-233)+(S2-10); (I-233)+(S3-1); (I-233)+(S3-2); (I-233)+(S3-3); (I-233)+(S3-4); (I-233)+(S3-5); (I-233)+(S3-6); (I-233)+(S3-7); (I-233)+(S3-8); (I-233)+(S3-9); (I-233)+(S3-10); (I-233)+(S3-11); (I-233)+(S4-1); (I-233)+(S4-2); (I-233)+(S4-3); (I-233)+(S4-4); (I-233)+(S4-5); (I-233)+(S7-1); (I-233)+(S11-1); (I-233)+(S11-2); (I-233)+(S11-3); (I-233)+(S12-1); (I-233)+(S13-1); (I-233)+(S13-2); (I-233)+(S13-3); (I-233)+(S13-4): (I-233)+(S13-5); (I-233)+(S13-6); (I-233)+(S13-7); (I-233)+(S13-8); (I-233)+(S13-9); (I-233)+(S14-1)

(I-234)+(S1-1); (I-234)+(S1-2); (I-234)+(S1-3); (I-234)+(S1-4); (I-234)+(S1-5); (I-234)+(S1-6); (I-234)+(S1-7); (I-234)+(S1-8); (I-234)+(S1-9); (I-234)+(S1-10); (I-234)+(S1-11); (I-234)+(S1-12); (I-234)+(S1-13); (I-234)+(S2-1); (I-234)+(S2-2); (I-234)+(S2-3); (I-234)+(S2-4); (I-234)+(S2-5); (I-234)+(S2-6); (I-234)+(S2-7); (I-234)+(S2-8); (I-234)+(S2-9); (I-234)+(S2-10); (I-234)+(S3-1); (I-234)+(S3-2); (I-234)+(S3-3); (I-234)+(S3-4); (I-234)+(S3-5); (I-234)+(S3-6); (I-234)+(S3-7); (I-234)+(S3-8); (I-234)+(S3-9); (I-234)+(S3-10); (I-234)+(S3-11); (I-234)+(S4-1); (I-234)+(S4-2); (I-234)+(S4-3); (I-234)+(S4-4); (I-234)+(S4-5); (I-234)+(S7-1); (I-234)+(S11-1); (I-234)+(S11-2); (I-234)+(S11-3); (I-234)+(S12-1); (I-234)+(S13-1); (I-234)+(S13-2); (I-234)+(S13-3); (I-234)+(S13-4): (I-234)+(S13-5); (I-234)+(S13-6); (I-234)+(S13-7); (I-234)+(S13-8); (I-234)+(S13-9); (I-234)+(S14-1)

(I-235)+(S1-1); (I-235)+(S1-2); (I-235)+(S1-3); (I-235)+(S1-4); (I-235)+(S1-5); (I-235)+(S1-6); (I-235)+(S1-7); (I-235)+(S1-8); (I-235)+(S1-9); (I-235)+(S1-10); (I-235)+(S1-11); (I-235)+(S1-12); (I-235)+(S1-13); (I-235)+(S2-1); (I-235)+(S2-2); (I-235)+(S2-3); (I-235)+(S2-4); (I-235)+(S2-5); (I-235)+(S2-6); (I-235)+(S2-7); (I-235)+(S2-8);

(I-235)+(S2-9); (I-235)+(S2-10); (I-235)+(S3-1); (I-235)+
(S3-2); (I-235)+(S3-3); (I-235)+(S3-4); (I-235)+(S3-5);
(I-235)+(S3-6); (I-235)+(S3-7); (I-235)+(S3-8); (I-235)+
(S3-9); (I-235)+(S3-10); (I-235)+(S3-11); (I-235)+(S4-1);
(I-235)+(S4-2); (I-235)+(S4-3); (I-235)+(S4-4); (I-235)+
(S4-5); (I-235)+(S7-1); (I-235)+(S11-1); (I-235)+(S11-2);
(I-235)+(S11-3); (I-235)+(S12-1); (I-235)+(S13-1); (I-235)+
(S13-2); (I-235)+(S13-3); (I-235)+(S13-4): (I-235)+(S13-5);
(I-235)+(S13-6); (I-235)+(S13-7); (I-235)+(S13-8); (I-235)+
(S13-9); (I-235)+(S14-1)

(I-236)+(S1-1); (I-236)+(S1-2); (I-236)+(S1-3); (I-236)+
(S1-4); (I-236)+(S1-5); (I-236)+(S1-6); (I-236)+(S1-7);
(I-236)+(S1-8); (I-236)+(S1-9); (I-236)+(S1-10); (I-236)+
(S1-11); (I-236)+(S1-12); (I-236)+(S1-13); (I-236)+(S2-1);
(I-236)+(S2-2); (I-236)+(S2-3); (I-236)+(S2-4); (I-236)+
(S2-5); (I-236)+(S2-6); (I-236)+(S2-7); (I-236)+(S2-8);
(I-236)+(S2-9); (I-236)+(S2-10); (I-236)+(S3-1); (I-236)+
(S3-2); (I-236)+(S3-3); (I-236)+(S3-4); (I-236)+(S3-5);
(I-236)+(S3-6); (I-236)+(S3-7); (I-236)+(S3-8); (I-236)+
(S3-9); (I-236)+(S3-10); (I-236)+(S3-11); (I-236)+(S4-1);
(I-236)+(S4-2); (I-236)+(S4-3); (I-236)+(S4-4); (I-236)+
(S4-5); (I-236)+(S7-1); (I-236)+(S11-1); (I-236)+(S11-2);
(I-236)+(S11-3); (I-236)+(S12-1); (I-236)+(S13-1); (I-236)+
(S13-2); (I-236)+(S13-3); (I-236)+(S13-4): (I-236)+(S13-5);
(I-236)+(S13-6); (I-236)+(S13-7); (I-236)+(S13-8); (I-236)+
(S13-9); (I-236)+(S14-1)

(I-237)+(S1-1); (I-237)+(S1-2); (I-237)+(S1-3); (I-237)+
(S1-4); (I-237)+(S1-5); (I-237)+(S1-6); (I-237)+(S1-7);
(I-237)+(S1-8); (I-237)+(S1-9); (I-237)+(S1-10); (I-237)+
(S1-11); (I-237)+(S1-12); (I-237)+(S1-13); (I-237)+(S2-1);
(I-237)+(S2-2); (I-237)+(S2-3); (I-237)+(S2-4); (I-237)+
(S2-5); (I-237)+(S2-6); (I-237)+(S2-7); (I-237)+(S2-8);
(I-237)+(S2-9); (I-237)+(S2-10); (I-237)+(S3-1); (I-237)+
(S3-2); (I-237)+(S3-3); (I-237)+(S3-4); (I-237)+(S3-5);
(I-237)+(S3-6); (I-237)+(S3-7); (I-237)+(S3-8); (I-237)+
(S3-9); (I-237)+(S3-10); (I-237)+(S3-11); (I-237)+(S4-1);
(I-237)+(S4-2); (I-237)+(S4-3); (I-237)+(S4-4); (I-237)+
(S4-5); (I-237)+(S7-1); (I-237)+(S11-1); (I-237)+(S11-2);
(I-237)+(S11-3); (I-237)+(S12-1); (I-237)+(S13-1); (I-237)+
(S13-2); (I-237)+(S13-3); (I-237)+(S13-4): (I-237)+(S13-5);
(I-237)+(S13-6); (I-237)+(S13-7); (I-237)+(S13-8); (I-237)+
(S13-9); (I-237)+(S14-1)

(I-238)+(S1-1); (I-238)+(S1-2); (I-238)+(S1-3); (I-238)+
(S1-4); (I-238)+(S1-5); (I-238)+(S1-6); (I-238)+(S1-7);
(I-238)+(S1-8); (I-238)+(S1-9); (I-238)+(S1-10); (I-238)+
(S1-11); (I-238)+(S1-12); (I-238)+(S1-13); (I-238)+(S2-1);
(I-238)+(S2-2); (I-238)+(S2-3); (I-238)+(S2-4); (I-238)+
(S2-5); (I-238)+(S2-6); (I-238)+(S2-7); (I-238)+(S2-8);
(I-238)+(S2-9); (I-238)+(S2-10); (I-238)+(S3-1); (I-238)+
(S3-2); (I-238)+(S3-3); (I-238)+(S3-4); (I-238)+(S3-5);
(I-238)+(S3-6); (I-238)+(S3-7); (I-238)+(S3-8); (I-238)+
(S3-9); (I-238)+(S3-10); (I-238)+(S3-11); (I-238)+(S4-1);
(I-238)+(S4-2); (I-238)+(S4-3); (I-238)+(S4-4); (I-238)+
(S4-5); (I-238)+(S7-1); (I-238)+(S11-1); (I-238)+(S11-2);
(I-238)+(S11-3); (I-238)+(S12-1); (I-238)+(S13-1); (I-238)+
(S13-2); (I-238)+(S13-3); (I-238)+(S13-4): (I-238)+(S13-5);
(I-238)+(S13-6); (I-238)+(S13-7); (I-238)+(S13-8); (I-238)+
(S13-9); (I-238)+(S14-1)

(I-239)+(S1-1); (I-239)+(S1-2); (I-239)+(S1-3); (I-239)+
(S1-4); (I-239)+(S1-5); (I-239)+(S1-6); (I-239)+(S1-7);
(I-239)+(S1-8); (I-239)+(S1-9); (I-239)+(S1-10); (I-239)+
(S1-11); (I-239)+(S1-12); (I-239)+(S1-13); (I-239)+(S2-1);
(I-239)+(S2-2); (I-239)+(S2-3); (I-239)+(S2-4); (I-239)+
(S2-5); (I-239)+(S2-6); (I-239)+(S2-7); (I-239)+(S2-8);
(I-239)+(S2-9); (I-239)+(S2-10); (I-239)+(S3-1); (I-239)+
(S3-2); (I-239)+(S3-3); (I-239)+(S3-4); (I-239)+(S3-5);
(I-239)+(S3-6); (I-239)+(S3-7); (I-239)+(S3-8); (I-239)+
(S3-9); (I-239)+(S3-10); (I-239)+(S3-11); (I-239)+(S4-1);
(I-239)+(S4-2); (I-239)+(S4-3); (I-239)+(S4-4); (I-239)+
(S4-5); (I-239)+(S7-1); (I-239)+(S11-1); (I-239)+(S11-2);
(I-239)+(S11-3); (I-239)+(S12-1); (I-239)+(S13-1); (I-239)+
(S13-2); (I-239)+(S13-3); (I-239)+(S13-4): (I-239)+(S13-5);
(I-239)+(S13-6); (I-239)+(S13-7); (I-239)+(S13-8); (I-239)+
(S13-9); (I-239)+(S14-1)

(I-240)+(S1-1); (I-240)+(S1-2); (I-240)+(S1-3); (I-240)+
(S1-4); (I-240)+(S1-5); (I-240)+(S1-6); (I-240)+(S1-7);
(I-240)+(S1-8); (I-240)+(S1-9); (I-240)+(S1-10); (I-240)+
(S1-11); (I-240)+(S1-12); (I-240)+(S1-13); (I-240)+(S2-1);
(I-240)+(S2-2); (I-240)+(S2-3); (I-240)+(S2-4); (I-240)+
(S2-5); (I-240)+(S2-6); (I-240)+(S2-7); (I-240)+(S2-8);
(I-240)+(S2-9); (I-240)+(S2-10); (I-240)+(S3-1); (I-240)+
(S3-2); (I-240)+(S3-3); (I-240)+(S3-4); (I-240)+(S3-5);
(I-240)+(S3-6); (I-240)+(S3-7); (I-240)+(S3-8); (I-240)+
(S3-9); (I-240)+(S3-10); (I-240)+(S3-11); (I-240)+(S4-1);
(I-240)+(S4-2); (I-240)+(S4-3); (I-240)+(S4-4); (I-240)+
(S4-5); (I-240)+(S7-1); (I-240)+(S11-1); (I-240)+(S11-2);
(I-240)+(S11-3); (I-240)+(S12-1); (I-240)+(S13-1); (I-240)+
(S13-2); (I-240)+(S13-3); (I-240)+(S13-4): (I-240)+(S13-5);
(I-240)+(S13-6); (I-240)+(S13-7); (I-240)+(S13-8); (I-240)+
(S13-9); (I-240)+(S14-1)

(I-241)+(S1-1); (I-241)+(S1-2); (I-241)+(S1-3); (I-241)+
(S1-4); (I-241)+(S1-5); (I-241)+(S1-6); (I-241)+(S1-7);
(I-241)+(S1-8); (I-241)+(S1-9); (I-241)+(S1-10); (I-241)+
(S1-11); (I-241)+(S1-12); (I-241)+(S1-13); (I-241)+(S2-1);
(I-241)+(S2-2); (I-241)+(S2-3); (I-241)+(S2-4); (I-241)+
(S2-5); (I-241)+(S2-6); (I-241)+(S2-7); (I-241)+(S2-8);
(I-241)+(S2-9); (I-241)+(S2-10); (I-241)+(S3-1); (I-241)+
(S3-2); (I-241)+(S3-3); (I-241)+(S3-4); (I-241)+(S3-5);
(I-241)+(S3-6); (I-241)+(S3-7); (I-241)+(S3-8); (I-241)+
(S3-9); (I-241)+(S3-10); (I-241)+(S3-11); (I-241)+(S4-1);
(I-241)+(S4-2); (I-241)+(S4-3); (I-241)+(S4-4); (I-241)+
(S4-5); (I-241)+(S7-1); (I-241)+(S11-1); (I-241)+(S11-2);
(I-241)+(S11-3); (I-241)+(S12-1); (I-241)+(S13-1); (I-241)+
(S13-2); (I-241)+(S13-3); (I-241)+(S13-4): (I-241)+(S13-5);
(I-241)+(S13-6); (I-241)+(S13-7); (I-241)+(S13-8); (I-241)+
(S13-9); (I-241)+(S14-1)

(I-242)+(S1-1); (I-242)+(S1-2); (I-242)+(S1-3); (I-242)+
(S1-4); (I-242)+(S1-5); (I-242)+(S1-6); (I-242)+(S1-7);
(I-242)+(S1-8); (I-242)+(S1-9); (I-242)+(S1-10); (I-242)+
(S1-11); (I-242)+(S1-12); (I-242)+(S1-13); (I-242)+(S2-1);
(I-242)+(S2-2); (I-242)+(S2-3); (I-242)+(S2-4); (I-242)+
(S2-5); (I-242)+(S2-6); (I-242)+(S2-7); (I-242)+(S2-8);
(I-242)+(S2-9); (I-242)+(S2-10); (I-242)+(S3-1); (I-242)+
(S3-2); (I-242)+(S3-3); (I-242)+(S3-4); (I-242)+(S3-5);
(I-242)+(S3-6); (I-242)+(S3-7); (I-242)+(S3-8); (I-242)+
(S3-9); (I-242)+(S3-10); (I-242)+(S3-11); (I-242)+(S4-1);
(I-242)+(S4-2); (I-242)+(S4-3); (I-242)+(S4-4); (I-242)+
(S4-5); (I-242)+(S7-1); (I-242)+(S11-1); (I-242)+(S11-2);
(I-242)+(S11-3); (I-242)+(S12-1); (I-242)+(S13-1); (I-242)+
(S13-2); (I-242)+(S13-3); (I-242)+(S13-4): (I-242)+(S13-5);
(I-242)+(S13-6); (I-242)+(S13-7); (I-242)+(S13-8); (I-242)+
(S13-9); (I-242)+(S14-1)

(I-243)+(S1-1); (I-243)+(S1-2); (I-243)+(S1-3); (I-243)+
(S1-4); (I-243)+(S1-5); (I-243)+(S1-6); (I-243)+(S1-7);
(I-243)+(S1-8); (I-243)+(S1-9); (I-243)+(S1-10); (I-243)+
(S1-11); (I-243)+(S1-12); (I-243)+(S1-13); (I-243)+(S2-1);
(I-243)+(S2-2); (I-243)+(S2-3); (I-243)+(S2-4); (I-243)+
(S2-5); (I-243)+(S2-6); (I-243)+(S2-7); (I-243)+(S2-8);
(I-243)+(S2-9); (I-243)+(S2-10); (I-243)+(S3-1); (I-243)+
(S3-2); (I-243)+(S3-3); (I-243)+(S3-4); (I-243)+(S3-5);
(I-243)+(S3-6); (I-243)+(S3-7); (I-243)+(S3-8); (I-243)+
(S3-9); (I-243)+(S3-10); (I-243)+(S3-11); (I-243)+(S4-1);
(I-243)+(S4-2); (I-243)+(S4-3); (I-243)+(S4-4); (I-243)+
(S4-5); (I-243)+(S7-1); (I-243)+(S11-1); (I-243)+(S11-2);

(I-243)+(S11-3); (I-243)+(S12-1); (I-243)+(S13-1); (I-243)+(S13-2); (I-243)+(S13-3); (I-243)+(S13-4): (I-243)+(S13-5); (I-243)+(S13-6); (I-243)+(S13-7); (I-243)+(S13-8); (I-243)+(S13-9); (I-243)+(S14-1)

(I-244)+(S1-1); (I-244)+(S1-2); (I-244)+(S1-3); (I-244)+(S1-4); (I-244)+(S1-5); (I-244)+(S1-6); (I-244)+(S1-7); (I-244)+(S1-8); (I-244)+(S1-9); (I-244)+(S1-10); (I-244)+(S1-11); (I-244)+(S1-12); (I-244)+(S1-13); (I-244)+(S2-1); (I-244)+(S2-2); (I-244)+(S2-3); (I-244)+(S2-4); (I-244)+(S2-5); (I-244)+(S2-6); (I-244)+(S2-7); (I-244)+(S2-8); (I-244)+(S2-9); (I-244)+(S2-10); (I-244)+(S3-1); (I-244)+(S3-2); (I-244)+(S3-3); (I-244)+(S3-4); (I-244)+(S3-5); (I-244)+(S3-6); (I-244)+(S3-7); (I-244)+(S3-8); (I-244)+(S3-9); (I-244)+(S3-10); (I-244)+(S3-11); (I-244)+(S4-1); (I-244)+(S4-2); (I-244)+(S4-3); (I-244)+(S4-4); (I-244)+(S4-5); (I-244)+(S7-1); (I-244)+(S11-1); (I-244)+(S11-2); (I-244)+(S11-3); (I-244)+(S12-1); (I-244)+(S13-1); (I-244)+(S13-2); (I-244)+(S13-3); (I-244)+(S13-4): (I-244)+(S13-5); (I-244)+(S13-6); (I-244)+(S13-7); (I-244)+(S13-8); (I-244)+(S13-9); (I-244)+(S14-1)

(I-245)+(S1-1); (I-245)+(S1-2); (I-245)+(S1-3); (I-245)+(S1-4); (I-245)+(S1-5); (I-245)+(S1-6); (I-245)+(S1-7); (I-245)+(S1-8); (I-245)+(S1-9); (I-245)+(S1-10); (I-245)+(S1-11); (I-245)+(S1-12); (I-245)+(S1-13); (I-245)+(S2-1); (I-245)+(S2-2); (I-245)+(S2-3); (I-245)+(S2-4); (I-245)+(S2-5); (I-245)+(S2-6); (I-245)+(S2-7); (I-245)+(S2-8); (I-245)+(S2-9); (I-245)+(S2-10); (I-245)+(S3-1); (I-245)+(S3-2); (I-245)+(S3-3); (I-245)+(S3-4); (I-245)+(S3-5); (I-245)+(S3-6); (I-245)+(S3-7); (I-245)+(S3-8); (I-245)+(S3-9); (I-245)+(S3-10); (I-245)+(S3-11); (I-245)+(S4-1); (I-245)+(S4-2); (I-245)+(S4-3); (I-245)+(S4-4); (I-245)+(S4-5); (I-245)+(S7-1); (I-245)+(S11-1); (I-245)+(S11-2); (I-245)+(S11-3); (I-245)+(S12-1); (I-245)+(S13-1); (I-245)+(S13-2); (I-245)+(S13-3); (I-245)+(S13-4): (I-245)+(S13-5); (I-245)+(S13-6); (I-245)+(S13-7); (I-245)+(S13-8); (I-245)+(S13-9); (I-245)+(S14-1)

(I-246)+(S1-1); (I-246)+(S1-2); (I-246)+(S1-3); (I-246)+(S1-4); (I-246)+(S1-5); (I-246)+(S1-6); (I-246)+(S1-7); (I-246)+(S1-8); (I-246)+(S1-9); (I-246)+(S1-10); (I-246)+(S1-11); (I-246)+(S1-12); (I-246)+(S1-13); (I-246)+(S2-1); (I-246)+(S2-2); (I-246)+(S2-3); (I-246)+(S2-4); (I-246)+(S2-5); (I-246)+(S2-6); (I-246)+(S2-7); (I-246)+(S2-8); (I-246)+(S2-9); (I-246)+(S2-10); (I-246)+(S3-1); (I-246)+(S3-2); (I-246)+(S3-3); (I-246)+(S3-4); (I-246)+(S3-5); (I-246)+(S3-6); (I-246)+(S3-7); (I-246)+(S3-8); (I-246)+(S3-9); (I-246)+(S3-10); (I-246)+(S3-11); (I-246)+(S4-1); (I-246)+(S4-2); (I-246)+(S4-3); (I-246)+(S4-4); (I-246)+(S4-5); (I-246)+(S7-1); (I-246)+(S11-1); (I-246)+(S11-2); (I-246)+(S11-3); (I-246)+(S12-1); (I-246)+(S13-1); (I-246)+(S13-2); (I-246)+(S13-3); (I-246)+(S13-4): (I-246)+(S13-5); (I-246)+(S13-6); (I-246)+(S13-7); (I-246)+(S13-8); (I-246)+(S13-9); (I-246)+(S14-1)

(I-247)+(S1-1); (I-247)+(S1-2); (I-247)+(S1-3); (I-247)+(S1-4); (I-247)+(S1-5); (I-247)+(S1-6); (I-247)+(S1-7); (I-247)+(S1-8); (I-247)+(S1-9); (I-247)+(S1-10); (I-247)+(S1-11); (I-247)+(S1-12); (I-247)+(S1-13); (I-247)+(S2-1); (I-247)+(S2-2); (I-247)+(S2-3); (I-247)+(S2-4); (I-247)+(S2-5); (I-247)+(S2-6); (I-247)+(S2-7); (I-247)+(S2-8); (I-247)+(S2-9); (I-247)+(S2-10); (I-247)+(S3-1); (I-247)+(S3-2); (I-247)+(S3-3); (I-247)+(S3-4); (I-247)+(S3-5); (I-247)+(S3-6); (I-247)+(S3-7); (I-247)+(S3-8); (I-247)+(S3-9); (I-247)+(S3-10); (I-247)+(S3-11); (I-247)+(S4-1); (I-247)+(S4-2); (I-247)+(S4-3); (I-247)+(S4-4); (I-247)+(S4-5); (I-247)+(S7-1); (I-247)+(S11-1); (I-247)+(S11-2); (I-247)+(S11-3); (I-247)+(S12-1); (I-247)+(S13-1); (I-247)+(S13-2); (I-247)+(S13-3); (I-247)+(S13-4): (I-247)+(S13-5); (I-247)+(S13-6); (I-247)+(S13-7); (I-247)+(S13-8); (I-247)+(S13-9); (I-247)+(S14-1)

(I-248)+(S1-1); (I-248)+(S1-2); (I-248)+(S1-3); (I-248)+(S1-4); (I-248)+(S1-5); (I-248)+(S1-6); (I-248)+(S1-7); (I-248)+(S1-8); (I-248)+(S1-9); (I-248)+(S1-10); (I-248)+(S1-11); (I-248)+(S1-12); (I-248)+(S1-13); (I-248)+(S2-1); (I-248)+(S2-2); (I-248)+(S2-3); (I-248)+(S2-4); (I-248)+(S2-5); (I-248)+(S2-6); (I-248)+(S2-7); (I-248)+(S2-8); (I-248)+(S2-9); (I-248)+(S2-10); (I-248)+(S3-1); (I-248)+(S3-2); (I-248)+(S3-3); (I-248)+(S3-4); (I-248)+(S3-5); (I-248)+(S3-6); (I-248)+(S3-7); (I-248)+(S3-8); (I-248)+(S3-9); (I-248)+(S3-10); (I-248)+(S3-11); (I-248)+(S4-1); (I-248)+(S4-2); (I-248)+(S4-3); (I-248)+(S4-4); (I-248)+(S4-5); (I-248)+(S7-1); (I-248)+(S11-1); (I-248)+(S11-2); (I-248)+(S11-3); (I-248)+(S12-1); (I-248)+(S13-1); (I-248)+(S13-2); (I-248)+(S13-3); (I-248)+(S13-4): (I-248)+(S13-5); (I-248)+(S13-6); (I-248)+(S13-7); (I-248)+(S13-8); (I-248)+(S13-9); (I-248)+(S14-1)

(I-249)+(S1-1); (I-249)+(S1-2); (I-249)+(S1-3); (I-249)+(S1-4); (I-249)+(S1-5); (I-249)+(S1-6); (I-249)+(S1-7); (I-249)+(S1-8); (I-249)+(S1-9); (I-249)+(S1-10); (I-249)+(S1-11); (I-249)+(S1-12); (I-249)+(S1-13); (I-249)+(S2-1); (I-249)+(S2-2); (I-249)+(S2-3); (I-249)+(S2-4); (I-249)+(S2-5); (I-249)+(S2-6); (I-249)+(S2-7); (I-249)+(S2-8); (I-249)+(S2-9); (I-249)+(S2-10); (I-249)+(S3-1); (I-249)+(S3-2); (I-249)+(S3-3); (I-249)+(S3-4); (I-249)+(S3-5); (I-249)+(S3-6); (I-249)+(S3-7); (I-249)+(S3-8); (I-249)+(S3-9); (I-249)+(S3-10); (I-249)+(S3-11); (I-249)+(S4-1); (I-249)+(S4-2); (I-249)+(S4-3); (I-249)+(S4-4); (I-249)+(S4-5); (I-249)+(S7-1); (I-249)+(S11-1); (I-249)+(S11-2); (I-249)+(S11-3); (I-249)+(S12-1); (I-249)+(S13-1); (I-249)+(S13-2); (I-249)+(S13-3); (I-249)+(S13-4): (I-249)+(S13-5); (I-249)+(S13-6); (I-249)+(S13-7); (I-249)+(S13-8); (I-249)+(S13-9); (I-249)+(S14-1)

(I-250)+(S1-1); (I-250)+(S1-2); (I-250)+(S1-3); (I-250)+(S1-4); (I-250)+(S1-5); (I-250)+(S1-6); (I-250)+(S1-7); (I-250)+(S1-8); (I-250)+(S1-9); (I-250)+(S1-10); (I-250)+(S1-11); (I-250)+(S1-12); (I-250)+(S1-13); (I-250)+(S2-1); (I-250)+(S2-2); (I-250)+(S2-3); (I-250)+(S2-4); (I-250)+(S2-5); (I-250)+(S2-6); (I-250)+(S2-7); (I-250)+(S2-8); (I-250)+(S2-9); (I-250)+(S2-10); (I-250)+(S3-1); (I-250)+(S3-2); (I-250)+(S3-3); (I-250)+(S3-4); (I-250)+(S3-5); (I-250)+(S3-6); (I-250)+(S3-7); (I-250)+(S3-8); (I-250)+(S3-9); (I-250)+(S3-10); (I-250)+(S3-11); (I-250)+(S4-1); (I-250)+(S4-2); (I-250)+(S4-3); (I-250)+(S4-4); (I-250)+(S4-5); (I-250)+(S7-1); (I-250)+(S11-1); (I-250)+(S11-2); (I-250)+(S11-3); (I-250)+(S12-1); (I-250)+(S13-1); (I-250)+(S13-2); (I-250)+(S13-3); (I-250)+(S13-4): (I-250)+(S13-5); (I-250)+(S13-6); (I-250)+(S13-7); (I-250)+(S13-8); (I-250)+(S13-9); (I-250)+(S14-1)

(I-251)+(S1-1); (I-251)+(S1-2); (I-251)+(S1-3); (I-251)+(S1-4); (I-251)+(S1-5); (I-251)+(S1-6); (I-251)+(S1-7); (I-251)+(S1-8); (I-251)+(S1-9); (I-251)+(S1-10); (I-251)+(S1-11); (I-251)+(S1-12); (I-251)+(S1-13); (I-251)+(S2-1); (I-251)+(S2-2); (I-251)+(S2-3); (I-251)+(S2-4); (I-251)+(S2-5); (I-251)+(S2-6); (I-251)+(S2-7); (I-251)+(S2-8); (I-251)+(S2-9); (I-251)+(S2-10); (I-251)+(S3-1); (I-251)+(S3-2); (I-251)+(S3-3); (I-251)+(S3-4); (I-251)+(S3-5); (I-251)+(S3-6); (I-251)+(S3-7); (I-251)+(S3-8); (I-251)+(S3-9); (I-251)+(S3-10); (I-251)+(S3-11); (I-251)+(S4-1); (I-251)+(S4-2); (I-251)+(S4-3); (I-251)+(S4-4); (I-251)+(S4-5); (I-251)+(S7-1); (I-251)+(S11-1); (I-251)+(S11-2); (I-251)+(S11-3); (I-251)+(S12-1); (I-251)+(S13-1); (I-251)+(S13-2); (I-251)+(S13-3); (I-251)+(S13-4): (I-251)+(S13-5); (I-251)+(S13-6); (I-251)+(S13-7); (I-251)+(S13-8); (I-251)+(S13-9); (I-251)+(S14-1)

(I-252)+(S1-1); (I-252)+(S1-2); (I-252)+(S1-3); (I-252)+(S1-4); (I-252)+(S1-5); (I-252)+(S1-6); (I-252)+(S1-7); (I-252)+(S1-8); (I-252)+(S1-9); (I-252)+(S1-10); (I-252)+(S1-11); (I-252)+(S1-12); (I-252)+(S1-13); (I-252)+(S2-1); (I-252)+(S2-2); (I-252)+(S2-3); (I-252)+(S2-4); (I-252)+(S2-5); (I-252)+(S2-6); (I-252)+(S2-7); (I-252)+(S2-8); (I-252)+(S2-9); (I-252)+(S2-10); (I-252)+(S3-1); (I-252)+(S3-2); (I-252)+(S3-3); (I-252)+(S3-4); (I-252)+(S3-5); (I-252)+(S3-6); (I-252)+(S3-7); (I-252)+(S3-8); (I-252)+(S3-9); (I-252)+(S3-10); (I-252)+(S3-11); (I-252)+(S4-1); (I-252)+(S4-2); (I-252)+(S4-3); (I-252)+(S4-4); (I-252)+(S4-5); (I-252)+(S7-1); (I-252)+(S11-1); (I-252)+(S11-2); (I-252)+(S11-3); (I-252)+(S12-1); (I-252)+(S13-1); (I-252)+(S13-2); (I-252)+(S13-3); (I-252)+(S13-4): (I-252)+(S13-5); (I-252)+(S13-6); (I-252)+(S13-7); (I-252)+(S13-8); (I-252)+(S13-9); (I-252)+(S14-1)

(I-253)+(S1-1); (I-253)+(S1-2); (I-253)+(S1-3); (I-253)+(S1-4); (I-253)+(S1-5); (I-253)+(S1-6); (I-253)+(S1-7); (I-253)+(S1-8); (I-253)+(S1-9); (I-253)+(S1-10); (I-253)+(S1-11); (I-253)+(S1-12); (I-253)+(S1-13); (I-253)+(S2-1); (I-253)+(S2-2); (I-253)+(S2-3); (I-253)+(S2-4); (I-253)+(S2-5); (I-253)+(S2-6); (I-253)+(S2-7); (I-253)+(S2-8); (I-253)+(S2-9); (I-253)+(S2-10); (I-253)+(S3-1); (I-253)+(S3-2); (I-253)+(S3-3); (I-253)+(S3-4); (I-253)+(S3-5); (I-253)+(S3-6); (I-253)+(S3-7); (I-253)+(S3-8); (I-253)+(S3-9); (I-253)+(S3-10); (I-253)+(S3-11); (I-253)+(S4-1); (I-253)+(S4-2); (I-253)+(S4-3); (I-253)+(S4-4); (I-253)+(S4-5); (I-253)+(S7-1); (I-253)+(S11-1); (I-253)+(S11-2); (I-253)+(S11-3); (I-253)+(S12-1); (I-253)+(S13-1); (I-253)+(S13-2); (I-253)+(S13-3); (I-253)+(S13-4): (I-253)+(S13-5); (I-253)+(S13-6); (I-253)+(S13-7); (I-253)+(S13-8); (I-253)+(S13-9); (I-253)+(S14-1)

(I-254)+(S1-1); (I-254)+(S1-2); (I-254)+(S1-3); (I-254)+(S1-4); (I-254)+(S1-5); (I-254)+(S1-6); (I-254)+(S1-7); (I-254)+(S1-8); (I-254)+(S1-9); (I-254)+(S1-10); (I-254)+(S1-11); (I-254)+(S1-12); (I-254)+(S1-13); (I-254)+(S2-1); (I-254)+(S2-2); (I-254)+(S2-3); (I-254)+(S2-4); (I-254)+(S2-5); (I-254)+(S2-6); (I-254)+(S2-7); (I-254)+(S2-8); (I-254)+(S2-9); (I-254)+(S2-10); (I-254)+(S3-1); (I-254)+(S3-2); (I-254)+(S3-3); (I-254)+(S3-4); (I-254)+(S3-5); (I-254)+(S3-6); (I-254)+(S3-7); (I-254)+(S3-8); (I-254)+(S3-9); (I-254)+(S3-10); (I-254)+(S3-11); (I-254)+(S4-1); (I-254)+(S4-2); (I-254)+(S4-3); (I-254)+(S4-4); (I-254)+(S4-5); (I-254)+(S7-1); (I-254)+(S11-1); (I-254)+(S11-2); (I-254)+(S11-3); (I-254)+(S12-1); (I-254)+(S13-1); (I-254)+(S13-2); (I-254)+(S13-3); (I-254)+(S13-4): (I-254)+(S13-5); (I-254)+(S13-6); (I-254)+(S13-7); (I-254)+(S13-8); (I-254)+(S13-9); (I-254)+(S14-1)

(I-255)+(S1-1); (I-255)+(S1-2); (I-255)+(S1-3); (I-255)+(S1-4); (I-255)+(S1-5); (I-255)+(S1-6); (I-255)+(S1-7); (I-255)+(S1-8); (I-255)+(S1-9); (I-255)+(S1-10); (I-255)+(S1-11); (I-255)+(S1-12); (I-255)+(S1-13); (I-255)+(S2-1); (I-255)+(S2-2); (I-255)+(S2-3); (I-255)+(S2-4); (I-255)+(S2-5); (I-255)+(S2-6); (I-255)+(S2-7); (I-255)+(S2-8); (I-255)+(S2-9); (I-255)+(S2-10); (I-255)+(S3-1); (I-255)+(S3-2); (I-255)+(S3-3); (I-255)+(S3-4); (I-255)+(S3-5); (I-255)+(S3-6); (I-255)+(S3-7); (I-255)+(S3-8); (I-255)+(S3-9); (I-255)+(S3-10); (I-255)+(S3-11); (I-255)+(S4-1); (I-255)+(S4-2); (I-255)+(S4-3); (I-255)+(S4-4); (I-255)+(S4-5); (I-255)+(S7-1); (I-255)+(S11-1); (I-255)+(S11-2); (I-255)+(S11-3); (I-255)+(S12-1); (I-255)+(S13-1); (I-255)+(S13-2); (I-255)+(S13-3); (I-255)+(S13-4): (I-255)+(S13-5); (I-255)+(S13-6); (I-255)+(S13-7); (I-255)+(S13-8); (I-255)+(S13-9); (I-255)+(S14-1)

(I-256)+(S1-1); (I-256)+(S1-2); (I-256)+(S1-3); (I-256)+(S1-4); (I-256)+(S1-5); (I-256)+(S1-6); (I-256)+(S1-7); (I-256)+(S1-8); (I-256)+(S1-9); (I-256)+(S1-10); (I-256)+(S1-11); (I-256)+(S1-12); (I-256)+(S1-13); (I-256)+(S2-1); (I-256)+(S2-2); (I-256)+(S2-3); (I-256)+(S2-4); (I-256)+(S2-5); (I-256)+(S2-6); (I-256)+(S2-7); (I-256)+(S2-8); (I-256)+(S2-9); (I-256)+(S2-10); (I-256)+(S3-1); (I-256)+(S3-2); (I-256)+(S3-3); (I-256)+(S3-4); (I-256)+(S3-5); (I-256)+(S3-6); (I-256)+(S3-7); (I-256)+(S3-8); (I-256)+(S3-9); (I-256)+(S3-10); (I-256)+(S3-11); (I-256)+(S4-1); (I-256)+(S4-2); (I-256)+(S4-3); (I-256)+(S4-4); (I-256)+(S4-5); (I-256)+(S7-1); (I-256)+(S11-1); (I-256)+(S11-2); (I-256)+(S11-3); (I-256)+(S12-1); (I-256)+(S13-1); (I-256)+(S13-2); (I-256)+(S13-3); (I-256)+(S13-4): (I-256)+(S13-5); (I-256)+(S13-6); (I-256)+(S13-7); (I-256)+(S13-8); (I-256)+(S13-9); (I-256)+(S14-1)

(I-257)+(S1-1); (I-257)+(S1-2); (I-257)+(S1-3); (I-257)+(S1-4); (I-257)+(S1-5); (I-257)+(S1-6); (I-257)+(S1-7); (I-257)+(S1-8); (I-257)+(S1-9); (I-257)+(S1-10); (I-257)+(S1-11); (I-257)+(S1-12); (I-257)+(S1-13); (I-257)+(S2-1); (I-257)+(S2-2); (I-257)+(S2-3); (I-257)+(S2-4); (I-257)+(S2-5); (I-257)+(S2-6); (I-257)+(S2-7); (I-257)+(S2-8); (I-257)+(S2-9); (I-257)+(S2-10); (I-257)+(S3-1); (I-257)+(S3-2); (I-257)+(S3-3); (I-257)+(S3-4); (I-257)+(S3-5); (I-257)+(S3-6); (I-257)+(S3-7); (I-257)+(S3-8); (I-257)+(S3-9); (I-257)+(S3-10); (I-257)+(S3-11); (I-257)+(S4-1); (I-257)+(S4-2); (I-257)+(S4-3); (I-257)+(S4-4); (I-257)+(S4-5); (I-257)+(S7-1); (I-257)+(S11-1); (I-257)+(S11-2); (I-257)+(S11-3); (I-257)+(S12-1); (I-257)+(S13-1); (I-257)+(S13-2); (I-257)+(S13-3); (I-257)+(S13-4): (I-257)+(S13-5); (I-257)+(S13-6); (I-257)+(S13-7); (I-257)+(S13-8); (I-257)+(S13-9); (I-257)+(S14-1)

(I-258)+(S1-1); (I-258)+(S1-2); (I-258)+(S1-3); (I-258)+(S1-4); (I-258)+(S1-5); (I-258)+(S1-6); (I-258)+(S1-7); (I-258)+(S1-8); (I-258)+(S1-9); (I-258)+(S1-10); (I-258)+(S1-11); (I-258)+(S1-12); (I-258)+(S1-13); (I-258)+(S2-1); (I-258)+(S2-2); (I-258)+(S2-3); (I-258)+(S2-4); (I-258)+(S2-5); (I-258)+(S2-6); (I-258)+(S2-7); (I-258)+(S2-8); (I-258)+(S2-9); (I-258)+(S2-10); (I-258)+(S3-1); (I-258)+(S3-2); (I-258)+(S3-3); (I-258)+(S3-4); (I-258)+(S3-5); (I-258)+(S3-6); (I-258)+(S3-7); (I-258)+(S3-8); (I-258)+(S3-9); (I-258)+(S3-10); (I-258)+(S3-11); (I-258)+(S4-1); (I-258)+(S4-2); (I-258)+(S4-3); (I-258)+(S4-4); (I-258)+(S4-5); (I-258)+(S7-1); (I-258)+(S11-1); (I-258)+(S11-2); (I-258)+(S11-3); (I-258)+(S12-1); (I-258)+(S13-1); (I-258)+(S13-2); (I-258)+(S13-3); (I-258)+(S13-4): (I-258)+(S13-5); (I-258)+(S13-6); (I-258)+(S13-7); (I-258)+(S13-8); (I-258)+(S13-9); (I-258)+(S14-1)

(I-259)+(S1-1); (I-259)+(S1-2); (I-259)+(S1-3); (I-259)+(S1-4); (I-259)+(S1-5); (I-259)+(S1-6); (I-259)+(S1-7); (I-259)+(S1-8); (I-259)+(S1-9); (I-259)+(S1-10); (I-259)+(S1-11); (I-259)+(S1-12); (I-259)+(S1-13); (I-259)+(S2-1); (I-259)+(S2-2); (I-259)+(S2-3); (I-259)+(S2-4); (I-259)+(S2-5); (I-259)+(S2-6); (I-259)+(S2-7); (I-259)+(S2-8); (I-259)+(S2-9); (I-259)+(S2-10); (I-259)+(S3-1); (I-259)+(S3-2); (I-259)+(S3-3); (I-259)+(S3-4); (I-259)+(S3-5); (I-259)+(S3-6); (I-259)+(S3-7); (I-259)+(S3-8); (I-259)+(S3-9); (I-259)+(S3-10); (I-259)+(S3-11); (I-259)+(S4-1); (I-259)+(S4-2); (I-259)+(S4-3); (I-259)+(S4-4); (I-259)+(S4-5); (I-259)+(S7-1); (I-259)+(S11-1); (I-259)+(S11-2); (I-259)+(S11-3); (I-259)+(S12-1); (I-259)+(S13-1); (I-259)+(S13-2); (I-259)+(S13-3); (I-259)+(S13-4): (I-259)+(S13-5); (I-259)+(S13-6); (I-259)+(S13-7); (I-259)+(S13-8); (I-259)+(S13-9); (I-259)+(S14-1)

(I-260)+(S1-1); (I-260)+(S1-2); (I-260)+(S1-3); (I-260)+(S1-4); (I-260)+(S1-5); (I-260)+(S1-6); (I-260)+(S1-7); (I-260)+(S1-8); (I-260)+(S1-9); (I-260)+(S1-10); (I-260)+(S1-11); (I-260)+(S1-12); (I-260)+(S1-13); (I-260)+(S2-1); (I-260)+(S2-2); (I-260)+(S2-3); (I-260)+(S2-4); (I-260)+(S2-5); (I-260)+(S2-6); (I-260)+(S2-7); (I-260)+(S2-8);

(I-260)+(S2-9); (I-260)+(S2-10); (I-260)+(S3-1); (I-260)+(S3-2); (I-260)+(S3-3); (I-260)+(S3-4); (I-260)+(S3-5); (I-260)+(S3-6); (I-260)+(S3-7); (I-260)+(S3-8); (I-260)+(S3-9); (I-260)+(S3-10); (I-260)+(S3-11); (I-260)+(S4-1); (I-260)+(S4-2); (I-260)+(S4-3); (I-260)+(S4-4); (I-260)+(S4-5); (I-260)+(S7-1); (I-260)+(S11-1); (I-260)+(S11-2); (I-260)+(S11-3); (I-260)+(S12-1); (I-260)+(S13-1); (I-260)+(S13-2); (I-260)+(S13-3); (I-260)+(S13-4): (I-260)+(S13-5); (I-260)+(S13-6); (I-260)+(S13-7); (I-260)+(S13-8); (I-260)+(S13-9); (I-260)+(S14-1)

(I-261)+(S1-1); (I-261)+(S1-2); (I-261)+(S1-3); (I-261)+(S1-4); (I-261)+(S1-5); (I-261)+(S1-6); (I-261)+(S1-7); (I-261)+(S1-8); (I-261)+(S1-9); (I-261)+(S1-10); (I-261)+(S1-11); (I-261)+(S1-12); (I-261)+(S1-13); (I-261)+(S2-1); (I-261)+(S2-2); (I-261)+(S2-3); (I-261)+(S2-4); (I-261)+(S2-5); (I-261)+(S2-6); (I-261)+(S2-7); (I-261)+(S2-8); (I-261)+(S2-9); (I-261)+(S2-10); (I-261)+(S3-1); (I-261)+(S3-2); (I-261)+(S3-3); (I-261)+(S3-4); (I-261)+(S3-5); (I-261)+(S3-6); (I-261)+(S3-7); (I-261)+(S3-8); (I-261)+(S3-9); (I-261)+(S3-10); (I-261)+(S3-11); (I-261)+(S4-1); (I-261)+(S4-2); (I-261)+(S4-3); (I-261)+(S4-4); (I-261)+(S4-5); (I-261)+(S7-1); (I-261)+(S11-1); (I-261)+(S11-2); (I-261)+(S11-3); (I-261)+(S12-1); (I-261)+(S13-1); (I-261)+(S13-2); (I-261)+(S13-3); (I-261)+(S13-4): (I-261)+(S13-5); (I-261)+(S13-6); (I-261)+(S13-7); (I-261)+(S13-8); (I-261)+(S13-9); (I-261)+(S14-1)

(I-262)+(S1-1); (I-262)+(S1-2); (I-262)+(S1-3); (I-262)+(S1-4); (I-262)+(S1-5); (I-262)+(S1-6); (I-262)+(S1-7); (I-262)+(S1-8); (I-262)+(S1-9); (I-262)+(S1-10); (I-262)+(S1-11); (I-262)+(S1-12); (I-262)+(S1-13); (I-262)+(S2-1); (I-262)+(S2-2); (I-262)+(S2-3); (I-262)+(S2-4); (I-262)+(S2-5); (I-262)+(S2-6); (I-262)+(S2-7); (I-262)+(S2-8); (I-262)+(S2-9); (I-262)+(S2-10); (I-262)+(S3-1); (I-262)+(S3-2); (I-262)+(S3-3); (I-262)+(S3-4); (I-262)+(S3-5); (I-262)+(S3-6); (I-262)+(S3-7); (I-262)+(S3-8); (I-262)+(S3-9); (I-262)+(S3-10); (I-262)+(S3-11); (I-262)+(S4-1); (I-262)+(S4-2); (I-262)+(S4-3); (I-262)+(S4-4); (I-262)+(S4-5); (I-262)+(S7-1); (I-262)+(S11-1); (I-262)+(S11-2); (I-262)+(S11-3); (I-262)+(S12-1); (I-262)+(S13-1); (I-262)+(S13-2); (I-262)+(S13-3); (I-262)+(S13-4): (I-262)+(S13-5); (I-262)+(S13-6); (I-262)+(S13-7); (I-262)+(S13-8); (I-262)+(S13-9); (I-262)+(S14-1)

(I-263)+(S1-1); (I-263)+(S1-2); (I-263)+(S1-3); (I-263)+(S1-4); (I-263)+(S1-5); (I-263)+(S1-6); (I-263)+(S1-7); (I-263)+(S1-8); (I-263)+(S1-9); (I-263)+(S1-10); (I-263)+(S1-11); (I-263)+(S1-12); (I-263)+(S1-13); (I-263)+(S2-1); (I-263)+(S2-2); (I-263)+(S2-3); (I-263)+(S2-4); (I-263)+(S2-5); (I-263)+(S2-6); (I-263)+(S2-7); (I-263)+(S2-8); (I-263)+(S2-9); (I-263)+(S2-10); (I-263)+(S3-1); (I-263)+(S3-2); (I-263)+(S3-3); (I-263)+(S3-4); (I-263)+(S3-5); (I-263)+(S3-6); (I-263)+(S3-7); (I-263)+(S3-8); (I-263)+(S3-9); (I-263)+(S3-10); (I-263)+(S3-11); (I-263)+(S4-1); (I-263)+(S4-2); (I-263)+(S4-3); (I-263)+(S4-4); (I-263)+(S4-5); (I-263)+(S7-1); (I-263)+(S11-1); (I-263)+(S11-2); (I-263)+(S11-3); (I-263)+(S12-1); (I-263)+(S13-1); (I-263)+(S13-2); (I-263)+(S13-3); (I-263)+(S13-4): (I-263)+(S13-5); (I-263)+(S13-6); (I-263)+(S13-7); (I-263)+(S13-8); (I-263)+(S13-9); (I-263)+(S14-1)

(I-264)+(S1-1); (I-264)+(S1-2); (I-264)+(S1-3); (I-264)+(S1-4); (I-264)+(S1-5); (I-264)+(S1-6); (I-264)+(S1-7); (I-264)+(S1-8); (I-264)+(S1-9); (I-264)+(S1-10); (I-264)+(S1-11); (I-264)+(S1-12); (I-264)+(S1-13); (I-264)+(S2-1); (I-264)+(S2-2); (I-264)+(S2-3); (I-264)+(S2-4); (I-264)+(S2-5); (I-264)+(S2-6); (I-264)+(S2-7); (I-264)+(S2-8); (I-264)+(S2-9); (I-264)+(S2-10); (I-264)+(S3-1); (I-264)+(S3-2); (I-264)+(S3-3); (I-264)+(S3-4); (I-264)+(S3-5); (I-264)+(S3-6); (I-264)+(S3-7); (I-264)+(S3-8); (I-264)+(S3-9); (I-264)+(S3-10); (I-264)+(S3-11); (I-264)+(S4-1); (I-264)+(S4-2); (I-264)+(S4-3); (I-264)+(S4-4); (I-264)+(S4-5); (I-264)+(S7-1); (I-264)+(S11-1); (I-264)+(S11-2); (I-264)+(S11-3); (I-264)+(S12-1); (I-264)+(S13-1); (I-264)+(S13-2); (I-264)+(S13-3); (I-264)+(S13-4): (I-264)+(S13-5); (I-264)+(S13-6); (I-264)+(S13-7); (I-264)+(S13-8); (I-264)+(S13-9); (I-264)+(S14-1)

(I-265)+(S1-1); (I-265)+(S1-2); (I-265)+(S1-3); (I-265)+(S1-4); (I-265)+(S1-5); (I-265)+(S1-6); (I-265)+(S1-7); (I-265)+(S1-8); (I-265)+(S1-9); (I-265)+(S1-10); (I-265)+(S1-11); (I-265)+(S1-12); (I-265)+(S1-13); (I-265)+(S2-1); (I-265)+(S2-2); (I-265)+(S2-3); (I-265)+(S2-4); (I-265)+(S2-5); (I-265)+(S2-6); (I-265)+(S2-7); (I-265)+(S2-8); (I-265)+(S2-9); (I-265)+(S2-10); (I-265)+(S3-1); (I-265)+(S3-2); (I-265)+(S3-3); (I-265)+(S3-4); (I-265)+(S3-5); (I-265)+(S3-6); (I-265)+(S3-7); (I-265)+(S3-8); (I-265)+(S3-9); (I-265)+(S3-10); (I-265)+(S3-11); (I-265)+(S4-1); (I-265)+(S4-2); (I-265)+(S4-3); (I-265)+(S4-4); (I-265)+(S4-5); (I-265)+(S7-1); (I-265)+(S11-1); (I-265)+(S11-2); (I-265)+(S11-3); (I-265)+(S12-1); (I-265)+(S13-1); (I-265)+(S13-2); (I-265)+(S13-3); (I-265)+(S13-4): (I-265)+(S13-5); (I-265)+(S13-6); (I-265)+(S13-7); (I-265)+(S13-8); (I-265)+(S13-9); (I-265)+(S14-1)

(I-266)+(S1-1); (I-266)+(S1-2); (I-266)+(S1-3); (I-266)+(S1-4); (I-266)+(S1-5); (I-266)+(S1-6); (I-266)+(S1-7); (I-266)+(S1-8); (I-266)+(S1-9); (I-266)+(S1-10); (I-266)+(S1-11); (I-266)+(S1-12); (I-266)+(S1-13); (I-266)+(S2-1); (I-266)+(S2-2); (I-266)+(S2-3); (I-266)+(S2-4); (I-266)+(S2-5); (I-266)+(S2-6); (I-266)+(S2-7); (I-266)+(S2-8); (I-266)+(S2-9); (I-266)+(S2-10); (I-266)+(S3-1); (I-266)+(S3-2); (I-266)+(S3-3); (I-266)+(S3-4); (I-266)+(S3-5); (I-266)+(S3-6); (I-266)+(S3-7); (I-266)+(S3-8); (I-266)+(S3-9); (I-266)+(S3-10); (I-266)+(S3-11); (I-266)+(S4-1); (I-266)+(S4-2); (I-266)+(S4-3); (I-266)+(S4-4); (I-266)+(S4-5); (I-266)+(S7-1); (I-266)+(S11-1); (I-266)+(S11-2); (I-266)+(S11-3); (I-266)+(S12-1); (I-266)+(S13-1); (I-266)+(S13-2); (I-266)+(S13-3); (I-266)+(S13-4): (I-266)+(S13-5); (I-266)+(S13-6); (I-266)+(S13-7); (I-266)+(S13-8); (I-266)+(S13-9); (I-266)+(S14-1)

(I-267)+(S1-1); (I-267)+(S1-2); (I-267)+(S1-3); (I-267)+(S1-4); (I-267)+(S1-5); (I-267)+(S1-6); (I-267)+(S1-7); (I-267)+(S1-8); (I-267)+(S1-9); (I-267)+(S1-10); (I-267)+(S1-11); (I-267)+(S1-12); (I-267)+(S1-13); (I-267)+(S2-1); (I-267)+(S2-2); (I-267)+(S2-3); (I-267)+(S2-4); (I-267)+(S2-5); (I-267)+(S2-6); (I-267)+(S2-7); (I-267)+(S2-8); (I-267)+(S2-9); (I-267)+(S2-10); (I-267)+(S3-1); (I-267)+(S3-2); (I-267)+(S3-3); (I-267)+(S3-4); (I-267)+(S3-5); (I-267)+(S3-6); (I-267)+(S3-7); (I-267)+(S3-8); (I-267)+(S3-9); (I-267)+(S3-10); (I-267)+(S3-11); (I-267)+(S4-1); (I-267)+(S4-2); (I-267)+(S4-3); (I-267)+(S4-4); (I-267)+(S4-5); (I-267)+(S7-1); (I-267)+(S11-1); (I-267)+(S11-2); (I-267)+(S11-3); (I-267)+(S12-1); (I-267)+(S13-1); (I-267)+(S13-2); (I-267)+(S13-3); (I-267)+(S13-4): (I-267)+(S13-5); (I-267)+(S13-6); (I-267)+(S13-7); (I-267)+(S13-8); (I-267)+(S13-9); (I-267)+(S14-1)

(I-268)+(S1-1); (I-268)+(S1-2); (I-268)+(S1-3); (I-268)+(S1-4); (I-268)+(S1-5); (I-268)+(S1-6); (I-268)+(S1-7); (I-268)+(S1-8); (I-268)+(S1-9); (I-268)+(S1-10); (I-268)+(S1-11); (I-268)+(S1-12); (I-268)+(S1-13); (I-268)+(S2-1); (I-268)+(S2-2); (I-268)+(S2-3); (I-268)+(S2-4); (I-268)+(S2-5); (I-268)+(S2-6); (I-268)+(S2-7); (I-268)+(S2-8); (I-268)+(S2-9); (I-268)+(S2-10); (I-268)+(S3-1); (I-268)+(S3-2); (I-268)+(S3-3); (I-268)+(S3-4); (I-268)+(S3-5); (I-268)+(S3-6); (I-268)+(S3-7); (I-268)+(S3-8); (I-268)+(S3-9); (I-268)+(S3-10); (I-268)+(S3-11); (I-268)+(S4-1); (I-268)+(S4-2); (I-268)+(S4-3); (I-268)+(S4-4); (I-268)+(S4-5); (I-268)+(S7-1); (I-268)+(S11-1); (I-268)+(S11-2);

(I-268)+(S11-3); (I-268)+(S12-1); (I-268)+(S13-1); (I-268)+(S13-2); (I-268)+(S13-3); (I-268)+(S13-4): (I-268)+(S13-5); (I-268)+(S13-6); (I-268)+(S13-7); (I-268)+(S13-8); (I-268)+(S13-9); (I-268)+(S14-1)

(I-269)+(S1-1); (I-269)+(S1-2); (I-269)+(S1-3); (I-269)+(S1-4); (I-269)+(S1-5); (I-269)+(S1-6); (I-269)+(S1-7); (I-269)+(S1-8); (I-269)+(S1-9); (I-269)+(S1-10); (I-269)+(S1-11); (I-269)+(S1-12); (I-269)+(S1-13); (I-269)+(S2-1); (I-269)+(S2-2); (I-269)+(S2-3); (I-269)+(S2-4); (I-269)+(S2-5); (I-269)+(S2-6); (I-269)+(S2-7); (I-269)+(S2-8); (I-269)+(S2-9); (I-269)+(S2-10); (I-269)+(S3-1); (I-269)+(S3-2); (I-269)+(S3-3); (I-269)+(S3-4); (I-269)+(S3-5); (I-269)+(S3-6); (I-269)+(S3-7); (I-269)+(S3-8); (I-269)+(S3-9); (I-269)+(S3-10); (I-269)+(S3-11); (I-269)+(S4-1); (I-269)+(S4-2); (I-269)+(S4-3); (I-269)+(S4-4); (I-269)+(S4-5); (I-269)+(S7-1); (I-269)+(S11-1); (I-269)+(S11-2); (I-269)+(S11-3); (I-269)+(S12-1); (I-269)+(S13-1); (I-269)+(S13-2); (I-269)+(S13-3); (I-269)+(S13-4): (I-269)+(S13-5); (I-269)+(S13-6); (I-269)+(S13-7); (I-269)+(S13-8); (I-269)+(S13-9); (I-269)+(S14-1)

(I-270)+(S1-1); (I-270)+(S1-2); (I-270)+(S1-3); (I-270)+(S1-4); (I-270)+(S1-5); (I-270)+(S1-6); (I-270)+(S1-7); (I-270)+(S1-8); (I-270)+(S1-9); (I-270)+(S1-10); (I-270)+(S1-11); (I-270)+(S1-12); (I-270)+(S1-13); (I-270)+(S2-1); (I-270)+(S2-2); (I-270)+(S2-3); (I-270)+(S2-4); (I-270)+(S2-5); (I-270)+(S2-6); (I-270)+(S2-7); (I-270)+(S2-8); (I-270)+(S2-9); (I-270)+(S2-10); (I-270)+(S3-1); (I-270)+(S3-2); (I-270)+(S3-3); (I-270)+(S3-4); (I-270)+(S3-5); (I-270)+(S3-6); (I-270)+(S3-7); (I-270)+(S3-8); (I-270)+(S3-9); (I-270)+(S3-10); (I-270)+(S3-11); (I-270)+(S4-1); (I-270)+(S4-2); (I-270)+(S4-3); (I-270)+(S4-4); (I-270)+(S4-5); (I-270)+(S7-1); (I-270)+(S11-1); (I-270)+(S11-2); (I-270)+(S11-3); (I-270)+(S12-1); (I-270)+(S13-1); (I-270)+(S13-2); (I-270)+(S13-3); (I-270)+(S13-4): (I-270)+(S13-5); (I-270)+(S13-6); (I-270)+(S13-7); (I-270)+(S13-8); (I-270)+(S13-9); (I-270)+(S14-1)

(I-271)+(S1-1); (I-271)+(S1-2); (I-271)+(S1-3); (I-271)+(S1-4); (I-271)+(S1-5); (I-271)+(S1-6); (I-271)+(S1-7); (I-271)+(S1-8); (I-271)+(S1-9); (I-271)+(S1-10); (I-271)+(S1-11); (I-271)+(S1-12); (I-271)+(S1-13); (I-271)+(S2-1); (I-271)+(S2-2); (I-271)+(S2-3); (I-271)+(S2-4); (I-271)+(S2-5); (I-271)+(S2-6); (I-271)+(S2-7); (I-271)+(S2-8); (I-271)+(S2-9); (I-271)+(S2-10); (I-271)+(S3-1); (I-271)+(S3-2); (I-271)+(S3-3); (I-271)+(S3-4); (I-271)+(S3-5); (I-271)+(S3-6); (I-271)+(S3-7); (I-271)+(S3-8); (I-271)+(S3-9); (I-271)+(S3-10); (I-271)+(S3-11); (I-271)+(S4-1); (I-271)+(S4-2); (I-271)+(S4-3); (I-271)+(S4-4); (I-271)+(S4-5); (I-271)+(S7-1); (I-271)+(S11-1); (I-271)+(S11-2); (I-271)+(S11-3); (I-271)+(S12-1); (I-271)+(S13-1); (I-271)+(S13-2); (I-271)+(S13-3); (I-271)+(S13-4): (I-271)+(S13-5); (I-271)+(S13-6); (I-271)+(S13-7); (I-271)+(S13-8); (I-271)+(S13-9); (I-271)+(S14-1)

(I-272)+(S1-1); (I-272)+(S1-2); (I-272)+(S1-3); (I-272)+(S1-4); (I-272)+(S1-5); (I-272)+(S1-6); (I-272)+(S1-7); (I-272)+(S1-8); (I-272)+(S1-9); (I-272)+(S1-10); (I-272)+(S1-11); (I-272)+(S1-12); (I-272)+(S1-13); (I-272)+(S2-1); (I-272)+(S2-2); (I-272)+(S2-3); (I-272)+(S2-4); (I-272)+(S2-5); (I-272)+(S2-6); (I-272)+(S2-7); (I-272)+(S2-8); (I-272)+(S2-9); (I-272)+(S2-10); (I-272)+(S3-1); (I-272)+(S3-2); (I-272)+(S3-3); (I-272)+(S3-4); (I-272)+(S3-5); (I-272)+(S3-6); (I-272)+(S3-7); (I-272)+(S3-8); (I-272)+(S3-9); (I-272)+(S3-10); (I-272)+(S3-11); (I-272)+(S4-1); (I-272)+(S4-2); (I-272)+(S4-3); (I-272)+(S4-4); (I-272)+(S4-5); (I-272)+(S7-1); (I-272)+(S11-1); (I-272)+(S11-2); (I-272)+(S11-3); (I-272)+(S12-1); (I-272)+(S13-1); (I-272)+(S13-2); (I-272)+(S13-3); (I-272)+(S13-4): (I-272)+(S13-5); (I-272)+(S13-6); (I-272)+(S13-7); (I-272)+(S13-8); (I-272)+(S13-9); (I-272)+(S14-1)

(I-273)+(S1-1); (I-273)+(S1-2); (I-273)+(S1-3); (I-273)+(S1-4); (I-273)+(S1-5); (I-273)+(S1-6); (I-273)+(S1-7); (I-273)+(S1-8); (I-273)+(S1-9); (I-273)+(S1-10); (I-273)+(S1-11); (I-273)+(S1-12); (I-273)+(S1-13); (I-273)+(S2-1); (I-273)+(S2-2); (I-273)+(S2-3); (I-273)+(S2-4); (I-273)+(S2-5); (I-273)+(S2-6); (I-273)+(S2-7); (I-273)+(S2-8); (I-273)+(S2-9); (I-273)+(S2-10); (I-273)+(S3-1); (I-273)+(S3-2); (I-273)+(S3-3); (I-273)+(S3-4); (I-273)+(S3-5); (I-273)+(S3-6); (I-273)+(S3-7); (I-273)+(S3-8); (I-273)+(S3-9); (I-273)+(S3-10); (I-273)+(S3-11); (I-273)+(S4-1); (I-273)+(S4-2); (I-273)+(S4-3); (I-273)+(S4-4); (I-273)+(S4-5); (I-273)+(S7-1); (I-273)+(S11-1); (I-273)+(S11-2); (I-273)+(S11-3); (I-273)+(S12-1); (I-273)+(S13-1); (I-273)+(S13-2); (I-273)+(S13-3); (I-273)+(S13-4): (I-273)+(S13-5); (I-273)+(S13-6); (I-273)+(S13-7); (I-273)+(S13-8); (I-273)+(S13-9); (I-273)+(S14-1)

(I-274)+(S1-1); (I-274)+(S1-2); (I-274)+(S1-3); (I-274)+(S1-4); (I-274)+(S1-5); (I-274)+(S1-6); (I-274)+(S1-7); (I-274)+(S1-8); (I-274)+(S1-9); (I-274)+(S1-10); (I-274)+(S1-11); (I-274)+(S1-12); (I-274)+(S1-13); (I-274)+(S2-1); (I-274)+(S2-2); (I-274)+(S2-3); (I-274)+(S2-4); (I-274)+(S2-5); (I-274)+(S2-6); (I-274)+(S2-7); (I-274)+(S2-8); (I-274)+(S2-9); (I-274)+(S2-10); (I-274)+(S3-1); (I-274)+(S3-2); (I-274)+(S3-3); (I-274)+(S3-4); (I-274)+(S3-5); (I-274)+(S3-6); (I-274)+(S3-7); (I-274)+(S3-8); (I-274)+(S3-9); (I-274)+(S3-10); (I-274)+(S3-11); (I-274)+(S4-1); (I-274)+(S4-2); (I-274)+(S4-3); (I-274)+(S4-4); (I-274)+(S4-5); (I-274)+(S7-1); (I-274)+(S11-1); (I-274)+(S11-2); (I-274)+(S11-3); (I-274)+(S12-1); (I-274)+(S13-1); (I-274)+(S13-2); (I-274)+(S13-3); (I-274)+(S13-4): (I-274)+(S13-5); (I-274)+(S13-6); (I-274)+(S13-7); (I-274)+(S13-8); (I-274)+(S13-9); (I-274)+(S14-1)

(I-275)+(S1-1); (I-275)+(S1-2); (I-275)+(S1-3); (I-275)+(S1-4); (I-275)+(S1-5); (I-275)+(S1-6); (I-275)+(S1-7); (I-275)+(S1-8); (I-275)+(S1-9); (I-275)+(S1-10); (I-275)+(S1-11); (I-275)+(S1-12); (I-275)+(S1-13); (I-275)+(S2-1); (I-275)+(S2-2); (I-275)+(S2-3); (I-275)+(S2-4); (I-275)+(S2-5); (I-275)+(S2-6); (I-275)+(S2-7); (I-275)+(S2-8); (I-275)+(S2-9); (I-275)+(S2-10); (I-275)+(S3-1); (I-275)+(S3-2); (I-275)+(S3-3); (I-275)+(S3-4); (I-275)+(S3-5); (I-275)+(S3-6); (I-275)+(S3-7); (I-275)+(S3-8); (I-275)+(S3-9); (I-275)+(S3-10); (I-275)+(S3-11); (I-275)+(S4-1); (I-275)+(S4-2); (I-275)+(S4-3); (I-275)+(S4-4); (I-275)+(S4-5); (I-275)+(S7-1); (I-275)+(S11-1); (I-275)+(S11-2); (I-275)+(S11-3); (I-275)+(S12-1); (I-275)+(S13-1); (I-275)+(S13-2); (I-275)+(S13-3); (I-275)+(S13-4): (I-275)+(S13-5); (I-275)+(S13-6); (I-275)+(S13-7); (I-275)+(S13-8); (I-275)+(S13-9); (I-275)+(S14-1)

(I-276)+(S1-1); (I-276)+(S1-2); (I-276)+(S1-3); (I-276)+(S1-4); (I-276)+(S1-5); (I-276)+(S1-6); (I-276)+(S1-7); (I-276)+(S1-8); (I-276)+(S1-9); (I-276)+(S1-10); (I-276)+(S1-11); (I-276)+(S1-12); (I-276)+(S1-13); (I-276)+(S2-1); (I-276)+(S2-2); (I-276)+(S2-3); (I-276)+(S2-4); (I-276)+(S2-5); (I-276)+(S2-6); (I-276)+(S2-7); (I-276)+(S2-8); (I-276)+(S2-9); (I-276)+(S2-10); (I-276)+(S3-1); (I-276)+(S3-2); (I-276)+(S3-3); (I-276)+(S3-4); (I-276)+(S3-5); (I-276)+(S3-6); (I-276)+(S3-7); (I-276)+(S3-8); (I-276)+(S3-9); (I-276)+(S3-10); (I-276)+(S3-11); (I-276)+(S4-1); (I-276)+(S4-2); (I-276)+(S4-3); (I-276)+(S4-4); (I-276)+(S4-5); (I-276)+(S7-1); (I-276)+(S11-1); (I-276)+(S11-2); (I-276)+(S11-3); (I-276)+(S12-1); (I-276)+(S13-1); (I-276)+(S13-2); (I-276)+(S13-3); (I-276)+(S13-4): (I-276)+(S13-5); (I-276)+(S13-6); (I-276)+(S13-7); (I-276)+(S13-8); (I-276)+(S13-9); (I-276)+(S14-1)

(I-277)+(S1-1); (I-277)+(S1-2); (I-277)+(S1-3); (I-277)+(S1-4); (I-277)+(S1-5); (I-277)+(S1-6); (I-277)+(S1-7); (I-277)+(S1-8); (I-277)+(S1-9); (I-277)+(S1-10); (I-277)+(S1-11); (I-277)+(S1-12); (I-277)+(S1-13); (I-277)+(S2-1); (I-277)+(S2-2); (I-277)+(S2-3); (I-277)+(S2-4); (I-277)+(S2-5); (I-277)+(S2-6); (I-277)+(S2-7); (I-277)+(S2-8); (I-277)+(S2-9); (I-277)+(S2-10); (I-277)+(S3-1); (I-277)+(S3-2); (I-277)+(S3-3); (I-277)+(S3-4); (I-277)+(S3-5); (I-277)+(S3-6); (I-277)+(S3-7); (I-277)+(S3-8); (I-277)+(S3-9); (I-277)+(S3-10); (I-277)+(S3-11); (I-277)+(S4-1); (I-277)+(S4-2); (I-277)+(S4-3); (I-277)+(S4-4); (I-277)+(S4-5); (I-277)+(S7-1); (I-277)+(S11-1); (I-277)+(S11-2); (I-277)+(S11-3); (I-277)+(S12-1); (I-277)+(S13-1); (I-277)+(S13-2); (I-277)+(S13-3); (I-277)+(S13-4): (I-277)+(S13-5); (I-277)+(S13-6); (I-277)+(S13-7); (I-277)+(S13-8); (I-277)+(S13-9); (I-277)+(S14-1)

(I-278)+(S1-1); (I-278)+(S1-2); (I-278)+(S1-3); (I-278)+(S1-4); (I-278)+(S1-5); (I-278)+(S1-6); (I-278)+(S1-7); (I-278)+(S1-8); (I-278)+(S1-9); (I-278)+(S1-10); (I-278)+(S1-11); (I-278)+(S1-12); (I-278)+(S1-13); (I-278)+(S2-1); (I-278)+(S2-2); (I-278)+(S2-3); (I-278)+(S2-4); (I-278)+(S2-5); (I-278)+(S2-6); (I-278)+(S2-7); (I-278)+(S2-8); (I-278)+(S2-9); (I-278)+(S2-10); (I-278)+(S3-1); (I-278)+(S3-2); (I-278)+(S3-3); (I-278)+(S3-4); (I-278)+(S3-5); (I-278)+(S3-6); (I-278)+(S3-7); (I-278)+(S3-8); (I-278)+(S3-9); (I-278)+(S3-10); (I-278)+(S3-11); (I-278)+(S4-1); (I-278)+(S4-2); (I-278)+(S4-3); (I-278)+(S4-4); (I-278)+(S4-5); (I-278)+(S7-1); (I-278)+(S11-1); (I-278)+(S11-2); (I-278)+(S11-3); (I-278)+(S12-1); (I-278)+(S13-1); (I-278)+(S13-2); (I-278)+(S13-3); (I-278)+(S13-4): (I-278)+(S13-5); (I-278)+(S13-6); (I-278)+(S13-7); (I-278)+(S13-8); (I-278)+(S13-9); (I-278)+(S14-1)

(I-279)+(S1-1); (I-279)+(S1-2); (I-279)+(S1-3); (I-279)+(S1-4); (I-279)+(S1-5); (I-279)+(S1-6); (I-279)+(S1-7); (I-279)+(S1-8); (I-279)+(S1-9); (I-279)+(S1-10); (I-279)+(S1-11); (I-279)+(S1-12); (I-279)+(S1-13); (I-279)+(S2-1); (I-279)+(S2-2); (I-279)+(S2-3); (I-279)+(S2-4); (I-279)+(S2-5); (I-279)+(S2-6); (I-279)+(S2-7); (I-279)+(S2-8); (I-279)+(S2-9); (I-279)+(S2-10); (I-279)+(S3-1); (I-279)+(S3-2); (I-279)+(S3-3); (I-279)+(S3-4); (I-279)+(S3-5); (I-279)+(S3-6); (I-279)+(S3-7); (I-279)+(S3-8); (I-279)+(S3-9); (I-279)+(S3-10); (I-279)+(S3-11); (I-279)+(S4-1); (I-279)+(S4-2); (I-279)+(S4-3); (I-279)+(S4-4); (I-279)+(S4-5); (I-279)+(S7-1); (I-279)+(S11-1); (I-279)+(S11-2); (I-279)+(S11-3); (I-279)+(S12-1); (I-279)+(S13-1); (I-279)+(S13-2); (I-279)+(S13-3); (I-279)+(S13-4): (I-279)+(S13-5); (I-279)+(S13-6); (I-279)+(S13-7); (I-279)+(S13-8); (I-279)+(S13-9); (I-279)+(S14-1)

(I-280)+(S1-1); (I-280)+(S1-2); (I-280)+(S1-3); (I-280)+(S1-4); (I-280)+(S1-5); (I-280)+(S1-6); (I-280)+(S1-7); (I-280)+(S1-8); (I-280)+(S1-9); (I-280)+(S1-10); (I-280)+(S1-11); (I-280)+(S1-12); (I-280)+(S1-13); (I-280)+(S2-1); (I-280)+(S2-2); (I-280)+(S2-3); (I-280)+(S2-4); (I-280)+(S2-5); (I-280)+(S2-6); (I-280)+(S2-7); (I-280)+(S2-8); (I-280)+(S2-9); (I-280)+(S2-10); (I-280)+(S3-1); (I-280)+(S3-2); (I-280)+(S3-3); (I-280)+(S3-4); (I-280)+(S3-5); (I-280)+(S3-6); (I-280)+(S3-7); (I-280)+(S3-8); (I-280)+(S3-9); (I-280)+(S3-10); (I-280)+(S3-11); (I-280)+(S4-1); (I-280)+(S4-2); (I-280)+(S4-3); (I-280)+(S4-4); (I-280)+(S4-5); (I-280)+(S7-1); (I-280)+(S11-1); (I-280)+(S11-2); (I-280)+(S11-3); (I-280)+(S12-1); (I-280)+(S13-1); (I-280)+(S13-2); (I-280)+(S13-3); (I-280)+(S13-4): (I-280)+(S13-5); (I-280)+(S13-6); (I-280)+(S13-7); (I-280)+(S13-8); (I-280)+(S13-9); (I-280)+(S14-1)

(I-281)+(S1-1); (I-281)+(S1-2); (I-281)+(S1-3); (I-281)+(S1-4); (I-281)+(S1-5); (I-281)+(S1-6); (I-281)+(S1-7); (I-281)+(S1-8); (I-281)+(S1-9); (I-281)+(S1-10); (I-281)+(S1-11); (I-281)+(S1-12); (I-281)+(S1-13); (I-281)+(S2-1); (I-281)+(S2-2); (I-281)+(S2-3); (I-281)+(S2-4); (I-281)+(S2-5); (I-281)+(S2-6); (I-281)+(S2-7); (I-281)+(S2-8); (I-281)+(S2-9); (I-281)+(S2-10); (I-281)+(S3-1); (I-281)+(S3-2); (I-281)+(S3-3); (I-281)+(S3-4); (I-281)+(S3-5); (I-281)+(S3-6); (I-281)+(S3-7); (I-281)+(S3-8); (I-281)+(S3-9); (I-281)+(S3-10); (I-281)+(S3-11); (I-281)+(S4-1); (I-281)+(S4-2); (I-281)+(S4-3); (I-281)+(S4-4); (I-281)+(S4-5); (I-281)+(S7-1); (I-281)+(S11-1); (I-281)+(S11-2); (I-281)+(S11-3); (I-281)+(S12-1); (I-281)+(S13-1); (I-281)+(S13-2); (I-281)+(S13-3); (I-281)+(S13-4): (I-281)+(S13-5); (I-281)+(S13-6); (I-281)+(S13-7); (I-281)+(S13-8); (I-281)+(S13-9); (I-281)+(S14-1)

(I-282)+(S1-1); (I-282)+(S1-2); (I-282)+(S1-3); (I-282)+(S1-4); (I-282)+(S1-5); (I-282)+(S1-6); (I-282)+(S1-7); (I-282)+(S1-8); (I-282)+(S1-9); (I-282)+(S1-10); (I-282)+(S1-11); (I-282)+(S1-12); (I-282)+(S1-13); (I-282)+(S2-1); (I-282)+(S2-2); (I-282)+(S2-3); (I-282)+(S2-4); (I-282)+(S2-5); (I-282)+(S2-6); (I-282)+(S2-7); (I-282)+(S2-8); (I-282)+(S2-9); (I-282)+(S2-10); (I-282)+(S3-1); (I-282)+(S3-2); (I-282)+(S3-3); (I-282)+(S3-4); (I-282)+(S3-5); (I-282)+(S3-6); (I-282)+(S3-7); (I-282)+(S3-8); (I-282)+(S3-9); (I-282)+(S3-10); (I-282)+(S3-11); (I-282)+(S4-1); (I-282)+(S4-2); (I-282)+(S4-3); (I-282)+(S4-4); (I-282)+(S4-5); (I-282)+(S7-1); (I-282)+(S11-1); (I-282)+(S11-2); (I-282)+(S11-3); (I-282)+(S12-1); (I-282)+(S13-1); (I-282)+(S13-2); (I-282)+(S13-3); (I-282)+(S13-4): (I-282)+(S13-5); (I-282)+(S13-6); (I-282)+(S13-7); (I-282)+(S13-8); (I-282)+(S13-9); (I-282)+(S14-1)

(I-283)+(S1-1); (I-283)+(S1-2); (I-283)+(S1-3); (I-283)+(S1-4); (I-283)+(S1-5); (I-283)+(S1-6); (I-283)+(S1-7); (I-283)+(S1-8); (I-283)+(S1-9); (I-283)+(S1-10); (I-283)+(S1-11); (I-283)+(S1-12); (I-283)+(S1-13); (I-283)+(S2-1); (I-283)+(S2-2); (I-283)+(S2-3); (I-283)+(S2-4); (I-283)+(S2-5); (I-283)+(S2-6); (I-283)+(S2-7); (I-283)+(S2-8); (I-283)+(S2-9); (I-283)+(S2-10); (I-283)+(S3-1); (I-283)+(S3-2); (I-283)+(S3-3); (I-283)+(S3-4); (I-283)+(S3-5); (I-283)+(S3-6); (I-283)+(S3-7); (I-283)+(S3-8); (I-283)+(S3-9); (I-283)+(S3-10); (I-283)+(S3-11); (I-283)+(S4-1); (I-283)+(S4-2); (I-283)+(S4-3); (I-283)+(S4-4); (I-283)+(S4-5); (I-283)+(S7-1); (I-283)+(S11-1); (I-283)+(S11-2); (I-283)+(S11-3); (I-283)+(S12-1); (I-283)+(S13-1); (I-283)+(S13-2); (I-283)+(S13-3); (I-283)+(S13-4): (I-283)+(S13-5); (I-283)+(S13-6); (I-283)+(S13-7); (I-283)+(S13-8); (I-283)+(S13-9); (I-283)+(S14-1)

(I-284)+(S1-1); (I-284)+(S1-2); (I-284)+(S1-3); (I-284)+(S1-4); (I-284)+(S1-5); (I-284)+(S1-6); (I-284)+(S1-7); (I-284)+(S1-8); (I-284)+(S1-9); (I-284)+(S1-10); (I-284)+(S1-11); (I-284)+(S1-12); (I-284)+(S1-13); (I-284)+(S2-1); (I-284)+(S2-2); (I-284)+(S2-3); (I-284)+(S2-4); (I-284)+(S2-5); (I-284)+(S2-6); (I-284)+(S2-7); (I-284)+(S2-8); (I-284)+(S2-9); (I-284)+(S2-10); (I-284)+(S3-1); (I-284)+(S3-2); (I-284)+(S3-3); (I-284)+(S3-4); (I-284)+(S3-5); (I-284)+(S3-6); (I-284)+(S3-7); (I-284)+(S3-8); (I-284)+(S3-9); (I-284)+(S3-10); (I-284)+(S3-11); (I-284)+(S4-1); (I-284)+(S4-2); (I-284)+(S4-3); (I-284)+(S4-4); (I-284)+(S4-5); (I-284)+(S7-1); (I-284)+(S11-1); (I-284)+(S11-2); (I-284)+(S11-3); (I-284)+(S12-1); (I-284)+(S13-1); (I-284)+(S13-2); (I-284)+(S13-3); (I-284)+(S13-4): (I-284)+(S13-5); (I-284)+(S13-6); (I-284)+(S13-7); (I-284)+(S13-8); (I-284)+(S13-9); (I-284)+(S14-1)

(I-285)+(S1-1); (I-285)+(S1-2); (I-285)+(S1-3); (I-285)+(S1-4); (I-285)+(S1-5); (I-285)+(S1-6); (I-285)+(S1-7); (I-285)+(S1-8); (I-285)+(S1-9); (I-285)+(S1-10); (I-285)+(S1-11); (I-285)+(S1-12); (I-285)+(S1-13); (I-285)+(S2-1); (I-285)+(S2-2); (I-285)+(S2-3); (I-285)+(S2-4); (I-285)+(S2-5); (I-285)+(S2-6); (I-285)+(S2-7); (I-285)+(S2-8);

(I-285)+(S2-9); (I-285)+(S2-10); (I-285)+(S3-1); (I-285)+(S3-2); (I-285)+(S3-3); (I-285)+(S3-4); (I-285)+(S3-5); (I-285)+(S3-6); (I-285)+(S3-7); (I-285)+(S3-8); (I-285)+(S3-9); (I-285)+(S3-10); (I-285)+(S3-11); (I-285)+(S4-1); (I-285)+(S4-2); (I-285)+(S4-3); (I-285)+(S4-4); (I-285)+(S4-5); (I-285)+(S7-1); (I-285)+(S11-1); (I-285)+(S11-2); (I-285)+(S11-3); (I-285)+(S12-1); (I-285)+(S13-1); (I-285)+(S13-2); (I-285)+(S13-3); (I-285)+(S13-4): (I-285)+(S13-5); (I-285)+(S13-6); (I-285)+(S13-7); (I-285)+(S13-8); (I-285)+(S13-9); (I-285)+(S14-1)

(I-286)+(S1-1); (I-286)+(S1-2); (I-286)+(S1-3); (I-286)+(S1-4); (I-286)+(S1-5); (I-286)+(S1-6); (I-286)+(S1-7); (I-286)+(S1-8); (I-286)+(S1-9); (I-286)+(S1-10); (I-286)+(S1-11); (I-286)+(S1-12); (I-286)+(S1-13); (I-286)+(S2-1); (I-286)+(S2-2); (I-286)+(S2-3); (I-286)+(S2-4); (I-286)+(S2-5); (I-286)+(S2-6); (I-286)+(S2-7); (I-286)+(S2-8); (I-286)+(S2-9); (I-286)+(S2-10); (I-286)+(S3-1); (I-286)+(S3-2); (I-286)+(S3-3); (I-286)+(S3-4); (I-286)+(S3-5); (I-286)+(S3-6); (I-286)+(S3-7); (I-286)+(S3-8); (I-286)+(S3-9); (I-286)+(S3-10); (I-286)+(S3-11); (I-286)+(S4-1); (I-286)+(S4-2); (I-286)+(S4-3); (I-286)+(S4-4); (I-286)+(S4-5); (I-286)+(S7-1); (I-286)+(S11-1); (I-286)+(S11-2); (I-286)+(S11-3); (I-286)+(S12-1); (I-286)+(S13-1); (I-286)+(S13-2); (I-286)+(S13-3); (I-286)+(S13-4): (I-286)+(S13-5); (I-286)+(S13-6); (I-286)+(S13-7); (I-286)+(S13-8); (I-286)+(S13-9); (I-286)+(S14-1)

(I-287)+(S1-1); (I-287)+(S1-2); (I-287)+(S1-3); (I-287)+(S1-4); (I-287)+(S1-5); (I-287)+(S1-6); (I-287)+(S1-7); (I-287)+(S1-8); (I-287)+(S1-9); (I-287)+(S1-10); (I-287)+(S1-11); (I-287)+(S1-12); (I-287)+(S1-13); (I-287)+(S2-1); (I-287)+(S2-2); (I-287)+(S2-3); (I-287)+(S2-4); (I-287)+(S2-5); (I-287)+(S2-6); (I-287)+(S2-7); (I-287)+(S2-8); (I-287)+(S2-9); (I-287)+(S2-10); (I-287)+(S3-1); (I-287)+(S3-2); (I-287)+(S3-3); (I-287)+(S3-4); (I-287)+(S3-5); (I-287)+(S3-6); (I-287)+(S3-7); (I-287)+(S3-8); (I-287)+(S3-9); (I-287)+(S3-10); (I-287)+(S3-11); (I-287)+(S4-1); (I-287)+(S4-2); (I-287)+(S4-3); (I-287)+(S4-4); (I-287)+(S4-5); (I-287)+(S7-1); (I-287)+(S11-1); (I-287)+(S11-2); (I-287)+(S11-3); (I-287)+(S12-1); (I-287)+(S13-1); (I-287)+(S13-2); (I-287)+(S13-3); (I-287)+(S13-4): (I-287)+(S13-5); (I-287)+(S13-6); (I-287)+(S13-7); (I-287)+(S13-8); (I-287)+(S13-9); (I-287)+(S14-1)

(I-288)+(S1-1); (I-288)+(S1-2); (I-288)+(S1-3); (I-288)+(S1-4); (I-288)+(S1-5); (I-288)+(S1-6); (I-288)+(S1-7); (I-288)+(S1-8); (I-288)+(S1-9); (I-288)+(S1-10); (I-288)+(S1-11); (I-288)+(S1-12); (I-288)+(S1-13); (I-288)+(S2-1); (I-288)+(S2-2); (I-288)+(S2-3); (I-288)+(S2-4); (I-288)+(S2-5); (I-288)+(S2-6); (I-288)+(S2-7); (I-288)+(S2-8); (I-288)+(S2-9); (I-288)+(S2-10); (I-288)+(S3-1); (I-288)+(S3-2); (I-288)+(S3-3); (I-288)+(S3-4); (I-288)+(S3-5); (I-288)+(S3-6); (I-288)+(S3-7); (I-288)+(S3-8); (I-288)+(S3-9); (I-288)+(S3-10); (I-288)+(S3-11); (I-288)+(S4-1); (I-288)+(S4-2); (I-288)+(S4-3); (I-288)+(S4-4); (I-288)+(S4-5); (I-288)+(S7-1); (I-288)+(S11-1); (I-288)+(S11-2); (I-288)+(S11-3); (I-288)+(S12-1); (I-288)+(S13-1); (I-288)+(S13-2); (I-288)+(S13-3); (I-288)+(S13-4): (I-288)+(S13-5); (I-288)+(S13-6); (I-288)+(S13-7); (I-288)+(S13-8); (I-288)+(S13-9); (I-288)+(S14-1)

(I-289)+(S1-1); (I-289)+(S1-2); (I-289)+(S1-3); (I-289)+(S1-4); (I-289)+(S1-5); (I-289)+(S1-6); (I-289)+(S1-7); (I-289)+(S1-8); (I-289)+(S1-9); (I-289)+(S1-10); (I-289)+(S1-11); (I-289)+(S1-12); (I-289)+(S1-13); (I-289)+(S2-1); (I-289)+(S2-2); (I-289)+(S2-3); (I-289)+(S2-4); (I-289)+(S2-5); (I-289)+(S2-6); (I-289)+(S2-7); (I-289)+(S2-8); (I-289)+(S2-9); (I-289)+(S2-10); (I-289)+(S3-1); (I-289)+(S3-2); (I-289)+(S3-3); (I-289)+(S3-4); (I-289)+(S3-5); (I-289)+(S3-6); (I-289)+(S3-7); (I-289)+(S3-8); (I-289)+(S3-9); (I-289)+(S3-10); (I-289)+(S3-11); (I-289)+(S4-1); (I-289)+(S4-2); (I-289)+(S4-3); (I-289)+(S4-4); (I-289)+(S4-5); (I-289)+(S7-1); (I-289)+(S11-1); (I-289)+(S11-2); (I-289)+(S11-3); (I-289)+(S12-1); (I-289)+(S13-1); (I-289)+(S13-2); (I-289)+(S13-3); (I-289)+(S13-4): (I-289)+(S13-5); (I-289)+(S13-6); (I-289)+(S13-7); (I-289)+(S13-8); (I-289)+(S13-9); (I-289)+(S14-1)

(I-290)+(S1-1); (I-290)+(S1-2); (I-290)+(S1-3); (I-290)+(S1-4); (I-290)+(S1-5); (I-290)+(S1-6); (I-290)+(S1-7); (I-290)+(S1-8); (I-290)+(S1-9); (I-290)+(S1-10); (I-290)+(S1-11); (I-290)+(S1-12); (I-290)+(S1-13); (I-290)+(S2-1); (I-290)+(S2-2); (I-290)+(S2-3); (I-290)+(S2-4); (I-290)+(S2-5); (I-290)+(S2-6); (I-290)+(S2-7); (I-290)+(S2-8); (I-290)+(S2-9); (I-290)+(S2-10); (I-290)+(S3-1); (I-290)+(S3-2); (I-290)+(S3-3); (I-290)+(S3-4); (I-290)+(S3-5); (I-290)+(S3-6); (I-290)+(S3-7); (I-290)+(S3-8); (I-290)+(S3-9); (I-290)+(S3-10); (I-290)+(S3-11); (I-290)+(S4-1); (I-290)+(S4-2); (I-290)+(S4-3); (I-290)+(S4-4); (I-290)+(S4-5); (I-290)+(S7-1); (I-290)+(S11-1); (I-290)+(S11-2); (I-290)+(S11-3); (I-290)+(S12-1); (I-290)+(S13-1); (I-290)+(S13-2); (I-290)+(S13-3); (I-290)+(S13-4): (I-290)+(S13-5); (I-290)+(S13-6); (I-290)+(S13-7); (I-290)+(S13-8); (I-290)+(S13-9); (I-290)+(S14-1)

(I-291)+(S1-1); (I-291)+(S1-2); (I-291)+(S1-3); (I-291)+(S1-4); (I-291)+(S1-5); (I-291)+(S1-6); (I-291)+(S1-7); (I-291)+(S1-8); (I-291)+(S1-9); (I-291)+(S1-10); (I-291)+(S1-11); (I-291)+(S1-12); (I-291)+(S1-13); (I-291)+(S2-1); (I-291)+(S2-2); (I-291)+(S2-3); (I-291)+(S2-4); (I-291)+(S2-5); (I-291)+(S2-6); (I-291)+(S2-7); (I-291)+(S2-8); (I-291)+(S2-9); (I-291)+(S2-10); (I-291)+(S3-1); (I-291)+(S3-2); (I-291)+(S3-3); (I-291)+(S3-4); (I-291)+(S3-5); (I-291)+(S3-6); (I-291)+(S3-7); (I-291)+(S3-8); (I-291)+(S3-9); (I-291)+(S3-10); (I-291)+(S3-11); (I-291)+(S4-1); (I-291)+(S4-2); (I-291)+(S4-3); (I-291)+(S4-4); (I-291)+(S4-5); (I-291)+(S7-1); (I-291)+(S11-1); (I-291)+(S11-2); (I-291)+(S11-3); (I-291)+(S12-1); (I-291)+(S13-1); (I-291)+(S13-2); (I-291)+(S13-3); (I-291)+(S13-4): (I-291)+(S13-5); (I-291)+(S13-6); (I-291)+(S13-7); (I-291)+(S13-8); (I-291)+(S13-9); (I-291)+(S14-1)

(I-292)+(S1-1); (I-292)+(S1-2); (I-292)+(S1-3); (I-292)+(S1-4); (I-292)+(S1-5); (I-292)+(S1-6); (I-292)+(S1-7); (I-292)+(S1-8); (I-292)+(S1-9); (I-292)+(S1-10); (I-292)+(S1-11); (I-292)+(S1-12); (I-292)+(S1-13); (I-292)+(S2-1); (I-292)+(S2-2); (I-292)+(S2-3); (I-292)+(S2-4); (I-292)+(S2-5); (I-292)+(S2-6); (I-292)+(S2-7); (I-292)+(S2-8); (I-292)+(S2-9); (I-292)+(S2-10); (I-292)+(S3-1); (I-292)+(S3-2); (I-292)+(S3-3); (I-292)+(S3-4); (I-292)+(S3-5); (I-292)+(S3-6); (I-292)+(S3-7); (I-292)+(S3-8); (I-292)+(S3-9); (I-292)+(S3-10); (I-292)+(S3-11); (I-292)+(S4-1); (I-292)+(S4-2); (I-292)+(S4-3); (I-292)+(S4-4); (I-292)+(S4-5); (I-292)+(S7-1); (I-292)+(S11-1); (I-292)+(S11-2); (I-292)+(S11-3); (I-292)+(S12-1); (I-292)+(S13-1); (I-292)+(S13-2); (I-292)+(S13-3); (I-292)+(S13-4): (I-292)+(S13-5); (I-292)+(S13-6); (I-292)+(S13-7); (I-292)+(S13-8); (I-292)+(S13-9); (I-292)+(S14-1)

(I-293)+(S1-1); (I-293)+(S1-2); (I-293)+(S1-3); (I-293)+(S1-4); (I-293)+(S1-5); (I-293)+(S1-6); (I-293)+(S1-7); (I-293)+(S1-8); (I-293)+(S1-9); (I-293)+(S1-10); (I-293)+(S1-11); (I-293)+(S1-12); (I-293)+(S1-13); (I-293)+(S2-1); (I-293)+(S2-2); (I-293)+(S2-3); (I-293)+(S2-4); (I-293)+(S2-5); (I-293)+(S2-6); (I-293)+(S2-7); (I-293)+(S2-8); (I-293)+(S2-9); (I-293)+(S2-10); (I-293)+(S3-1); (I-293)+(S3-2); (I-293)+(S3-3); (I-293)+(S3-4); (I-293)+(S3-5); (I-293)+(S3-6); (I-293)+(S3-7); (I-293)+(S3-8); (I-293)+(S3-9); (I-293)+(S3-10); (I-293)+(S3-11); (I-293)+(S4-1); (I-293)+(S4-2); (I-293)+(S4-3); (I-293)+(S4-4); (I-293)+(S4-5); (I-293)+(S7-1); (I-293)+(S11-1); (I-293)+(S11-2);

(I-293)+(S11-3); (I-293)+(S12-1); (I-293)+(S13-1); (I-293)+(S13-2); (I-293)+(S13-3); (I-293)+(S13-4): (I-293)+(S13-5); (I-293)+(S13-6); (I-293)+(S13-7); (I-293)+(S13-8); (I-293)+(S13-9); (I-293)+(S14-1)

(I-294)+(S1-1); (I-294)+(S1-2); (I-294)+(S1-3); (I-294)+(S1-4); (I-294)+(S1-5); (I-294)+(S1-6); (I-294)+(S1-7); (I-294)+(S1-8); (I-294)+(S1-9); (I-294)+(S1-10); (I-294)+(S1-11); (I-294)+(S1-12); (I-294)+(S1-13); (I-294)+(S2-1); (I-294)+(S2-2); (I-294)+(S2-3); (I-294)+(S2-4); (I-294)+(S2-5); (I-294)+(S2-6); (I-294)+(S2-7); (I-294)+(S2-8); (I-294)+(S2-9); (I-294)+(S2-10); (I-294)+(S3-1); (I-294)+(S3-2); (I-294)+(S3-3); (I-294)+(S3-4); (I-294)+(S3-5); (I-294)+(S3-6); (I-294)+(S3-7); (I-294)+(S3-8); (I-294)+(S3-9); (I-294)+(S3-10); (I-294)+(S3-11); (I-294)+(S4-1); (I-294)+(S4-2); (I-294)+(S4-3); (I-294)+(S4-4); (I-294)+(S4-5); (I-294)+(S7-1); (I-294)+(S11-1); (I-294)+(S11-2); (I-294)+(S11-3); (I-294)+(S12-1); (I-294)+(S13-1); (I-294)+(S13-2); (I-294)+(S13-3); (I-294)+(S13-4): (I-294)+(S13-5); (I-294)+(S13-6); (I-294)+(S13-7); (I-294)+(S13-8); (I-294)+(S13-9); (I-294)+(S14-1)

(I-295)+(S1-1); (I-295)+(S1-2); (I-295)+(S1-3); (I-295)+(S1-4); (I-295)+(S1-5); (I-295)+(S1-6); (I-295)+(S1-7); (I-295)+(S1-8); (I-295)+(S1-9); (I-295)+(S1-10); (I-295)+(S1-11); (I-295)+(S1-12); (I-295)+(S1-13); (I-295)+(S2-1); (I-295)+(S2-2); (I-295)+(S2-3); (I-295)+(S2-4); (I-295)+(S2-5); (I-295)+(S2-6); (I-295)+(S2-7); (I-295)+(S2-8); (I-295)+(S2-9); (I-295)+(S2-10); (I-295)+(S3-1); (I-295)+(S3-2); (I-295)+(S3-3); (I-295)+(S3-4); (I-295)+(S3-5); (I-295)+(S3-6); (I-295)+(S3-7); (I-295)+(S3-8); (I-295)+(S3-9); (I-295)+(S3-10); (I-295)+(S3-11); (I-295)+(S4-1); (I-295)+(S4-2); (I-295)+(S4-3); (I-295)+(S4-4); (I-295)+(S4-5); (I-295)+(S7-1); (I-295)+(S11-1); (I-295)+(S11-2); (I-295)+(S11-3); (I-295)+(S12-1); (I-295)+(S13-1); (I-295)+(S13-2); (I-295)+(S13-3); (I-295)+(S13-4): (I-295)+(S13-5); (I-295)+(S13-6); (I-295)+(S13-7); (I-295)+(S13-8); (I-295)+(S13-9); (I-295)+(S14-1)

(I-296)+(S1-1); (I-296)+(S1-2); (I-296)+(S1-3); (I-296)+(S1-4); (I-296)+(S1-5); (I-296)+(S1-6); (I-296)+(S1-7); (I-296)+(S1-8); (I-296)+(S1-9); (I-296)+(S1-10); (I-296)+(S1-11); (I-296)+(S1-12); (I-296)+(S1-13); (I-296)+(S2-1); (I-296)+(S2-2); (I-296)+(S2-3); (I-296)+(S2-4); (I-296)+(S2-5); (I-296)+(S2-6); (I-296)+(S2-7); (I-296)+(S2-8); (I-296)+(S2-9); (I-296)+(S2-10); (I-296)+(S3-1); (I-296)+(S3-2); (I-296)+(S3-3); (I-296)+(S3-4); (I-296)+(S3-5); (I-296)+(S3-6); (I-296)+(S3-7); (I-296)+(S3-8); (I-296)+(S3-9); (I-296)+(S3-10); (I-296)+(S3-11); (I-296)+(S4-1); (I-296)+(S4-2); (I-296)+(S4-3); (I-296)+(S4-4); (I-296)+(S4-5); (I-296)+(S7-1); (I-296)+(S11-1); (I-296)+(S11-2); (I-296)+(S11-3); (I-296)+(S12-1); (I-296)+(S13-1); (I-296)+(S13-2); (I-296)+(S13-3); (I-296)+(S13-4): (I-296)+(S13-5); (I-296)+(S13-6); (I-296)+(S13-7); (I-296)+(S13-8); (I-296)+(S13-9); (I-296)+(S14-1)

(I-297)+(S1-1); (I-297)+(S1-2); (I-297)+(S1-3); (I-297)+(S1-4); (I-297)+(S1-5); (I-297)+(S1-6); (I-297)+(S1-7); (I-297)+(S1-8); (I-297)+(S1-9); (I-297)+(S1-10); (I-297)+(S1-11); (I-297)+(S1-12); (I-297)+(S1-13); (I-297)+(S2-1); (I-297)+(S2-2); (I-297)+(S2-3); (I-297)+(S2-4); (I-297)+(S2-5); (I-297)+(S2-6); (I-297)+(S2-7); (I-297)+(S2-8); (I-297)+(S2-9); (I-297)+(S2-10); (I-297)+(S3-1); (I-297)+(S3-2); (I-297)+(S3-3); (I-297)+(S3-4); (I-297)+(S3-5); (I-297)+(S3-6); (I-297)+(S3-7); (I-297)+(S3-8); (I-297)+(S3-9); (I-297)+(S3-10); (I-297)+(S3-11); (I-297)+(S4-1); (I-297)+(S4-2); (I-297)+(S4-3); (I-297)+(S4-4); (I-297)+(S4-5); (I-297)+(S7-1); (I-297)+(S11-1); (I-297)+(S11-2); (I-297)+(S11-3); (I-297)+(S12-1); (I-297)+(S13-1); (I-297)+(S13-2); (I-297)+(S13-3); (I-297)+(S13-4): (I-297)+(S13-5); (I-297)+(S13-6); (I-297)+(S13-7); (I-297)+(S13-8); (I-297)+(S13-9); (I-297)+(S14-1)

(I-298)+(S1-1); (I-298)+(S1-2); (I-298)+(S1-3); (I-298)+(S1-4); (I-298)+(S1-5); (I-298)+(S1-6); (I-298)+(S1-7); (I-298)+(S1-8); (I-298)+(S1-9); (I-298)+(S1-10); (I-298)+(S1-11); (I-298)+(S1-12); (I-298)+(S1-13); (I-298)+(S2-1); (I-298)+(S2-2); (I-298)+(S2-3); (I-298)+(S2-4); (I-298)+(S2-5); (I-298)+(S2-6); (I-298)+(S2-7); (I-298)+(S2-8); (I-298)+(S2-9); (I-298)+(S2-10); (I-298)+(S3-1); (I-298)+(S3-2); (I-298)+(S3-3); (I-298)+(S3-4); (I-298)+(S3-5); (I-298)+(S3-6); (I-298)+(S3-7); (I-298)+(S3-8); (I-298)+(S3-9); (I-298)+(S3-10); (I-298)+(S3-11); (I-298)+(S4-1); (I-298)+(S4-2); (I-298)+(S4-3); (I-298)+(S4-4); (I-298)+(S4-5); (I-298)+(S7-1); (I-298)+(S11-1); (I-298)+(S11-2); (I-298)+(S11-3); (I-298)+(S12-1); (I-298)+(S13-1); (I-298)+(S13-2); (I-298)+(S13-3); (I-298)+(S13-4): (I-298)+(S13-5); (I-298)+(S13-6); (I-298)+(S13-7); (I-298)+(S13-8); (I-298)+(S13-9); (I-298)+(S14-1)

(I-299)+(S1-1); (I-299)+(S1-2); (I-299)+(S1-3); (I-299)+(S1-4); (I-299)+(S1-5); (I-299)+(S1-6); (I-299)+(S1-7); (I-299)+(S1-8); (I-299)+(S1-9); (I-299)+(S1-10); (I-299)+(S1-11); (I-299)+(S1-12); (I-299)+(S1-13); (I-299)+(S2-1); (I-299)+(S2-2); (I-299)+(S2-3); (I-299)+(S2-4); (I-299)+(S2-5); (I-299)+(S2-6); (I-299)+(S2-7); (I-299)+(S2-8); (I-299)+(S2-9); (I-299)+(S2-10); (I-299)+(S3-1); (I-299)+(S3-2); (I-299)+(S3-3); (I-299)+(S3-4); (I-299)+(S3-5); (I-299)+(S3-6); (I-299)+(S3-7); (I-299)+(S3-8); (I-299)+(S3-9); (I-299)+(S3-10); (I-299)+(S3-11); (I-299)+(S4-1); (I-299)+(S4-2); (I-299)+(S4-3); (I-299)+(S4-4); (I-299)+(S4-5); (I-299)+(S7-1); (I-299)+(S11-1); (I-299)+(S11-2); (I-299)+(S11-3); (I-299)+(S12-1); (I-299)+(S13-1); (I-299)+(S13-2); (I-299)+(S13-3); (I-299)+(S13-4): (I-299)+(S13-5); (I-299)+(S13-6); (I-299)+(S13-7); (I-299)+(S13-8); (I-299)+(S13-9); (I-299)+(S14-1)

(I-300)+(S1-1); (I-300)+(S1-2); (I-300)+(S1-3); (I-300)+(S1-4); (I-300)+(S1-5); (I-300)+(S1-6); (I-300)+(S1-7); (I-300)+(S1-8); (I-300)+(S1-9); (I-300)+(S1-10); (I-300)+(S1-11); (I-300)+(S1-12); (I-300)+(S1-13); (I-300)+(S2-1); (I-300)+(S2-2); (I-300)+(S2-3); (I-300)+(S2-4); (I-300)+(S2-5); (I-300)+(S2-6); (I-300)+(S2-7); (I-300)+(S2-8); (I-300)+(S2-9); (I-300)+(S2-10); (I-300)+(S3-1); (I-300)+(S3-2); (I-300)+(S3-3); (I-300)+(S3-4); (I-300)+(S3-5); (I-300)+(S3-6); (I-300)+(S3-7); (I-300)+(S3-8); (I-300)+(S3-9); (I-300)+(S3-10); (I-300)+(S3-11); (I-300)+(S4-1); (I-300)+(S4-2); (I-300)+(S4-3); (I-300)+(S4-4); (I-300)+(S4-5); (I-300)+(S7-1); (I-300)+(S11-1); (I-300)+(S11-2); (I-300)+(S11-3); (I-300)+(S12-1); (I-300)+(S13-1); (I-300)+(S13-2); (I-300)+(S13-3); (I-300)+(S13-4): (I-300)+(S13-5); (I-300)+(S13-6); (I-300)+(S13-7); (I-300)+(S13-8); (I-300)+(S13-9); (I-300)+(S14-1)

(I-301)+(S1-1); (I-301)+(S1-2); (I-301)+(S1-3); (I-301)+(S1-4); (I-301)+(S1-5); (I-301)+(S1-6); (I-301)+(S1-7); (I-301)+(S1-8); (I-301)+(S1-9); (I-301)+(S1-10); (I-301)+(S1-11); (I-301)+(S1-12); (I-301)+(S1-13); (I-301)+(S2-1); (I-301)+(S2-2); (I-301)+(S2-3); (I-301)+(S2-4); (I-301)+(S2-5); (I-301)+(S2-6); (I-301)+(S2-7); (I-301)+(S2-8); (I-301)+(S2-9); (I-301)+(S2-10); (I-301)+(S3-1); (I-301)+(S3-2); (I-301)+(S3-3); (I-301)+(S3-4); (I-301)+(S3-5); (I-301)+(S3-6); (I-301)+(S3-7); (I-301)+(S3-8); (I-301)+(S3-9); (I-301)+(S3-10); (I-301)+(S3-11); (I-301)+(S4-1); (I-301)+(S4-2); (I-301)+(S4-3); (I-301)+(S4-4); (I-301)+(S4-5); (I-301)+(S7-1); (I-301)+(S11-1); (I-301)+(S11-2); (I-301)+(S11-3); (I-301)+(S12-1); (I-301)+(S13-1); (I-301)+(S13-2); (I-301)+(S13-3); (I-301)+(S13-4): (I-301)+(S13-5); (I-301)+(S13-6); (I-301)+(S13-7); (I-301)+(S13-8); (I-301)+(S13-9); (I-301)+(S14-1)

(I-302)+(S1-1); (I-302)+(S1-2); (I-302)+(S1-3); (I-302)+(S1-4); (I-302)+(S1-5); (I-302)+(S1-6); (I-302)+(S1-7); (I-302)+(S1-8); (I-302)+(S1-9); (I-302)+(S1-10); (I-302)+(S1-11); (I-302)+(S1-12); (I-302)+(S1-13); (I-302)+(S2-1); (I-302)+(S2-2); (I-302)+(S2-3); (I-302)+(S2-4); (I-302)+(S2-5); (I-302)+(S2-6); (I-302)+(S2-7); (I-302)+(S2-8); (I-302)+(S2-9); (I-302)+(S2-10); (I-302)+(S3-1); (I-302)+(S3-2); (I-302)+(S3-3); (I-302)+(S3-4); (I-302)+(S3-5); (I-302)+(S3-6); (I-302)+(S3-7); (I-302)+(S3-8); (I-302)+(S3-9); (I-302)+(S3-10); (I-302)+(S3-11); (I-302)+(S4-1); (I-302)+(S4-2); (I-302)+(S4-3); (I-302)+(S4-4); (I-302)+(S4-5); (I-302)+(S7-1); (I-302)+(S11-1); (I-302)+(S11-2); (I-302)+(S11-3); (I-302)+(S12-1); (I-302)+(S13-1); (I-302)+(S13-2); (I-302)+(S13-3); (I-302)+(S13-4): (I-302)+(S13-5); (I-302)+(S13-6); (I-302)+(S13-7); (I-302)+(S13-8); (I-302)+(S13-9); (I-302)+(S14-1)

(I-303)+(S1-1); (I-303)+(S1-2); (I-303)+(S1-3); (I-303)+(S1-4); (I-303)+(S1-5); (I-303)+(S1-6); (I-303)+(S1-7); (I-303)+(S1-8); (I-303)+(S1-9); (I-303)+(S1-10); (I-303)+(S1-11); (I-303)+(S1-12); (I-303)+(S1-13); (I-303)+(S2-1); (I-303)+(S2-2); (I-303)+(S2-3); (I-303)+(S2-4); (I-303)+(S2-5); (I-303)+(S2-6); (I-303)+(S2-7); (I-303)+(S2-8); (I-303)+(S2-9); (I-303)+(S2-10); (I-303)+(S3-1); (I-303)+(S3-2); (I-303)+(S3-3); (I-303)+(S3-4); (I-303)+(S3-5); (I-303)+(S3-6); (I-303)+(S3-7); (I-303)+(S3-8); (I-303)+(S3-9); (I-303)+(S3-10); (I-303)+(S3-11); (I-303)+(S4-1); (I-303)+(S4-2); (I-303)+(S4-3); (I-303)+(S4-4); (I-303)+(S4-5); (I-303)+(S7-1); (I-303)+(S11-1); (I-303)+(S11-2); (I-303)+(S11-3); (I-303)+(S12-1); (I-303)+(S13-1); (I-303)+(S13-2); (I-303)+(S13-3); (I-303)+(S13-4): (I-303)+(S13-5); (I-303)+(S13-6); (I-303)+(S13-7); (I-303)+(S13-8); (I-303)+(S13-9); (I-303)+(S14-1)

(I-304)+(S1-1); (I-304)+(S1-2); (I-304)+(S1-3); (I-304)+(S1-4); (I-304)+(S1-5); (I-304)+(S1-6); (I-304)+(S1-7); (I-304)+(S1-8); (I-304)+(S1-9); (I-304)+(S1-10); (I-304)+(S1-11); (I-304)+(S1-12); (I-304)+(S1-13); (I-304)+(S2-1); (I-304)+(S2-2); (I-304)+(S2-3); (I-304)+(S2-4); (I-304)+(S2-5); (I-304)+(S2-6); (I-304)+(S2-7); (I-304)+(S2-8); (I-304)+(S2-9); (I-304)+(S2-10); (I-304)+(S3-1); (I-304)+(S3-2); (I-304)+(S3-3); (I-304)+(S3-4); (I-304)+(S3-5); (I-304)+(S3-6); (I-304)+(S3-7); (I-304)+(S3-8); (I-304)+(S3-9); (I-304)+(S3-10); (I-304)+(S3-11); (I-304)+(S4-1); (I-304)+(S4-2); (I-304)+(S4-3); (I-304)+(S4-4); (I-304)+(S4-5); (I-304)+(S7-1); (I-304)+(S11-1); (I-304)+(S11-2); (I-304)+(S11-3); (I-304)+(S12-1); (I-304)+(S13-1); (I-304)+(S13-2); (I-304)+(S13-3); (I-304)+(S13-4): (I-304)+(S13-5); (I-304)+(S13-6); (I-304)+(S13-7); (I-304)+(S13-8); (I-304)+(S13-9); (I-304)+(S14-1)

(I-305)+(S1-1); (I-305)+(S1-2); (I-305)+(S1-3); (I-305)+(S1-4); (I-305)+(S1-5); (I-305)+(S1-6); (I-305)+(S1-7); (I-305)+(S1-8); (I-305)+(S1-9); (I-305)+(S1-10); (I-305)+(S1-11); (I-305)+(S1-12); (I-305)+(S1-13); (I-305)+(S2-1); (I-305)+(S2-2); (I-305)+(S2-3); (I-305)+(S2-4); (I-305)+(S2-5); (I-305)+(S2-6); (I-305)+(S2-7); (I-305)+(S2-8); (I-305)+(S2-9); (I-305)+(S2-10); (I-305)+(S3-1); (I-305)+(S3-2); (I-305)+(S3-3); (I-305)+(S3-4); (I-305)+(S3-5); (I-305)+(S3-6); (I-305)+(S3-7); (I-305)+(S3-8); (I-305)+(S3-9); (I-305)+(S3-10); (I-305)+(S3-11); (I-305)+(S4-1); (I-305)+(S4-2); (I-305)+(S4-3); (I-305)+(S4-4); (I-305)+(S4-5); (I-305)+(S7-1); (I-305)+(S11-1); (I-305)+(S11-2); (I-305)+(S11-3); (I-305)+(S12-1); (I-305)+(S13-1); (I-305)+(S13-2); (I-305)+(S13-3); (I-305)+(S13-4): (I-305)+(S13-5); (I-305)+(S13-6); (I-305)+(S13-7); (I-305)+(S13-8); (I-305)+(S13-9); (I-305)+(S14-1)

(I-306)+(S1-1); (I-306)+(S1-2); (I-306)+(S1-3); (I-306)+(S1-4); (I-306)+(S1-5); (I-306)+(S1-6); (I-306)+(S1-7); (I-306)+(S1-8); (I-306)+(S1-9); (I-306)+(S1-10); (I-306)+(S1-11); (I-306)+(S1-12); (I-306)+(S1-13); (I-306)+(S2-1); (I-306)+(S2-2); (I-306)+(S2-3); (I-306)+(S2-4); (I-306)+(S2-5); (I-306)+(S2-6); (I-306)+(S2-7); (I-306)+(S2-8); (I-306)+(S2-9); (I-306)+(S2-10); (I-306)+(S3-1); (I-306)+(S3-2); (I-306)+(S3-3); (I-306)+(S3-4); (I-306)+(S3-5); (I-306)+(S3-6); (I-306)+(S3-7); (I-306)+(S3-8); (I-306)+(S3-9); (I-306)+(S3-10); (I-306)+(S3-11); (I-306)+(S4-1); (I-306)+(S4-2); (I-306)+(S4-3); (I-306)+(S4-4); (I-306)+(S4-5); (I-306)+(S7-1); (I-306)+(S11-1); (I-306)+(S11-2); (I-306)+(S11-3); (I-306)+(S12-1); (I-306)+(S13-1); (I-306)+(S13-2); (I-306)+(S13-3); (I-306)+(S13-4): (I-306)+(S13-5); (I-306)+(S13-6); (I-306)+(S13-7); (I-306)+(S13-8); (I-306)+(S13-9); (I-306)+(S14-1)

(I-307)+(S1-1); (I-307)+(S1-2); (I-307)+(S1-3); (I-307)+(S1-4); (I-307)+(S1-5); (I-307)+(S1-6); (I-307)+(S1-7); (I-307)+(S1-8); (I-307)+(S1-9); (I-307)+(S1-10); (I-307)+(S1-11); (I-307)+(S1-12); (I-307)+(S1-13); (I-307)+(S2-1); (I-307)+(S2-2); (I-307)+(S2-3); (I-307)+(S2-4); (I-307)+(S2-5); (I-307)+(S2-6); (I-307)+(S2-7); (I-307)+(S2-8); (I-307)+(S2-9); (I-307)+(S2-10); (I-307)+(S3-1); (I-307)+(S3-2); (I-307)+(S3-3); (I-307)+(S3-4); (I-307)+(S3-5); (I-307)+(S3-6); (I-307)+(S3-7); (I-307)+(S3-8); (I-307)+(S3-9); (I-307)+(S3-10); (I-307)+(S3-11); (I-307)+(S4-1); (I-307)+(S4-2); (I-307)+(S4-3); (I-307)+(S4-4); (I-307)+(S4-5); (I-307)+(S7-1); (I-307)+(S11-1); (I-307)+(S11-2); (I-307)+(S11-3); (I-307)+(S12-1); (I-307)+(S13-1); (I-307)+(S13-2); (I-307)+(S13-3); (I-307)+(S13-4): (I-307)+(S13-5); (I-307)+(S13-6); (I-307)+(S13-7); (I-307)+(S13-8); (I-307)+(S13-9); (I-307)+(S14-1)

(I-308)+(S1-1); (I-308)+(S1-2); (I-308)+(S1-3); (I-308)+(S1-4); (I-308)+(S1-5); (I-308)+(S1-6); (I-308)+(S1-7); (I-308)+(S1-8); (I-308)+(S1-9); (I-308)+(S1-10); (I-308)+(S1-11); (I-308)+(S1-12); (I-308)+(S1-13); (I-308)+(S2-1); (I-308)+(S2-2); (I-308)+(S2-3); (I-308)+(S2-4); (I-308)+(S2-5); (I-308)+(S2-6); (I-308)+(S2-7); (I-308)+(S2-8); (I-308)+(S2-9); (I-308)+(S2-10); (I-308)+(S3-1); (I-308)+(S3-2); (I-308)+(S3-3); (I-308)+(S3-4); (I-308)+(S3-5); (I-308)+(S3-6); (I-308)+(S3-7); (I-308)+(S3-8); (I-308)+(S3-9); (I-308)+(S3-10); (I-308)+(S3-11); (I-308)+(S4-1); (I-308)+(S4-2); (I-308)+(S4-3); (I-308)+(S4-4); (I-308)+(S4-5); (I-308)+(S7-1); (I-308)+(S11-1); (I-308)+(S11-2); (I-308)+(S11-3); (I-308)+(S12-1); (I-308)+(S13-1); (I-308)+(S13-2); (I-308)+(S13-3); (I-308)+(S13-4): (I-308)+(S13-5); (I-308)+(S13-6); (I-308)+(S13-7); (I-308)+(S13-8); (I-308)+(S13-9); (I-308)+(S14-1)

(I-309)+(S1-1); (I-309)+(S1-2); (I-309)+(S1-3); (I-309)+(S1-4); (I-309)+(S1-5); (I-309)+(S1-6); (I-309)+(S1-7); (I-309)+(S1-8); (I-309)+(S1-9); (I-309)+(S1-10); (I-309)+(S1-11); (I-309)+(S1-12); (I-309)+(S1-13); (I-309)+(S2-1); (I-309)+(S2-2); (I-309)+(S2-3); (I-309)+(S2-4); (I-309)+(S2-5); (I-309)+(S2-6); (I-309)+(S2-7); (I-309)+(S2-8); (I-309)+(S2-9); (I-309)+(S2-10); (I-309)+(S3-1); (I-309)+(S3-2); (I-309)+(S3-3); (I-309)+(S3-4); (I-309)+(S3-5); (I-309)+(S3-6); (I-309)+(S3-7); (I-309)+(S3-8); (I-309)+(S3-9); (I-309)+(S3-10); (I-309)+(S3-11); (I-309)+(S4-1); (I-309)+(S4-2); (I-309)+(S4-3); (I-309)+(S4-4); (I-309)+(S4-5); (I-309)+(S7-1); (I-309)+(S11-1); (I-309)+(S11-2); (I-309)+(S11-3); (I-309)+(S12-1); (I-309)+(S13-1); (I-309)+(S13-2); (I-309)+(S13-3); (I-309)+(S13-4): (I-309)+(S13-5); (I-309)+(S13-6); (I-309)+(S13-7); (I-309)+(S13-8); (I-309)+(S13-9); (I-309)+(S14-1)

(I-310)+(S1-1); (I-310)+(S1-2); (I-310)+(S1-3); (I-310)+(S1-4); (I-310)+(S1-5); (I-310)+(S1-6); (I-310)+(S1-7); (I-310)+(S1-8); (I-310)+(S1-9); (I-310)+(S1-10); (I-310)+(S1-11); (I-310)+(S1-12); (I-310)+(S1-13); (I-310)+(S2-1); (I-310)+(S2-2); (I-310)+(S2-3); (I-310)+(S2-4); (I-310)+(S2-5); (I-310)+(S2-6); (I-310)+(S2-7); (I-310)+(S2-8);

(I-310)+(S2-9); (I-310)+(S2-10); (I-310)+(S3-1); (I-310)+(S3-2); (I-310)+(S3-3); (I-310)+(S3-4); (I-310)+(S3-5); (I-310)+(S3-6); (I-310)+(S3-7); (I-310)+(S3-8); (I-310)+(S3-9); (I-310)+(S3-10); (I-310)+(S3-11); (I-310)+(S4-1); (I-310)+(S4-2); (I-310)+(S4-3); (I-310)+(S4-4); (I-310)+(S4-5); (I-310)+(S7-1); (I-310)+(S11-1); (I-310)+(S11-2); (I-310)+(S11-3); (I-310)+(S12-1); (I-310)+(S13-1); (I-310)+(S13-2); (I-310)+(S13-3); (I-310)+(S13-4): (I-310)+(S13-5); (I-310)+(S13-6); (I-310)+(S13-7); (I-310)+(S13-8); (I-310)+(S13-9); (I-310)+(S14-1)

(I-311)+(S1-1); (I-311)+(S1-2); (I-311)+(S1-3); (I-311)+(S1-4); (I-311)+(S1-5); (I-311)+(S1-6); (I-311)+(S1-7); (I-311)+(S1-8); (I-311)+(S1-9); (I-311)+(S1-10); (I-311)+(S1-11); (I-311)+(S1-12); (I-311)+(S1-13); (I-311)+(S2-1); (I-311)+(S2-2); (I-311)+(S2-3); (I-311)+(S2-4); (I-311)+(S2-5); (I-311)+(S2-6); (I-311)+(S2-7); (I-311)+(S2-8); (I-311)+(S2-9); (I-311)+(S2-10); (I-311)+(S3-1); (I-311)+(S3-2); (I-311)+(S3-3); (I-311)+(S3-4); (I-311)+(S3-5); (I-311)+(S3-6); (I-311)+(S3-7); (I-311)+(S3-8); (I-311)+(S3-9); (I-311)+(S3-10); (I-311)+(S3-11); (I-311)+(S4-1); (I-311)+(S4-2); (I-311)+(S4-3); (I-311)+(S4-4); (I-311)+(S4-5); (I-311)+(S7-1); (I-311)+(S11-1); (I-311)+(S11-2); (I-311)+(S11-3); (I-311)+(S12-1); (I-311)+(S13-1); (I-311)+(S13-2); (I-311)+(S13-3); (I-311)+(S13-4): (I-311)+(S13-5); (I-311)+(S13-6); (I-311)+(S13-7); (I-311)+(S13-8); (I-311)+(S13-9); (I-311)+(S14-1)

(I-312)+(S1-1); (I-312)+(S1-2); (I-312)+(S1-3); (I-312)+(S1-4); (I-312)+(S1-5); (I-312)+(S1-6); (I-312)+(S1-7); (I-312)+(S1-8); (I-312)+(S1-9); (I-312)+(S1-10); (I-312)+(S1-11); (I-312)+(S1-12); (I-312)+(S1-13); (I-312)+(S2-1); (I-312)+(S2-2); (I-312)+(S2-3); (I-312)+(S2-4); (I-312)+(S2-5); (I-312)+(S2-6); (I-312)+(S2-7); (I-312)+(S2-8); (I-312)+(S2-9); (I-312)+(S2-10); (I-312)+(S3-1); (I-312)+(S3-2); (I-312)+(S3-3); (I-312)+(S3-4); (I-312)+(S3-5); (I-312)+(S3-6); (I-312)+(S3-7); (I-312)+(S3-8); (I-312)+(S3-9); (I-312)+(S3-10); (I-312)+(S3-11); (I-312)+(S4-1); (I-312)+(S4-2); (I-312)+(S4-3); (I-312)+(S4-4); (I-312)+(S4-5); (I-312)+(S7-1); (I-312)+(S11-1); (I-312)+(S11-2); (I-312)+(S11-3); (I-312)+(S12-1); (I-312)+(S13-1); (I-312)+(S13-2); (I-312)+(S13-3); (I-312)+(S13-4): (I-312)+(S13-5); (I-312)+(S13-6); (I-312)+(S13-7); (I-312)+(S13-8); (I-312)+(S13-9); (I-312)+(S14-1)

(I-313)+(S1-1); (I-313)+(S1-2); (I-313)+(S1-3); (I-313)+(S1-4); (I-313)+(S1-5); (I-313)+(S1-6); (I-313)+(S1-7); (I-313)+(S1-8); (I-313)+(S1-9); (I-313)+(S1-10); (I-313)+(S1-11); (I-313)+(S1-12); (I-313)+(S1-13); (I-313)+(S2-1); (I-313)+(S2-2); (I-313)+(S2-3); (I-313)+(S2-4); (I-313)+(S2-5); (I-313)+(S2-6); (I-313)+(S2-7); (I-313)+(S2-8); (I-313)+(S2-9); (I-313)+(S2-10); (I-313)+(S3-1); (I-313)+(S3-2); (I-313)+(S3-3); (I-313)+(S3-4); (I-313)+(S3-5); (I-313)+(S3-6); (I-313)+(S3-7); (I-313)+(S3-8); (I-313)+(S3-9); (I-313)+(S3-10); (I-313)+(S3-11); (I-313)+(S4-1); (I-313)+(S4-2); (I-313)+(S4-3); (I-313)+(S4-4); (I-313)+(S4-5); (I-313)+(S7-1); (I-313)+(S11-1); (I-313)+(S11-2); (I-313)+(S11-3); (I-313)+(S12-1); (I-313)+(S13-1); (I-313)+(S13-2); (I-313)+(S13-3); (I-313)+(S13-4): (I-313)+(S13-5); (I-313)+(S13-6); (I-313)+(S13-7); (I-313)+(S13-8); (I-313)+(S13-9); (I-313)+(S14-1)

(I-314)+(S1-1); (I-314)+(S1-2); (I-314)+(S1-3); (I-314)+(S1-4); (I-314)+(S1-5); (I-314)+(S1-6); (I-314)+(S1-7); (I-314)+(S1-8); (I-314)+(S1-9); (I-314)+(S1-10); (I-314)+(S1-11); (I-314)+(S1-12); (I-314)+(S1-13); (I-314)+(S2-1); (I-314)+(S2-2); (I-314)+(S2-3); (I-314)+(S2-4); (I-314)+(S2-5); (I-314)+(S2-6); (I-314)+(S2-7); (I-314)+(S2-8); (I-314)+(S2-9); (I-314)+(S2-10); (I-314)+(S3-1); (I-314)+(S3-2); (I-314)+(S3-3); (I-314)+(S3-4); (I-314)+(S3-5); (I-314)+(S3-6); (I-314)+(S3-7); (I-314)+(S3-8); (I-314)+(S3-9); (I-314)+(S3-10); (I-314)+(S3-11); (I-314)+(S4-1); (I-314)+(S4-2); (I-314)+(S4-3); (I-314)+(S4-4); (I-314)+(S4-5); (I-314)+(S7-1); (I-314)+(S11-1); (I-314)+(S11-2); (I-314)+(S11-3); (I-314)+(S12-1); (I-314)+(S13-1); (I-314)+(S13-2); (I-314)+(S13-3); (I-314)+(S13-4): (I-314)+(S13-5); (I-314)+(S13-6); (I-314)+(S13-7); (I-314)+(S13-8); (I-314)+(S13-9); (I-314)+(S14-1)

(I-315)+(S1-1); (I-315)+(S1-2); (I-315)+(S1-3); (I-315)+(S1-4); (I-315)+(S1-5); (I-315)+(S1-6); (I-315)+(S1-7); (I-315)+(S1-8); (I-315)+(S1-9); (I-315)+(S1-10); (I-315)+(S1-11); (I-315)+(S1-12); (I-315)+(S1-13); (I-315)+(S2-1); (I-315)+(S2-2); (I-315)+(S2-3); (I-315)+(S2-4); (I-315)+(S2-5); (I-315)+(S2-6); (I-315)+(S2-7); (I-315)+(S2-8); (I-315)+(S2-9); (I-315)+(S2-10); (I-315)+(S3-1); (I-315)+(S3-2); (I-315)+(S3-3); (I-315)+(S3-4); (I-315)+(S3-5); (I-315)+(S3-6); (I-315)+(S3-7); (I-315)+(S3-8); (I-315)+(S3-9); (I-315)+(S3-10); (I-315)+(S3-11); (I-315)+(S4-1); (I-315)+(S4-2); (I-315)+(S4-3); (I-315)+(S4-4); (I-315)+(S4-5); (I-315)+(S7-1); (I-315)+(S11-1); (I-315)+(S11-2); (I-315)+(S11-3); (I-315)+(S12-1); (I-315)+(S13-1); (I-315)+(S13-2); (I-315)+(S13-3); (I-315)+(S13-4): (I-315)+(S13-5); (I-315)+(S13-6); (I-315)+(S13-7); (I-315)+(S13-8); (I-315)+(S13-9); (I-315)+(S14-1)

(I-316)+(S1-1); (I-316)+(S1-2); (I-316)+(S1-3); (I-316)+(S1-4); (I-316)+(S1-5); (I-316)+(S1-6); (I-316)+(S1-7); (I-316)+(S1-8); (I-316)+(S1-9); (I-316)+(S1-10); (I-316)+(S1-11); (I-316)+(S1-12); (I-316)+(S1-13); (I-316)+(S2-1); (I-316)+(S2-2); (I-316)+(S2-3); (I-316)+(S2-4); (I-316)+(S2-5); (I-316)+(S2-6); (I-316)+(S2-7); (I-316)+(S2-8); (I-316)+(S2-9); (I-316)+(S2-10); (I-316)+(S3-1); (I-316)+(S3-2); (I-316)+(S3-3); (I-316)+(S3-4); (I-316)+(S3-5); (I-316)+(S3-6); (I-316)+(S3-7); (I-316)+(S3-8); (I-316)+(S3-9); (I-316)+(S3-10); (I-316)+(S3-11); (I-316)+(S4-1); (I-316)+(S4-2); (I-316)+(S4-3); (I-316)+(S4-4); (I-316)+(S4-5); (I-316)+(S7-1); (I-316)+(S11-1); (I-316)+(S11-2); (I-316)+(S11-3); (I-316)+(S12-1); (I-316)+(S13-1); (I-316)+(S13-2); (I-316)+(S13-3); (I-316)+(S13-4): (I-316)+(S13-5); (I-316)+(S13-6); (I-316)+(S13-7); (I-316)+(S13-8); (I-316)+(S13-9); (I-316)+(S14-1)

(I-317)+(S1-1); (I-317)+(S1-2); (I-317)+(S1-3); (I-317)+(S1-4); (I-317)+(S1-5); (I-317)+(S1-6); (I-317)+(S1-7); (I-317)+(S1-8); (I-317)+(S1-9); (I-317)+(S1-10); (I-317)+(S1-11); (I-317)+(S1-12); (I-317)+(S1-13); (I-317)+(S2-1); (I-317)+(S2-2); (I-317)+(S2-3); (I-317)+(S2-4); (I-317)+(S2-5); (I-317)+(S2-6); (I-317)+(S2-7); (I-317)+(S2-8); (I-317)+(S2-9); (I-317)+(S2-10); (I-317)+(S3-1); (I-317)+(S3-2); (I-317)+(S3-3); (I-317)+(S3-4); (I-317)+(S3-5); (I-317)+(S3-6); (I-317)+(S3-7); (I-317)+(S3-8); (I-317)+(S3-9); (I-317)+(S3-10); (I-317)+(S3-11); (I-317)+(S4-1); (I-317)+(S4-2); (I-317)+(S4-3); (I-317)+(S4-4); (I-317)+(S4-5); (I-317)+(S7-1); (I-317)+(S11-1); (I-317)+(S11-2); (I-317)+(S11-3); (I-317)+(S12-1); (I-317)+(S13-1); (I-317)+(S13-2); (I-317)+(S13-3); (I-317)+(S13-4): (I-317)+(S13-5); (I-317)+(S13-6); (I-317)+(S13-7); (I-317)+(S13-8); (I-317)+(S13-9); (I-317)+(S14-1)

(I-318)+(S1-1); (I-318)+(S1-2); (I-318)+(S1-3); (I-318)+(S1-4); (I-318)+(S1-5); (I-318)+(S1-6); (I-318)+(S1-7); (I-318)+(S1-8); (I-318)+(S1-9); (I-318)+(S1-10); (I-318)+(S1-11); (I-318)+(S1-12); (I-318)+(S1-13); (I-318)+(S2-1); (I-318)+(S2-2); (I-318)+(S2-3); (I-318)+(S2-4); (I-318)+(S2-5); (I-318)+(S2-6); (I-318)+(S2-7); (I-318)+(S2-8); (I-318)+(S2-9); (I-318)+(S2-10); (I-318)+(S3-1); (I-318)+(S3-2); (I-318)+(S3-3); (I-318)+(S3-4); (I-318)+(S3-5); (I-318)+(S3-6); (I-318)+(S3-7); (I-318)+(S3-8); (I-318)+(S3-9); (I-318)+(S3-10); (I-318)+(S3-11); (I-318)+(S4-1); (I-318)+(S4-2); (I-318)+(S4-3); (I-318)+(S4-4); (I-318)+(S4-5); (I-318)+(S7-1); (I-318)+(S11-1); (I-318)+(S11-2);

(I-318)+(S11-3); (I-318)+(S12-1); (I-318)+(S13-1); (I-318)+(S13-2); (I-318)+(S13-3); (I-318)+(S13-4): (I-318)+(S13-5); (I-318)+(S13-6); (I-318)+(S13-7); (I-318)+(S13-8); (I-318)+(S13-9); (I-318)+(S14-1)

(I-319)+(S1-1); (I-319)+(S1-2); (I-319)+(S1-3); (I-319)+(S1-4); (I-319)+(S1-5); (I-319)+(S1-6); (I-319)+(S1-7); (I-319)+(S1-8); (I-319)+(S1-9); (I-319)+(S1-10); (I-319)+(S1-11); (I-319)+(S1-12); (I-319)+(S1-13); (I-319)+(S2-1); (I-319)+(S2-2); (I-319)+(S2-3); (I-319)+(S2-4); (I-319)+(S2-5); (I-319)+(S2-6); (I-319)+(S2-7); (I-319)+(S2-8); (I-319)+(S2-9); (I-319)+(S2-10); (I-319)+(S3-1); (I-319)+(S3-2); (I-319)+(S3-3); (I-319)+(S3-4); (I-319)+(S3-5); (I-319)+(S3-6); (I-319)+(S3-7); (I-319)+(S3-8); (I-319)+(S3-9); (I-319)+(S3-10); (I-319)+(S3-11); (I-319)+(S4-1); (I-319)+(S4-2); (I-319)+(S4-3); (I-319)+(S4-4); (I-319)+(S4-5); (I-319)+(S7-1); (I-319)+(S11-1); (I-319)+(S11-2); (I-319)+(S11-3); (I-319)+(S12-1); (I-319)+(S13-1); (I-319)+(S13-2); (I-319)+(S13-3); (I-319)+(S13-4): (I-319)+(S13-5); (I-319)+(S13-6); (I-319)+(S13-7); (I-319)+(S13-8); (I-319)+(S13-9); (I-319)+(S14-1)

(I-320)+(S1-1); (I-320)+(S1-2); (I-320)+(S1-3); (I-320)+(S1-4); (I-320)+(S1-5); (I-320)+(S1-6); (I-320)+(S1-7); (I-320)+(S1-8); (I-320)+(S1-9); (I-320)+(S1-10); (I-320)+(S1-11); (I-320)+(S1-12); (I-320)+(S1-13); (I-320)+(S2-1); (I-320)+(S2-2); (I-320)+(S2-3); (I-320)+(S2-4); (I-320)+(S2-5); (I-320)+(S2-6); (I-320)+(S2-7); (I-320)+(S2-8); (I-320)+(S2-9); (I-320)+(S2-10); (I-320)+(S3-1); (I-320)+(S3-2); (I-320)+(S3-3); (I-320)+(S3-4); (I-320)+(S3-5); (I-320)+(S3-6); (I-320)+(S3-7); (I-320)+(S3-8); (I-320)+(S3-9); (I-320)+(S3-10); (I-320)+(S3-11); (I-320)+(S4-1); (I-320)+(S4-2); (I-320)+(S4-3); (I-320)+(S4-4); (I-320)+(S4-5); (I-320)+(S7-1); (I-320)+(S11-1); (I-320)+(S11-2); (I-320)+(S11-3); (I-320)+(S12-1); (I-320)+(S13-1); (I-320)+(S13-2); (I-320)+(S13-3); (I-320)+(S13-4): (I-320)+(S13-5); (I-320)+(S13-6); (I-320)+(S13-7); (I-320)+(S13-8); (I-320)+(S13-9); (I-320)+(S14-1)

(I-321)+(S1-1); (I-321)+(S1-2); (I-321)+(S1-3); (I-321)+(S1-4); (I-321)+(S1-5); (I-321)+(S1-6); (I-321)+(S1-7); (I-321)+(S1-8); (I-321)+(S1-9); (I-321)+(S1-10); (I-321)+(S1-11); (I-321)+(S1-12); (I-321)+(S1-13); (I-321)+(S2-1); (I-321)+(S2-2); (I-321)+(S2-3); (I-321)+(S2-4); (I-321)+(S2-5); (I-321)+(S2-6); (I-321)+(S2-7); (I-321)+(S2-8); (I-321)+(S2-9); (I-321)+(S2-10); (I-321)+(S3-1); (I-321)+(S3-2); (I-321)+(S3-3); (I-321)+(S3-4); (I-321)+(S3-5); (I-321)+(S3-6); (I-321)+(S3-7); (I-321)+(S3-8); (I-321)+(S3-9); (I-321)+(S3-10); (I-321)+(S3-11); (I-321)+(S4-1); (I-321)+(S4-2); (I-321)+(S4-3); (I-321)+(S4-4); (I-321)+(S4-5); (I-321)+(S7-1); (I-321)+(S11-1); (I-321)+(S11-2); (I-321)+(S11-3); (I-321)+(S12-1); (I-321)+(S13-1); (I-321)+(S13-2); (I-321)+(S13-3); (I-321)+(S13-4): (I-321)+(S13-5); (I-321)+(S13-6); (I-321)+(S13-7); (I-321)+(S13-8); (I-321)+(S13-9); (I-321)+(S14-1)

(I-322)+(S1-1); (I-322)+(S1-2); (I-322)+(S1-3); (I-322)+(S1-4); (I-322)+(S1-5); (I-322)+(S1-6); (I-322)+(S1-7); (I-322)+(S1-8); (I-322)+(S1-9); (I-322)+(S1-10); (I-322)+(S1-11); (I-322)+(S1-12); (I-322)+(S1-13); (I-322)+(S2-1); (I-322)+(S2-2); (I-322)+(S2-3); (I-322)+(S2-4); (I-322)+(S2-5); (I-322)+(S2-6); (I-322)+(S2-7); (I-322)+(S2-8); (I-322)+(S2-9); (I-322)+(S2-10); (I-322)+(S3-1); (I-322)+(S3-2); (I-322)+(S3-3); (I-322)+(S3-4); (I-322)+(S3-5); (I-322)+(S3-6); (I-322)+(S3-7); (I-322)+(S3-8); (I-322)+(S3-9); (I-322)+(S3-10); (I-322)+(S3-11); (I-322)+(S4-1); (I-322)+(S4-2); (I-322)+(S4-3); (I-322)+(S4-4); (I-322)+(S4-5); (I-322)+(S7-1); (I-322)+(S11-1); (I-322)+(S11-2); (I-322)+(S11-3); (I-322)+(S12-1); (I-322)+(S13-1); (I-322)+(S13-2); (I-322)+(S13-3); (I-322)+(S13-4): (I-322)+(S13-5); (I-322)+(S13-6); (I-322)+(S13-7); (I-322)+(S13-8); (I-322)+(S13-9); (I-322)+(S14-1)

(I-323)+(S1-1); (I-323)+(S1-2); (I-323)+(S1-3); (I-323)+(S1-4); (I-323)+(S1-5); (I-323)+(S1-6); (I-323)+(S1-7); (I-323)+(S1-8); (I-323)+(S1-9); (I-323)+(S1-10); (I-323)+(S1-11); (I-323)+(S1-12); (I-323)+(S1-13); (I-323)+(S2-1); (I-323)+(S2-2); (I-323)+(S2-3); (I-323)+(S2-4); (I-323)+(S2-5); (I-323)+(S2-6); (I-323)+(S2-7); (I-323)+(S2-8); (I-323)+(S2-9); (I-323)+(S2-10); (I-323)+(S3-1); (I-323)+(S3-2); (I-323)+(S3-3); (I-323)+(S3-4); (I-323)+(S3-5); (I-323)+(S3-6); (I-323)+(S3-7); (I-323)+(S3-8); (I-323)+(S3-9); (I-323)+(S3-10); (I-323)+(S3-11); (I-323)+(S4-1); (I-323)+(S4-2); (I-323)+(S4-3); (I-323)+(S4-4); (I-323)+(S4-5); (I-323)+(S7-1); (I-323)+(S11-1); (I-323)+(S11-2); (I-323)+(S11-3); (I-323)+(S12-1); (I-323)+(S13-1); (I-323)+(S13-2); (I-323)+(S13-3); (I-323)+(S13-4): (I-323)+(S13-5); (I-323)+(S13-6); (I-323)+(S13-7); (I-323)+(S13-8); (I-323)+(S13-9); (I-323)+(S14-1)

(I-324)+(S1-1); (I-324)+(S1-2); (I-324)+(S1-3); (I-324)+(S1-4); (I-324)+(S1-5); (I-324)+(S1-6); (I-324)+(S1-7); (I-324)+(S1-8); (I-324)+(S1-9); (I-324)+(S1-10); (I-324)+(S1-11); (I-324)+(S1-12); (I-324)+(S1-13); (I-324)+(S2-1); (I-324)+(S2-2); (I-324)+(S2-3); (I-324)+(S2-4); (I-324)+(S2-5); (I-324)+(S2-6); (I-324)+(S2-7); (I-324)+(S2-8); (I-324)+(S2-9); (I-324)+(S2-10); (I-324)+(S3-1); (I-324)+(S3-2); (I-324)+(S3-3); (I-324)+(S3-4); (I-324)+(S3-5); (I-324)+(S3-6); (I-324)+(S3-7); (I-324)+(S3-8); (I-324)+(S3-9); (I-324)+(S3-10); (I-324)+(S3-11); (I-324)+(S4-1); (I-324)+(S4-2); (I-324)+(S4-3); (I-324)+(S4-4); (I-324)+(S4-5); (I-324)+(S7-1); (I-324)+(S11-1); (I-324)+(S11-2); (I-324)+(S11-3); (I-324)+(S12-1); (I-324)+(S13-1); (I-324)+(S13-2); (I-324)+(S13-3); (I-324)+(S13-4): (I-324)+(S13-5); (I-324)+(S13-6); (I-324)+(S13-7); (I-324)+(S13-8); (I-324)+(S13-9); (I-324)+(S14-1)

(I-325)+(S1-1); (I-325)+(S1-2); (I-325)+(S1-3); (I-325)+(S1-4); (I-325)+(S1-5); (I-325)+(S1-6); (I-325)+(S1-7); (I-325)+(S1-8); (I-325)+(S1-9); (I-325)+(S1-10); (I-325)+(S1-11); (I-325)+(S1-12); (I-325)+(S1-13); (I-325)+(S2-1); (I-325)+(S2-2); (I-325)+(S2-3); (I-325)+(S2-4); (I-325)+(S2-5); (I-325)+(S2-6); (I-325)+(S2-7); (I-325)+(S2-8); (I-325)+(S2-9); (I-325)+(S2-10); (I-325)+(S3-1); (I-325)+(S3-2); (I-325)+(S3-3); (I-325)+(S3-4); (I-325)+(S3-5); (I-325)+(S3-6); (I-325)+(S3-7); (I-325)+(S3-8); (I-325)+(S3-9); (I-325)+(S3-10); (I-325)+(S3-11); (I-325)+(S4-1); (I-325)+(S4-2); (I-325)+(S4-3); (I-325)+(S4-4); (I-325)+(S4-5); (I-325)+(S7-1); (I-325)+(S11-1); (I-325)+(S11-2); (I-325)+(S11-3); (I-325)+(S12-1); (I-325)+(S13-1); (I-325)+(S13-2); (I-325)+(S13-3); (I-325)+(S13-4): (I-325)+(S13-5); (I-325)+(S13-6); (I-325)+(S13-7); (I-325)+(S13-8); (I-325)+(S13-9); (I-325)+(S14-1)

(I-326)+(S1-1); (I-326)+(S1-2); (I-326)+(S1-3); (I-326)+(S1-4); (I-326)+(S1-5); (I-326)+(S1-6); (I-326)+(S1-7); (I-326)+(S1-8); (I-326)+(S1-9); (I-326)+(S1-10); (I-326)+(S1-11); (I-326)+(S1-12); (I-326)+(S1-13); (I-326)+(S2-1); (I-326)+(S2-2); (I-326)+(S2-3); (I-326)+(S2-4); (I-326)+(S2-5); (I-326)+(S2-6); (I-326)+(S2-7); (I-326)+(S2-8); (I-326)+(S2-9); (I-326)+(S2-10); (I-326)+(S3-1); (I-326)+(S3-2); (I-326)+(S3-3); (I-326)+(S3-4); (I-326)+(S3-5); (I-326)+(S3-6); (I-326)+(S3-7); (I-326)+(S3-8); (I-326)+(S3-9); (I-326)+(S3-10); (I-326)+(S3-11); (I-326)+(S4-1); (I-326)+(S4-2); (I-326)+(S4-3); (I-326)+(S4-4); (I-326)+(S4-5); (I-326)+(S7-1); (I-326)+(S11-1); (I-326)+(S11-2); (I-326)+(S11-3); (I-326)+(S12-1); (I-326)+(S13-1); (I-326)+(S13-2); (I-326)+(S13-3); (I-326)+(S13-4): (I-326)+(S13-5); (I-326)+(S13-6); (I-326)+(S13-7); (I-326)+(S13-8); (I-326)+(S13-9); (I-326)+(S14-1)

(I-327)+(S1-1); (I-327)+(S1-2); (I-327)+(S1-3); (I-327)+(S1-4); (I-327)+(S1-5); (I-327)+(S1-6); (I-327)+(S1-7); (I-327)+(S1-8); (I-327)+(S1-9); (I-327)+(S1-10); (I-327)+(S1-11); (I-327)+(S1-12); (I-327)+(S1-13); (I-327)+(S2-1); (I-327)+(S2-2); (I-327)+(S2-3); (I-327)+(S2-4); (I-327)+(S2-5); (I-327)+(S2-6); (I-327)+(S2-7); (I-327)+(S2-8); (I-327)+(S2-9); (I-327)+(S2-10); (I-327)+(S3-1); (I-327)+(S3-2); (I-327)+(S3-3); (I-327)+(S3-4); (I-327)+(S3-5); (I-327)+(S3-6); (I-327)+(S3-7); (I-327)+(S3-8); (I-327)+(S3-9); (I-327)+(S3-10); (I-327)+(S3-11); (I-327)+(S4-1); (I-327)+(S4-2); (I-327)+(S4-3); (I-327)+(S4-4); (I-327)+(S4-5); (I-327)+(S7-1); (I-327)+(S11-1); (I-327)+(S11-2); (I-327)+(S11-3); (I-327)+(S12-1); (I-327)+(S13-1); (I-327)+(S13-2); (I-327)+(S13-3); (I-327)+(S13-4): (I-327)+(S13-5); (I-327)+(S13-6); (I-327)+(S13-7); (I-327)+(S13-8); (I-327)+(S13-9); (I-327)+(S14-1)

(I-328)+(S1-1); (I-328)+(S1-2); (I-328)+(S1-3); (I-328)+(S1-4); (I-328)+(S1-5); (I-328)+(S1-6); (I-328)+(S1-7); (I-328)+(S1-8); (I-328)+(S1-9); (I-328)+(S1-10); (I-328)+(S1-11); (I-328)+(S1-12); (I-328)+(S1-13); (I-328)+(S2-1); (I-328)+(S2-2); (I-328)+(S2-3); (I-328)+(S2-4); (I-328)+(S2-5); (I-328)+(S2-6); (I-328)+(S2-7); (I-328)+(S2-8); (I-328)+(S2-9); (I-328)+(S2-10); (I-328)+(S3-1); (I-328)+(S3-2); (I-328)+(S3-3); (I-328)+(S3-4); (I-328)+(S3-5); (I-328)+(S3-6); (I-328)+(S3-7); (I-328)+(S3-8); (I-328)+(S3-9); (I-328)+(S3-10); (I-328)+(S3-11); (I-328)+(S4-1); (I-328)+(S4-2); (I-328)+(S4-3); (I-328)+(S4-4); (I-328)+(S4-5); (I-328)+(S7-1); (I-328)+(S11-1); (I-328)+(S11-2); (I-328)+(S11-3); (I-328)+(S12-1); (I-328)+(S13-1); (I-328)+(S13-2); (I-328)+(S13-3); (I-328)+(S13-4): (I-328)+(S13-5); (I-328)+(S13-6); (I-328)+(S13-7); (I-328)+(S13-8); (I-328)+(S13-9); (I-328)+(S14-1)

(I-329)+(S1-1); (I-329)+(S1-2); (I-329)+(S1-3); (I-329)+(S1-4); (I-329)+(S1-5); (I-329)+(S1-6); (I-329)+(S1-7); (I-329)+(S1-8); (I-329)+(S1-9); (I-329)+(S1-10); (I-329)+(S1-11); (I-329)+(S1-12); (I-329)+(S1-13); (I-329)+(S2-1); (I-329)+(S2-2); (I-329)+(S2-3); (I-329)+(S2-4); (I-329)+(S2-5); (I-329)+(S2-6); (I-329)+(S2-7); (I-329)+(S2-8); (I-329)+(S2-9); (I-329)+(S2-10); (I-329)+(S3-1); (I-329)+(S3-2); (I-329)+(S3-3); (I-329)+(S3-4); (I-329)+(S3-5); (I-329)+(S3-6); (I-329)+(S3-7); (I-329)+(S3-8); (I-329)+(S3-9); (I-329)+(S3-10); (I-329)+(S3-11); (I-329)+(S4-1); (I-329)+(S4-2); (I-329)+(S4-3); (I-329)+(S4-4); (I-329)+(S4-5); (I-329)+(S7-1); (I-329)+(S11-1); (I-329)+(S11-2); (I-329)+(S11-3); (I-329)+(S12-1); (I-329)+(S13-1); (I-329)+(S13-2); (I-329)+(S13-3); (I-329)+(S13-4): (I-329)+(S13-5); (I-329)+(S13-6); (I-329)+(S13-7); (I-329)+(S13-8); (I-329)+(S13-9); (I-329)+(S14-1)

(I-330)+(S1-1); (I-330)+(S1-2); (I-330)+(S1-3); (I-330)+(S1-4); (I-330)+(S1-5); (I-330)+(S1-6); (I-330)+(S1-7); (I-330)+(S1-8); (I-330)+(S1-9); (I-330)+(S1-10); (I-330)+(S1-11); (I-330)+(S1-12); (I-330)+(S1-13); (I-330)+(S2-1); (I-330)+(S2-2); (I-330)+(S2-3); (I-330)+(S2-4); (I-330)+(S2-5); (I-330)+(S2-6); (I-330)+(S2-7); (I-330)+(S2-8); (I-330)+(S2-9); (I-330)+(S2-10); (I-330)+(S3-1); (I-330)+(S3-2); (I-330)+(S3-3); (I-330)+(S3-4); (I-330)+(S3-5); (I-330)+(S3-6); (I-330)+(S3-7); (I-330)+(S3-8); (I-330)+(S3-9); (I-330)+(S3-10); (I-330)+(S3-11); (I-330)+(S4-1); (I-330)+(S4-2); (I-330)+(S4-3); (I-330)+(S4-4); (I-330)+(S4-5); (I-330)+(S7-1); (I-330)+(S11-1); (I-330)+(S11-2); (I-330)+(S11-3); (I-330)+(S12-1); (I-330)+(S13-1); (I-330)+(S13-2); (I-330)+(S13-3); (I-330)+(S13-4): (I-330)+(S13-5); (I-330)+(S13-6); (I-330)+(S13-7); (I-330)+(S13-8); (I-330)+(S13-9); (I-330)+(S14-1)

(I-331)+(S1-1); (I-331)+(S1-2); (I-331)+(S1-3); (I-331)+(S1-4); (I-331)+(S1-5); (I-331)+(S1-6); (I-331)+(S1-7); (I-331)+(S1-8); (I-331)+(S1-9); (I-331)+(S1-10); (I-331)+(S1-11); (I-331)+(S1-12); (I-331)+(S1-13); (I-331)+(S2-1); (I-331)+(S2-2); (I-331)+(S2-3); (I-331)+(S2-4); (I-331)+(S2-5); (I-331)+(S2-6); (I-331)+(S2-7); (I-331)+(S2-8); (I-331)+(S2-9); (I-331)+(S2-10); (I-331)+(S3-1); (I-331)+(S3-2); (I-331)+(S3-3); (I-331)+(S3-4); (I-331)+(S3-5); (I-331)+(S3-6); (I-331)+(S3-7); (I-331)+(S3-8); (I-331)+(S3-9); (I-331)+(S3-10); (I-331)+(S3-11); (I-331)+(S4-1); (I-331)+(S4-2); (I-331)+(S4-3); (I-331)+(S4-4); (I-331)+(S4-5); (I-331)+(S7-1); (I-331)+(S11-1); (I-331)+(S11-2); (I-331)+(S11-3); (I-331)+(S12-1); (I-331)+(S13-1); (I-331)+(S13-2); (I-331)+(S13-3); (I-331)+(S13-4): (I-331)+(S13-5); (I-331)+(S13-6); (I-331)+(S13-7); (I-331)+(S13-8); (I-331)+(S13-9); (I-331)+(S14-1)

(I-332)+(S1-1); (I-332)+(S1-2); (I-332)+(S1-3); (I-332)+(S1-4); (I-332)+(S1-5); (I-332)+(S1-6); (I-332)+(S1-7); (I-332)+(S1-8); (I-332)+(S1-9); (I-332)+(S1-10); (I-332)+(S1-11); (I-332)+(S1-12); (I-332)+(S1-13); (I-332)+(S2-1); (I-332)+(S2-2); (I-332)+(S2-3); (I-332)+(S2-4); (I-332)+(S2-5); (I-332)+(S2-6); (I-332)+(S2-7); (I-332)+(S2-8); (I-332)+(S2-9); (I-332)+(S2-10); (I-332)+(S3-1); (I-332)+(S3-2); (I-332)+(S3-3); (I-332)+(S3-4); (I-332)+(S3-5); (I-332)+(S3-6); (I-332)+(S3-7); (I-332)+(S3-8); (I-332)+(S3-9); (I-332)+(S3-10); (I-332)+(S3-11); (I-332)+(S4-1); (I-332)+(S4-2); (I-332)+(S4-3); (I-332)+(S4-4); (I-332)+(S4-5); (I-332)+(S7-1); (I-332)+(S11-1); (I-332)+(S11-2); (I-332)+(S11-3); (I-332)+(S12-1); (I-332)+(S13-1); (I-332)+(S13-2); (I-332)+(S13-3); (I-332)+(S13-4): (I-332)+(S13-5); (I-332)+(S13-6); (I-332)+(S13-7); (I-332)+(S13-8); (I-332)+(S13-9); (I-332)+(S14-1)

(I-333)+(S1-1); (I-333)+(S1-2); (I-333)+(S1-3); (I-333)+(S1-4); (I-333)+(S1-5); (I-333)+(S1-6); (I-333)+(S1-7); (I-333)+(S1-8); (I-333)+(S1-9); (I-333)+(S1-10); (I-333)+(S1-11); (I-333)+(S1-12); (I-333)+(S1-13); (I-333)+(S2-1); (I-333)+(S2-2); (I-333)+(S2-3); (I-333)+(S2-4); (I-333)+(S2-5); (I-333)+(S2-6); (I-333)+(S2-7); (I-333)+(S2-8); (I-333)+(S2-9); (I-333)+(S2-10); (I-333)+(S3-1); (I-333)+(S3-2); (I-333)+(S3-3); (I-333)+(S3-4); (I-333)+(S3-5); (I-333)+(S3-6); (I-333)+(S3-7); (I-333)+(S3-8); (I-333)+(S3-9); (I-333)+(S3-10); (I-333)+(S3-11); (I-333)+(S4-1); (I-333)+(S4-2); (I-333)+(S4-3); (I-333)+(S4-4); (I-333)+(S4-5); (I-333)+(S7-1); (I-333)+(S11-1); (I-333)+(S11-2); (I-333)+(S11-3); (I-333)+(S12-1); (I-333)+(S13-1); (I-333)+(S13-2); (I-333)+(S13-3); (I-333)+(S13-4): (I-333)+(S13-5); (I-333)+(S13-6); (I-333)+(S13-7); (I-333)+(S13-8); (I-333)+(S13-9); (I-333)+(S14-1)

(I-334)+(S1-1); (I-334)+(S1-2); (I-334)+(S1-3); (I-334)+(S1-4); (I-334)+(S1-5); (I-334)+(S1-6); (I-334)+(S1-7); (I-334)+(S1-8); (I-334)+(S1-9); (I-334)+(S1-10); (I-334)+(S1-11); (I-334)+(S1-12); (I-334)+(S1-13); (I-334)+(S2-1); (I-334)+(S2-2); (I-334)+(S2-3); (I-334)+(S2-4); (I-334)+(S2-5); (I-334)+(S2-6); (I-334)+(S2-7); (I-334)+(S2-8); (I-334)+(S2-9); (I-334)+(S2-10); (I-334)+(S3-1); (I-334)+(S3-2); (I-334)+(S3-3); (I-334)+(S3-4); (I-334)+(S3-5); (I-334)+(S3-6); (I-334)+(S3-7); (I-334)+(S3-8); (I-334)+(S3-9); (I-334)+(S3-10); (I-334)+(S3-11); (I-334)+(S4-1); (I-334)+(S4-2); (I-334)+(S4-3); (I-334)+(S4-4); (I-334)+(S4-5); (I-334)+(S7-1); (I-334)+(S11-1); (I-334)+(S11-2); (I-334)+(S11-3); (I-334)+(S12-1); (I-334)+(S13-1); (I-334)+(S13-2); (I-334)+(S13-3); (I-334)+(S13-4): (I-334)+(S13-5); (I-334)+(S13-6); (I-334)+(S13-7); (I-334)+(S13-8); (I-334)+(S13-9); (I-334)+(S14-1)

(I-335)+(S1-1); (I-335)+(S1-2); (I-335)+(S1-3); (I-335)+(S1-4); (I-335)+(S1-5); (I-335)+(S1-6); (I-335)+(S1-7); (I-335)+(S1-8); (I-335)+(S1-9); (I-335)+(S1-10); (I-335)+(S1-11); (I-335)+(S1-12); (I-335)+(S1-13); (I-335)+(S2-1); (I-335)+(S2-2); (I-335)+(S2-3); (I-335)+(S2-4); (I-335)+(S2-5); (I-335)+(S2-6); (I-335)+(S2-7); (I-335)+(S2-8);

(I-335)+(S2-9); (I-335)+(S2-10); (I-335)+(S3-1); (I-335)+(S3-2); (I-335)+(S3-3); (I-335)+(S3-4); (I-335)+(S3-5); (I-335)+(S3-6); (I-335)+(S3-7); (I-335)+(S3-8); (I-335)+(S3-9); (I-335)+(S3-10); (I-335)+(S3-11); (I-335)+(S4-1); (I-335)+(S4-2); (I-335)+(S4-3); (I-335)+(S4-4); (I-335)+(S4-5); (I-335)+(S7-1); (I-335)+(S11-1); (I-335)+(S11-2); (I-335)+(S11-3); (I-335)+(S12-1); (I-335)+(S13-1); (I-335)+(S13-2); (I-335)+(S13-3); (I-335)+(S13-4): (I-335)+(S13-5); (I-335)+(S13-6); (I-335)+(S13-7); (I-335)+(S13-8); (I-335)+(S13-9); (I-335)+(S14-1)

(I-336)+(S1-1); (I-336)+(S1-2); (I-336)+(S1-3); (I-336)+(S1-4); (I-336)+(S1-5); (I-336)+(S1-6); (I-336)+(S1-7); (I-336)+(S1-8); (I-336)+(S1-9); (I-336)+(S1-10); (I-336)+(S1-11); (I-336)+(S1-12); (I-336)+(S1-13); (I-336)+(S2-1); (I-336)+(S2-2); (I-336)+(S2-3); (I-336)+(S2-4); (I-336)+(S2-5); (I-336)+(S2-6); (I-336)+(S2-7); (I-336)+(S2-8); (I-336)+(S2-9); (I-336)+(S2-10); (I-336)+(S3-1); (I-336)+(S3-2); (I-336)+(S3-3); (I-336)+(S3-4); (I-336)+(S3-5); (I-336)+(S3-6); (I-336)+(S3-7); (I-336)+(S3-8); (I-336)+(S3-9); (I-336)+(S3-10); (I-336)+(S3-11); (I-336)+(S4-1); (I-336)+(S4-2); (I-336)+(S4-3); (I-336)+(S4-4); (I-336)+(S4-5); (I-336)+(S7-1); (I-336)+(S11-1); (I-336)+(S11-2); (I-336)+(S11-3); (I-336)+(S12-1); (I-336)+(S13-1); (I-336)+(S13-2); (I-336)+(S13-3); (I-336)+(S13-4): (I-336)+(S13-5); (I-336)+(S13-6); (I-336)+(S13-7); (I-336)+(S13-8); (I-336)+(S13-9); (I-336)+(S14-1)

(I-337)+(S1-1); (I-337)+(S1-2); (I-337)+(S1-3); (I-337)+(S1-4); (I-337)+(S1-5); (I-337)+(S1-6); (I-337)+(S1-7); (I-337)+(S1-8); (I-337)+(S1-9); (I-337)+(S1-10); (I-337)+(S1-11); (I-337)+(S1-12); (I-337)+(S1-13); (I-337)+(S2-1); (I-337)+(S2-2); (I-337)+(S2-3); (I-337)+(S2-4); (I-337)+(S2-5); (I-337)+(S2-6); (I-337)+(S2-7); (I-337)+(S2-8); (I-337)+(S2-9); (I-337)+(S2-10); (I-337)+(S3-1); (I-337)+(S3-2); (I-337)+(S3-3); (I-337)+(S3-4); (I-337)+(S3-5); (I-337)+(S3-6); (I-337)+(S3-7); (I-337)+(S3-8); (I-337)+(S3-9); (I-337)+(S3-10); (I-337)+(S3-11); (I-337)+(S4-1); (I-337)+(S4-2); (I-337)+(S4-3); (I-337)+(S4-4); (I-337)+(S4-5); (I-337)+(S7-1); (I-337)+(S11-1); (I-337)+(S11-2); (I-337)+(S11-3); (I-337)+(S12-1); (I-337)+(S13-1); (I-337)+(S13-2); (I-337)+(S13-3); (I-337)+(S13-4): (I-337)+(S13-5); (I-337)+(S13-6); (I-337)+(S13-7); (I-337)+(S13-8); (I-337)+(S13-9); (I-337)+(S14-1)

(I-338)+(S1-1); (I-338)+(S1-2); (I-338)+(S1-3); (I-338)+(S1-4); (I-338)+(S1-5); (I-338)+(S1-6); (I-338)+(S1-7); (I-338)+(S1-8); (I-338)+(S1-9); (I-338)+(S1-10); (I-338)+(S1-11); (I-338)+(S1-12); (I-338)+(S1-13); (I-338)+(S2-1); (I-338)+(S2-2); (I-338)+(S2-3); (I-338)+(S2-4); (I-338)+(S2-5); (I-338)+(S2-6); (I-338)+(S2-7); (I-338)+(S2-8); (I-338)+(S2-9); (I-338)+(S2-10); (I-338)+(S3-1); (I-338)+(S3-2); (I-338)+(S3-3); (I-338)+(S3-4); (I-338)+(S3-5); (I-338)+(S3-6); (I-338)+(S3-7); (I-338)+(S3-8); (I-338)+(S3-9); (I-338)+(S3-10); (I-338)+(S3-11); (I-338)+(S4-1); (I-338)+(S4-2); (I-338)+(S4-3); (I-338)+(S4-4); (I-338)+(S4-5); (I-338)+(S7-1); (I-338)+(S11-1); (I-338)+(S11-2); (I-338)+(S11-3); (I-338)+(S12-1); (I-338)+(S13-1); (I-338)+(S13-2); (I-338)+(S13-3); (I-338)+(S13-4): (I-338)+(S13-5); (I-338)+(S13-6); (I-338)+(S13-7); (I-338)+(S13-8); (I-338)+(S13-9); (I-338)+(S14-1)

(I-339)+(S1-1); (I-339)+(S1-2); (I-339)+(S1-3); (I-339)+(S1-4); (I-339)+(S1-5); (I-339)+(S1-6); (I-339)+(S1-7); (I-339)+(S1-8); (I-339)+(S1-9); (I-339)+(S1-10); (I-339)+(S1-11); (I-339)+(S1-12); (I-339)+(S1-13); (I-339)+(S2-1); (I-339)+(S2-2); (I-339)+(S2-3); (I-339)+(S2-4); (I-339)+(S2-5); (I-339)+(S2-6); (I-339)+(S2-7); (I-339)+(S2-8); (I-339)+(S2-9); (I-339)+(S2-10); (I-339)+(S3-1); (I-339)+(S3-2); (I-339)+(S3-3); (I-339)+(S3-4); (I-339)+(S3-5); (I-339)+(S3-6); (I-339)+(S3-7); (I-339)+(S3-8); (I-339)+(S3-9); (I-339)+(S3-10); (I-339)+(S3-11); (I-339)+(S4-1); (I-339)+(S4-2); (I-339)+(S4-3); (I-339)+(S4-4); (I-339)+(S4-5); (I-339)+(S7-1); (I-339)+(S11-1); (I-339)+(S11-2); (I-339)+(S11-3); (I-339)+(S12-1); (I-339)+(S13-1); (I-339)+(S13-2); (I-339)+(S13-3); (I-339)+(S13-4): (I-339)+(S13-5); (I-339)+(S13-6); (I-339)+(S13-7); (I-339)+(S13-8); (I-339)+(S13-9); (I-339)+(S14-1)

(I-340)+(S1-1); (I-340)+(S1-2); (I-340)+(S1-3); (I-340)+(S1-4); (I-340)+(S1-5); (I-340)+(S1-6); (I-340)+(S1-7); (I-340)+(S1-8); (I-340)+(S1-9); (I-340)+(S1-10); (I-340)+(S1-11); (I-340)+(S1-12); (I-340)+(S1-13); (I-340)+(S2-1); (I-340)+(S2-2); (I-340)+(S2-3); (I-340)+(S2-4); (I-340)+(S2-5); (I-340)+(S2-6); (I-340)+(S2-7); (I-340)+(S2-8); (I-340)+(S2-9); (I-340)+(S2-10); (I-340)+(S3-1); (I-340)+(S3-2); (I-340)+(S3-3); (I-340)+(S3-4); (I-340)+(S3-5); (I-340)+(S3-6); (I-340)+(S3-7); (I-340)+(S3-8); (I-340)+(S3-9); (I-340)+(S3-10); (I-340)+(S3-11); (I-340)+(S4-1); (I-340)+(S4-2); (I-340)+(S4-3); (I-340)+(S4-4); (I-340)+(S4-5); (I-340)+(S7-1); (I-340)+(S11-1); (I-340)+(S11-2); (I-340)+(S11-3); (I-340)+(S12-1); (I-340)+(S13-1); (I-340)+(S13-2); (I-340)+(S13-3); (I-340)+(S13-4): (I-340)+(S13-5); (I-340)+(S13-6); (I-340)+(S13-7); (I-340)+(S13-8); (I-340)+(S13-9); (I-340)+(S14-1)

(I-341)+(S1-1); (I-341)+(S1-2); (I-341)+(S1-3); (I-341)+(S1-4); (I-341)+(S1-5); (I-341)+(S1-6); (I-341)+(S1-7); (I-341)+(S1-8); (I-341)+(S1-9); (I-341)+(S1-10); (I-341)+(S1-11); (I-341)+(S1-12); (I-341)+(S1-13); (I-341)+(S2-1); (I-341)+(S2-2); (I-341)+(S2-3); (I-341)+(S2-4); (I-341)+(S2-5); (I-341)+(S2-6); (I-341)+(S2-7); (I-341)+(S2-8); (I-341)+(S2-9); (I-341)+(S2-10); (I-341)+(S3-1); (I-341)+(S3-2); (I-341)+(S3-3); (I-341)+(S3-4); (I-341)+(S3-5); (I-341)+(S3-6); (I-341)+(S3-7); (I-341)+(S3-8); (I-341)+(S3-9); (I-341)+(S3-10); (I-341)+(S3-11); (I-341)+(S4-1); (I-341)+(S4-2); (I-341)+(S4-3); (I-341)+(S4-4); (I-341)+(S4-5); (I-341)+(S7-1); (I-341)+(S11-1); (I-341)+(S11-2); (I-341)+(S11-3); (I-341)+(S12-1); (I-341)+(S13-1); (I-341)+(S13-2); (I-341)+(S13-3); (I-341)+(S13-4): (I-341)+(S13-5); (I-341)+(S13-6); (I-341)+(S13-7); (I-341)+(S13-8); (I-341)+(S14-1)

(I-342)+(S1-1); (I-342)+(S1-2); (I-342)+(S1-3); (I-342)+(S1-4); (I-342)+(S1-5); (I-342)+(S1-6); (I-342)+(S1-7); (I-342)+(S1-8); (I-342)+(S1-9); (I-342)+(S1-10); (I-342)+(S1-11); (I-342)+(S1-12); (I-342)+(S1-13); (I-342)+(S2-1); (I-342)+(S2-2); (I-342)+(S2-3); (I-342)+(S2-4); (I-342)+(S2-5); (I-342)+(S2-6); (I-342)+(S2-7); (I-342)+(S2-8); (I-342)+(S2-9); (I-342)+(S2-10); (I-342)+(S3-1); (I-342)+(S3-2); (I-342)+(S3-3); (I-342)+(S3-4); (I-342)+(S3-5); (I-342)+(S3-6); (I-342)+(S3-7); (I-342)+(S3-8); (I-342)+(S3-9); (I-342)+(S3-10); (I-342)+(S3-11); (I-342)+(S4-1); (I-342)+(S4-2); (I-342)+(S4-3); (I-342)+(S4-4); (I-342)+(S4-5); (I-342)+(S7-1); (I-342)+(S11-1); (I-342)+(S11-2); (I-342)+(S11-3); (I-342)+(S12-1); (I-342)+(S13-1); (I-342)+(S13-2); (I-342)+(S13-3); (I-342)+(S13-4): (I-342)+(S13-5); (I-342)+(S13-6); (I-342)+(S13-7); (I-342)+(S13-8); (I-342)+(S13-9); (I-342)+(S14-1)

(I-343)+(S1-1); (I-343)+(S1-2); (I-343)+(S1-3); (I-343)+(S1-4); (I-343)+(S1-5); (I-343)+(S1-6); (I-343)+(S1-7); (I-343)+(S1-8); (I-343)+(S1-9); (I-343)+(S1-10); (I-343)+(S1-11); (I-343)+(S1-12); (I-343)+(S1-13); (I-343)+(S2-1); (I-343)+(S2-2); (I-343)+(S2-3); (I-343)+(S2-4); (I-343)+(S2-5); (I-343)+(S2-6); (I-343)+(S2-7); (I-343)+(S2-8); (I-343)+(S2-9); (I-343)+(S2-10); (I-343)+(S3-1); (I-343)+(S3-2); (I-343)+(S3-3); (I-343)+(S3-4); (I-343)+(S3-5); (I-343)+(S3-6); (I-343)+(S3-7); (I-343)+(S3-8); (I-343)+(S3-9); (I-343)+(S3-10); (I-343)+(S3-11); (I-343)+(S4-1); (I-343)+(S4-2); (I-343)+(S4-3); (I-343)+(S4-4); (I-343)+(S4-5); (I-343)+(S7-1); (I-343)+(S11-1); (I-343)+(S11-2);

(I-343)+(S11-3); (I-343)+(S12-1); (I-343)+(S13-1); (I-343)+(S13-2); (I-343)+(S13-3); (I-343)+(S13-4): (I-343)+(S13-5); (I-343)+(S13-6); (I-343)+(S13-7); (I-343)+(S13-8); (I-343)+(S13-9); (I-343)+(S14-1)

(I-344)+(S1-1); (I-344)+(S1-2); (I-344)+(S1-3); (I-344)+(S1-4); (I-344)+(S1-5); (I-344)+(S1-6); (I-344)+(S1-7); (I-344)+(S1-8); (I-344)+(S1-9); (I-344)+(S1-10); (I-344)+(S1-11); (I-344)+(S1-12); (I-344)+(S1-13); (I-344)+(S2-1); (I-344)+(S2-2); (I-344)+(S2-3); (I-344)+(S2-4); (I-344)+(S2-5); (I-344)+(S2-6); (I-344)+(S2-7); (I-344)+(S2-8); (I-344)+(S2-9); (I-344)+(S2-10); (I-344)+(S3-1); (I-344)+(S3-2); (I-344)+(S3-3); (I-344)+(S3-4); (I-344)+(S3-5); (I-344)+(S3-6); (I-344)+(S3-7); (I-344)+(S3-8); (I-344)+(S3-9); (I-344)+(S3-10); (I-344)+(S3-11); (I-344)+(S4-1); (I-344)+(S4-2); (I-344)+(S4-3); (I-344)+(S4-4); (I-344)+(S4-5); (I-344)+(S7-1); (I-344)+(S11-1); (I-344)+(S11-2); (I-344)+(S11-3); (I-344)+(S12-1); (I-344)+(S13-1); (I-344)+(S13-2); (I-344)+(S13-3); (I-344)+(S13-4): (I-344)+(S13-5); (I-344)+(S13-6); (I-344)+(S13-7); (I-344)+(S13-8); (I-344)+(S13-9); (I-344)+(S14-1)

(I-345)+(S1-1); (I-345)+(S1-2); (I-345)+(S1-3); (I-345)+(S1-4); (I-345)+(S1-5); (I-345)+(S1-6); (I-345)+(S1-7); (I-345)+(S1-8); (I-345)+(S1-9); (I-345)+(S1-10); (I-345)+(S1-11); (I-345)+(S1-12); (I-345)+(S1-13); (I-345)+(S2-1); (I-345)+(S2-2); (I-345)+(S2-3); (I-345)+(S2-4); (I-345)+(S2-5); (I-345)+(S2-6); (I-345)+(S2-7); (I-345)+(S2-8); (I-345)+(S2-9); (I-345)+(S2-10); (I-345)+(S3-1); (I-345)+(S3-2); (I-345)+(S3-3); (I-345)+(S3-4); (I-345)+(S3-5); (I-345)+(S3-6); (I-345)+(S3-7); (I-345)+(S3-8); (I-345)+(S3-9); (I-345)+(S3-10); (I-345)+(S3-11); (I-345)+(S4-1); (I-345)+(S4-2); (I-345)+(S4-3); (I-345)+(S4-4); (I-345)+(S4-5); (I-345)+(S7-1); (I-345)+(S11-1); (I-345)+(S11-2); (I-345)+(S11-3); (I-345)+(S12-1); (I-345)+(S13-1); (I-345)+(S13-2); (I-345)+(S13-3); (I-345)+(S13-4): (I-345)+(S13-5); (I-345)+(S13-6); (I-345)+(S13-7); (I-345)+(S13-8); (I-345)+(S13-9); (I-345)+(S14-1)

(I-346)+(S1-1); (I-346)+(S1-2); (I-346)+(S1-3); (I-346)+(S1-4); (I-346)+(S1-5); (I-346)+(S1-6); (I-346)+(S1-7); (I-346)+(S1-8); (I-346)+(S1-9); (I-346)+(S1-10); (I-346)+(S1-11); (I-346)+(S1-12); (I-346)+(S1-13); (I-346)+(S2-1); (I-346)+(S2-2); (I-346)+(S2-3); (I-346)+(S2-4); (I-346)+(S2-5); (I-346)+(S2-6); (I-346)+(S2-7); (I-346)+(S2-8); (I-346)+(S2-9); (I-346)+(S2-10); (I-346)+(S3-1); (I-346)+(S3-2); (I-346)+(S3-3); (I-346)+(S3-4); (I-346)+(S3-5); (I-346)+(S3-6); (I-346)+(S3-7); (I-346)+(S3-8); (I-346)+(S3-9); (I-346)+(S3-10); (I-346)+(S3-11); (I-346)+(S4-1); (I-346)+(S4-2); (I-346)+(S4-3); (I-346)+(S4-4); (I-346)+(S4-5); (I-346)+(S7-1); (I-346)+(S11-1); (I-346)+(S11-2); (I-346)+(S11-3); (I-346)+(S12-1); (I-346)+(S13-1); (I-346)+(S13-2); (I-346)+(S13-3); (I-346)+(S13-4): (I-346)+(S13-5); (I-346)+(S13-6); (I-346)+(S13-7); (I-346)+(S13-8); (I-346)+(S13-9); (I-346)+(S14-1)

(I-347)+(S1-1); (I-347)+(S1-2); (I-347)+(S1-3); (I-347)+(S1-4); (I-347)+(S1-5); (I-347)+(S1-6); (I-347)+(S1-7); (I-347)+(S1-8); (I-347)+(S1-9); (I-347)+(S1-10); (I-347)+(S1-11); (I-347)+(S1-12); (I-347)+(S1-13); (I-347)+(S2-1); (I-347)+(S2-2); (I-347)+(S2-3); (I-347)+(S2-4); (I-347)+(S2-5); (I-347)+(S2-6); (I-347)+(S2-7); (I-347)+(S2-8); (I-347)+(S2-9); (I-347)+(S2-10); (I-347)+(S3-1); (I-347)+(S3-2); (I-347)+(S3-3); (I-347)+(S3-4); (I-347)+(S3-5); (I-347)+(S3-6); (I-347)+(S3-7); (I-347)+(S3-8); (I-347)+(S3-9); (I-347)+(S3-10); (I-347)+(S3-11); (I-347)+(S4-1); (I-347)+(S4-2); (I-347)+(S4-3); (I-347)+(S4-4); (I-347)+(S4-5); (I-347)+(S7-1); (I-347)+(S11-1); (I-347)+(S11-2); (I-347)+(S11-3); (I-347)+(S12-1); (I-347)+(S13-1); (I-347)+(S13-2); (I-347)+(S13-3); (I-347)+(S13-4): (I-347)+(S13-5); (I-347)+(S13-6); (I-347)+(S13-7); (I-347)+(S13-8); (I-347)+(S13-9); (I-347)+(S14-1)

(I-348)+(S1-1); (I-348)+(S1-2); (I-348)+(S1-3); (I-348)+(S1-4); (I-348)+(S1-5); (I-348)+(S1-6); (I-348)+(S1-7); (I-348)+(S1-8); (I-348)+(S1-9); (I-348)+(S1-10); (I-348)+(S1-11); (I-348)+(S1-12); (I-348)+(S1-13); (I-348)+(S2-1); (I-348)+(S2-2); (I-348)+(S2-3); (I-348)+(S2-4); (I-348)+(S2-5); (I-348)+(S2-6); (I-348)+(S2-7); (I-348)+(S2-8); (I-348)+(S2-9); (I-348)+(S2-10); (I-348)+(S3-1); (I-348)+(S3-2); (I-348)+(S3-3); (I-348)+(S3-4); (I-348)+(S3-5); (I-348)+(S3-6); (I-348)+(S3-7); (I-348)+(S3-8); (I-348)+(S3-9); (I-348)+(S3-10); (I-348)+(S3-11); (I-348)+(S4-1); (I-348)+(S4-2); (I-348)+(S4-3); (I-348)+(S4-4); (I-348)+(S4-5); (I-348)+(S7-1); (I-348)+(S11-1); (I-348)+(S11-2); (I-348)+(S11-3); (I-348)+(S12-1); (I-348)+(S13-1); (I-348)+(S13-2); (I-348)+(S13-3); (I-348)+(S13-4): (I-348)+(S13-5); (I-348)+(S13-6); (I-348)+(S13-7); (I-348)+(S13-8); (I-348)+(S13-9); (I-348)+(S14-1)

(I-349)+(S1-1); (I-349)+(S1-2); (I-349)+(S1-3); (I-349)+(S1-4); (I-349)+(S1-5); (I-349)+(S1-6); (I-349)+(S1-7); (I-349)+(S1-8); (I-349)+(S1-9); (I-349)+(S1-10); (I-349)+(S1-11); (I-349)+(S1-12); (I-349)+(S1-13); (I-349)+(S2-1); (I-349)+(S2-2); (I-349)+(S2-3); (I-349)+(S2-4); (I-349)+(S2-5); (I-349)+(S2-6); (I-349)+(S2-7); (I-349)+(S2-8); (I-349)+(S2-9); (I-349)+(S2-10); (I-349)+(S3-1); (I-349)+(S3-2); (I-349)+(S3-3); (I-349)+(S3-4); (I-349)+(S3-5); (I-349)+(S3-6); (I-349)+(S3-7); (I-349)+(S3-8); (I-349)+(S3-9); (I-349)+(S3-10); (I-349)+(S3-11); (I-349)+(S4-1); (I-349)+(S4-2); (I-349)+(S4-3); (I-349)+(S4-4); (I-349)+(S4-5); (I-349)+(S7-1); (I-349)+(S11-1); (I-349)+(S11-2); (I-349)+(S11-3); (I-349)+(S12-1); (I-349)+(S13-1); (I-349)+(S13-2); (I-349)+(S13-3); (I-349)+(S13-4): (I-349)+(S13-5); (I-349)+(S13-6); (I-349)+(S13-7); (I-349)+(S13-8); (I-349)+(S13-9); (I-349)+(S14-1)

(I-350)+(S1-1); (I-350)+(S1-2); (I-350)+(S1-3); (I-350)+(S1-4); (I-350)+(S1-5); (I-350)+(S1-6); (I-350)+(S1-7); (I-350)+(S1-8); (I-350)+(S1-9); (I-350)+(S1-10); (I-350)+(S1-11); (I-350)+(S1-12); (I-350)+(S1-13); (I-350)+(S2-1); (I-350)+(S2-2); (I-350)+(S2-3); (I-350)+(S2-4); (I-350)+(S2-5); (I-350)+(S2-6); (I-350)+(S2-7); (I-350)+(S2-8); (I-350)+(S2-9); (I-350)+(S2-10); (I-350)+(S3-1); (I-350)+(S3-2); (I-350)+(S3-3); (I-350)+(S3-4); (I-350)+(S3-5); (I-350)+(S3-6); (I-350)+(S3-7); (I-350)+(S3-8); (I-350)+(S3-9); (I-350)+(S3-10); (I-350)+(S3-11); (I-350)+(S4-1); (I-350)+(S4-2); (I-350)+(S4-3); (I-350)+(S4-4); (I-350)+(S4-5); (I-350)+(S7-1); (I-350)+(S11-1); (I-350)+(S11-2); (I-350)+(S11-3); (I-350)+(S12-1); (I-350)+(S13-1); (I-350)+(S13-2); (I-350)+(S13-3); (I-350)+(S13-4): (I-350)+(S13-5); (I-350)+(S13-6); (I-350)+(S13-7); (I-350)+(S13-8); (I-350)+(S13-9); (I-350)+(S14-1)

(I-351)+(S1-1); (I-351)+(S1-2); (I-351)+(S1-3); (I-351)+(S1-4); (I-351)+(S1-5); (I-351)+(S1-6); (I-351)+(S1-7); (I-351)+(S1-8); (I-351)+(S1-9); (I-351)+(S1-10); (I-351)+(S1-11); (I-351)+(S1-12); (I-351)+(S1-13); (I-351)+(S2-1); (I-351)+(S2-2); (I-351)+(S2-3); (I-351)+(S2-4); (I-351)+(S2-5); (I-351)+(S2-6); (I-351)+(S2-7); (I-351)+(S2-8); (I-351)+(S2-9); (I-351)+(S2-10); (I-351)+(S3-1); (I-351)+(S3-2); (I-351)+(S3-3); (I-351)+(S3-4); (I-351)+(S3-5); (I-351)+(S3-6); (I-351)+(S3-7); (I-351)+(S3-8); (I-351)+(S3-9); (I-351)+(S3-10); (I-351)+(S3-11); (I-351)+(S4-1); (I-351)+(S4-2); (I-351)+(S4-3); (I-351)+(S4-4); (I-351)+(S4-5); (I-351)+(S7-1); (I-351)+(S11-1); (I-351)+(S11-2); (I-351)+(S11-3); (I-351)+(S12-1); (I-351)+(S13-1); (I-351)+(S13-2); (I-351)+(S13-3); (I-351)+(S13-4): (I-351)+(S13-5); (I-351)+(S13-6); (I-351)+(S13-7); (I-351)+(S13-8); (I-351)+(S13-9); (I-351)+(S14-1)

(I-352)+(S1-1); (I-352)+(S1-2); (I-352)+(S1-3); (I-352)+(S1-4); (I-352)+(S1-5); (I-352)+(S1-6); (I-352)+(S1-7); (I-352)+(S1-8); (I-352)+(S1-9); (I-352)+(S1-10); (I-352)+(S1-11); (I-352)+(S1-12); (I-352)+(S1-13); (I-352)+(S2-1); (I-352)+(S2-2); (I-352)+(S2-3); (I-352)+(S2-4); (I-352)+(S2-5); (I-352)+(S2-6); (I-352)+(S2-7); (I-352)+(S2-8); (I-352)+(S2-9); (I-352)+(S2-10); (I-352)+(S3-1); (I-352)+(S3-2); (I-352)+(S3-3); (I-352)+(S3-4); (I-352)+(S3-5); (I-352)+(S3-6); (I-352)+(S3-7); (I-352)+(S3-8); (I-352)+(S3-9); (I-352)+(S3-10); (I-352)+(S3-11); (I-352)+(S4-1); (I-352)+(S4-2); (I-352)+(S4-3); (I-352)+(S4-4); (I-352)+(S4-5); (I-352)+(S7-1); (I-352)+(S11-1); (I-352)+(S11-2); (I-352)+(S11-3); (I-352)+(S12-1); (I-352)+(S13-1); (I-352)+(S13-2); (I-352)+(S13-3); (I-352)+(S13-4): (I-352)+(S13-5); (I-352)+(S13-6); (I-352)+(S13-7); (I-352)+(S13-8); (I-352)+(S13-9); (I-352)+(S14-1)

(I-353)+(S1-1); (I-353)+(S1-2); (I-353)+(S1-3); (I-353)+(S1-4); (I-353)+(S1-5); (I-353)+(S1-6); (I-353)+(S1-7); (I-353)+(S1-8); (I-353)+(S1-9); (I-353)+(S1-10); (I-353)+(S1-11); (I-353)+(S1-12); (I-353)+(S1-13); (I-353)+(S2-1); (I-353)+(S2-2); (I-353)+(S2-3); (I-353)+(S2-4); (I-353)+(S2-5); (I-353)+(S2-6); (I-353)+(S2-7); (I-353)+(S2-8); (I-353)+(S2-9); (I-353)+(S2-10); (I-353)+(S3-1); (I-353)+(S3-2); (I-353)+(S3-3); (I-353)+(S3-4); (I-353)+(S3-5); (I-353)+(S3-6); (I-353)+(S3-7); (I-353)+(S3-8); (I-353)+(S3-9); (I-353)+(S3-10); (I-353)+(S3-11); (I-353)+(S4-1); (I-353)+(S4-2); (I-353)+(S4-3); (I-353)+(S4-4); (I-353)+(S4-5); (I-353)+(S7-1); (I-353)+(S11-1); (I-353)+(S11-2); (I-353)+(S11-3); (I-353)+(S12-1); (I-353)+(S13-1); (I-353)+(S13-2); (I-353)+(S13-3); (I-353)+(S13-4): (I-353)+(S13-5); (I-353)+(S13-6); (I-353)+(S13-7); (I-353)+(S13-8); (I-353)+(S13-9); (I-353)+(S14-1)

(I-354)+(S1-1); (I-354)+(S1-2); (I-354)+(S1-3); (I-354)+(S1-4); (I-354)+(S1-5); (I-354)+(S1-6); (I-354)+(S1-7); (I-354)+(S1-8); (I-354)+(S1-9); (I-354)+(S1-10); (I-354)+(S1-11); (I-354)+(S1-12); (I-354)+(S1-13); (I-354)+(S2-1); (I-354)+(S2-2); (I-354)+(S2-3); (I-354)+(S2-4); (I-354)+(S2-5); (I-354)+(S2-6); (I-354)+(S2-7); (I-354)+(S2-8); (I-354)+(S2-9); (I-354)+(S2-10); (I-354)+(S3-1); (I-354)+(S3-2); (I-354)+(S3-3); (I-354)+(S3-4); (I-354)+(S3-5); (I-354)+(S3-6); (I-354)+(S3-7); (I-354)+(S3-8); (I-354)+(S3-9); (I-354)+(S3-10); (I-354)+(S3-11); (I-354)+(S4-1); (I-354)+(S4-2); (I-354)+(S4-3); (I-354)+(S4-4); (I-354)+(S4-5); (I-354)+(S7-1); (I-354)+(S11-1); (I-354)+(S11-2); (I-354)+(S11-3); (I-354)+(S12-1); (I-354)+(S13-1); (I-354)+(S13-2); (I-354)+(S13-3); (I-354)+(S13-4): (I-354)+(S13-5); (I-354)+(S13-6); (I-354)+(S13-7); (I-354)+(S13-8); (I-354)+(S13-9); (I-354)+(S14-1)

(I-355)+(S1-1); (I-355)+(S1-2); (I-355)+(S1-3); (I-355)+(S1-4); (I-355)+(S1-5); (I-355)+(S1-6); (I-355)+(S1-7); (I-355)+(S1-8); (I-355)+(S1-9); (I-355)+(S1-10); (I-355)+(S1-11); (I-355)+(S1-12); (I-355)+(S1-13); (I-355)+(S2-1); (I-355)+(S2-2); (I-355)+(S2-3); (I-355)+(S2-4); (I-355)+(S2-5); (I-355)+(S2-6); (I-355)+(S2-7); (I-355)+(S2-8); (I-355)+(S2-9); (I-355)+(S2-10); (I-355)+(S3-1); (I-355)+(S3-2); (I-355)+(S3-3); (I-355)+(S3-4); (I-355)+(S3-5); (I-355)+(S3-6); (I-355)+(S3-7); (I-355)+(S3-8); (I-355)+(S3-9); (I-355)+(S3-10); (I-355)+(S3-11); (I-355)+(S4-1); (I-355)+(S4-2); (I-355)+(S4-3); (I-355)+(S4-4); (I-355)+(S4-5); (I-355)+(S7-1); (I-355)+(S11-1); (I-355)+(S11-2); (I-355)+(S11-3); (I-355)+(S12-1); (I-355)+(S13-1); (I-355)+(S13-2); (I-355)+(S13-3); (I-355)+(S13-4): (I-355)+(S13-5); (I-355)+(S13-6); (I-355)+(S13-7); (I-355)+(S13-8); (I-355)+(S13-9); (I-355)+(S14-1)

(I-356)+(S1-1); (I-356)+(S1-2); (I-356)+(S1-3); (I-356)+(S1-4); (I-356)+(S1-5); (I-356)+(S1-6); (I-356)+(S1-7); (I-356)+(S1-8); (I-356)+(S1-9); (I-356)+(S1-10); (I-356)+(S1-11); (I-356)+(S1-12); (I-356)+(S1-13); (I-356)+(S2-1); (I-356)+(S2-2); (I-356)+(S2-3); (I-356)+(S2-4); (I-356)+(S2-5); (I-356)+(S2-6); (I-356)+(S2-7); (I-356)+(S2-8); (I-356)+(S2-9); (I-356)+(S2-10); (I-356)+(S3-1); (I-356)+(S3-2); (I-356)+(S3-3); (I-356)+(S3-4); (I-356)+(S3-5); (I-356)+(S3-6); (I-356)+(S3-7); (I-356)+(S3-8); (I-356)+(S3-9); (I-356)+(S3-10); (I-356)+(S3-11); (I-356)+(S4-1); (I-356)+(S4-2); (I-356)+(S4-3); (I-356)+(S4-4); (I-356)+(S4-5); (I-356)+(S7-1); (I-356)+(S11-1); (I-356)+(S11-2); (I-356)+(S11-3); (I-356)+(S12-1); (I-356)+(S13-1); (I-356)+(S13-2); (I-356)+(S13-3); (I-356)+(S13-4): (I-356)+(S13-5); (I-356)+(S13-6); (I-356)+(S13-7); (I-356)+(S13-8); (I-356)+(S13-9); (I-356)+(S14-1)

(I-357)+(S1-1); (I-357)+(S1-2); (I-357)+(S1-3); (I-357)+(S1-4); (I-357)+(S1-5); (I-357)+(S1-6); (I-357)+(S1-7); (I-357)+(S1-8); (I-357)+(S1-9); (I-357)+(S1-10); (I-357)+(S1-11); (I-357)+(S1-12); (I-357)+(S1-13); (I-357)+(S2-1); (I-357)+(S2-2); (I-357)+(S2-3); (I-357)+(S2-4); (I-357)+(S2-5); (I-357)+(S2-6); (I-357)+(S2-7); (I-357)+(S2-8); (I-357)+(S2-9); (I-357)+(S2-10); (I-357)+(S3-1); (I-357)+(S3-2); (I-357)+(S3-3); (I-357)+(S3-4); (I-357)+(S3-5); (I-357)+(S3-6); (I-357)+(S3-7); (I-357)+(S3-8); (I-357)+(S3-9); (I-357)+(S3-10); (I-357)+(S3-11); (I-357)+(S4-1); (I-357)+(S4-2); (I-357)+(S4-3); (I-357)+(S4-4); (I-357)+(S4-5); (I-357)+(S7-1); (I-357)+(S11-1); (I-357)+(S11-2); (I-357)+(S11-3); (I-357)+(S12-1); (I-357)+(S13-1); (I-357)+(S13-2); (I-357)+(S13-3); (I-357)+(S13-4): (I-357)+(S13-5); (I-357)+(S13-6); (I-357)+(S13-7); (I-357)+(S13-8); (I-357)+(S13-9); (I-357)+(S14-1)

(I-358)+(S1-1); (I-358)+(S1-2); (I-358)+(S1-3); (I-358)+(S1-4); (I-358)+(S1-5); (I-358)+(S1-6); (I-358)+(S1-7); (I-358)+(S1-8); (I-358)+(S1-9); (I-358)+(S1-10); (I-358)+(S1-11); (I-358)+(S1-12); (I-358)+(S1-13); (I-358)+(S2-1); (I-358)+(S2-2); (I-358)+(S2-3); (I-358)+(S2-4); (I-358)+(S2-5); (I-358)+(S2-6); (I-358)+(S2-7); (I-358)+(S2-8); (I-358)+(S2-9); (I-358)+(S2-10); (I-358)+(S3-1); (I-358)+(S3-2); (I-358)+(S3-3); (I-358)+(S3-4); (I-358)+(S3-5); (I-358)+(S3-6); (I-358)+(S3-7); (I-358)+(S3-8); (I-358)+(S3-9); (I-358)+(S3-10); (I-358)+(S3-11); (I-358)+(S4-1); (I-358)+(S4-2); (I-358)+(S4-3); (I-358)+(S4-4); (I-358)+(S4-5); (I-358)+(S7-1); (I-358)+(S11-1); (I-358)+(S11-2); (I-358)+(S11-3); (I-358)+(S12-1); (I-358)+(S13-1); (I-358)+(S13-2); (I-358)+(S13-3); (I-358)+(S13-4): (I-358)+(S13-5); (I-358)+(S13-6); (I-358)+(S13-7); (I-358)+(S13-8); (I-358)+(S13-9); (I-358)+(S14-1)

(I-359)+(S1-1); (I-359)+(S1-2); (I-359)+(S1-3); (I-359)+(S1-4); (I-359)+(S1-5); (I-359)+(S1-6); (I-359)+(S1-7); (I-359)+(S1-8); (I-359)+(S1-9); (I-359)+(S1-10); (I-359)+(S1-11); (I-359)+(S1-12); (I-359)+(S1-13); (I-359)+(S2-1); (I-359)+(S2-2); (I-359)+(S2-3); (I-359)+(S2-4); (I-359)+(S2-5); (I-359)+(S2-6); (I-359)+(S2-7); (I-359)+(S2-8); (I-359)+(S2-9); (I-359)+(S2-10); (I-359)+(S3-1); (I-359)+(S3-2); (I-359)+(S3-3); (I-359)+(S3-4); (I-359)+(S3-5); (I-359)+(S3-6); (I-359)+(S3-7); (I-359)+(S3-8); (I-359)+(S3-9); (I-359)+(S3-10); (I-359)+(S3-11); (I-359)+(S4-1); (I-359)+(S4-2); (I-359)+(S4-3); (I-359)+(S4-4); (I-359)+(S4-5); (I-359)+(S7-1); (I-359)+(S11-1); (I-359)+(S11-2); (I-359)+(S11-3); (I-359)+(S12-1); (I-359)+(S13-1); (I-359)+(S13-2); (I-359)+(S13-3); (I-359)+(S13-4): (I-359)+(S13-5); (I-359)+(S13-6); (I-359)+(S13-7); (I-359)+(S13-8); (I-359)+(S13-9); (I-359)+(S14-1)

(I-360)+(S1-1); (I-360)+(S1-2); (I-360)+(S1-3); (I-360)+(S1-4); (I-360)+(S1-5); (I-360)+(S1-6); (I-360)+(S1-7); (I-360)+(S1-8); (I-360)+(S1-9); (I-360)+(S1-10); (I-360)+(S1-11); (I-360)+(S1-12); (I-360)+(S1-13); (I-360)+(S2-1); (I-360)+(S2-2); (I-360)+(S2-3); (I-360)+(S2-4); (I-360)+(S2-5); (I-360)+(S2-6); (I-360)+(S2-7); (I-360)+(S2-8);

(I-360)+(S2-9); (I-360)+(S2-10); (I-360)+(S3-1); (I-360)+(S3-2); (I-360)+(S3-3); (I-360)+(S3-4); (I-360)+(S3-5); (I-360)+(S3-6); (I-360)+(S3-7); (I-360)+(S3-8); (I-360)+(S3-9); (I-360)+(S3-10); (I-360)+(S3-11); (I-360)+(S4-1); (I-360)+(S4-2); (I-360)+(S4-3); (I-360)+(S4-4); (I-360)+(S4-5); (I-360)+(S7-1); (I-360)+(S11-1); (I-360)+(S11-2); (I-360)+(S11-3); (I-360)+(S12-1); (I-360)+(S13-1); (I-360)+(S13-2); (I-360)+(S13-3); (I-360)+(S13-4): (I-360)+(S13-5); (I-360)+(S13-6); (I-360)+(S13-7); (I-360)+(S13-8); (I-360)+(S13-9); (I-360)+(S14-1)

(I-361)+(S1-1); (I-361)+(S1-2); (I-361)+(S1-3); (I-361)+(S1-4); (I-361)+(S1-5); (I-361)+(S1-6); (I-361)+(S1-7); (I-361)+(S1-8); (I-361)+(S1-9); (I-361)+(S1-10); (I-361)+(S1-11); (I-361)+(S1-12); (I-361)+(S1-13); (I-361)+(S2-1); (I-361)+(S2-2); (I-361)+(S2-3); (I-361)+(S2-4); (I-361)+(S2-5); (I-361)+(S2-6); (I-361)+(S2-7); (I-361)+(S2-8); (I-361)+(S2-9); (I-361)+(S2-10); (I-361)+(S3-1); (I-361)+(S3-2); (I-361)+(S3-3); (I-361)+(S3-4); (I-361)+(S3-5); (I-361)+(S3-6); (I-361)+(S3-7); (I-361)+(S3-8); (I-361)+(S3-9); (I-361)+(S3-10); (I-361)+(S3-11); (I-361)+(S4-1); (I-361)+(S4-2); (I-361)+(S4-3); (I-361)+(S4-4); (I-361)+(S4-5); (I-361)+(S7-1); (I-361)+(S11-1); (I-361)+(S11-2); (I-361)+(S11-3); (I-361)+(S12-1); (I-361)+(S13-1); (I-361)+(S13-2); (I-361)+(S13-3); (I-361)+(S13-4): (I-361)+(S13-5); (I-361)+(S13-6); (I-361)+(S13-7); (I-361)+(S13-8); (I-361)+(S13-9); (I-361)+(S14-1)

(I-362)+(S1-1); (I-362)+(S1-2); (I-362)+(S1-3); (I-362)+(S1-4); (I-362)+(S1-5); (I-362)+(S1-6); (I-362)+(S1-7); (I-362)+(S1-8); (I-362)+(S1-9); (I-362)+(S1-10); (I-362)+(S1-11); (I-362)+(S1-12); (I-362)+(S1-13); (I-362)+(S2-1); (I-362)+(S2-2); (I-362)+(S2-3); (I-362)+(S2-4); (I-362)+(S2-5); (I-362)+(S2-6); (I-362)+(S2-7); (I-362)+(S2-8); (I-362)+(S2-9); (I-362)+(S2-10); (I-362)+(S3-1); (I-362)+(S3-2); (I-362)+(S3-3); (I-362)+(S3-4); (I-362)+(S3-5); (I-362)+(S3-6); (I-362)+(S3-7); (I-362)+(S3-8); (I-362)+(S3-9); (I-362)+(S3-10); (I-362)+(S3-11); (I-362)+(S4-1); (I-362)+(S4-2); (I-362)+(S4-3); (I-362)+(S4-4); (I-362)+(S4-5); (I-362)+(S7-1); (I-362)+(S11-1); (I-362)+(S11-2); (I-362)+(S11-3); (I-362)+(S12-1); (I-362)+(S13-1); (I-362)+(S13-2); (I-362)+(S13-3); (I-362)+(S13-4): (I-362)+(S13-5); (I-362)+(S13-6); (I-362)+(S13-7); (I-362)+(S13-8); (I-362)+(S13-9); (I-362)+(S14-1)

(I-363)+(S1-1); (I-363)+(S1-2); (I-363)+(S1-3); (I-363)+(S1-4); (I-363)+(S1-5); (I-363)+(S1-6); (I-363)+(S1-7); (I-363)+(S1-8); (I-363)+(S1-9); (I-363)+(S1-10); (I-363)+(S1-11); (I-363)+(S1-12); (I-363)+(S1-13); (I-363)+(S2-1); (I-363)+(S2-2); (I-363)+(S2-3); (I-363)+(S2-4); (I-363)+(S2-5); (I-363)+(S2-6); (I-363)+(S2-7); (I-363)+(S2-8); (I-363)+(S2-9); (I-363)+(S2-10); (I-363)+(S3-1); (I-363)+(S3-2); (I-363)+(S3-3); (I-363)+(S3-4); (I-363)+(S3-5); (I-363)+(S3-6); (I-363)+(S3-7); (I-363)+(S3-8); (I-363)+(S3-9); (I-363)+(S3-10); (I-363)+(S3-11); (I-363)+(S4-1); (I-363)+(S4-2); (I-363)+(S4-3); (I-363)+(S4-4); (I-363)+(S4-5); (I-363)+(S7-1); (I-363)+(S11-1); (I-363)+(S11-2); (I-363)+(S11-3); (I-363)+(S12-1); (I-363)+(S13-1); (I-363)+(S13-2); (I-363)+(S13-3); (I-363)+(S13-4): (I-363)+(S13-5); (I-363)+(S13-6); (I-363)+(S13-7); (I-363)+(S13-8); (I-363)+(S13-9); (I-363)+(S14-1)

(I-364)+(S1-1); (I-364)+(S1-2); (I-364)+(S1-3); (I-364)+(S1-4); (I-364)+(S1-5); (I-364)+(S1-6); (I-364)+(S1-7); (I-364)+(S1-8); (I-364)+(S1-9); (I-364)+(S1-10); (I-364)+(S1-11); (I-364)+(S1-12); (I-364)+(S1-13); (I-364)+(S2-1); (I-364)+(S2-2); (I-364)+(S2-3); (I-364)+(S2-4); (I-364)+(S2-5); (I-364)+(S2-6); (I-364)+(S2-7); (I-364)+(S2-8); (I-364)+(S2-9); (I-364)+(S2-10); (I-364)+(S3-1); (I-364)+(S3-2); (I-364)+(S3-3); (I-364)+(S3-4); (I-364)+(S3-5); (I-364)+(S3-6); (I-364)+(S3-7); (I-364)+(S3-8); (I-364)+(S3-9); (I-364)+(S3-10); (I-364)+(S3-11); (I-364)+(S4-1); (I-364)+(S4-2); (I-364)+(S4-3); (I-364)+(S4-4); (I-364)+(S4-5); (I-364)+(S7-1); (I-364)+(S11-1); (I-364)+(S11-2); (I-364)+(S11-3); (I-364)+(S12-1); (I-364)+(S13-1); (I-364)+(S13-2); (I-364)+(S13-3); (I-364)+(S13-4): (I-364)+(S13-5); (I-364)+(S13-6); (I-364)+(S13-7); (I-364)+(S13-8); (I-364)+(S13-9); (I-364)+(S14-1)

(I-365)+(S1-1); (I-365)+(S1-2); (I-365)+(S1-3); (I-365)+(S1-4); (I-365)+(S1-5); (I-365)+(S1-6); (I-365)+(S1-7); (I-365)+(S1-8); (I-365)+(S1-9); (I-365)+(S1-10); (I-365)+(S1-11); (I-365)+(S1-12); (I-365)+(S1-13); (I-365)+(S2-1); (I-365)+(S2-2); (I-365)+(S2-3); (I-365)+(S2-4); (I-365)+(S2-5); (I-365)+(S2-6); (I-365)+(S2-7); (I-365)+(S2-8); (I-365)+(S2-9); (I-365)+(S2-10); (I-365)+(S3-1); (I-365)+(S3-2); (I-365)+(S3-3); (I-365)+(S3-4); (I-365)+(S3-5); (I-365)+(S3-6); (I-365)+(S3-7); (I-365)+(S3-8); (I-365)+(S3-9); (I-365)+(S3-10); (I-365)+(S3-11); (I-365)+(S4-1); (I-365)+(S4-2); (I-365)+(S4-3); (I-365)+(S4-4); (I-365)+(S4-5); (I-365)+(S7-1); (I-365)+(S11-1); (I-365)+(S11-2); (I-365)+(S11-3); (I-365)+(S12-1); (I-365)+(S13-1); (I-365)+(S13-2); (I-365)+(S13-3); (I-365)+(S13-4): (I-365)+(S13-5); (I-365)+(S13-6); (I-365)+(S13-7); (I-365)+(S13-8); (I-365)+(S13-9); (I-365)+(S14-1)

(I-366)+(S1-1); (I-366)+(S1-2); (I-366)+(S1-3); (I-366)+(S1-4); (I-366)+(S1-5); (I-366)+(S1-6); (I-366)+(S1-7); (I-366)+(S1-8); (I-366)+(S1-9); (I-366)+(S1-10); (I-366)+(S1-11); (I-366)+(S1-12); (I-366)+(S1-13); (I-366)+(S2-1); (I-366)+(S2-2); (I-366)+(S2-3); (I-366)+(S2-4); (I-366)+(S2-5); (I-366)+(S2-6); (I-366)+(S2-7); (I-366)+(S2-8); (I-366)+(S2-9); (I-366)+(S2-10); (I-366)+(S3-1); (I-366)+(S3-2); (I-366)+(S3-3); (I-366)+(S3-4); (I-366)+(S3-5); (I-366)+(S3-6); (I-366)+(S3-7); (I-366)+(S3-8); (I-366)+(S3-9); (I-366)+(S3-10); (I-366)+(S3-11); (I-366)+(S4-1); (I-366)+(S4-2); (I-366)+(S4-3); (I-366)+(S4-4); (I-366)+(S4-5); (I-366)+(S7-1); (I-366)+(S11-1); (I-366)+(S11-2); (I-366)+(S11-3); (I-366)+(S12-1); (I-366)+(S13-1); (I-366)+(S13-2); (I-366)+(S13-3); (I-366)+(S13-4): (I-366)+(S13-5); (I-366)+(S13-6); (I-366)+(S13-7); (I-366)+(S13-8); (I-366)+(S13-9); (I-366)+(S14-1)

(I-367)+(S1-1); (I-367)+(S1-2); (I-367)+(S1-3); (I-367)+(S1-4); (I-367)+(S1-5); (I-367)+(S1-6); (I-367)+(S1-7); (I-367)+(S1-8); (I-367)+(S1-9); (I-367)+(S1-10); (I-367)+(S1-11); (I-367)+(S1-12); (I-367)+(S1-13); (I-367)+(S2-1); (I-367)+(S2-2); (I-367)+(S2-3); (I-367)+(S2-4); (I-367)+(S2-5); (I-367)+(S2-6); (I-367)+(S2-7); (I-367)+(S2-8); (I-367)+(S2-9); (I-367)+(S2-10); (I-367)+(S3-1); (I-367)+(S3-2); (I-367)+(S3-3); (I-367)+(S3-4); (I-367)+(S3-5); (I-367)+(S3-6); (I-367)+(S3-7); (I-367)+(S3-8); (I-367)+(S3-9); (I-367)+(S3-10); (I-367)+(S3-11); (I-367)+(S4-1); (I-367)+(S4-2); (I-367)+(S4-3); (I-367)+(S4-4); (I-367)+(S4-5); (I-367)+(S7-1); (I-367)+(S11-1); (I-367)+(S11-2); (I-367)+(S11-3); (I-367)+(S12-1); (I-367)+(S13-1); (I-367)+(S13-2); (I-367)+(S13-3); (I-367)+(S13-4): (I-367)+(S13-5); (I-367)+(S13-6); (I-367)+(S13-7); (I-367)+(S13-8); (I-367)+(S13-9); (I-367)+(S14-1)

(I-368)+(S1-1); (I-368)+(S1-2); (I-368)+(S1-3); (I-368)+(S1-4); (I-368)+(S1-5); (I-368)+(S1-6); (I-368)+(S1-7); (I-368)+(S1-8); (I-368)+(S1-9); (I-368)+(S1-10); (I-368)+(S1-11); (I-368)+(S1-12); (I-368)+(S1-13); (I-368)+(S2-1); (I-368)+(S2-2); (I-368)+(S2-3); (I-368)+(S2-4); (I-368)+(S2-5); (I-368)+(S2-6); (I-368)+(S2-7); (I-368)+(S2-8); (I-368)+(S2-9); (I-368)+(S2-10); (I-368)+(S3-1); (I-368)+(S3-2); (I-368)+(S3-3); (I-368)+(S3-4); (I-368)+(S3-5); (I-368)+(S3-6); (I-368)+(S3-7); (I-368)+(S3-8); (I-368)+(S3-9); (I-368)+(S3-10); (I-368)+(S3-11); (I-368)+(S4-1); (I-368)+(S4-2); (I-368)+(S4-3); (I-368)+(S4-4); (I-368)+(S4-5); (I-368)+(S7-1); (I-368)+(S11-1); (I-368)+(S11-2);

(I-368)+(S11-3); (I-368)+(S12-1); (I-368)+(S13-1); (I-368)+(S13-2); (I-368)+(S13-3); (I-368)+(S13-4): (I-368)+(S13-5); (I-368)+(S13-6); (I-368)+(S13-7); (I-368)+(S13-8); (I-368)+(S13-9); (I-368)+(S14-1)

(I-369)+(S1-1); (I-369)+(S1-2); (I-369)+(S1-3); (I-369)+(S1-4); (I-369)+(S1-5); (I-369)+(S1-6); (I-369)+(S1-7); (I-369)+(S1-8); (I-369)+(S1-9); (I-369)+(S1-10); (I-369)+(S1-11); (I-369)+(S1-12); (I-369)+(S1-13); (I-369)+(S2-1); (I-369)+(S2-2); (I-369)+(S2-3); (I-369)+(S2-4); (I-369)+(S2-5); (I-369)+(S2-6); (I-369)+(S2-7); (I-369)+(S2-8); (I-369)+(S2-9); (I-369)+(S2-10); (I-369)+(S3-1); (I-369)+(S3-2); (I-369)+(S3-3); (I-369)+(S3-4); (I-369)+(S3-5); (I-369)+(S3-6); (I-369)+(S3-7); (I-369)+(S3-8); (I-369)+(S3-9); (I-369)+(S3-10); (I-369)+(S3-11); (I-369)+(S4-1); (I-369)+(S4-2); (I-369)+(S4-3); (I-369)+(S4-4); (I-369)+(S4-5); (I-369)+(S7-1); (I-369)+(S11-1); (I-369)+(S11-2); (I-369)+(S11-3); (I-369)+(S12-1); (I-369)+(S13-1); (I-369)+(S13-2); (I-369)+(S13-3); (I-369)+(S13-4): (I-369)+(S13-5); (I-369)+(S13-6); (I-369)+(S13-7); (I-369)+(S13-8); (I-369)+(S13-9); (I-369)+(S14-1)

(I-370)+(S1-1); (I-370)+(S1-2); (I-370)+(S1-3); (I-370)+(S1-4); (I-370)+(S1-5); (I-370)+(S1-6); (I-370)+(S1-7); (I-370)+(S1-8); (I-370)+(S1-9); (I-370)+(S1-10); (I-370)+(S1-11); (I-370)+(S1-12); (I-370)+(S1-13); (I-370)+(S2-1); (I-370)+(S2-2); (I-370)+(S2-3); (I-370)+(S2-4); (I-370)+(S2-5); (I-370)+(S2-6); (I-370)+(S2-7); (I-370)+(S2-8); (I-370)+(S2-9); (I-370)+(S2-10); (I-370)+(S3-1); (I-370)+(S3-2); (I-370)+(S3-3); (I-370)+(S3-4); (I-370)+(S3-5); (I-370)+(S3-6); (I-370)+(S3-7); (I-370)+(S3-8); (I-370)+(S3-9); (I-370)+(S3-10); (I-370)+(S3-11); (I-370)+(S4-1); (I-370)+(S4-2); (I-370)+(S4-3); (I-370)+(S4-4); (I-370)+(S4-5); (I-370)+(S7-1); (I-370)+(S11-1); (I-370)+(S11-2); (I-370)+(S11-3); (I-370)+(S12-1); (I-370)+(S13-1); (I-370)+(S13-2); (I-370)+(S13-3); (I-370)+(S13-4): (I-370)+(S13-5); (I-370)+(S13-6); (I-370)+(S13-7); (I-370)+(S13-8); (I-370)+(S13-9); (I-370)+(S14-1)

(I-371)+(S1-1); (I-371)+(S1-2); (I-371)+(S1-3); (I-371)+(S1-4); (I-371)+(S1-5); (I-371)+(S1-6); (I-371)+(S1-7); (I-371)+(S1-8); (I-371)+(S1-9); (I-371)+(S1-10); (I-371)+(S1-11); (I-371)+(S1-12); (I-371)+(S1-13); (I-371)+(S2-1); (I-371)+(S2-2); (I-371)+(S2-3); (I-371)+(S2-4); (I-371)+(S2-5); (I-371)+(S2-6); (I-371)+(S2-7); (I-371)+(S2-8); (I-371)+(S2-9); (I-371)+(S2-10); (I-371)+(S3-1); (I-371)+(S3-2); (I-371)+(S3-3); (I-371)+(S3-4); (I-371)+(S3-5); (I-371)+(S3-6); (I-371)+(S3-7); (I-371)+(S3-8); (I-371)+(S3-9); (I-371)+(S3-10); (I-371)+(S3-11); (I-371)+(S4-1); (I-371)+(S4-2); (I-371)+(S4-3); (I-371)+(S4-4); (I-371)+(S4-5); (I-371)+(S7-1); (I-371)+(S11-1); (I-371)+(S11-2); (I-371)+(S11-3); (I-371)+(S12-1); (I-371)+(S13-1); (I-371)+(S13-2); (I-371)+(S13-3); (I-371)+(S13-4): (I-371)+(S13-5); (I-371)+(S13-6); (I-371)+(S13-7); (I-371)+(S13-8); (I-371)+(S13-9); (I-371)+(S14-1)

(I-372)+(S1-1); (I-372)+(S1-2); (I-372)+(S1-3); (I-372)+(S1-4); (I-372)+(S1-5); (I-372)+(S1-6); (I-372)+(S1-7); (I-372)+(S1-8); (I-372)+(S1-9); (I-372)+(S1-10); (I-372)+(S1-11); (I-372)+(S1-12); (I-372)+(S1-13); (I-372)+(S2-1); (I-372)+(S2-2); (I-372)+(S2-3); (I-372)+(S2-4); (I-372)+(S2-5); (I-372)+(S2-6); (I-372)+(S2-7); (I-372)+(S2-8); (I-372)+(S2-9); (I-372)+(S2-10); (I-372)+(S3-1); (I-372)+(S3-2); (I-372)+(S3-3); (I-372)+(S3-4); (I-372)+(S3-5); (I-372)+(S3-6); (I-372)+(S3-7); (I-372)+(S3-8); (I-372)+(S3-9); (I-372)+(S3-10); (I-372)+(S3-11); (I-372)+(S4-1); (I-372)+(S4-2); (I-372)+(S4-3); (I-372)+(S4-4); (I-372)+(S4-5); (I-372)+(S7-1); (I-372)+(S11-1); (I-372)+(S11-2); (I-372)+(S11-3); (I-372)+(S12-1); (I-372)+(S13-1); (I-372)+(S13-2); (I-372)+(S13-3); (I-372)+(S13-4): (I-372)+(S13-5); (I-372)+(S13-6); (I-372)+(S13-7); (I-372)+(S13-8); (I-372)+(S13-9); (I-372)+(S14-1)

(I-373)+(S1-1); (I-373)+(S1-2); (I-373)+(S1-3); (I-373)+(S1-4); (I-373)+(S1-5); (I-373)+(S1-6); (I-373)+(S1-7); (I-373)+(S1-8); (I-373)+(S1-9); (I-373)+(S1-10); (I-373)+(S1-11); (I-373)+(S1-12); (I-373)+(S1-13); (I-373)+(S2-1); (I-373)+(S2-2); (I-373)+(S2-3); (I-373)+(S2-4); (I-373)+(S2-5); (I-373)+(S2-6); (I-373)+(S2-7); (I-373)+(S2-8); (I-373)+(S2-9); (I-373)+(S2-10); (I-373)+(S3-1); (I-373)+(S3-2); (I-373)+(S3-3); (I-373)+(S3-4); (I-373)+(S3-5); (I-373)+(S3-6); (I-373)+(S3-7); (I-373)+(S3-8); (I-373)+(S3-9); (I-373)+(S3-10); (I-373)+(S3-11); (I-373)+(S4-1); (I-373)+(S4-2); (I-373)+(S4-3); (I-373)+(S4-4); (I-373)+(S4-5); (I-373)+(S7-1); (I-373)+(S11-1); (I-373)+(S11-2); (I-373)+(S11-3); (I-373)+(S12-1); (I-373)+(S13-1); (I-373)+(S13-2); (I-373)+(S13-3); (I-373)+(S13-4): (I-373)+(S13-5); (I-373)+(S13-6); (I-373)+(S13-7); (I-373)+(S13-8); (I-373)+(S13-9); (I-373)+(S14-1)

(I-374)+(S1-1); (I-374)+(S1-2); (I-374)+(S1-3); (I-374)+(S1-4); (I-374)+(S1-5); (I-374)+(S1-6); (I-374)+(S1-7); (I-374)+(S1-8); (I-374)+(S1-9); (I-374)+(S1-10); (I-374)+(S1-11); (I-374)+(S1-12); (I-374)+(S1-13); (I-374)+(S2-1); (I-374)+(S2-2); (I-374)+(S2-3); (I-374)+(S2-4); (I-374)+(S2-5); (I-374)+(S2-6); (I-374)+(S2-7); (I-374)+(S2-8); (I-374)+(S2-9); (I-374)+(S2-10); (I-374)+(S3-1); (I-374)+(S3-2); (I-374)+(S3-3); (I-374)+(S3-4); (I-374)+(S3-5); (I-374)+(S3-6); (I-374)+(S3-7); (I-374)+(S3-8); (I-374)+(S3-9); (I-374)+(S3-10); (I-374)+(S3-11); (I-374)+(S4-1); (I-374)+(S4-2); (I-374)+(S4-3); (I-374)+(S4-4); (I-374)+(S4-5); (I-374)+(S7-1); (I-374)+(S11-1); (I-374)+(S11-2); (I-374)+(S11-3); (I-374)+(S12-1); (I-374)+(S13-1); (I-374)+(S13-2); (I-374)+(S13-3); (I-374)+(S13-4): (I-374)+(S13-5); (I-374)+(S13-6); (I-374)+(S13-7); (I-374)+(S13-8); (I-374)+(S13-9); (I-374)+(S14-1)

(I-375)+(S1-1); (I-375)+(S1-2); (I-375)+(S1-3); (I-375)+(S1-4); (I-375)+(S1-5); (I-375)+(S1-6); (I-375)+(S1-7); (I-375)+(S1-8); (I-375)+(S1-9); (I-375)+(S1-10); (I-375)+(S1-11); (I-375)+(S1-12); (I-375)+(S1-13); (I-375)+(S2-1); (I-375)+(S2-2); (I-375)+(S2-3); (I-375)+(S2-4); (I-375)+(S2-5); (I-375)+(S2-6); (I-375)+(S2-7); (I-375)+(S2-8); (I-375)+(S2-9); (I-375)+(S2-10); (I-375)+(S3-1); (I-375)+(S3-2); (I-375)+(S3-3); (I-375)+(S3-4); (I-375)+(S3-5); (I-375)+(S3-6); (I-375)+(S3-7); (I-375)+(S3-8); (I-375)+(S3-9); (I-375)+(S3-10); (I-375)+(S3-11); (I-375)+(S4-1); (I-375)+(S4-2); (I-375)+(S4-3); (I-375)+(S4-4); (I-375)+(S4-5); (I-375)+(S7-1); (I-375)+(S11-1); (I-375)+(S11-2); (I-375)+(S11-3); (I-375)+(S12-1); (I-375)+(S13-1); (I-375)+(S13-2); (I-375)+(S13-3); (I-375)+(S13-4): (I-375)+(S13-5); (I-375)+(S13-6); (I-375)+(S13-7); (I-375)+(S13-8); (I-375)+(S13-9); (I-375)+(S14-1)

(I-376)+(S1-1); (I-376)+(S1-2); (I-376)+(S1-3); (I-376)+(S1-4); (I-376)+(S1-5); (I-376)+(S1-6); (I-376)+(S1-7); (I-376)+(S1-8); (I-376)+(S1-9); (I-376)+(S1-10); (I-376)+(S1-11); (I-376)+(S1-12); (I-376)+(S1-13); (I-376)+(S2-1); (I-376)+(S2-2); (I-376)+(S2-3); (I-376)+(S2-4); (I-376)+(S2-5); (I-376)+(S2-6); (I-376)+(S2-7); (I-376)+(S2-8); (I-376)+(S2-9); (I-376)+(S2-10); (I-376)+(S3-1); (I-376)+(S3-2); (I-376)+(S3-3); (I-376)+(S3-4); (I-376)+(S3-5); (I-376)+(S3-6); (I-376)+(S3-7); (I-376)+(S3-8); (I-376)+(S3-9); (I-376)+(S3-10); (I-376)+(S3-11); (I-376)+(S4-1); (I-376)+(S4-2); (I-376)+(S4-3); (I-376)+(S4-4); (I-376)+(S4-5); (I-376)+(S7-1); (I-376)+(S11-1); (I-376)+(S11-2); (I-376)+(S11-3); (I-376)+(S12-1); (I-376)+(S13-1); (I-376)+(S13-2); (I-376)+(S13-3); (I-376)+(S13-4): (I-376)+(S13-5); (I-376)+(S13-6); (I-376)+(S13-7); (I-376)+(S13-8); (I-376)+(S13-9); (I-376)+(S14-1)

(I-377)+(S1-1); (I-377)+(S1-2); (I-377)+(S1-3); (I-377)+(S1-4); (I-377)+(S1-5); (I-377)+(S1-6); (I-377)+(S1-7); (I-377)+(S1-8); (I-377)+(S1-9); (I-377)+(S1-10); (I-377)+(S1-11); (I-377)+(S1-12); (I-377)+(S1-13); (I-377)+(S2-1); (I-377)+(S2-2); (I-377)+(S2-3); (I-377)+(S2-4); (I-377)+(S2-5); (I-377)+(S2-6); (I-377)+(S2-7); (I-377)+(S2-8); (I-377)+(S2-9); (I-377)+(S2-10); (I-377)+(S3-1); (I-377)+(S3-2); (I-377)+(S3-3); (I-377)+(S3-4); (I-377)+(S3-5); (I-377)+(S3-6); (I-377)+(S3-7); (I-377)+(S3-8); (I-377)+(S3-9); (I-377)+(S3-10); (I-377)+(S3-11); (I-377)+(S4-1); (I-377)+(S4-2); (I-377)+(S4-3); (I-377)+(S4-4); (I-377)+(S4-5); (I-377)+(S7-1); (I-377)+(S11-1); (I-377)+(S11-2); (I-377)+(S11-3); (I-377)+(S12-1); (I-377)+(S13-1); (I-377)+(S13-2); (I-377)+(S13-3); (I-377)+(S13-4): (I-377)+(S13-5); (I-377)+(S13-6); (I-377)+(S13-7); (I-377)+(S13-8); (I-377)+(S13-9); (I-377)+(S14-1)

(I-378)+(S1-1); (I-378)+(S1-2); (I-378)+(S1-3); (I-378)+(S1-4); (I-378)+(S1-5); (I-378)+(S1-6); (I-378)+(S1-7); (I-378)+(S1-8); (I-378)+(S1-9); (I-378)+(S1-10); (I-378)+(S1-11); (I-378)+(S1-12); (I-378)+(S1-13); (I-378)+(S2-1); (I-378)+(S2-2); (I-378)+(S2-3); (I-378)+(S2-4); (I-378)+(S2-5); (I-378)+(S2-6); (I-378)+(S2-7); (I-378)+(S2-8); (I-378)+(S2-9); (I-378)+(S2-10); (I-378)+(S3-1); (I-378)+(S3-2); (I-378)+(S3-3); (I-378)+(S3-4); (I-378)+(S3-5); (I-378)+(S3-6); (I-378)+(S3-7); (I-378)+(S3-8); (I-378)+(S3-9); (I-378)+(S3-10); (I-378)+(S3-11); (I-378)+(S4-1); (I-378)+(S4-2); (I-378)+(S4-3); (I-378)+(S4-4); (I-378)+(S4-5); (I-378)+(S7-1); (I-378)+(S11-1); (I-378)+(S11-2); (I-378)+(S11-3); (I-378)+(S12-1); (I-378)+(S13-1); (I-378)+(S13-2); (I-378)+(S13-3); (I-378)+(S13-4): (I-378)+(S13-5); (I-378)+(S13-6); (I-378)+(S13-7); (I-378)+(S13-8); (I-378)+(S13-9); (I-378)+(S14-1)

(I-379)+(S1-1); (I-379)+(S1-2); (I-379)+(S1-3); (I-379)+(S1-4); (I-379)+(S1-5); (I-379)+(S1-6); (I-379)+(S1-7); (I-379)+(S1-8); (I-379)+(S1-9); (I-379)+(S1-10); (I-379)+(S1-11); (I-379)+(S1-12); (I-379)+(S1-13); (I-379)+(S2-1); (I-379)+(S2-2); (I-379)+(S2-3); (I-379)+(S2-4); (I-379)+(S2-5); (I-379)+(S2-6); (I-379)+(S2-7); (I-379)+(S2-8); (I-379)+(S2-9); (I-379)+(S2-10); (I-379)+(S3-1); (I-379)+(S3-2); (I-379)+(S3-3); (I-379)+(S3-4); (I-379)+(S3-5); (I-379)+(S3-6); (I-379)+(S3-7); (I-379)+(S3-8); (I-379)+(S3-9); (I-379)+(S3-10); (I-379)+(S3-11); (I-379)+(S4-1); (I-379)+(S4-2); (I-379)+(S4-3); (I-379)+(S4-4); (I-379)+(S4-5); (I-379)+(S7-1); (I-379)+(S11-1); (I-379)+(S11-2); (I-379)+(S11-3); (I-379)+(S12-1); (I-379)+(S13-1); (I-379)+(S13-2); (I-379)+(S13-3); (I-379)+(S13-4): (I-379)+(S13-5); (I-379)+(S13-6); (I-379)+(S13-7); (I-379)+(S13-8); (I-379)+(S13-9); (I-379)+(S14-1)

(I-380)+(S1-1); (I-380)+(S1-2); (I-380)+(S1-3); (I-380)+(S1-4); (I-380)+(S1-5); (I-380)+(S1-6); (I-380)+(S1-7); (I-380)+(S1-8); (I-380)+(S1-9); (I-380)+(S1-10); (I-380)+(S1-11); (I-380)+(S1-12); (I-380)+(S1-13); (I-380)+(S2-1); (I-380)+(S2-2); (I-380)+(S2-3); (I-380)+(S2-4); (I-380)+(S2-5); (I-380)+(S2-6); (I-380)+(S2-7); (I-380)+(S2-8); (I-380)+(S2-9); (I-380)+(S2-10); (I-380)+(S3-1); (I-380)+(S3-2); (I-380)+(S3-3); (I-380)+(S3-4); (I-380)+(S3-5); (I-380)+(S3-6); (I-380)+(S3-7); (I-380)+(S3-8); (I-380)+(S3-9); (I-380)+(S3-10); (I-380)+(S3-11); (I-380)+(S4-1); (I-380)+(S4-2); (I-380)+(S4-3); (I-380)+(S4-4); (I-380)+(S4-5); (I-380)+(S7-1); (I-380)+(S11-1); (I-380)+(S11-2); (I-380)+(S11-3); (I-380)+(S12-1); (I-380)+(S13-1); (I-380)+(S13-2); (I-380)+(S13-3); (I-380)+(S13-4): (I-380)+(S13-5); (I-380)+(S13-6); (I-380)+(S13-7); (I-380)+(S13-8); (I-380)+(S13-9); (I-380)+(S14-1)

(I-381)+(S1-1); (I-381)+(S1-2); (I-381)+(S1-3); (I-381)+(S1-4); (I-381)+(S1-5); (I-381)+(S1-6); (I-381)+(S1-7); (I-381)+(S1-8); (I-381)+(S1-9); (I-381)+(S1-10); (I-381)+(S1-11); (I-381)+(S1-12); (I-381)+(S1-13); (I-381)+(S2-1); (I-381)+(S2-2); (I-381)+(S2-3); (I-381)+(S2-4); (I-381)+(S2-5); (I-381)+(S2-6); (I-381)+(S2-7); (I-381)+(S2-8); (I-381)+(S2-9); (I-381)+(S2-10); (I-381)+(S3-1); (I-381)+(S3-2); (I-381)+(S3-3); (I-381)+(S3-4); (I-381)+(S3-5); (I-381)+(S3-6); (I-381)+(S3-7); (I-381)+(S3-8); (I-381)+(S3-9); (I-381)+(S3-10); (I-381)+(S3-11); (I-381)+(S4-1); (I-381)+(S4-2); (I-381)+(S4-3); (I-381)+(S4-4); (I-381)+(S4-5); (I-381)+(S7-1); (I-381)+(S11-1); (I-381)+(S11-2); (I-381)+(S11-3); (I-381)+(S12-1); (I-381)+(S13-1); (I-381)+(S13-2); (I-381)+(S13-3); (I-381)+(S13-4): (I-381)+(S13-5); (I-381)+(S13-6); (I-381)+(S13-7); (I-381)+(S13-8); (I-381)+(S13-9); (I-381)+(S14-1)

(I-382)+(S1-1); (I-382)+(S1-2); (I-382)+(S1-3); (I-382)+(S1-4); (I-382)+(S1-5); (I-382)+(S1-6); (I-382)+(S1-7); (I-382)+(S1-8); (I-382)+(S1-9); (I-382)+(S1-10); (I-382)+(S1-11); (I-382)+(S1-12); (I-382)+(S1-13); (I-382)+(S2-1); (I-382)+(S2-2); (I-382)+(S2-3); (I-382)+(S2-4); (I-382)+(S2-5); (I-382)+(S2-6); (I-382)+(S2-7); (I-382)+(S2-8); (I-382)+(S2-9); (I-382)+(S2-10); (I-382)+(S3-1); (I-382)+(S3-2); (I-382)+(S3-3); (I-382)+(S3-4); (I-382)+(S3-5); (I-382)+(S3-6); (I-382)+(S3-7); (I-382)+(S3-8); (I-382)+(S3-9); (I-382)+(S3-10); (I-382)+(S3-11); (I-382)+(S4-1); (I-382)+(S4-2); (I-382)+(S4-3); (I-382)+(S4-4); (I-382)+(S4-5); (I-382)+(S7-1); (I-382)+(S11-1); (I-382)+(S11-2); (I-382)+(S11-3); (I-382)+(S12-1); (I-382)+(S13-1); (I-382)+(S13-2); (I-382)+(S13-3); (I-382)+(S13-4): (I-382)+(S13-5); (I-382)+(S13-6); (I-382)+(S13-7); (I-382)+(S13-8); (I-382)+(S13-9); (I-382)+(S14-1)

(I-383)+(S1-1); (I-383)+(S1-2); (I-383)+(S1-3); (I-383)+(S1-4); (I-383)+(S1-5); (I-383)+(S1-6); (I-383)+(S1-7); (I-383)+(S1-8); (I-383)+(S1-9); (I-383)+(S1-10); (I-383)+(S1-11); (I-383)+(S1-12); (I-383)+(S1-13); (I-383)+(S2-1); (I-383)+(S2-2); (I-383)+(S2-3); (I-383)+(S2-4); (I-383)+(S2-5); (I-383)+(S2-6); (I-383)+(S2-7); (I-383)+(S2-8); (I-383)+(S2-9); (I-383)+(S2-10); (I-383)+(S3-1); (I-383)+(S3-2); (I-383)+(S3-3); (I-383)+(S3-4); (I-383)+(S3-5); (I-383)+(S3-6); (I-383)+(S3-7); (I-383)+(S3-8); (I-383)+(S3-9); (I-383)+(S3-10); (I-383)+(S3-11); (I-383)+(S4-1); (I-383)+(S4-2); (I-383)+(S4-3); (I-383)+(S4-4); (I-383)+(S4-5); (I-383)+(S7-1); (I-383)+(S11-1); (I-383)+(S11-2); (I-383)+(S11-3); (I-383)+(S12-1); (I-383)+(S13-1); (I-383)+(S13-2); (I-383)+(S13-3); (I-383)+(S13-4): (I-383)+(S13-5); (I-383)+(S13-6); (I-383)+(S13-7); (I-383)+(S13-8); (I-383)+(S13-9); (I-383)+(S14-1)

(I-384)+(S1-1); (I-384)+(S1-2); (I-384)+(S1-3); (I-384)+(S1-4); (I-384)+(S1-5); (I-384)+(S1-6); (I-384)+(S1-7); (I-384)+(S1-8); (I-384)+(S1-9); (I-384)+(S1-10); (I-384)+(S1-11); (I-384)+(S1-12); (I-384)+(S1-13); (I-384)+(S2-1); (I-384)+(S2-2); (I-384)+(S2-3); (I-384)+(S2-4); (I-384)+(S2-5); (I-384)+(S2-6); (I-384)+(S2-7); (I-384)+(S2-8);

(I-384)+(S2-9); (I-384)+(S2-10); (I-384)+(S3-1); (I-384)+(S3-2); (I-384)+(S3-3); (I-384)+(S3-4); (I-384)+(S3-5); (I-384)+(S3-6); (I-384)+(S3-7); (I-384)+(S3-8); (I-384)+(S3-9); (I-384)+(S3-10); (I-384)+(S3-11); (I-384)+(S4-1); (I-384)+(S4-2); (I-384)+(S4-3); (I-384)+(S4-4); (I-384)+(S4-5); (I-384)+(S7-1); (I-384)+(S11-1); (I-384)+(S11-2); (I-384)+(S11-3); (I-384)+(S12-1); (I-384)+(S13-1); (I-384)+(S13-2); (I-384)+(S13-3); (I-384)+(S13-4): (I-384)+(S13-5); (I-384)+(S13-6); (I-384)+(S13-7); (I-384)+(S13-8); (I-384)+(S13-9); (I-384)+(S14-1)

(I-385)+(S1-1); (I-385)+(S1-2); (I-385)+(S1-3); (I-385)+(S1-4); (I-385)+(S1-5); (I-385)+(S1-6); (I-385)+(S1-7); (I-385)+(S1-8); (I-385)+(S1-9); (I-385)+(S1-10); (I-385)+(S1-11); (I-385)+(S1-12); (I-385)+(S1-13); (I-385)+(S2-1); (I-385)+(S2-2); (I-385)+(S2-3); (I-385)+(S2-4); (I-385)+(S2-5); (I-385)+(S2-6); (I-385)+(S2-7); (I-385)+(S2-8); (I-385)+(S2-9); (I-385)+(S2-10); (I-385)+(S3-1); (I-385)+(S3-2); (I-385)+(S3-3); (I-385)+(S3-4); (I-385)+(S3-5); (I-385)+(S3-6); (I-385)+(S3-7); (I-385)+(S3-8); (I-385)+(S3-9); (I-385)+(S3-10); (I-385)+(S3-11); (I-385)+(S4-1); (I-385)+(S4-2); (I-385)+(S4-3); (I-385)+(S4-4); (I-385)+(S4-5); (I-385)+(S7-1); (I-385)+(S11-1); (I-385)+(S11-2); (I-385)+(S11-3); (I-385)+(S12-1); (I-385)+(S13-1); (I-385)+(S13-2); (I-385)+(S13-3); (I-385)+(S13-4): (I-385)+(S13-5); (I-385)+(S13-6); (I-385)+(S13-7); (I-385)+(S13-8); (I-385)+(S13-9); (I-385)+(S14-1)

(I-386)+(S1-1); (I-386)+(S1-2); (I-386)+(S1-3); (I-386)+(S1-4); (I-386)+(S1-5); (I-386)+(S1-6); (I-386)+(S1-7); (I-386)+(S1-8); (I-386)+(S1-9); (I-386)+(S1-10); (I-386)+(S1-11); (I-386)+(S1-12); (I-386)+(S1-13); (I-386)+(S2-1); (I-386)+(S2-2); (I-386)+(S2-3); (I-386)+(S2-4); (I-386)+(S2-5); (I-386)+(S2-6); (I-386)+(S2-7); (I-386)+(S2-8); (I-386)+(S2-9); (I-386)+(S2-10); (I-386)+(S3-1); (I-386)+(S3-2); (I-386)+(S3-3); (I-386)+(S3-4); (I-386)+(S3-5); (I-386)+(S3-6); (I-386)+(S3-7); (I-386)+(S3-8); (I-386)+(S3-9); (I-386)+(S3-10); (I-386)+(S3-11); (I-386)+(S4-1); (I-386)+(S4-2); (I-386)+(S4-3); (I-386)+(S4-4); (I-386)+(S4-5); (I-386)+(S7-1); (I-386)+(S11-1); (I-386)+(S11-2); (I-386)+(S11-3); (I-386)+(S12-1); (I-386)+(S13-1); (I-386)+(S13-2); (I-386)+(S13-3); (I-386)+(S13-4): (I-386)+(S13-5); (I-386)+(S13-6); (I-386)+(S13-7); (I-386)+(S13-8); (I-386)+(S14-1)

(I-387)+(S1-1); (I-387)+(S1-2); (I-387)+(S1-3); (I-387)+(S1-4); (I-387)+(S1-5); (I-387)+(S1-6); (I-387)+(S1-7); (I-387)+(S1-8); (I-387)+(S1-9); (I-387)+(S1-10); (I-387)+(S1-11); (I-387)+(S1-12); (I-387)+(S1-13); (I-387)+(S2-1); (I-387)+(S2-2); (I-387)+(S2-3); (I-387)+(S2-4); (I-387)+(S2-5); (I-387)+(S2-6); (I-387)+(S2-7); (I-387)+(S2-8); (I-387)+(S2-9); (I-387)+(S2-10); (I-387)+(S3-1); (I-387)+(S3-2); (I-387)+(S3-3); (I-387)+(S3-4); (I-387)+(S3-5); (I-387)+(S3-6); (I-387)+(S3-7); (I-387)+(S3-8); (I-387)+(S3-9); (I-387)+(S3-10); (I-387)+(S3-11); (I-387)+(S4-1); (I-387)+(S4-2); (I-387)+(S4-3); (I-387)+(S4-4); (I-387)+(S4-5); (I-387)+(S7-1); (I-387)+(S11-1); (I-387)+(S11-2); (I-387)+(S11-3); (I-387)+(S12-1); (I-387)+(S13-1); (I-387)+(S13-2); (I-387)+(S13-3); (I-387)+(S13-4): (I-387)+(S13-5); (I-387)+(S13-6); (I-387)+(S13-7); (I-387)+(S13-8); (I-387)+(S13-9); (I-387)+(S14-1)

(I-388)+(S1-1); (I-388)+(S1-2); (I-388)+(S1-3); (I-388)+(S1-4); (I-388)+(S1-5); (I-388)+(S1-6); (I-388)+(S1-7); (I-388)+(S1-8); (I-388)+(S1-9); (I-388)+(S1-10); (I-388)+(S1-11); (I-388)+(S1-12); (I-388)+(S1-13); (I-388)+(S2-1); (I-388)+(S2-2); (I-388)+(S2-3); (I-388)+(S2-4); (I-388)+(S2-5); (I-388)+(S2-6); (I-388)+(S2-7); (I-388)+(S2-8); (I-388)+(S2-9); (I-388)+(S2-10); (I-388)+(S3-1); (I-388)+(S3-2); (I-388)+(S3-3); (I-388)+(S3-4); (I-388)+(S3-5); (I-388)+(S3-6); (I-388)+(S3-7); (I-388)+(S3-8); (I-388)+(S3-9); (I-388)+(S3-10); (I-388)+(S3-11); (I-388)+(S4-1); (I-388)+(S4-2); (I-388)+(S4-3); (I-388)+(S4-4); (I-388)+(S4-5); (I-388)+(S7-1); (I-388)+(S11-1); (I-388)+(S11-2); (I-388)+(S11-3); (I-388)+(S12-1); (I-388)+(S13-1); (I-388)+(S13-2); (I-388)+(S13-3); (I-388)+(S13-4): (I-388)+(S13-5); (I-388)+(S13-6); (I-388)+(S13-7); (I-388)+(S13-8); (I-388)+(S13-9); (I-388)+(S14-1)

(I-389)+(S1-1); (I-389)+(S1-2); (I-389)+(S1-3); (I-389)+(S1-4); (I-389)+(S1-5); (I-389)+(S1-6); (I-389)+(S1-7); (I-389)+(S1-8); (I-389)+(S1-9); (I-389)+(S1-10); (I-389)+(S1-11); (I-389)+(S1-12); (I-389)+(S1-13); (I-389)+(S2-1); (I-389)+(S2-2); (I-389)+(S2-3); (I-389)+(S2-4); (I-389)+(S2-5); (I-389)+(S2-6); (I-389)+(S2-7); (I-389)+(S2-8); (I-389)+(S2-9); (I-389)+(S2-10); (I-389)+(S3-1); (I-389)+(S3-2); (I-389)+(S3-3); (I-389)+(S3-4); (I-389)+(S3-5); (I-389)+(S3-6); (I-389)+(S3-7); (I-389)+(S3-8); (I-389)+(S3-9); (I-389)+(S3-10); (I-389)+(S3-11); (I-389)+(S4-1); (I-389)+(S4-2); (I-389)+(S4-3); (I-389)+(S4-4); (I-389)+(S4-5); (I-389)+(S7-1); (I-389)+(S11-1); (I-389)+(S11-2); (I-389)+(S11-3); (I-389)+(S12-1); (I-389)+(S13-1); (I-389)+(S13-2); (I-389)+(S13-3); (I-389)+(S13-4): (I-389)+(S13-5); (I-389)+(S13-6); (I-389)+(S13-7); (I-389)+(S13-8); (I-389)+(S13-9); (I-389)+(S14-1)

(I-390)+(S1-1); (I-390)+(S1-2); (I-390)+(S1-3); (I-390)+(S1-4); (I-390)+(S1-5); (I-390)+(S1-6); (I-390)+(S1-7); (I-390)+(S1-8); (I-390)+(S1-9); (I-390)+(S1-10); (I-390)+(S1-11); (I-390)+(S1-12); (I-390)+(S1-13); (I-390)+(S2-1); (I-390)+(S2-2); (I-390)+(S2-3); (I-390)+(S2-4); (I-390)+(S2-5); (I-390)+(S2-6); (I-390)+(S2-7); (I-390)+(S2-8); (I-390)+(S2-9); (I-390)+(S2-10); (I-390)+(S3-1); (I-390)+(S3-2); (I-390)+(S3-3); (I-390)+(S3-4); (I-390)+(S3-5); (I-390)+(S3-6); (I-390)+(S3-7); (I-390)+(S3-8); (I-390)+(S3-9); (I-390)+(S3-10); (I-390)+(S3-11); (I-390)+(S4-1); (I-390)+(S4-2); (I-390)+(S4-3); (I-390)+(S4-4); (I-390)+(S4-5); (I-390)+(S7-1); (I-390)+(S11-1); (I-390)+(S11-2); (I-390)+(S11-3); (I-390)+(S12-1); (I-390)+(S13-1); (I-390)+(S13-2); (I-390)+(S13-3); (I-390)+(S13-4): (I-390)+(S13-5); (I-390)+(S13-6); (I-390)+(S13-7); (I-390)+(S13-8); (I-390)+(S14-1)

(I-391)+(S1-1); (I-391)+(S1-2); (I-391)+(S1-3); (I-391)+(S1-4); (I-391)+(S1-5); (I-391)+(S1-6); (I-391)+(S1-7); (I-391)+(S1-8); (I-391)+(S1-9); (I-391)+(S1-10); (I-391)+(S1-11); (I-391)+(S1-12); (I-391)+(S1-13); (I-391)+(S2-1); (I-391)+(S2-2); (I-391)+(S2-3); (I-391)+(S2-4); (I-391)+(S2-5); (I-391)+(S2-6); (I-391)+(S2-7); (I-391)+(S2-8); (I-391)+(S2-9); (I-391)+(S2-10); (I-391)+(S3-1); (I-391)+(S3-2); (I-391)+(S3-3); (I-391)+(S3-4); (I-391)+(S3-5); (I-391)+(S3-6); (I-391)+(S3-7); (I-391)+(S3-8); (I-391)+(S3-9); (I-391)+(S3-10); (I-391)+(S3-11); (I-391)+(S4-1); (I-391)+(S4-2); (I-391)+(S4-3); (I-391)+(S4-4); (I-391)+(S4-5); (I-391)+(S7-1); (I-391)+(S11-1); (I-391)+(S11-2); (I-391)+(S11-3); (I-391)+(S12-1); (I-391)+(S13-1); (I-391)+(S13-2); (I-391)+(S13-3); (I-391)+(S13-4): (I-391)+(S13-5); (I-391)+(S13-6); (I-391)+(S13-7); (I-391)+(S13-8); (I-391)+(S13-9); (I-391)+(S14-1)

(I-392)+(S1-1); (I-392)+(S1-2); (I-392)+(S1-3); (I-392)+(S1-4); (I-392)+(S1-5); (I-392)+(S1-6); (I-392)+(S1-7); (I-392)+(S1-8); (I-392)+(S1-9); (I-392)+(S1-10); (I-392)+(S1-11); (I-392)+(S1-12); (I-392)+(S1-13); (I-392)+(S2-1); (I-392)+(S2-2); (I-392)+(S2-3); (I-392)+(S2-4); (I-392)+(S2-5); (I-392)+(S2-6); (I-392)+(S2-7); (I-392)+(S2-8); (I-392)+(S2-9); (I-392)+(S2-10); (I-392)+(S3-1); (I-392)+(S3-2); (I-392)+(S3-3); (I-392)+(S3-4); (I-392)+(S3-5); (I-392)+(S3-6); (I-392)+(S3-7); (I-392)+(S3-8); (I-392)+(S3-9); (I-392)+(S3-10); (I-392)+(S3-11); (I-392)+(S4-1); (I-392)+(S4-2); (I-392)+(S4-3); (I-392)+(S4-4); (I-392)+(S4-5); (I-392)+(S7-1); (I-392)+(S11-1); (I-392)+(S11-2);

(I-392)+(S11-3); (I-392)+(S12-1); (I-392)+(S13-1); (I-392)+(S13-2); (I-392)+(S13-3); (I-392)+(S13-4): (I-392)+(S13-5); (I-392)+(S13-6); (I-392)+(S13-7); (I-392)+(S13-8); (I-392)+(S13-9); (I-392)+(S14-1)

(I-393)+(S1-1); (I-393)+(S1-2); (I-393)+(S1-3); (I-393)+(S1-4); (I-393)+(S1-5); (I-393)+(S1-6); (I-393)+(S1-7); (I-393)+(S1-8); (I-393)+(S1-9); (I-393)+(S1-10); (I-393)+(S1-11); (I-393)+(S1-12); (I-393)+(S1-13); (I-393)+(S2-1); (I-393)+(S2-2); (I-393)+(S2-3); (I-393)+(S2-4); (I-393)+(S2-5); (I-393)+(S2-6); (I-393)+(S2-7); (I-393)+(S2-8); (I-393)+(S2-9); (I-393)+(S2-10); (I-393)+(S3-1); (I-393)+(S3-2); (I-393)+(S3-3); (I-393)+(S3-4); (I-393)+(S3-5); (I-393)+(S3-6); (I-393)+(S3-7); (I-393)+(S3-8); (I-393)+(S3-9); (I-393)+(S3-10); (I-393)+(S3-11); (I-393)+(S4-1); (I-393)+(S4-2); (I-393)+(S4-3); (I-393)+(S4-4); (I-393)+(S4-5); (I-393)+(S7-1); (I-393)+(S11-1); (I-393)+(S11-2); (I-393)+(S11-3); (I-393)+(S12-1); (I-393)+(S13-1); (I-393)+(S13-2); (I-393)+(S13-3); (I-393)+(S13-4): (I-393)+(S13-5); (I-393)+(S13-6); (I-393)+(S13-7); (I-393)+(S13-8); (I-393)+(S13-9); (I-393)+(S14-1)

(I-394)+(S1-1); (I-394)+(S1-2); (I-394)+(S1-3); (I-394)+(S1-4); (I-394)+(S1-5); (I-394)+(S1-6); (I-394)+(S1-7); (I-394)+(S1-8); (I-394)+(S1-9); (I-394)+(S1-10); (I-394)+(S1-11); (I-394)+(S1-12); (I-394)+(S1-13); (I-394)+(S2-1); (I-394)+(S2-2); (I-394)+(S2-3); (I-394)+(S2-4); (I-394)+(S2-5); (I-394)+(S2-6); (I-394)+(S2-7); (I-394)+(S2-8); (I-394)+(S2-9); (I-394)+(S2-10); (I-394)+(S3-1); (I-394)+(S3-2); (I-394)+(S3-3); (I-394)+(S3-4); (I-394)+(S3-5); (I-394)+(S3-6); (I-394)+(S3-7); (I-394)+(S3-8); (I-394)+(S3-9); (I-394)+(S3-10); (I-394)+(S3-11); (I-394)+(S4-1); (I-394)+(S4-2); (I-394)+(S4-3); (I-394)+(S4-4); (I-394)+(S4-5); (I-394)+(S7-1); (I-394)+(S11-1); (I-394)+(S11-2); (I-394)+(S11-3); (I-394)+(S12-1); (I-394)+(S13-1); (I-394)+(S13-2); (I-394)+(S13-3); (I-394)+(S13-4): (I-394)+(S13-5); (I-394)+(S13-6); (I-394)+(S13-7); (I-394)+(S13-8); (I-394)+(S13-9); (I-394)+(S14-1)

(I-395)+(S1-1); (I-395)+(S1-2); (I-395)+(S1-3); (I-395)+(S1-4); (I-395)+(S1-5); (I-395)+(S1-6); (I-395)+(S1-7); (I-395)+(S1-8); (I-395)+(S1-9); (I-395)+(S1-10); (I-395)+(S1-11); (I-395)+(S1-12); (I-395)+(S1-13); (I-395)+(S2-1); (I-395)+(S2-2); (I-395)+(S2-3); (I-395)+(S2-4); (I-395)+(S2-5); (I-395)+(S2-6); (I-395)+(S2-7); (I-395)+(S2-8); (I-395)+(S2-9); (I-395)+(S2-10); (I-395)+(S3-1); (I-395)+(S3-2); (I-395)+(S3-3); (I-395)+(S3-4); (I-395)+(S3-5); (I-395)+(S3-6); (I-395)+(S3-7); (I-395)+(S3-8); (I-395)+(S3-9); (I-395)+(S3-10); (I-395)+(S3-11); (I-395)+(S4-1); (I-395)+(S4-2); (I-395)+(S4-3); (I-395)+(S4-4); (I-395)+(S4-5); (I-395)+(S7-1); (I-395)+(S11-1); (I-395)+(S11-2); (I-395)+(S11-3); (I-395)+(S12-1); (I-395)+(S13-1); (I-395)+(S13-2); (I-395)+(S13-3); (I-395)+(S13-4): (I-395)+(S13-5); (I-395)+(S13-6); (I-395)+(S13-7); (I-395)+(S13-8); (I-395)+(S13-9); (I-395)+(S14-1)

(I-396)+(S1-1); (I-396)+(S1-2); (I-396)+(S1-3); (I-396)+(S1-4); (I-396)+(S1-5); (I-396)+(S1-6); (I-396)+(S1-7); (I-396)+(S1-8); (I-396)+(S1-9); (I-396)+(S1-10); (I-396)+(S1-11); (I-396)+(S1-12); (I-396)+(S1-13); (I-396)+(S2-1); (I-396)+(S2-2); (I-396)+(S2-3); (I-396)+(S2-4); (I-396)+(S2-5); (I-396)+(S2-6); (I-396)+(S2-7); (I-396)+(S2-8); (I-396)+(S2-9); (I-396)+(S2-10); (I-396)+(S3-1); (I-396)+(S3-2); (I-396)+(S3-3); (I-396)+(S3-4); (I-396)+(S3-5); (I-396)+(S3-6); (I-396)+(S3-7); (I-396)+(S3-8); (I-396)+(S3-9); (I-396)+(S3-10); (I-396)+(S3-11); (I-396)+(S4-1); (I-396)+(S4-2); (I-396)+(S4-3); (I-396)+(S4-4); (I-396)+(S4-5); (I-396)+(S7-1); (I-396)+(S11-1); (I-396)+(S11-2); (I-396)+(S11-3); (I-396)+(S12-1); (I-396)+(S13-1); (I-396)+(S13-2); (I-396)+(S13-3); (I-396)+(S13-4): (I-396)+(S13-5); (I-396)+(S13-6); (I-396)+(S13-7); (I-396)+(S13-8); (I-396)+(S13-9); (I-396)+(S14-1)

(I-397)+(S1-1); (I-397)+(S1-2); (I-397)+(S1-3); (I-397)+(S1-4); (I-397)+(S1-5); (I-397)+(S1-6); (I-397)+(S1-7); (I-397)+(S1-8); (I-397)+(S1-9); (I-397)+(S1-10); (I-397)+(S1-11); (I-397)+(S1-12); (I-397)+(S1-13); (I-397)+(S2-1); (I-397)+(S2-2); (I-397)+(S2-3); (I-397)+(S2-4); (I-397)+(S2-5); (I-397)+(S2-6); (I-397)+(S2-7); (I-397)+(S2-8); (I-397)+(S2-9); (I-397)+(S2-10); (I-397)+(S3-1); (I-397)+(S3-2); (I-397)+(S3-3); (I-397)+(S3-4); (I-397)+(S3-5); (I-397)+(S3-6); (I-397)+(S3-7); (I-397)+(S3-8); (I-397)+(S3-9); (I-397)+(S3-10); (I-397)+(S3-11); (I-397)+(S4-1); (I-397)+(S4-2); (I-397)+(S4-3); (I-397)+(S4-4); (I-397)+(S4-5); (I-397)+(S7-1); (I-397)+(S11-1); (I-397)+(S11-2); (I-397)+(S11-3); (I-397)+(S12-1); (I-397)+(S13-1); (I-397)+(S13-2); (I-397)+(S13-3); (I-397)+(S13-4): (I-397)+(S13-5); (I-397)+(S13-6); (I-397)+(S13-7); (I-397)+(S13-8); (I-397)+(S13-9); (I-397)+(S14-1)

(I-398)+(S1-1); (I-398)+(S1-2); (I-398)+(S1-3); (I-398)+(S1-4); (I-398)+(S1-5); (I-398)+(S1-6); (I-398)+(S1-7); (I-398)+(S1-8); (I-398)+(S1-9); (I-398)+(S1-10); (I-398)+(S1-11); (I-398)+(S1-12); (I-398)+(S1-13); (I-398)+(S2-1); (I-398)+(S2-2); (I-398)+(S2-3); (I-398)+(S2-4); (I-398)+(S2-5); (I-398)+(S2-6); (I-398)+(S2-7); (I-398)+(S2-8); (I-398)+(S2-9); (I-398)+(S2-10); (I-398)+(S3-1); (I-398)+(S3-2); (I-398)+(S3-3); (I-398)+(S3-4); (I-398)+(S3-5); (I-398)+(S3-6); (I-398)+(S3-7); (I-398)+(S3-8); (I-398)+(S3-9); (I-398)+(S3-10); (I-398)+(S3-11); (I-398)+(S4-1); (I-398)+(S4-2); (I-398)+(S4-3); (I-398)+(S4-4); (I-398)+(S4-5); (I-398)+(S7-1); (I-398)+(S11-1); (I-398)+(S11-2); (I-398)+(S11-3); (I-398)+(S12-1); (I-398)+(S13-1); (I-398)+(S13-2); (I-398)+(S13-3); (I-398)+(S13-4): (I-398)+(S13-5); (I-398)+(S13-6); (I-398)+(S13-7); (I-398)+(S13-8); (I-398)+(S13-9); (I-398)+(S14-1)

(I-399)+(S1-1); (I-399)+(S1-2); (I-399)+(S1-3); (I-399)+(S1-4); (I-399)+(S1-5); (I-399)+(S1-6); (I-399)+(S1-7); (I-399)+(S1-8); (I-399)+(S1-9); (I-399)+(S1-10); (I-399)+(S1-11); (I-399)+(S1-12); (I-399)+(S1-13); (I-399)+(S2-1); (I-399)+(S2-2); (I-399)+(S2-3); (I-399)+(S2-4); (I-399)+(S2-5); (I-399)+(S2-6); (I-399)+(S2-7); (I-399)+(S2-8); (I-399)+(S2-9); (I-399)+(S2-10); (I-399)+(S3-1); (I-399)+(S3-2); (I-399)+(S3-3); (I-399)+(S3-4); (I-399)+(S3-5); (I-399)+(S3-6); (I-399)+(S3-7); (I-399)+(S3-8); (I-399)+(S3-9); (I-399)+(S3-10); (I-399)+(S3-11); (I-399)+(S4-1); (I-399)+(S4-2); (I-399)+(S4-3); (I-399)+(S4-4); (I-399)+(S4-5); (I-399)+(S7-1); (I-399)+(S11-1); (I-399)+(S11-2); (I-399)+(S11-3); (I-399)+(S12-1); (I-399)+(S13-1); (I-399)+(S13-2); (I-399)+(S13-3); (I-399)+(S13-4): (I-399)+(S13-5); (I-399)+(S13-6); (I-399)+(S13-7); (I-399)+(S13-8); (I-399)+(S13-9); (I-399)+(S14-1)

(I-400)+(S1-1); (I-400)+(S1-2); (I-400)+(S1-3); (I-400)+(S1-4); (I-400)+(S1-5); (I-400)+(S1-6); (I-400)+(S1-7); (I-400)+(S1-8); (I-400)+(S1-9); (I-400)+(S1-10); (I-400)+(S1-11); (I-400)+(S1-12); (I-400)+(S1-13); (I-400)+(S2-1); (I-400)+(S2-2); (I-400)+(S2-3); (I-400)+(S2-4); (I-400)+(S2-5); (I-400)+(S2-6); (I-400)+(S2-7); (I-400)+(S2-8); (I-400)+(S2-9); (I-400)+(S2-10); (I-400)+(S3-1); (I-400)+(S3-2); (I-400)+(S3-3); (I-400)+(S3-4); (I-400)+(S3-5); (I-400)+(S3-6); (I-400)+(S3-7); (I-400)+(S3-8); (I-400)+(S3-9); (I-400)+(S3-10); (I-400)+(S3-11); (I-400)+(S4-1); (I-400)+(S4-2); (I-400)+(S4-3); (I-400)+(S4-4); (I-400)+(S4-5); (I-400)+(S7-1); (I-400)+(S11-1); (I-400)+(S11-2); (I-400)+(S11-3); (I-400)+(S12-1); (I-400)+(S13-1); (I-400)+(S13-2); (I-400)+(S13-3); (I-400)+(S13-4): (I-400)+(S13-5); (I-400)+(S13-6); (I-400)+(S13-7); (I-400)+(S13-8); (I-400)+(S13-9); (I-400)+(S14-1)

(I-401)+(S1-1); (I-401)+(S1-2); (I-401)+(S1-3); (I-401)+(S1-4); (I-401)+(S1-5); (I-401)+(S1-6); (I-401)+(S1-7); (I-401)+(S1-8); (I-401)+(S1-9); (I-401)+(S1-10); (I-401)+(S1-11); (I-401)+(S1-12); (I-401)+(S1-13); (I-401)+(S2-1); (I-401)+(S2-2); (I-401)+(S2-3); (I-401)+(S2-4); (I-401)+(S2-5); (I-401)+(S2-6); (I-401)+(S2-7); (I-401)+(S2-8); (I-401)+(S2-9); (I-401)+(S2-10); (I-401)+(S3-1); (I-401)+(S3-2); (I-401)+(S3-3); (I-401)+(S3-4); (I-401)+(S3-5); (I-401)+(S3-6); (I-401)+(S3-7); (I-401)+(S3-8); (I-401)+(S3-9); (I-401)+(S3-10); (I-401)+(S3-11); (I-401)+(S4-1); (I-401)+(S4-2); (I-401)+(S4-3); (I-401)+(S4-4); (I-401)+(S4-5); (I-401)+(S7-1); (I-401)+(S11-1); (I-401)+(S11-2); (I-401)+(S11-3); (I-401)+(S12-1); (I-401)+(S13-1); (I-401)+(S13-2); (I-401)+(S13-3); (I-401)+(S13-4): (I-401)+(S13-5); (I-401)+(S13-6); (I-401)+(S13-7); (I-401)+(S13-8); (I-401)+(S13-9); (I-401)+(S14-1)

(I-402)+(S1-1); (I-402)+(S1-2); (I-402)+(S1-3); (I-402)+(S1-4); (I-402)+(S1-5); (I-402)+(S1-6); (I-402)+(S1-7); (I-402)+(S1-8); (I-402)+(S1-9); (I-402)+(S1-10); (I-402)+(S1-11); (I-402)+(S1-12); (I-402)+(S1-13); (I-402)+(S2-1); (I-402)+(S2-2); (I-402)+(S2-3); (I-402)+(S2-4); (I-402)+(S2-5); (I-402)+(S2-6); (I-402)+(S2-7); (I-402)+(S2-8); (I-402)+(S2-9); (I-402)+(S2-10); (I-402)+(S3-1); (I-402)+(S3-2); (I-402)+(S3-3); (I-402)+(S3-4); (I-402)+(S3-5); (I-402)+(S3-6); (I-402)+(S3-7); (I-402)+(S3-8); (I-402)+(S3-9); (I-402)+(S3-10); (I-402)+(S3-11); (I-402)+(S4-1); (I-402)+(S4-2); (I-402)+(S4-3); (I-402)+(S4-4); (I-402)+(S4-5); (I-402)+(S7-1); (I-402)+(S11-1); (I-402)+(S11-2); (I-402)+(S11-3); (I-402)+(S12-1); (I-402)+(S13-1); (I-402)+(S13-2); (I-402)+(S13-3); (I-402)+(S13-4): (I-402)+(S13-5); (I-402)+(S13-6); (I-402)+(S13-7); (I-402)+(S13-8); (I-402)+(S13-9); (I-402)+(S14-1)

(I-403)+(S1-1); (I-403)+(S1-2); (I-403)+(S1-3); (I-403)+(S1-4); (I-403)+(S1-5); (I-403)+(S1-6); (I-403)+(S1-7); (I-403)+(S1-8); (I-403)+(S1-9); (I-403)+(S1-10); (I-403)+(S1-11); (I-403)+(S1-12); (I-403)+(S1-13); (I-403)+(S2-1); (I-403)+(S2-2); (I-403)+(S2-3); (I-403)+(S2-4); (I-403)+(S2-5); (I-403)+(S2-6); (I-403)+(S2-7); (I-403)+(S2-8); (I-403)+(S2-9); (I-403)+(S2-10); (I-403)+(S3-1); (I-403)+(S3-2); (I-403)+(S3-3); (I-403)+(S3-4); (I-403)+(S3-5); (I-403)+(S3-6); (I-403)+(S3-7); (I-403)+(S3-8); (I-403)+(S3-9); (I-403)+(S3-10); (I-403)+(S3-11); (I-403)+(S4-1); (I-403)+(S4-2); (I-403)+(S4-3); (I-403)+(S4-4); (I-403)+(S4-5); (I-403)+(S7-1); (I-403)+(S11-1); (I-403)+(S11-2); (I-403)+(S11-3); (I-403)+(S12-1); (I-403)+(S13-1); (I-403)+(S13-2); (I-403)+(S13-3); (I-403)+(S13-4): (I-403)+(S13-5); (I-403)+(S13-6); (I-403)+(S13-7); (I-403)+(S13-8); (I-403)+(S13-9); (I-403)+(S14-1)

(I-404)+(S1-1); (I-404)+(S1-2); (I-404)+(S1-3); (I-404)+(S1-4); (I-404)+(S1-5); (I-404)+(S1-6); (I-404)+(S1-7); (I-404)+(S1-8); (I-404)+(S1-9); (I-404)+(S1-10); (I-404)+(S1-11); (I-404)+(S1-12); (I-404)+(S1-13); (I-404)+(S2-1); (I-404)+(S2-2); (I-404)+(S2-3); (I-404)+(S2-4); (I-404)+(S2-5); (I-404)+(S2-6); (I-404)+(S2-7); (I-404)+(S2-8); (I-404)+(S2-9); (I-404)+(S2-10); (I-404)+(S3-1); (I-404)+(S3-2); (I-404)+(S3-3); (I-404)+(S3-4); (I-404)+(S3-5); (I-404)+(S3-6); (I-404)+(S3-7); (I-404)+(S3-8); (I-404)+(S3-9); (I-404)+(S3-10); (I-404)+(S3-11); (I-404)+(S4-1); (I-404)+(S4-2); (I-404)+(S4-3); (I-404)+(S4-4); (I-404)+(S4-5); (I-404)+(S7-1); (I-404)+(S11-1); (I-404)+(S11-2); (I-404)+(S11-3); (I-404)+(S12-1); (I-404)+(S13-1); (I-404)+(S13-2); (I-404)+(S13-3); (I-404)+(S13-4): (I-404)+(S13-5); (I-404)+(S13-6); (I-404)+(S13-7); (I-404)+(S13-8); (I-404)+(S13-9); (I-404)+(S14-1)

(I-405)+(S1-1); (I-405)+(S1-2); (I-405)+(S1-3); (I-405)+(S1-4); (I-405)+(S1-5); (I-405)+(S1-6); (I-405)+(S1-7); (I-405)+(S1-8); (I-405)+(S1-9); (I-405)+(S1-10); (I-405)+(S1-11); (I-405)+(S1-12); (I-405)+(S1-13); (I-405)+(S2-1); (I-405)+(S2-2); (I-405)+(S2-3); (I-405)+(S2-4); (I-405)+(S2-5); (I-405)+(S2-6); (I-405)+(S2-7); (I-405)+(S2-8); (I-405)+(S2-9); (I-405)+(S2-10); (I-405)+(S3-1); (I-405)+(S3-2); (I-405)+(S3-3); (I-405)+(S3-4); (I-405)+(S3-5); (I-405)+(S3-6); (I-405)+(S3-7); (I-405)+(S3-8); (I-405)+(S3-9); (I-405)+(S3-10); (I-405)+(S3-11); (I-405)+(S4-1); (I-405)+(S4-2); (I-405)+(S4-3); (I-405)+(S4-4); (I-405)+(S4-5); (I-405)+(S7-1); (I-405)+(S11-1); (I-405)+(S11-2); (I-405)+(S11-3); (I-405)+(S12-1); (I-405)+(S13-1); (I-405)+(S13-2); (I-405)+(S13-3); (I-405)+(S13-4): (I-405)+(S13-5); (I-405)+(S13-6); (I-405)+(S13-7); (I-405)+(S13-8); (I-405)+(S13-9); (I-405)+(S14-1)

(I-406)+(S1-1); (I-406)+(S1-2); (I-406)+(S1-3); (I-406)+(S1-4); (I-406)+(S1-5); (I-406)+(S1-6); (I-406)+(S1-7); (I-406)+(S1-8); (I-406)+(S1-9); (I-406)+(S1-10); (I-406)+(S1-11); (I-406)+(S1-12); (I-406)+(S1-13); (I-406)+(S2-1); (I-406)+(S2-2); (I-406)+(S2-3); (I-406)+(S2-4); (I-406)+(S2-5); (I-406)+(S2-6); (I-406)+(S2-7); (I-406)+(S2-8); (I-406)+(S2-9); (I-406)+(S2-10); (I-406)+(S3-1); (I-406)+(S3-2); (I-406)+(S3-3); (I-406)+(S3-4); (I-406)+(S3-5); (I-406)+(S3-6); (I-406)+(S3-7); (I-406)+(S3-8); (I-406)+(S3-9); (I-406)+(S3-10); (I-406)+(S3-11); (I-406)+(S4-1); (I-406)+(S4-2); (I-406)+(S4-3); (I-406)+(S4-4); (I-406)+(S4-5); (I-406)+(S7-1); (I-406)+(S11-1); (I-406)+(S11-2); (I-406)+(S11-3); (I-406)+(S12-1); (I-406)+(S13-1); (I-406)+(S13-2); (I-406)+(S13-3); (I-406)+(S13-4): (I-406)+(S13-5); (I-406)+(S13-6); (I-406)+(S13-7); (I-406)+(S13-8); (I-406)+(S13-9); (I-406)+(S14-1)

Within the context of the present invention, particular preference is given to combinations of the compounds of the formula (I) with the following safeners: daimuron (S14-1), benoxacor (S3-4), furilazole [(S3-10) or (S3-11)], fluxofenim (S11-2), fenchlorazole(-ethyl) (S1-7), mefenpyr-diethyl (S1-1), cloquintocet-mexyl (S2-1), isoxadifen-ethyl (S1-11), cyprosulfamide (S4-1), flurazole (S13-3), oxabetrinil (S11-1), dichlormid (S3-1) and dietholate (S13-8).

Within the context of the present invention, very particular preference is given to combinations of the compounds of the formula (I) with the following safeners: mefenpyr-diethyl (S1-1), isoxadifen-ethyl (S1-11), cyprosulfamide (S4-1), fenchlorazole-ethyl (S1-7), benoxacor (S3-4), cloquintocet-mexyl (S2-1), fluxofenim (S11-2) and furilazole [(S3-10) or (S3-11)].

Within the context of the present invention, combinations of the compounds of the formula (I) with the following safeners: isoxadifen-ethyl (S1-11) or cyprosulfamide (S4-1) are especially preferred.

Within the context of the present invention, combinations of the compounds of the formula (I) with the safener cyprosulfamide (S4-1) are emphasized.

Preference is given to herbicide/safener combinations comprising (A) a herbicidally effective amount of one or more compounds of the formula (I) or their salts, and (B) an antidotically effective amount of one or more safeners.

Within the context of the invention, herbicidally effective amount means an amount of one or more herbicides which is suitable for adversely affecting plant growth. Antidotically effective amount within the context of the invention means an amount of one or more safeners which is suitable for reducing the phytotoxic effect of crop protection composition active ingredients (e.g. of herbicides) on crop plants.

The safeners (B) are suitable for reducing phytotoxic effects which may occur when herbicides of the formula (I) are used in crops of useful plants without substantially impairing the effectiveness of these herbicidal active ingredients against harmful plants. As a result, it is possible to extend quite considerably the field of use of conventional crop protection compositions, for example to crops in which it has hitherto only been possible to use the herbicides to a limited extent, if at all.

Depending on indication and herbicidal active ingredient used, the required application rates of the safeners can vary within wide limits and are generally in the range from 0.001 to 5 kg, preferably 0.005 to 2.5 kg of active ingredient per hectare.

The herbicidal active ingredients (A) of the formula (I) and the safeners (B) can be applied together (e.g. as a ready mix or in the tank mix method) or sequentially in any desired order, for example in atomizing, pouring or spraying, or by scattering granules. The weight ratio of herbicide of the formula (I) (A):safener (B) can vary within wide limits and is preferably in the range from 1:10 000 to 10 000:1, in particular from 1:1000 to 1000:1. The optimum amounts in each case of the formula (I) (A) and safener (B) are dependent on the type of herbicide used and the type of safener used and also on the nature and the development stage of the plant stock to be treated and can be determined from case to case by simple routine preliminary experiments.

Depending on their properties, the safeners (B) contained in the herbicide/safener combination according to the invention can be used for pretreating the seed material of the crop plant (for example for seed dressing) or introduced into the seed furrows prior to sowing or be used together with the herbicide before or after the emergence of the plants. Pre-emergence treatment includes not only the treatment of the area under cultivation (including, if appropriate, water present on the area under cultivation, for example in the case of rice applications) before sowing, but also the treatment of the sown area of cultivation which does not yet sustain any growth. Joint application with the herbicide is preferred. For this purpose, it is possible to use tank mixes or ready mixes.

In a preferred embodiment, the seed material (e.g. grains, seeds or vegetative propagation organs, such as tubers or shoot parts with buds) or seedlings are pretreated with the safeners (B), if appropriate in combination with other agrochemical active ingredients. For the pretreatment of the seed material, the active ingredients can be applied to the seed material, for example, by dressing, or the active ingredients and the seed material can be introduced into water or other solvents, and the active ingredients are taken up, for example, by adduct formation or diffusion in a dip process or by swelling or pregermination. For the pretreatment of seedlings, the young plants can be brought into contact with the safeners, if appropriate in combination with other agrochemical active ingredients, for example by spraying, dipping or watering, and then be transplanted and, if appropriate, be subjected to a post-treatment with the herbicides (A).

The treatment of the seed material or seedlings can be carried out using the safeners (B) alone or together with other agrochemical active ingredients—such as fungicides, insecticides or agents for fortifying the plant, for fertilizing or for increasing the rate of the swelling and germination processes. Here, the safeners may, after the pretreatment application, be applied again before, after or together with one or more herbicides of the formula (I), possibly also in combination with other known herbicides. By pretreating the seed material or the seedlings, it is possible to achieve an improved long-term effect of the safeners.

Accordingly, the present invention further provides a method for controlling unwanted plants in crops of plants, which method comprises applying the components (A) and (B) of the herbicide/safener combination according to the invention to the plants (for example harmful plants, such as monocotyledonous or dicotyledonous weeds or undesired crop plants), the seed material (e.g. grains, seeds or vegetative propagation organs, such as tubers or shoot parts with buds) or the area on which the plants grow (e.g. the area under cultivation), for example together or separately. Here, it is possible to apply one or more safeners (B), preferably one or more, in particular one, compound of groups (S1) to (S14) before, after or at the same time as the herbicide(s) of the formula (I) (A) to the plants, the seed material or the area on which the plants grow (for example the area under cultivation). In a preferred embodiment, the safeners (B) are used for treating the seed material.

Undesired plants are to be understood as meaning all plants which grow where they are not wanted. These may be, for example, harmful plants (for example monocotyledonous or dicotyledonous weeds or undesired crop plants), including, for example, those which are resistant to certain herbicidal active ingredients, such as glyphosate, atrazine, glufosinates or imidazolinone herbicides.

Monocotyledonous weeds originate, for example, from the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera*. Dicotyledonous weeds originate, for example, from the genera *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia*.

In the method according to the invention, preferably an effective amount of components (A) and (B) is used for controlling harmful plants in plant crops, for example in economically important arable crops, for example monocotyledonous arable crops such as cereals (for example wheat, barley, rye, oats), rice, corn, millet, or dicotyledonous arable crops such as sugar beet, rapeseed, cotton, sunflowers and leguminous plants, for example of the genera *Glycine* (for example *Glycine max.*, such as non-transgenic *Glycine max.* (for example conventional cultivars, such as STS cultivars) or transgenic *Glycine max.* (for example RR-soybean or LL-soybean) and hybrids thereof, *Phaseolus, Pisum, Vicia* and *Arachis*, or vegetable crops of various botanical groups, such as potato, leek, cabbage, carrot, tomato, onion, and also permanent crops and plantation crops, such as pip and stone fruit, berry fruit, grapevine, Hevea, bananas, sugar cane, coffee, tea, citrus fruits, nut plantations, lawns, palm crops and forest plantations.

The invention also provides the use of the herbicide/safener combinations according to the invention for controlling undesired plant growth, preferably in plant crops.

The herbicide/safener combinations according to the invention can be prepared by known processes, for example as mix formulations of the individual components, if appropriate with further active ingredients, additives and/or customary formulation auxiliaries, which are then applied in a customary manner diluted with water, or they can be prepared as tank mixes by jointly diluting the individual components, formulated separately or partially formulated separately, with water. It is likewise possible to apply the individual components, formulated separately or partially formulated separately, at different times (splitting). It is also possible to apply the individual components or the herbicide/safener combinations in several portions (sequential application), for example pre-emergence applications, followed by post-emergence applications or early post-emergence applications, followed by medium or late post-emergence applications. Preference is given here to the joint or almost simultaneous application of the active ingredients of the combination in question.

The herbicide/safener combination according to the invention can also be used for controlling harmful plants in crops of known or still developing genetically modified plants.

The transgenic plants are usually characterized by particularly advantageous properties, for example by resistances to certain pesticides, primarily certain herbicides, resistances to plant diseases or pathogens of plant diseases such as certain insects or microorganisms such as fungi, bacteria or viruses. Other particular properties relate, for example, to the harvest material with regard to amount, quality, storability, composition and special ingredients. For example, transgenic plants with increased starch content or modified quality of the starch or those with a different fatty acid composition of the harvest material are known. Further particular properties may lie in a tolerance or resistance to abiotic stressors, for example heat, cold, dryness, salt and ultraviolet radiation.

Preferably, the application of the herbicide/safener combinations according to the invention, or salts thereof, is in economically important transgenic crops of useful plants and ornamental plants, e.g. of cereals such as wheat, barley, rye, oats, millet, rice, manioc and corn or else crops of sugar beet, cotton, soybean, rape, potatoes, tomatoes, peas and other vegetable crops.

The compounds of the formula (I) can preferably be used as herbicides in crops of useful plants which are resistant to the phytotoxic effects of the herbicides and/or have been rendered resistant by means of genetic engineering.

Conventional methods for producing new plants which have modified properties compared to existing plants consist, for example, in classical cultivation methods and the production of mutants. Alternatively, new plants with modified properties can be produced using genetic engineering methods (see e.g. EP-A-0221044, EP-A-0131624). For example, in several cases the following have been described:

genetic modifications of crop plants for the purpose of modifying the starch synthesized in the plants (e.g. WO 92/11376, WO 92/14827, WO 91/19806), transgenic crop plants which are resistant to certain herbicides of the glufosinate type (c.f. e.g. EP-A-0242236, EP-A-242246) or glyphosate type (WO 92/00377) or the sulfonylurea type (EP-A-0257993, U.S. Pat. No. 5,013, 659), transgenic crop plants, for example cotton, with the ability to produce *Bacillus thuringiensis* toxins (Bt toxins) which make the plants resistant to certain pests (EP-A-0142924, EP-A-0193259).

transgenic crop plants with a modified fatty acid composition (WO 91/13972).

genetically modified crop plants with new ingredients or secondary substances, for example new phytoalexins, which bring about an increased disease resistance (EPA 309862, EPA 0464461)

genetically modified plants with reduced photorespiration which have higher yields and higher stress tolerance (EPA 0305398).

transgenic crop plants which produce pharmaceutically or diagnostically important proteins ("molecular pharming")

transgenic crop plants which are characterized by higher yields or better quality transgenic crop plants which are characterized by a combination e.g. of the aforementioned new properties ("gene stacking").

Numerous molecular-biological techniques by means of which novel transgenic plants with modified properties can be produced are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For genetic manipulations of this type, nucleic acid molecules can be introduced into plasmids which permit a mutagenesis or a sequence modification through recombination of DNA sequences. With the help of standard methods it is possible, for example, to undertake base exchanges, remove part sequences or add natural or synthetic sequences. For joining the DNA fragments with one another, adapters or linkers can be attached to the fragments, see e.g. Sambrook et al., 1989, Molecular Cloning, A Laboratory Manual, 2nd edition, Cold Spring Harbor Laboratory Press, Cold Spring Harbor, N.Y.; or Winnacker "Gene and Klone [Genes and Clones]", VCH Weinheim 2nd edition 1996.

The production of plant cells with reduced activity of a gene product can be achieved, for example, through the expression of at least one corresponding antisense-RNA, of a sense-RNA for achieving a cosuppression effect or the expression of at least one correspondingly constructed ribozyme which cleaves specifically transcripts of the aforementioned gene product.

For this, firstly DNA molecules can be used which include the entire coding sequence for a gene product including any flanking sequences present, and also DNA molecules which only include parts of the coding sequence, in which case it is necessary for these parts to be long enough to bring about an antisense effect in the cells. It is also possible to use DNA sequences which have a high degree of homology to the coding sequences of a gene product, but are not completely identical.

During the expression of nucleic acid molecules in plants, the synthesized protein can be localized in any desired compartment of the plant cell. However, in order to achieve localization in a specific compartment, the coding region can, for example, be linked to DNA sequences which ensure localization in a specific compartment. Sequences of this type are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The expression of the nucleic acid molecules can also take place in the organelles of the plant cells.

The transgenic plant cells can be regenerated by known techniques to give whole plants. The transgenic plants may in principle be plants of any desired plant species, i.e. both monocotyledonous and also dicotyledonous plants.

Thus, transgenic plants are obtainable which have modified properties through overexpression, suppression or inhibition of homologous (=natural) genes or gene sequences or expression of heterologous (=foreign) genes or gene sequences.

Preferably, the herbicide/safener combinations according to the invention can be used in transgenic crops which are resistant to growth regulators such as, for example, dicamba or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of sulfonylureas, glyphosates, glufosinates or benzoylisoxazoles and analogous active ingredients.

When using the herbicide/safener combinations according to the invention in transgenic crops, besides the effects against harmful plants that are observed in other crops, effects often arise which are specific to the application in the particular transgenic crop, for example a modified or specifically expanded weed spectrum which can be controlled, modified application rates which can be used for the application, preferably good combinability with the herbicides against which the transgenic crop is resistant, and also influencing of growth and yield of the transgenic crop plants.

The invention therefore also provides the use of the herbicide/safener combinations according to the invention for controlling harmful plants in transgenic crop plants.

Preferably, the use of the combinations according to the invention is in economically important transgenic crops of useful plants and ornamental plants, e.g. of cereals (e.g. wheat, barley, rye, oats), millet, rice, manioc and corn or else cultures of sugar beet, cotton, soybean, rape, potatoes, tomatoes, peas and other vegetable crops.

The invention therefore also provides the use of the herbicide/safener combinations according to the invention for controlling harmful plants in transgenic crop plants or crop plants which are tolerant owing to selective cultivation.

The herbicides (A) and the safeners (B) can be converted jointly or separately into customary formulations, for example for application by atomization, pouring, spraying and seed dressing, such as solutions, emulsions, suspensions, powders, foams, pastes, granules, aerosols, natural and synthetic materials impregnated with active ingredient, and microencapsulations in polymeric substances. The formulations may comprise the customary auxiliaries and additives.

These formulations are produced in a known manner, for example by mixing the active ingredients with extenders, that is liquid solvents, liquefied gases under pressure, and/or solid carriers, optionally with the use of surface-active agents, that is emulsifiers and/or dispersants and/or foam formers.

If the extender used is water, it is also possible to use, for example, organic solvents as auxiliary solvents. Essentially, suitable liquid solvents are: aromatics such as xylene, toluene, or alkylnaphthalenes, chlorinated aromatics or chlorinated aliphatic hydrocarbons such as chlorobenzenes, chloroethylenes, or methylene chloride, aliphatic hydrocarbons such as cyclohexane or paraffins, e.g. mineral oil fractions, mineral and vegetable oils, alcohols, such as butanol or glycol and ethers and esters thereof, ketones, such as acetone, methyl ethyl ketone, methyl isobutyl ketone or cyclohexanone, strongly polar solvents such as dimethylformamide or dimethyl sulfoxide, and water.

Suitable solid carriers are: for example ammonium salts and ground natural minerals such as kaolins, clay earths, talc, chalk, quartz, attapulgite, montmorillonite or diatomaceous earth, and ground synthetic materials such as highly-dispersed silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, corn cobs and tobacco stalks; suitable emulsifiers and/or foam formers are: for example nonionogenic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignosulfite waste liquors and methylcellulose.

Tackifiers such as carboxymethylcellulose, natural and synthetic polymers in the form of powders, granules or latices, such as gum Arabic, polyvinyl alcohol and polyvinyl acetate, and also natural phospholipids, such as cephalins and lecithins, and synthetic phospholipids can be used in the formulations. Further additives may be mineral and vegetable oils.

Dyes such as inorganic pigments, for example iron oxide, titanium oxide, ferrocyan blue, and organic dyes such as alizarin dyes, azo dyes and metallophthalocyanine dyes and trace nutrients such as salts of iron, manganese, boron, copper, cobalt, molybdenum and zinc can be used.

The formulations comprise generally between 0.1 and 95% by weight of active ingredient, preferably between 0.5 and 90% by weight.

The herbicides (A) and the safeners (B) can be used as such or in their formulations also in a mixture with other agrochemical active ingredients, such as known herbicides, for controlling undesired plant growth, for example for controlling weeds or for controlling undesired crop plants, where, for example, ready mixes or tank mixes are possible.

Mixtures with other known active ingredients such as fungicides, insecticides, acaricides, nematicides, bird repellants, plant nutrients and soil structure improvers are also possible, likewise with additives and formulation auxiliaries customary in crop protection.

The herbicides (A) and the safeners (B) can be applied as such, in the form of their formulations and the application forms provided therefrom by further dilution, such as ready-to-use solutions, suspensions, emulsions, powders, pastes and granules. The application takes place in the customary manner, for example by pouring, atomizing, spraying, scattering.

The active ingredients can be applied to the plants, plant parts, the seed material or the area under cultivation (arable soil), preferably to the seed material or the green plants and plant parts and, if appropriate, additionally to the arable soil. One possible application is the joint application of the active ingredients in the form of tank mixes, where the optimally formulated concentrated formulations of the individual active ingredients are mixed together in the tank with water and the resulting spray liquor is applied.

A joint formulation of the combination according to the invention of active ingredients (A) and (B) has the advantage of easier application because the amounts of the components can already be adjusted in an optimal ratio relative to one another. Moreover, the auxiliaries in the formulation can be optimally matched to one another.

Combination partners which can be used for the herbicide/safener combination according to the invention in mixture formulations or in the tank mix are, for example, known, preferably herbicidal, active ingredients which are based on an inhibition of, for example, acetolactate synthase, acetyl-coenzyme-A-carboxylase, PS I, PS II, HPPD, phytoene desaturase, protoporphyrinogen oxidase, glutamine synthetase, cellulose biosynthesis, 5-enolpyruvylshikimate-3-phosphate synthetase. Such compounds and also other compounds that can be used, some of which have an unknown action mechanism or a different action mechanism, are described, for example, in Weed Research 26, 441-445 (1986), or in the handbook "The Pesticide Manual", 12th edition 2000, or 13th edition 2003 or 14th edition 2006/2007, or in the corresponding "e-Pesticide Manual", version 4.1 (2007-08), each published by the British Crop Protection Council (also referred to for short below as "PM"), and literature cited therein. Lists of "common names" are also available in "The Compendium of Pesticide Common Names" on the Internet. Known herbicides which can be combined with the mixtures according to the invention are, for example, the following active ingredients (note: the compounds are designated either with the "common name" in accordance with the International Organization for Standardization (ISO) or with the chemical name, optionally together with a customary code number, and always include all of the application forms such as acids, salts, esters and isomers such as stereoisomers and optical isomers. Here, one, and sometimes also more, application forms are specified):

2,4-D, acetochlor, acifluorfen, acifluorfen-sodium, aclonifen, alachlor, alloxydim, alloxydim-sodium, ametryn, amicarbazone, amidosulfuron, aminocyclopyrachlor, aminopyralid, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bicyclopyrone, bifenox, bilanafos, bispyribac-sodium, bromacil, bromobutide, bromofenoxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlorotoluron, chlorsulfuron, cinidon-ethyl, cinmethylin, cinosulfuron, clefoxydim, clethodim, clodinafop-propargyl, clomazone, clomeprop, clopyralid, cloransulam-methyl, cumyluron, cyanazine, cyclosulfamuron, cycloxydim, cyhalofop-butyl, desmedipham, dicamba, dichlobenil, dichlorprop, dichlorprop-P, diclofop-methyl, diclosulam, difenzoquat, diflufenican, diflufenzopyr, dikegulac-sodium, dimefuron, dimepiperate, dimethachlor, dimethametryn, dimethenamid, triaziflam, diquat-dibromide, dithiopyr, diuron, dymron, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fenoxasulfone, fentrazamide, flamprop-M-isopropyl, flamprop-M-methyl, flazasulfuron, florasulam, fluazifop, fluazifop-butyl, fluazifop-P-butyl, fluazolate, flucarbazone-sodium, flucetosulfuron, fluchloralin, flufenacet, flufenpyr, flumetsulam, flumiclorac-pentyl, flumioxazin, fluometuron, fluorochloridone, fluoroglycofen-ethyl, flupoxam, flupyrsulfuron-methyl-sodium, fluridone, fluoroxypyr, fluoroxypyr-butoxypropyl, fluoroxypyr-meptyl, flurprimidol, flurtamone, fluthiacet-methyl, fomesafen, foramsulfuron, glufosinate, glufosinate-P, glufosinate-ammonium, glufosinate-P-ammonium, glufosinate-P-sodium, glyphosate, halosulfuron-methyl, haloxyfop, haloxyfop-ethoxyethyl, haloxyfop-methyl, haloxyfop-P-methyl, hexazinone, imazamethabenz-methyl, imazamox, imazapic, imazapyr, imazaquin, imazethapyr, imazosulfuron, indanofan, indaziflam, iodosulfuron-methyl-sodium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, metazosulfuron, methabenzthiazuron, methiozolin, methyldymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxsulam, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyrisulfuron, propyzamide, prosulfocarb, pyrosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, saflufenacil, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenylchlor, thiazopyr, thifensulfuron-methyl, thiobencarb, tiocarbazil, tralkoxydim, triallate, triasulfuron, tribenuron-methyl, triclopyr, tridiphane, trifloxysulfuron, trifluralin, triflusulfuron-methyl and tritosulfuron.

Further possible mixing partners are pyroxasulfone, pyroxsulam, orthosulfamuron, pyrimisulfan, prohexadione-calcium, bencarbazone, SYN-523, IDH-100, SYP-249, monosulfuron, ipfencarbazone (HOK-201), pyribambenz-isopropyl, tefuryltrione, bencarbazone, tembotrione, pyrasulfotole and thiencarbazone-methyl.

For use, the formulations, which are present in a commercially available form, are, if appropriate, diluted in the customary manner, for example in the case of wettable powders, emulsifiable concentrates, dispersions and water-dispersible granules, by means of water. Preparations in the form of dusts, soil granules, granules for scattering, and sprayable solutions are usually not diluted further with other inert substances prior to use.

BIOLOGICAL EXAMPLES

Post-Emergence Herbicidal Effect and Safener Effect

Seeds or rhizome pieces of mono- and dicotyledonous harmful plants and of crop plants are planted in peat pots in sandy loam, covered with earth and grown in a greenhouse under good growth conditions. Alternatively to this, harmful plants occurring in the paddy rice cultivation are cultivated in pots in which water comes to 2 cm above the soil surface. 10 to 20 days after sowing, the test plants are treated in the one to three-leaf stage. The herbicide/safener active ingredient combinations according to the invention, formulated as water-soluble powders or suspensions, and, in parallel experiments, the correspondingly formulated individual active ingredients are sprayed onto the green plant parts in various dosages using an application rate of 300 l of water/ha (converted) and, after the test plants have remained in the greenhouse under optimum growth conditions for 2-3 weeks, the effect of the preparations is scored visually in comparison with untreated controls. In the case of rice or in the case of harmful plants which occur in the rice cultivation, the active ingredients are also placed directly into the irrigation water (application analogous to the so-called granules application) or sprayed onto plants and into the irrigation water.

Pre-Emergence Herbicidal Effect and Safener Effect

Seeds or rhizome pieces of mono- and dicotyledonous weed plants and crop plants were planted in peat pots in sandy loam and covered with earth. The herbicide/safener active ingredient combinations according to the invention, formulated as water-soluble powders or suspensions, and, in parallel experiments, the correspondingly formulated individual active ingredients were then applied to the surface of the covering earth at an application rate of 600 to 800 l of water/ha (converted) in a variety of dosages.

After the treatment, the pots were placed in the greenhouse and kept under good growth conditions for the weeds and the crop plants. Visual scoring of the plant damage or emergence damage was carried out after the test plants had emerged after a test period of 2 to 4 weeks, in comparison with untreated controls.

Treatment of Seed Material

Seed grains of crop plants were mixed in bottles with the safeners according to the invention, formulated as suspension concentrates or emulsion concentrates, and water and shaken well so that the seed grains were uniformly coated with the formulation of the particular safener. The seed grains and the emerged plants were then tested with herbicides in the pre-emergence or post-emergence method in accordance with the experiments according to examples 3.3 and 3.2.

Experimental series I (compound I-128):

Wheat (Triso)

| Administration | Herbicide | Herbicide dosage g (a.i./ha) | % Effect (without safener) | Safener (SA) | Safener dosage g of a.i./ha | % Effect (with safener) | % Reduction |
|---|---|---|---|---|---|---|---|
| Pre-emergence | I-128 | 100 | 50 | Mefenpyr-diethyl | 200 | 25 | 50 |
| Pre-emergence | I-128 | 100 | 50 | Isoxadifen-ethyl | 200 | 35 | 30 |
| Pre-emergence | I-128 | 100 | 50 | Cyprosulfamide | 200 | 35 | 30 |
| Pre-emergence | I-128 | 100 | 50 | Cloquintocet-mexyl | 200 | 30 | 40 |
| Pre-emergence | I-128 | 100 | 50 | Benoxacor | 200 | 20 | 60 |
| Pre-emergence | I-128 | 100 | 50 | Furilazole | 200 | 20 | 60 |
| Pre-emergence | I-128 | 100 | 50 | Fluxofenim | 200 | 40 | 20 |
| Pre-emergence | I-128 | 100 | 50 | Fenchlorazole | 200 | 30 | 40 |

Experimental series II (compound I-128):

Wheat (Triso)

| Administration | Herbicide | Herbicide dosage g (a.i./ha) | % Effect (without safener) | Safener (SA) | Safener dosage g of a.i./ha | % Effect (with safener) | % Reduction |
|---|---|---|---|---|---|---|---|
| Post-emergence | I-128 | 50 | 40 | Mefenpyr-diethyl | 100 | 30 | 25 |
| Post-emergence | I-128 | 50 | 40 | Benoxacor | 100 | 30 | 25 |
| Post-emergence | I-128 | 50 | 40 | Isoxadifen-ethyl | 100 | 30 | 25 |
| Post-emergence | I-128 | 50 | 40 | Cyprosulfamide | 100 | 20 | 50 |
| Post-emergence | I-128 | 50 | 40 | Cloquintocet-mexyl | 100 | 30 | 25 |
| Post-emergence | I-128 | 50 | 40 | Furilazole | 100 | 30 | 25 |
| Post-emergence | I-128 | 50 | 40 | Fluxofenim | 100 | 30 | 25 |
| Post-emergence | I-128 | 50 | 40 | Fenchlorazole | 100 | 30 | 25 |

Experimental series III (compound I-128):

Barley (Adonis)

| Administration | Herbicide | Herbicide dosage g (a.i./ha) | % Effect (without safener) | Safener (SA) | Safener dosage g of a.i./ha | % Effect (with safener) | % Reduction |
|---|---|---|---|---|---|---|---|
| Post-emergence | I-128 | 50 | 20 | Isoxadifen-ethyl | 100 | 10 | 50 |
| Post-emergence | I-128 | 25 | 30 | Cyprosulfamide | 50 | 20 | 33 |
| Post-emergence | I-128 | 25 | 30 | Cloquintocet-mexyl | 50 | 20 | 33 |
| Post-emergence | I-128 | 25 | 30 | Furilazole | 50 | 20 | 33 |
| Post-emergence | I-128 | 25 | 30 | Fluxofenim | 50 | 20 | 33 |
| Post-emergence | I-128 | 25 | 30 | Fenchlorazole | 50 | 20 | 33 |

Experimental series IV (compound I-128):

| | | | % Effect (without safener) | | | % Effect (with safener) | |
|---|---|---|---|---|---|---|---|
| | | Herbicide dosage | | | Safener dosage | | % |
| Administration | Herbicide | g (a.i./ha) | | Safener (SA) | g of a.i./ha | | Reduction |
| Pre-emergence | I-128 | 25 | 50 | Isoxadifen-ethyl | 50 | 40 | 20 |
| Pre-emergence | I-128 | 50 | 65 | Benoxacor | 100 | 50 | 23 |
| Post-emergence | I-128 | 100 | 40 | Mefenpyr-diethyl | 200 | 20 | 50 |
| Post-emergence | I-128 | 100 | 40 | Cyprosulfamide | 200 | 20 | 50 |
| Post-emergence | I-128 | 100 | 40 | Cloquintocet-mexyl | 200 | 10 | 75 |
| Post-emergence | I-128 | 100 | 40 | Furilazole | 200 | 20 | 50 |
| Post-emergence | I-128 | 100 | 40 | Fenchlorazole | 200 | 30 | 25 |

The invention claimed is:

1. A herbicidal composition to be used in corn comprising
(A)   4-amino-3-chloro-6-(4-chloro-2-fluoro-3-methoxyphenyl)pyridine-2-carboxylate or a salt, ester, acyl hydrazide, imidate, thioimidate, amidine, amide, orthoester, acyl cyanide, acyl halide, thio ester, thione ester, dithiol ester, or nitrile derivative thereof that (a) does not impair the herbicidal effect of the 4-amino-3-chloro-6-(4-chloro-2-fluoro-3-methoxyphenyl)pyridine-2-carboxylate or derivative thereof and (b) is or can be hydrolyzed, oxidized, or metabolized in plants or in the soil to give 4-amino-3-chloro-6-(4-chloro-2-fluoro-3-methoxyphenyl)pyridine-2-carboxylate, and
(B) one or more safeners selected from the group consisting of cyprosulfamide and 1-[4-(N-2-methoxybenzoylsulfamoyl)phenyl]-3-methylurea,
wherein said herbicidal composition reduces injury to corn.

2. The composition as claimed in claim 1, comprising, as component (A), the compound methyl 4-amino-3-chloro-6-(4-chloro-2-fluoro-3-methoxyphenyl)pyridine-2-carboxylate and, as component (B), cyprosulfamide.

3. The composition as claimed in claim 1 comprising an antidotically effective amount of one or more of said safeners, wherein an antidotically effective amount is an amount of one or more safeners which is suitable for reducing the phytotoxic effect on corn of 4-amino-3-chloro-6-(4-chloro-2-fluoro-3-methoxyphenyl)pyridine-2-carboxylate or a salt, ester, acyl hydrazide, imidate, thioimidate, amidine, amide, orthoester, acyl cyanide, acyl halide, thio ester, thione ester, dithiol ester, or nitrile derivative thereof that (a) does not impair the herbicidal effect of the 4-amino-3-chloro-6-(4-chloro-2-fluoro-3-methoxyphenyl)pyridine-2-carboxylate or derivative thereof and (b) is or can be hydrolyzed, oxidized, or metabolized in plants or in the soil to give 4-amino-3-chloro-6-(4-chloro-2-fluoro-3-methoxyphenyl)pyridine-2-carboxylate.

4. The composition as claimed in claim 1, wherein the safener is cyprosulfamide.

5. The composition as claimed in claim 1, wherein the safener is 1-[4-(N-2-methoxybenzoylsulfamoyl)phenyl]-3-methylurea.

6. The composition as claimed in claim 1, wherein component (A) is the compound methyl 4-amino-3-chloro-6-(4-chloro-2-fluoro-3-methoxyphenyl)pyridine-2-carboxylate.

7. The composition as claimed in claim 1, wherein component (A) is the compound 4-amino-3-chloro-6-(4-chloro-2-fluoro-3-methoxyphenyl)pyridine-2-carboxylic acid.

8. The composition as claimed in claim 1, wherein the weight ratio of (A) to (B) is 1:1000 to 1000:1.

9. A method for controlling undesired plants in corn, in which
(A)   4-amino-3-chloro-6-(4-chloro-2-fluoro-3-methoxyphenyl)pyridine-2-carboxylate or a salt, ester, acyl hydrazide, imidate, thioimidate, amidine, amide, orthoester, acyl cyanide, acyl halide, thio ester, thione ester, dithiol ester, or nitrile derivative thereof that (a) does not impair the herbicidal effect of the 4-amino-3-chloro-6-(4-chloro-2-fluoro-3-methoxyphenyl)pyridine-2-carboxylate or derivative thereof and (b) is or can be hydrolyzed, oxidized, or metabolized in plants or in the soil to give 4-amino-3-chloro-6-(4-chloro-2-fluoro-3-methoxyphenyl)pyridine-2-carboxylate, and
(B) one or more safeners selected from the group consisting of cyprosulfamide and 1-[4-(N-2-methoxybenzoylsulfamoyl)phenyl]-3-methylurea
are applied together or separately, to the undesired plants in the presence of corn, corn seed material, or the area on which the corn grows.

10. The method as claimed in claim 9, wherein the corn is transgenic or tolerant owing to selective cultivation.

11. The method as claimed in claim 9, wherein the application rate of (A) is 0.1 to 800 g of a.i./ha and the application rate of (B) is 0.001 to 5 kg of a.i./ha.

12. The method as claimed in claim 9, wherein the application rate of (A) is 10 to 400 g of a.i./ha and the application rate of (B) is 0.005 to 2.5 kg of a.i./ha.

13. A herbicidal composition to be used in corn comprising
(A) 4-amino-3-chloro-6-(6-chloro-3-pyridinyl)pyridine-2-carboxylate or a salt or ester thereof, and
(B) one or more safeners selected from the group consisting of cyprosulfamide and cloquintocet-mexyl,
wherein said herbicidal composition reduces injury to corn.

14. A method for controlling undesired plants in corn, in which
(A) the compound methyl 4-amino-3-chloro-6-(6-chloro-3-pyridinyl)pyridine-2-carboxylate or a salt or ester thereof,
and
(B) one or more safeners selected from the group consisting of cyprosulfamide and cloquintocet-mexyl,
are applied together or separately, to the undesired plants in the presence of corn, corn seed material, or the area on which the corn grows.

15. The method as claimed in claim 14, wherein the application rate of (A) is 25 to 100 g of a.i./ha and the application rate of (B) is 50 to 200 g of a.i./ha.

16. The method as claimed in claim 14, wherein the application rate of (A) is 0.1 to 800 g of a.i./ha and the application rate of (B) is 0.001 to 5 kg of a.i./ha.

\* \* \* \* \*